(12) United States Patent
Etter et al.

(10) Patent No.: US 12,016,961 B2
(45) Date of Patent: Jun. 25, 2024

(54) POINT OF CARE ULTRAVIOLET DISINFECTION SYSTEM

(71) Applicant: PuraCath Medical, Inc., San Francisco, CA (US)

(72) Inventors: Jeffrey Etter, Hayward, CA (US); John Ashley, Danville, CA (US); Ian Tran, Fremont, CA (US); Jochen Backs, San Francisco, CA (US); Julia Rasooly, San Francisco, CA (US); Michael Fourkas, Sunnyvale, CA (US)

(73) Assignee: PURACATH MEDICAL, INC., San Francisco, CA (US)

( * ) Notice: Subject to any disclaimer, the term of this patent is extended or adjusted under 35 U.S.C. 154(b) by 570 days.

(21) Appl. No.: 17/061,388

(22) Filed: Oct. 1, 2020

(65) Prior Publication Data

US 2021/0113725 A1 Apr. 22, 2021

Related U.S. Application Data

(60) Provisional application No. 62/911,004, filed on Oct. 4, 2019, provisional application No. 62/911,059, filed on Oct. 4, 2019.

(51) Int. Cl.
*A61L 2/10* (2006.01)
*A61L 2/24* (2006.01)
*G16H 10/60* (2018.01)

(52) U.S. Cl.
CPC ............ *A61L 2/10* (2013.01); *A61L 2/24* (2013.01); *G16H 10/60* (2018.01); *A61L 2202/11* (2013.01); *A61L 2202/14* (2013.01); *A61L 2202/16* (2013.01); *A61L 2202/24* (2013.01)

(58) Field of Classification Search
CPC .......... A61L 2/10; A61L 2/24; A61L 2202/11; A61L 2202/14; A61L 2202/16; A61L 2202/24; A61L 2202/121; A61L 2202/122; G16H 10/60; G16H 40/40; G16H 40/63; A61M 2025/0019
See application file for complete search history.

(56) References Cited

U.S. PATENT DOCUMENTS

| | | | |
|---|---|---|---|
| 5,360,413 | A | 11/1994 | Leason et al. |
| 5,423,791 | A | 6/1995 | Mark |
| 5,439,451 | A | 8/1995 | Collinson et al. |
| 5,730,418 | A | 3/1998 | Feith et al. |
| 5,782,816 | A | 7/1998 | Werschmidt et al. |
| 6,068,011 | A | 5/2000 | Paradis |

(Continued)

FOREIGN PATENT DOCUMENTS

| | | |
|---|---|---|
| CN | 105050627 A | 11/2015 |
| CN | 109641073 A | 4/2019 |

(Continued)

OTHER PUBLICATIONS

Office Action dated Aug. 30, 2021 from Japanese Patent Application No. 2019-522610 to Puracath Medical, Inc.

(Continued)

*Primary Examiner* — Regina M Yoo
(74) *Attorney, Agent, or Firm* — Vorys, Sater, Seymour and Pease LLP; Khaled Shami

(57) ABSTRACT

Hand held and portable disinfection units for use with patients having indwelling catheters or are hospitalized or under care in an intensive care unit.

5 Claims, 131 Drawing Sheets

(56) References Cited

U.S. PATENT DOCUMENTS

| | | |
|---|---|---|
| 6,245,048 B1 | 6/2001 | Fangrow, Jr. et al. |
| 6,482,188 B1 | 11/2002 | Rogers et al. |
| 6,491,668 B1 | 12/2002 | Paradis |
| 6,626,418 B2 | 9/2003 | Kiehne |
| 7,114,701 B2 | 10/2006 | Peppel |
| 7,591,449 B2 | 9/2009 | Raines et al. |
| 7,837,658 B2 | 11/2010 | Cote et al. |
| 7,867,204 B2 | 1/2011 | Bartholomew et al. |
| 8,038,123 B2 | 10/2011 | Ruschke et al. |
| 8,298,196 B1 | 10/2012 | Mansour |
| 8,636,720 B2 | 1/2014 | Truitt et al. |
| 8,708,976 B1 | 4/2014 | Yeh et al. |
| 8,715,247 B2 | 5/2014 | Mansour et al. |
| 8,801,678 B2 | 8/2014 | Panian et al. |
| 8,840,577 B1 | 9/2014 | Zollinger et al. |
| 9,017,295 B2 | 4/2015 | Pan |
| 9,056,147 B2 | 6/2015 | Ma |
| 9,067,049 B2 | 6/2015 | Panian et al. |
| 9,079,005 B2 | 7/2015 | Chelak et al. |
| 9,089,682 B2 | 7/2015 | Yeh et al. |
| 9,144,672 B2 | 9/2015 | Mansour et al. |
| 9,278,205 B2 | 3/2016 | Quach et al. |
| 9,370,651 B2 | 6/2016 | Zollinger et al. |
| 9,421,290 B2 | 8/2016 | Victor et al. |
| 9,695,953 B2 | 7/2017 | Burnard et al. |
| 10,016,588 B2 | 7/2018 | Mansour et al. |
| 10,610,609 B2 | 4/2020 | Swaney et al. |
| 2003/0017073 A1 | 1/2003 | Eckhardt et al. |
| 2003/0199835 A1 | 10/2003 | Leinsing et al. |
| 2007/0176117 A1 | 8/2007 | Redmond et al. |
| 2009/0012459 A1 | 1/2009 | Sobue et al. |
| 2011/0028914 A1 | 2/2011 | Mansour et al. |
| 2011/0062703 A1 | 3/2011 | Lopez et al. |
| 2013/0303996 A1 | 11/2013 | Rasooly et al. |
| 2013/0323120 A1 | 12/2013 | Ma |
| 2014/0264074 A1 | 9/2014 | Victor et al. |
| 2014/0276459 A1 | 9/2014 | Yeh et al. |
| 2014/0334974 A1 | 11/2014 | Rasooly et al. |
| 2015/0065956 A1 | 3/2015 | Huang et al. |
| 2015/0258230 A1 | 9/2015 | Victor et al. |
| 2015/0265829 A1 | 9/2015 | Truitt et al. |
| 2016/0030613 A1 | 2/2016 | Paul et al. |
| 2016/0082138 A1 | 3/2016 | Kermode et al. |
| 2017/0128713 A1 | 5/2017 | Panian et al. |
| 2019/0290791 A1* | 9/2019 | Baker .................... A61B 90/70 |
| 2020/0188543 A1 | 6/2020 | Etter et al. |

FOREIGN PATENT DOCUMENTS

| | | | |
|---|---|---|---|
| JP | 2010532238 A | 10/2010 | |
| JP | 2016518872 A | 6/2016 | |
| WO | 02/102421 A1 | 12/2002 | |
| WO | 2009006506 A1 | 1/2009 | |
| WO | 2010/036617 A1 | 4/2010 | |
| WO | WO-2014120620 A1 * | 8/2014 | ............... A61L 2/10 |
| WO | 2014159855 A1 | 10/2014 | |
| WO | 2015/157662 A1 | 10/2015 | |
| WO | 2016/044821 A1 | 3/2016 | |
| WO | 2017/192262 A1 | 11/2017 | |
| WO | 2018013581 A1 | 1/2018 | |
| WO | 2018089643 A1 | 5/2018 | |
| WO | WO2020198042 | 3/2020 | |

OTHER PUBLICATIONS

Chinese Search Report for Chinese Patent Application No. 201780052656.X dated Dec. 9, 2021, 2 pages.
Chinese Office Action for Chinese Patent Application No. 201780052656.X dated Jun. 14, 2022, 10 pages.
PCT International Search report, PCT App. No. PCT/US2020/054075, dated Dec. 22, 2020, 3 Pages.
Written Opinion of the International Searching Authority, PCT App. No. PCT/US2020/054075, dated Dec. 22, 2020, 8 Pages.

* cited by examiner

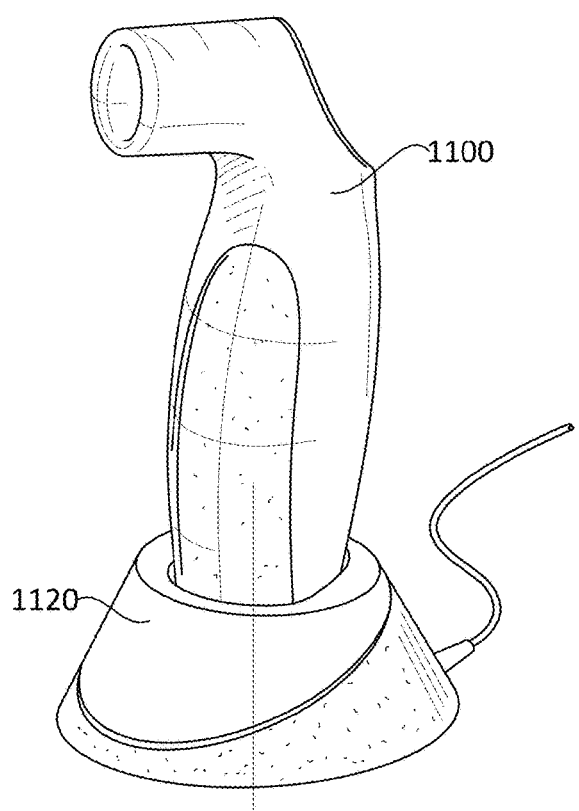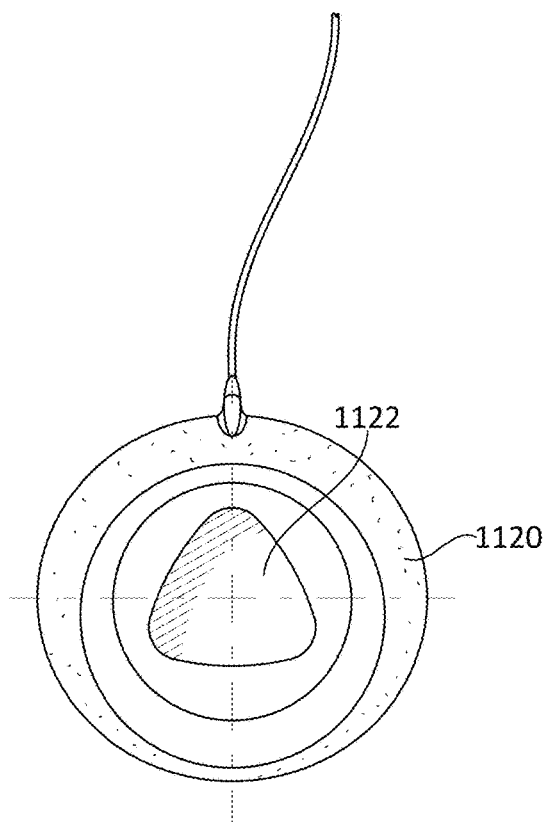
FIG. 11E                    FIG. 11F

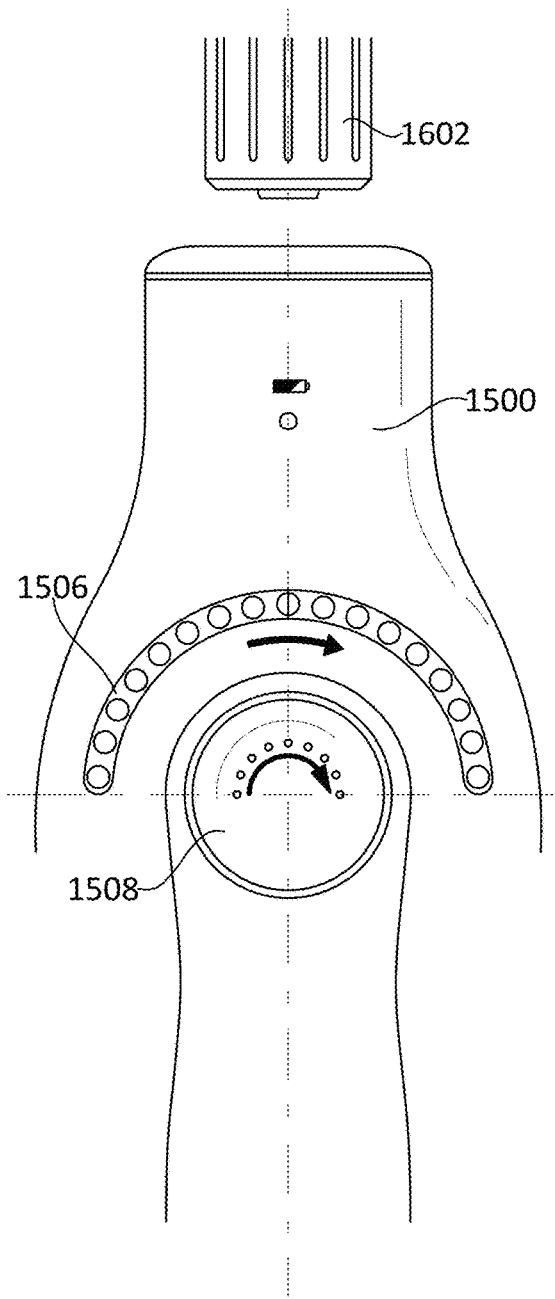
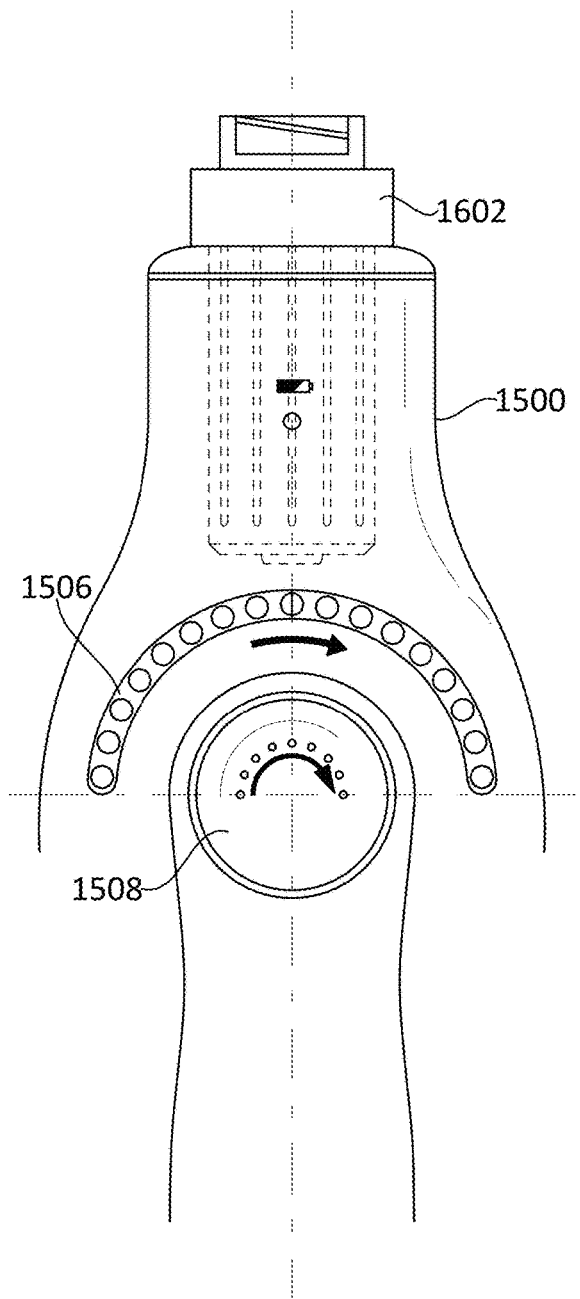
FIG. 16B
FIG. 16C

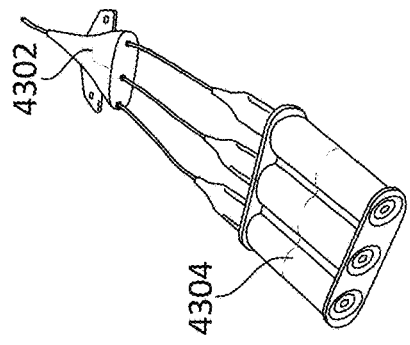
FIG. 43A
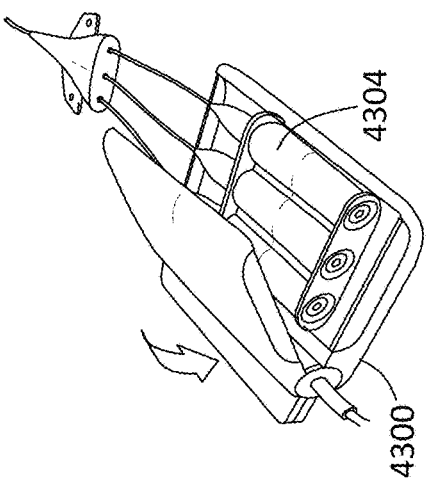
FIG. 43B
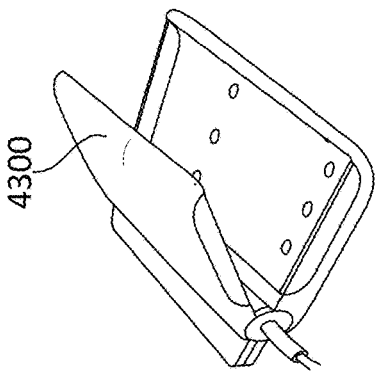
FIG. 43C
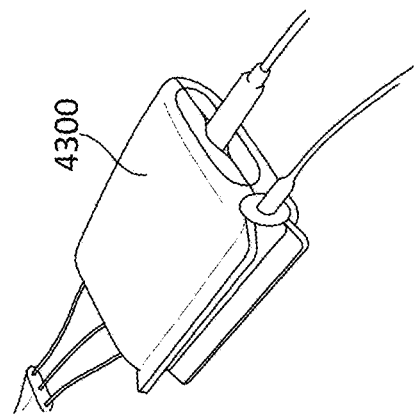
FIG. 43D
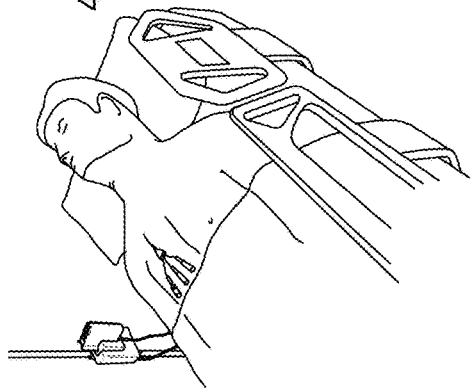
FIG. 43E
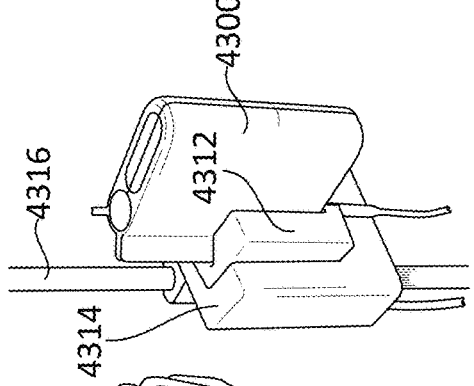
FIG. 43F
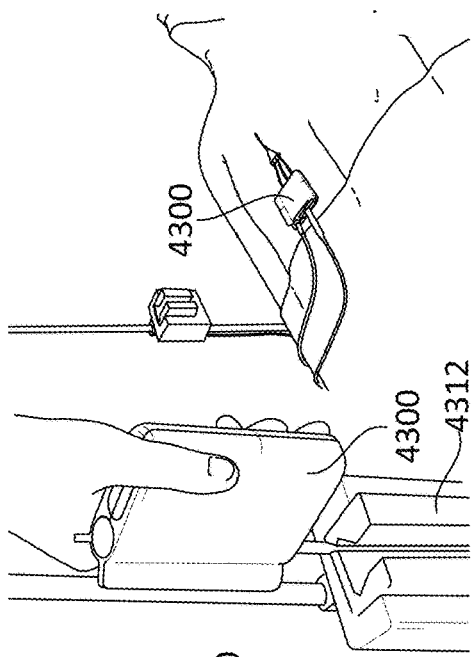
FIG. 43G
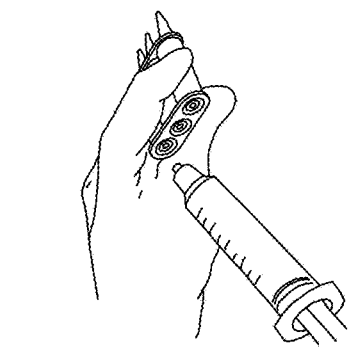
FIG. 43H
FIG. 43I

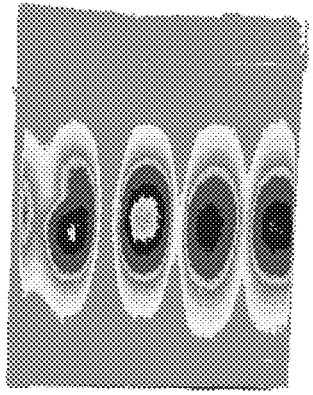
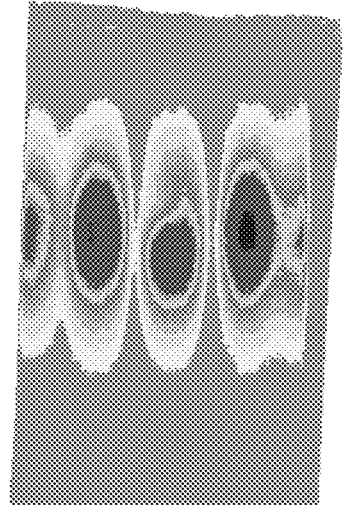
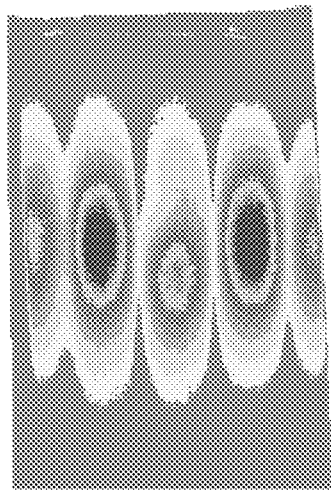
FIG. 64A  FIG. 64B  FIG. 64C
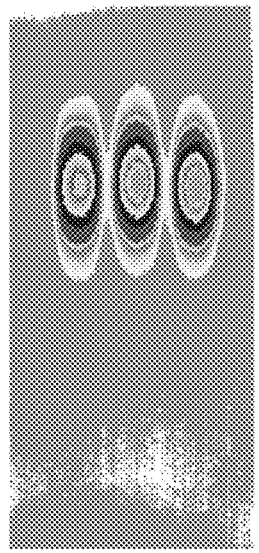
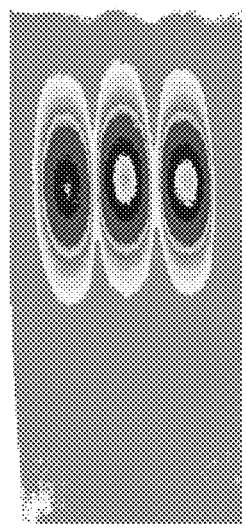
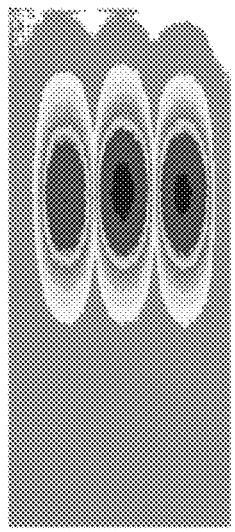
FIG. 64D  FIG. 64E  FIG. 64F

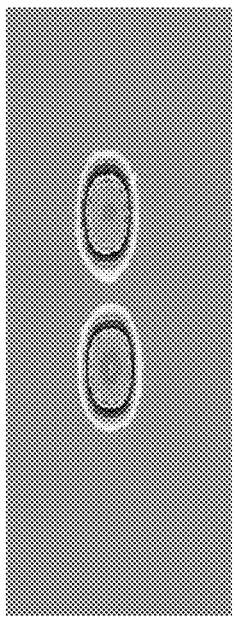 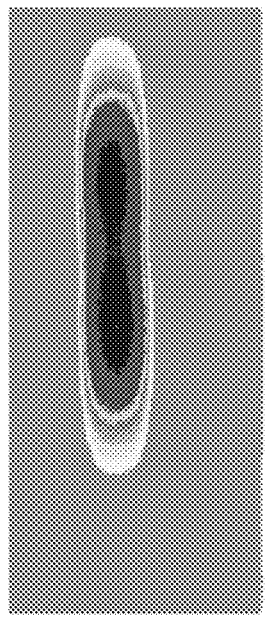 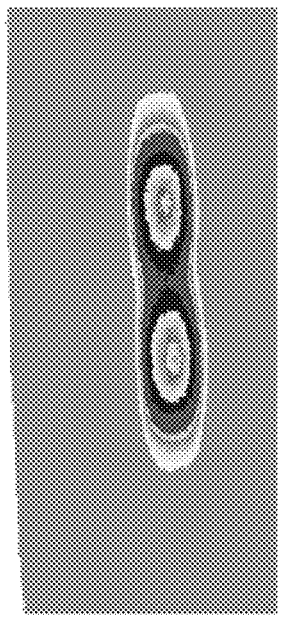
FIG. 64M                FIG. 64N                FIG. 64O
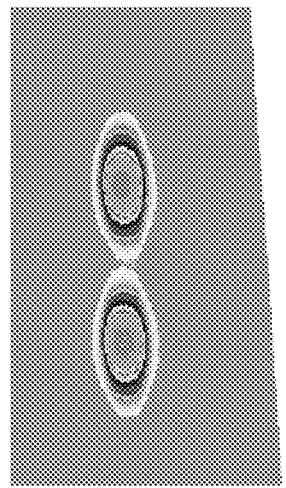 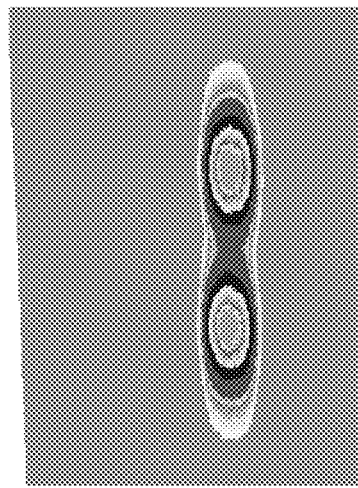
FIG. 64P                FIG. 64Q

6500

6505
Providing existing needleless connector design adapted for non-light based disinfection

6510
Fabricate needleless connector using precursor materials and process adapted for controllable transmissivity to enable UV-C based disinfection

6515
Obtain UV-C transmissivity signature for needleless connector fabricated for controllable transmissivity UV-C based disinfection

6520
Model/adapt UV-C sources, placement and dosing profile for desired disinfection profile for needleless connector fabricated for controllable transmissivity UV-C based disinfection

6525
Select UV-C disinfection unit

6530
Modify UV-C sources, placement, array and dose parameters in selected UV-C disinfection unit to key the disinfection chamber of the selected UV-C disinfection unit to the disinfection profile for the needleless connector fabricated for controllable transmissivity UV-C based disinfection

6535
Confirm keyed UV-C disinfection unit provides desired disinfection profile dosing parameters/achieves desired disinfection end point (i.e., 4 log reduction in less than 15 sec, less than 10 sec or less) for keyed needleless connector fabricated for controllable transmissivity UV-C based disinfection

6540
Release matched pair UV-C disinfection unit with disinfection chamber keyed to deliver the desired dosing profile and disinfection end point for the needleless connector fabricated for controllable transmissivity UV-C based disinfection

FIG. 65

POINT OF CARE ULTRAVIOLET DISINFECTION SYSTEM

CROSS REFERENCE TO RELATED APPLICATIONS

This application claims priority from U.S. Provisional Patent Application No. 62/911,059, entitled "NEEDLESS CONNECTOR VALVE FOR UV DISINIFECTION," and from U.S. Provisional Patent Application No. 62/911,004, entitled "POINT OF CARE ULTRA-VIOLET DISINFECTION SYSTEM," both filed on Oct. 4, 2019, the contents of both of which are incorporated herein by reference in their entirety.

This application may be considered related to U.S. patent application Ser. No. 16/316,918, entitled "POINT OF CARE ULTRAVIOLET DISINFECTION SYSTEM," filed Jul. 11, 2017; U.S. patent application Ser. No. 14/857,522, entitled "ULTRAVIOLET DISINFECTION UNIT," filed Sep. 17, 2015; U.S. patent application Ser. No. 15/074,854, entitled "CATHETER CONNECTION SYSTEM FOR ULTRAVIOLET LIGHT DISINFECTION," filed Mar. 18, 2016; U.S. patent application Ser. No. 16/316,930, entitled "CATHETER CONNECTION SYSTEM FOR ULTRAVIOLET LIGHT DISINFECTION," filed herewith on Jul. 11, 2017; and U.S. Provisional Patent Application No. 62/420,217, entitled "NEEDLESS CONNECTOR VALVE," filed Nov. 10, 2016, the contents of all which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Systems and methods related generally to uses for sterilizing access sites are described herein. More particularly, the various methods and devices for sterilizing intraluminal and percutaneous access sites using ultraviolet radiation delivered from any of the variously configured mobile disinfecting units or handheld disinfecting units.

BACKGROUND

One of the first interventions that occurs when a patient is admitted into a hospital is the placement of an intravenous access line (IV). This percutaneously-placed IV line gives the caregivers a direct path to the patient's bloodstream via a peripheral vein for rapid administration of fluids, medication or for drawing blood samples. In more serious cases, where direct access to a high blood flow supply is needed, for example, in chemotherapy delivery, temporary kidney dialysis or heart monitoring catheterization, a Central Venous Catheter (CVC or Central Line) is inserted. This line is typically inserted percutaneously into a major branching vessel, frequently the subclavian vein (but can also be placed in a peripheral vein), and then the distal segment of the catheter is directed into the superior vena cava.

Both peripheral and central catheterization procedures create an open pathway or lumen from an external access site into the bloodstream. This intraluminal access site provides an attachment point for various therapeutic or diagnostic medical devices, including, but not limited to, stopcocks, needle-less access sites, IV bags, infusion pumps, drug delivery pumps, kidney dialysis equipment, thermal dilution catheters, and the like. Unfortunately, this access site also provides an entry point for bacterial infections. Therefore, each time the access site is opened to accommodate the attachment of a medical device there is an opportunity for bacteria to enter the catheter lumen and be transferred into the bloodstream.

In addition to the contamination of the catheter lumen via the external access site, bacteria can also enter by the skin puncture and sub-cutaneous tract that is created by the catheter when the IV or CVC is placed. Bacteria can then find their way down the outside wall of the catheter to its distal end, infecting the tract along the catheter wall as they migrate.

In an attempt to mitigate the serious problems identified in the preceding paragraphs, conventional IV lines and CVCs use some type of molded plastic fitting at their proximal end terminated with a female Luer-lock or Luer-slip connector. These connectors must be closed by a Luer cap when not in use to prevent access site contamination. Each time the line is to be accessed, the Luer cap must be removed and discarded as it must be assumed that the outside of the Luer cap is contaminated and that once removed it is nearly impossible to prevent the male Luer configuration from touching a contaminated surface. Therefore, conventional infection control practice is to always replace the Luer cap whenever the line is accessed. This procedure is not only costly, but the removal and replacement process provides additional chances for bacteria to enter the lumen of the connector.

In some cases, IV access sites have been converted to needle-less access valves, which incorporate an elastomeric seal that can be opened via the tip of a male Luer connector mounted on a syringe or like device. These needle-less access valves are meant to be cleaned with an alcohol saturated swab before the valve is opened by the sterile male Luer tip of a syringe. Unfortunately, compliance with the swabbing procedures can be sporadic as it requires significant time, additional supplies and proper technique from the clinician performing the swabbing procedure.

As a result of the continued challenges related to preventing infection in patients having indwelling catheters, improvements in disinfecting and preventing infection are needed.

SUMMARY

In some embodiments, a UV disinfection device for disinfecting catheter connectors is provided. The device comprises a body having a first end and a second end, the body shaped to be held in a hand of a user; a generally barrel shaped opening positioned at or near the first end of the body, the opening shaped to receive a catheter connector; a generally cylindrical shaped kill zone within the opening; a UV-C transmissive lumen positioned within the kill zone; and a plurality of UV-C LEDs positioned around a circumference of the kill zone at at least two circumferential planes along a length of the kill zone.

In some embodiments, a UV disinfection device for disinfecting catheter connectors is provided. The device comprises a body having a first end and a second end, the body shaped to be held in a hand of a user; and a generally barrel shaped opening positioned at or near the first end of the body, the opening shaped to receive a catheter connector, the generally barrel shaped opening comprising a circumference and a length, the opening comprising a plurality of UV-C LEDs positioned near the circumference of the opening and at at least two circumferential planes along the length of the opening.

The device can comprise a disinfection progress indicator. The disinfection progress indicator can comprise a plurality of LEDs that change color, intensity or frequency of pulsing to indicate progress of disinfection. The device can comprise a battery charge indicator. The device can comprise a sensor near the opening to sense insertion of a component within the opening. In some embodiments, insertion of a component is configured to trigger at least one of activation, authentication, and logging disinfection information using a controller of the device. The sensor can be configured to interact with a tag on the component configured to be inserted within the opening. The device can comprise a head portion positioned at an angle relative to the body portion. In some embodiments, the device comprises a UV-C LED positioned towards an end of the opening. The device can comprise a charging dock. The dock can be configured to wirelessly charge the disinfection device. The dock can be configured to rest on a surface or be mounted to an IV pole. The charging dock can comprise a receptacle for receiving the first end of the device. The receptacle can comprise a UV-C LED. The dock can comprise a depression shaped to mate with the body portion. The device can comprise a display. In some embodiments, the device comprises an activation button. The device can comprise about 4-12 UV-C LEDs positioned within the opening. In some embodiments, the device comprises 8 LEDs positioned near a circumference at 2 circumferential planes along a length of the opening or kill zone. The UV-C LEDs can be equally spaced around a circumference of the kill zone or opening. In some embodiments, 4 UV-C LEDs are equally spaced near or around the circumference at two circumferential planes along a length of the opening or kill zone. The body portion can comprise a depression for a finger of a user. The device can comprise a mobile power pack. In some embodiments, the UV-C LEDs are symmetrical about a longitudinal axis of the opening. The device can comprise a rechargeable battery. In some embodiments, the device is configured to transmit data to a separate device or database through a wired or wireless connection.

In some embodiments, an apparatus for disinfecting a component or an universal adapter used in conjunction with an intravascular access site is provided. The apparatus comprises a catheter hub, a component or an universal adapter and a disinfecting unit adapted and configured for engaging with one or more of the component or the universal adapter by engagement to provide disinfection irradiating energy generated by the disinfecting unit to all or a portion of the component or the adapter via one or more specifically positioned substantially UV transparent surfaces in the component or universal adapter to facilitate disinfection of an end portion or an interior portion of the component or universal adapter sufficient to disinfect the same.

The disinfecting unit can engage with the component or the universal adapter by performing one or more of a closing a lid, sliding, inserting, clamping, or snapping action. The apparatus can comprise a UV-C transparent portion and an irradiating energy system for controllably irradiating a component or a universal adapter or a manifold adjacent to said UV-C transparent portion including plural sources of UV-C radiation disposed in a pattern for emitting UV-C radiation in a direction towards substantially all or a portion of the component or universal adapter and including a computer controller for controllably energizing said plural sources of UV radiation and to provide information related to operation of the disinfecting system to a local or remote user via a computer network. The disinfecting unit can include features adapted and configured for complementary engagement with the component, the manifold or the universal adapter to be disinfected. The features can be one or more of electronic, mechanical, friction or optical features.

In some embodiments, a device for disinfecting a universal adapter connector is provided. The device comprises a housing containing a UV light source, the UV light source being operably connected to a power source, the housing further comprising a receptacle for specifically receiving or engaging with the universal adapter connector, wherein the universal adapter connector is exposed to emitted light from the UV light source when the universal adapter connector is received by the receptacle.

The device can comprise a patient worn catheter hub configured to be selectively inserted by and retained within the receptacle, the patient worn catheter hub having an inner reflection portion or a transparent portion configured to reflect or permit passage of UV light emitted from the UV light source. The patient worn catheter hub can be configured to receive a manifold having an internal surface or features configured to receive one or more universal adapter connectors and to orient same for optimal interaction with UV light from the disinfecting unit. The device can further comprise a UV transparent shell in a friction fit, hinged or sliding arrangement to position over a patient worn catheter hub adapted and configured to interact with a handheld or portable disinfecting unit. In some embodiments, the patient worn catheter hub includes an adhesive backing or a frame to retain a component or universal connector. The device can comprise one or more attachment or engagement features configured to selectively attach, in a specifically desired orientation, a component, universal connector, catheter hub or patient worn access device in relation to a portable disinfection unit, a mobile disinfection unit or a disinfection unit integrated into a patient bed who has the vascular access site receiving the disinfection operation. The UV light source can include at least one or a plural arrangement of an UV-C LED. The device can comprise a timer electronically coupled to the irradiation source or the UV light source or one or more UV-LED to turn off the light source after a predetermined time period. The device can comprise a disinfection status indicator configured to communicate to a user a disinfection status of the disinfection operation performed by a disinfection unit including one or more lights configured into a bar, arc, ring or other shape to indicate a disinfection status. The device can comprise an input device for receiving an identification of at least one of the universal adapter connector, the disinfection unit, and the patient ID. In some embodiments, the device comprises an output for communicating the identification of at least one of the universal adapter connector, the disinfection unit and the patient ID.

In some embodiments, a method for disinfecting a connector for catheter connections is provided. The method comprises inserting the connector within a connector opening of a handheld UV disinfection device, the connector opening comprising a plurality of UV-C LEDs equidistantly positioned around a perimeter of the connector at two or more cross sectional planes along a length of the connector; and activating the device to irradiate the connector with UV-C light.

The method can comprise sensing insertion of the connector into the device using a sensor in the device. The device can initiate disinfection upon sensing insertion of the connector into the device. The method can comprise the device logging insertion of the connector into the device. In some embodiments, the method comprises the device logging complete disinfection cycles. The method can comprise the device logging incomplete disinfection cycles. In some embodiments, the method comprises the device sending disinfection information to a separate device. The method can comprise the device alerting the user to initiate a disinfection cycle. In some embodiments, the method comprises the device indicating disinfection progress. The method can comprise the device indicating battery charge level. In some embodiments, the method comprises placing the device in a charging dock following completion of disinfection. In some embodiments, placing the device in the charging dock activates an LED in the charging dock to disinfect the connector opening of the device. In some embodiments, placing the device in the charging dock activates the plurality of UV-C LEDs in the device to disinfect the connector opening of the device. Activating the device can comprise applying a current of about 200 mA to 800 mA. Activating the device can comprise applying a voltage of about 3V to about 10V. The UV-C LEDs can have a wavelength of about 350-300 nm. In some embodiments, activating the device comprises activating the device for about 10-20 seconds. Activating the device can comprise activating the device for about 15 seconds. The LEDs can emit light having a wavelength between 100 and 300 nm. In some embodiments the LEDs emit light having a wavelength of 250-290 nm. In some embodiments the activation time can be less than 10 seconds and preferentially 1 second or less.

In some embodiments, a method for disinfecting a universal adapter connector, component or manifold is provided. The method comprises inserting, sliding, clamping or covering a universal connector, manifold or component with a portion of a disinfection unit after performing a step of inserting, sliding, clamping or covering according to the operable requirements of the disinfection unit, exposing the universal adapter connector, component or manifold to light emitted from a UV light source of the disinfection unit for a predetermined length of time.

The UV light source can emit light in a portion of the UV-C spectrum or having a wavelength from approximately 290 nm to approximately 100 nm. The predetermined length of time can be approximately 1 second, 5 seconds, 10 seconds, 20 seconds, 30 seconds, 40 seconds or 50 seconds or less. The method can comprise a step for sending a disinfection status of the disinfection unit operation or an indication of operation to a remote computer system. The method can further comprise identifying the universal adapter connector, component or manifold; identifying a disinfection status of the disinfection unit; identifying the patient name, patient ID, or patient sate of birth, sending the disinfection status, the identification of the universal adapter connector, component or manifold, and the patient name, patient ID or patient date of birth to a remote computer system; and storing the sent information in an electronic medical record. In some embodiments, the electronic medical record is the electronic medical record of the patient. A step of sending the disinfection status and the identification of the disinfection unit or other information to a remote computer system can be achieved using at least one of a wireless antenna, an electrical connection, an RFID transmitter, a Bluetooth transmitter, an audio speaker, and a manual input device.

The devices described herein can be configured to include one or more of an editable electronic display, function indicators, status indicators, use indicators or patient information in a variety of different configurations with this view showing a patient name, a hospital ID, an editable electronic display and a frequency of use indicator. A disinfecting unit as described herein can include an aperture in a handheld unit adapted and configured to receive a selected portion or optionally all of a component to be disinfected using a disinfecting system contained within or operable to direct disinfecting energy into the component or portion thereof in the aperture. The disposable patient worn bases described herein can be configured to couple with a catheter hub or one or more connectors in order to maintain a relative position and orientation of the hub and connector to an intraluminal line in the patient and optionally in a position to enable coupling to a portable or handheld disinfecting unit for the disinfection of the one or more connectors individually or simultaneously while still connected to the patient.

The device can be configured to work with any standard male or female luer connection. Placing the luer connection into the UVC chamber and activating the UVC disinfection cycle applies UVC light to all of the surfaces exposed to UVC light for sufficient dosage. The exposed surfaces that are thus disinfected include the threads, lugs and other surfaces near the exposed port. The exposed surfaces can also include the surface of a needleless connector. In some embodiments the luer connection may be made from a UVC transmissive material. UVC light can transmit through the surfaces and therefore disinfect portions that would otherwise be shielded from the UVC light such as the internal surfaces of a connector.

In some embodiments a protective cap can be placed over the end of the luer connector. The protective cap can be fabricated from a UVC transmissive material. The luer connector with the protective cap on it can be positioned inside the UVC chamber. UVC light can then be used to disinfect the external surfaces of the protective cap and also the surfaces within the protective cap, in particular the luer connector surface that the protective cap is attached to. The luer connector surface would then be in a disinfected state and would be protected from contamination by the cap.

In some embodiments, a needleless connector valve is provided. The valve comprises an inlet; an outlet; a body; and a sealed core segment positioned within the body and positioned between the inlet and the outlet, wherein fluid entering the inlet is configured to flow around the sealed core segment, wherein the body comprises UV-C transmissive material.

In some embodiments, a needleless connector valve is provided. The valve comprises an inlet; an outlet; a body configured to allow 250 nm-300 nm wavelength light to propagate therethrough; and a sealed core positioned within the body.

The valve can comprise a cyclic olefin copolymer or a polymethylpentene.

In some embodiments, a method of providing a selective transmissivity connector for use in a light based disinfection system is provided. The method comprises providing a needleless connector design; and fabricating a needleless connector using precursor materials and a process adapted for controllable transmissivity to enable UV-C based disinfection.

The method can further comprise obtaining UV-C transmissivity signature for a needleless connector fabricated for controllable transmissivity UV-C based disinfection. The method can further comprise adapting UV-C sources, placement and dosing profile for a desired disinfection profile for the needleless connector design. The method can further comprise selecting a UV-C disinfection unit. The method can further comprise modifying the UV-C sources, placement, array and dose parameters in the selected UV-C disinfection unit to key the disinfection chamber of the selected UV-C disinfection unit to the disinfection profile for the needleless connector design. The method can further comprise confirming the keyed UV-C disinfection unit provides desired disinfection profile and/or achieves a desired disinfection end point. The method can further comprise releasing a matched pair UV-C disinfection unit with a disinfection chamber keyed to deliver the desired dosing profile and disinfection end point for the needleless connector fabricated for controllable transmissivity UV-C based disinfection.

In some embodiments, a method of fabricating a needleless connector is provided. The method comprises providing a mold for a needleless connector; placing a material comprising at least one of a cyclic olefin copolymer and polymethylpentene in the mold; and using a mold dwell time of one third or less than a manufacturer recommended dwell time.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 11E is a perspective view of the handheld UV disinfecting unit of FIG. 11A shown in a stowed position within a specifically configured charging dock.

FIG. 11F is a top down view of the charging dock of FIG. 11E with the hand held disinfecting unit removed.

FIGS. 16A and 16B are perspective and top views, respectively, of a connector or a component being advanced towards the portable disinfecting unit of FIG. 15A.

FIG. 16C is a top view showing the catheter or component inserted into the handheld disinfecting unit of FIG. 15A showing the differences in the status display as compared to FIG. 16B.

FIGS. 43A-43D are various views of a catheter hub and 3 port manifold and a UV LED disinfecting unit.

FIGS. 43E-43I illustrate the steps of disinfecting and delivery of a fluid via the three port manifold after use of a bedside mounted UV LED disinfecting unit as illustrated in FIGS. 43A-43D.

FIG. 65 illustrates an embodiment of a method of providing a selective transmissivity connector for use in a light based disinfection system.

DETAILED DESCRIPTION

Systems for light based disinfection of indwelling catheters and other similar tubes are described herein. In one embodiment, a disinfection system comprises a small or hand held light based disinfection unit which can be used to disinfect a UV transmissive connector used to infuse fluids or other substances into a patient. A number of various hand held light based disinfecting units are described herein. In particular, various different form factors for the use of UV-C lighting systems including in particular UV-LED based disinfecting systems are described. A number of UV transmissive connectors are also described herein. The light based disinfection achieved by the systems described herein can achieve a 4 log reduction in microbial growth within a desired amount of time.

The disinfection systems described herein find particular utility for use with indwelling catheters such as CVC, PICC and the like. Additionally, the various embodiments described herein may be applied to advantage to uses in ICU settings and more in a general way through various techniques and designs to integrate disinfection systems into bedside fluid delivery systems, hospital rooms, hospital beds or as a way of enhancing hospital room patient workflow.

The systems described herein can be 'smart' systems in that they allow tracking of disinfection information, and in turn, compliance information, and allow for providing alerts or adjusting workflow based on the tracked information. In certain embodiments the tracked information is linked to any one or more of a patient, treatment protocol, medical facility, medical personnel, and so on.

Figure 1C:
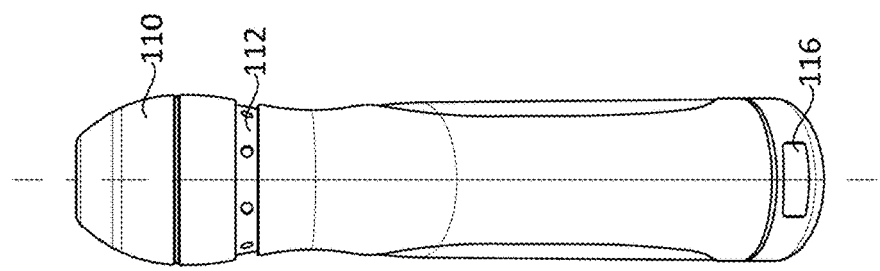
FIGS. 1A-1T illustrate various views of hand held UV disinfection units in accordance with certain embodiments.
Figure 1B:
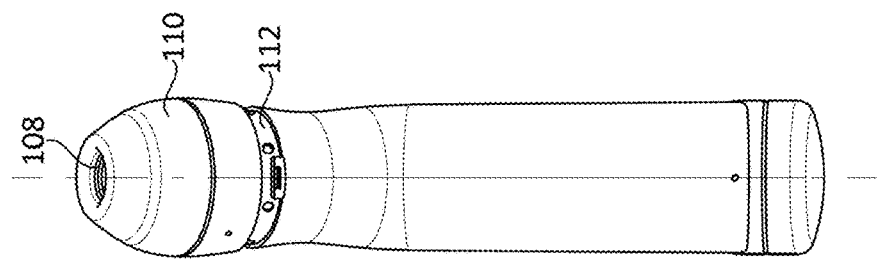
Figure 1A:
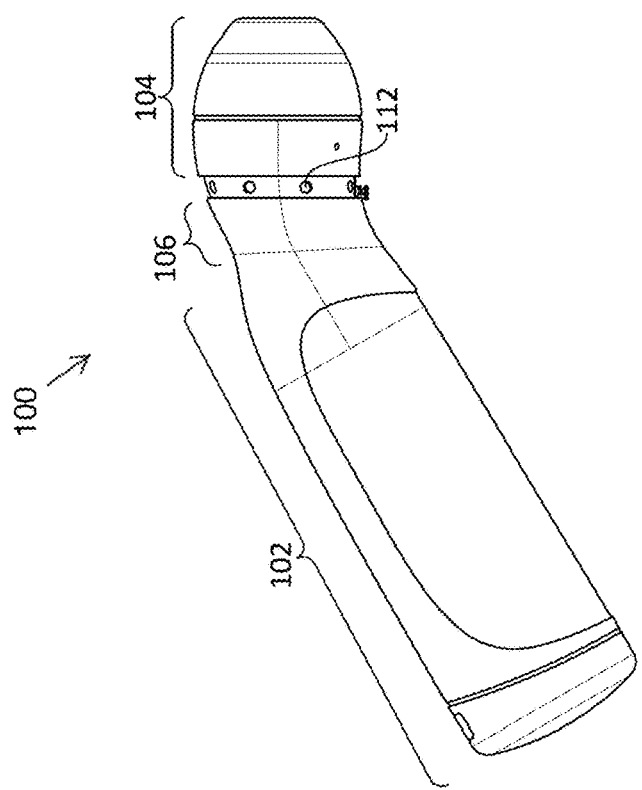
Figure 1F:
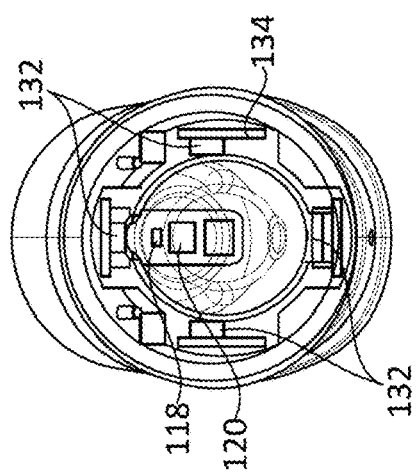
Figure 1E:
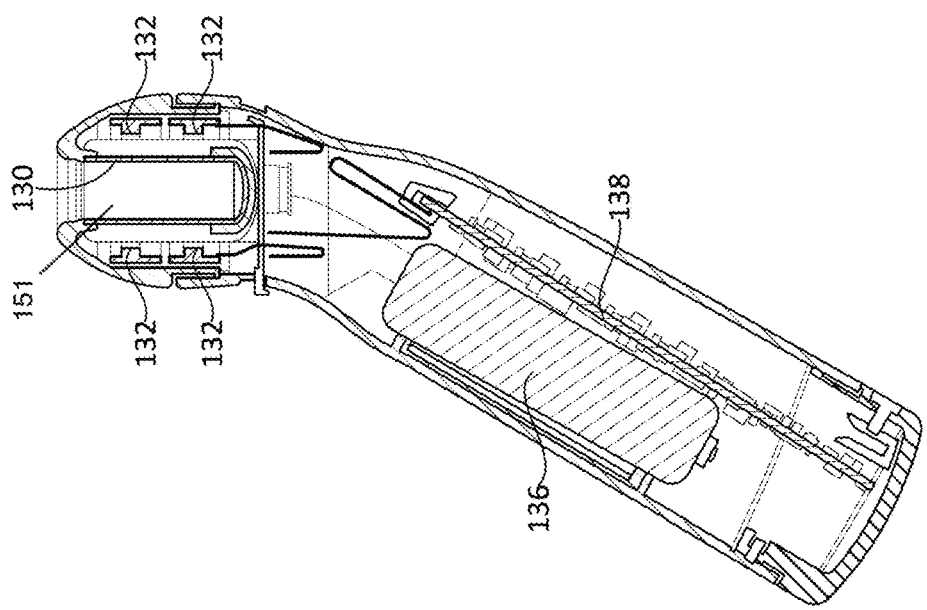
Figure 1D:
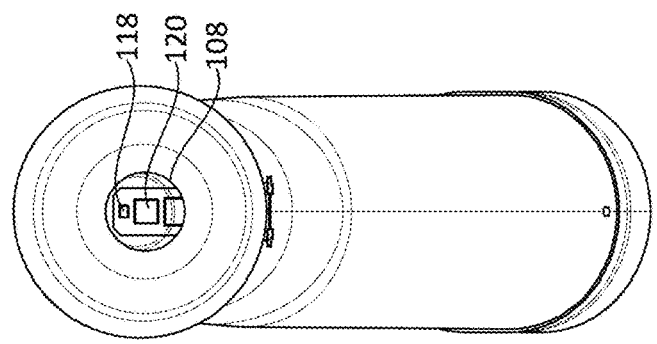

FIGS. 1A-D illustrate various views of a disinfection unit or handpiece 100. FIG. 1A shows a side view of the unit 100. The unit comprises a body portion 102 and a head portion 104. As also shown in the views of FIGS. 1B-D, the body portion 102 comprises a generally rounded cross-sectional shape (e.g., ovular, circular, etc.), making the body portion 102 comfortable to grip in either a left or right handed grip. The body portion 102 can be gripped in the way one would grip a bicycle handle. The body portion 102 transitions to the head portion 104 at a neck portion 106 having a reduced diameter as compared to the body portion and the neck portion. Similar to the body portion 102, the neck and head portions 104, 106 have a generally rounded cross-sectional shape (e.g., ovular, circular, etc.) The head portion 104 is arranged at an angle as compared to the body portion 102, with the angle occurring at or near the neck portion 106. The angle can be about 20 to 40 degrees. In the embodiment shown in FIGS. 1A-1D, the angle is about 30 degrees. This angle can provide a comfortable orientation for a user to grip the body portion 102 and insert a component to be disinfected into the connector insertion opening 108, shown in the front view of FIG. 1B. The head portion 104 comprises a nose portion 110 near an end of the head portion 104. The nose portion 110 extends from a midsection of the head portion 104 towards the connector insertion opening 108. A diameter of the nose portion decreases as it extends towards the connector insertion opening 108. The nose portion 110 can comprise a different material (e.g., aluminum) than the remainder of the disinfection unit. In other embodiments, the material of the nose portion can be the same as the remainder of the disinfection unit. The device can comprise commonly used plastics for molding including, but not limited to ABS (Acrylonitrile Butadiene Styrene), ABS/Polycarbonate blends, polypropylene, polycarbonate, and polyethylene. In some embodiments, the device can incorporate antimicrobial additives such as silver ions. A width of the nose cone can be about 25-60 mm. In some embodiments, a widest dimension of the nose cone is about 35 mm.

Portions of the system, and particularly the handpiece 100, that are exposed to UVC light may be made out of materials that have particular benefits relative to UVC light as applicable for disinfection. The materials that comprise the UVC chamber, shown below, are for example preferably fabricated from a material that was not physically affected by UVC exposure. The chamber could be made of aluminum or other metals for instance. The chamber may also be made out of Polyetherimide (such as Ultem). The construction of the chamber isolates UVC light so that materials or components are exposed to minimal UVC light such as by using a UVC opaque material and including physical barriers to minimize UVC exposure except where desired. The materials can be selected to be UVC reflective or UVC absorptive to control light as desired within the chamber. Through selection of UVC transparent materials, elimination of shadows, and optimal placement of UVC LEDs, in certain embodiments the system is able to disinfect a component in as fast as 1 second or even less.

In certain embodiments, head portion 104 includes a disinfection progress indicator 112. The indicator 112 comprises a series of lights spaced circumferentially around a portion of the disinfection unit 100. The indicator 112 can be configured to change color to indicate the progress of the disinfection cycle. In some embodiments, the indicator 112 is configured to sequentially illuminate the lights during the disinfection process to indicate progress of the disinfection cycle. In other embodiments the entire band could be configured to illuminate to indicate the start and end of the disinfection cycle. Circumferential illumination could provide status to the user regardless of hand piece orientation. The indicator 112 can also be configured to vary the intensity or frequency of the light to indicate progress of a disinfection cycle. Any combination of these light modulations are possible to indicate progress of the disinfection. Once all the lights are illuminated, the disinfection cycle is complete. In some embodiments, an audible alert can also be used. FIGS. 1A-1C show disinfection progress lights positioned the entire circumference of the device. In some embodiments, the disinfection progress indicator can comprise lights positioned around a portion of the circumference of the device. Examples of such embodiments are described below.

The back view of FIG. 1C shows a battery level indicator 116. The indicator can change color and/or flash at varying frequencies to indicate a charge level of the battery. In some embodiments, the indicator 116 can comprise a plurality of lights that sequentially illuminate to indicate the charge level of the battery. The indicator 116 can also vary an intensity of light to indicate charge level. Any combination of this light modulation can be used to indicate a battery level. In some embodiments, an audible alert can also be used. In some embodiments, the circumferentially positioned light 112 may be used to indicate battery level. The light can illuminate yellow light, and be steady or flash or blinking. In some embodiments the frequency (blinking rate) of the light can increase or change to indicate differences in the remaining battery charge. In some embodiments the color of the light can change to indicate differences in the remaining battery charge.

The top perspective view of FIG. 1D shows an interior of the nose portion 110. A sensor 118 is shown positioned within the nose portion 110. The sensor 118 is configured to read a corresponding tag on a connector or component to be disinfected. The sensor 118 can be an optical sensor, an RFID reader, a near field communication (NFC reader), and the like. Once the component is sufficiently inserted within the opening 108, the disinfection unit 100 can automatically activate a disinfection cycle. As noted elsewhere herein, the optical sensor 118 can also be used to authenticate the component, track compliance with disinfection protocols, and log user and patient information. FIG. 1D shows the sensor 118 positioned at an end of the nose portion 118. Other positions for the sensor are also possible. The sensor can be positioned at any position that will allow it to interact with a corresponding tag on a component to be disinfected to sense insertion of the component into the device 100. For example, in some embodiments, the component to be disinfected may have a tag positioned at a distal end of the component. In such embodiments, the sensor may be positioned closer to the connector insertion opening 108 as that is the area of the device 100 that will be nearest the tag on the component to be disinfected. In some embodiments, the sensor 118 is configured to sense full insertion of the component into the device 100. This allows the device 100 to sense full insertion and then trigger a disinfection cycle once full insertion has been verified. In some embodiments, the sensor may sense at least partial insertion of a component to be disinfected in the device. In such embodiments, the device 100 can alert the user if the component is not properly inserted to allow disinfection. The system can also log an event in which the component is partially inserted, but a disinfection cycle is not completed.

FIG. 1D also shows an UV LED 120 that can be used to disinfect the end of an inserted component, described in more detail below. In some embodiments 2 LEDs can be used or even more.

FIG. 1E shows a sectional side view of the disinfection unit 100. A tube 130 extends from the connector insertion opening 108 into the disinfection unit 100. The tube 130 can comprise a UV transmissive material (e.g., quartz) and can serve to define a chamber 151 and separate the connector insertion area from the LEDs and other internal components. In this view, UV LEDs 132 are shown surrounding the tube. In certain embodiments, there are 8 LEDs total. Pairs of LEDs 132 are positioned equally around a circumference of the tube at four positions along the circumference. Each pair is spaced along the length of the tube. As described in more detail below and with respect to FIGS. 63A-C, this configuration ensures that a component inserted within the tube 130 in chamber 151 will receive UV energy sufficient for desired microbial reduction or disinfection. FIG. 1E also shows rechargeable battery 136 and PCB 138.

FIG. 1F shows a sectional view of the head portion taken from an end of the head portion. This view shows four LEDs 132 spaced around the tube 130. This view also shows the end LED 120 used for disinfection of an end portion of a component inserted and to be disinfected. The end of the component may comprise a flat surface or surfaces that may not be sufficiently illuminated by LEDs 132. Thus, end LED 120 can serve to illuminate such surfaces. FIG. 1F also shows sensor 118. As shown in FIG. 1F, each LED can have an associated circuit board 134.

In certain embodiments, the disinfection unit 100 does not include an activation button. Instead, a disinfection cycle can be automatically triggered when the system senses insertion of a connector or other component to be disinfected within the head portion 104 of the device 100. Triggering the system can initiate a disinfection cycle of a desired time frame (e.g., about 1 second, 10 seconds, about 20 seconds, about 10-15 seconds, about 10-20 seconds, about 15-25 seconds, about 5-25 seconds, about 25-35 seconds, etc.). In some embodiments, the disinfection cycle is about 15 seconds. As described elsewhere herein, in some embodiments, the disinfection unit may comprise an activation control to allow manual initiation of a disinfection cycle. In some embodiments, the sensor that triggers the disinfection cycle could be an electrical contact switch, as described below, an optical sensor, magnetic sensor, and the like.

The design of the disinfection unit shown helps ensure compliance as the connector or component to be disinfected can be inserted into the disinfection unit at any angle and does not need to be in a particular configuration to be exposed to the UV light. Thus, a clinician reaching for the component does not need to spend any extra time making sure they are handling it properly, and can just grab it and insert it into the disinfection unit.

Figure 1I:
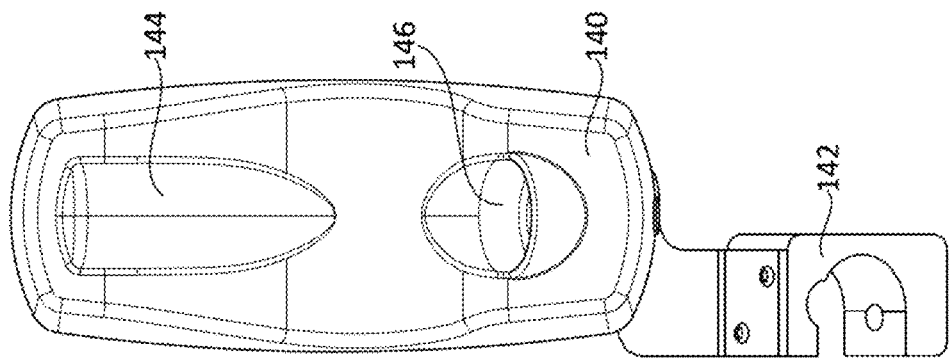
Figure 1G:
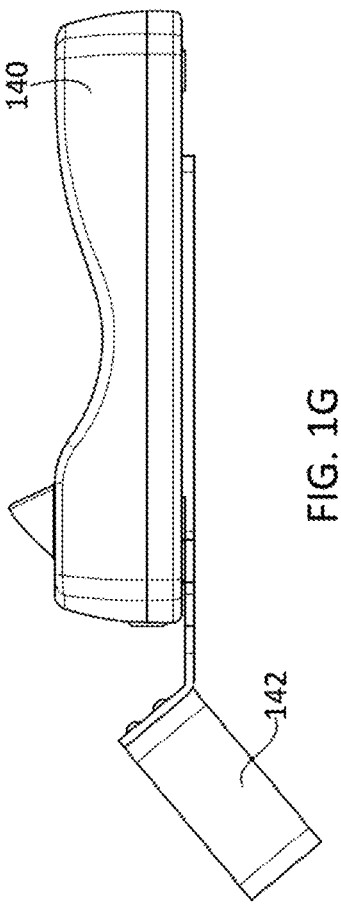
Figure 1H:
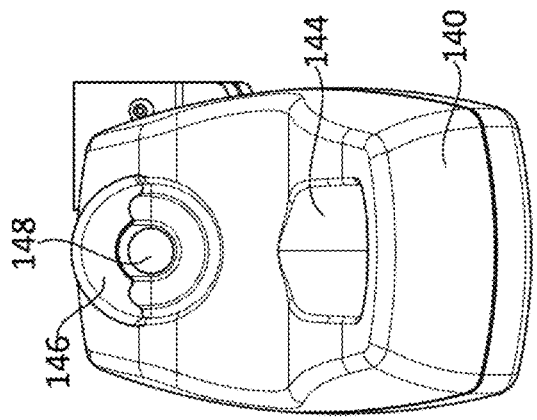

FIG. 1G shows an embodiment of a charging station or base 140 to be used with the disinfection unit 100. The base 140 can be designed to rest on a surface, or, as shown in FIG. 1G, the base 140 can be attached to a bracket 142 that can be used to mount the base 140 to an IV pole. FIG. 1H shows a top perspective view of the charging base 140. The base 140 comprises a depression 144 shaped to receive the body portion of the disinfection unit. The base 140 also comprises receptacle 146 configured to receive the head portion of the disinfection unit 100. The receptacle 146 comprises a window 148 that can comprise a UV transmissivity material (e.g., quartz). Behind the window 148 is an LED that can be used to disinfect the head portion 104 and opening 108 of the disinfection unit 100. When the unit 100 is charging in base 140, all of the LEDs 132, 120 in the head portion can also be configured to activate to disinfect the interior of the head portion of the unit 100. The base 140 can be configured to wirelessly charge the disinfection unit 100. FIG. 1I shows a top view of the charging base 140, showing depression 144, receptacle 146 and the bracket 142.

In certain embodiments, the handpiece 100 is charged in the charging station 140 using wireless charging. The handpiece and charging station can also have mating electronic connectors that contact in the charging station to recharge the batteries. The handpiece and charging station may also be geometrically designed so that movement or rotation of the charging station does not result in the handpiece becoming dislodged.

Figure 1K:
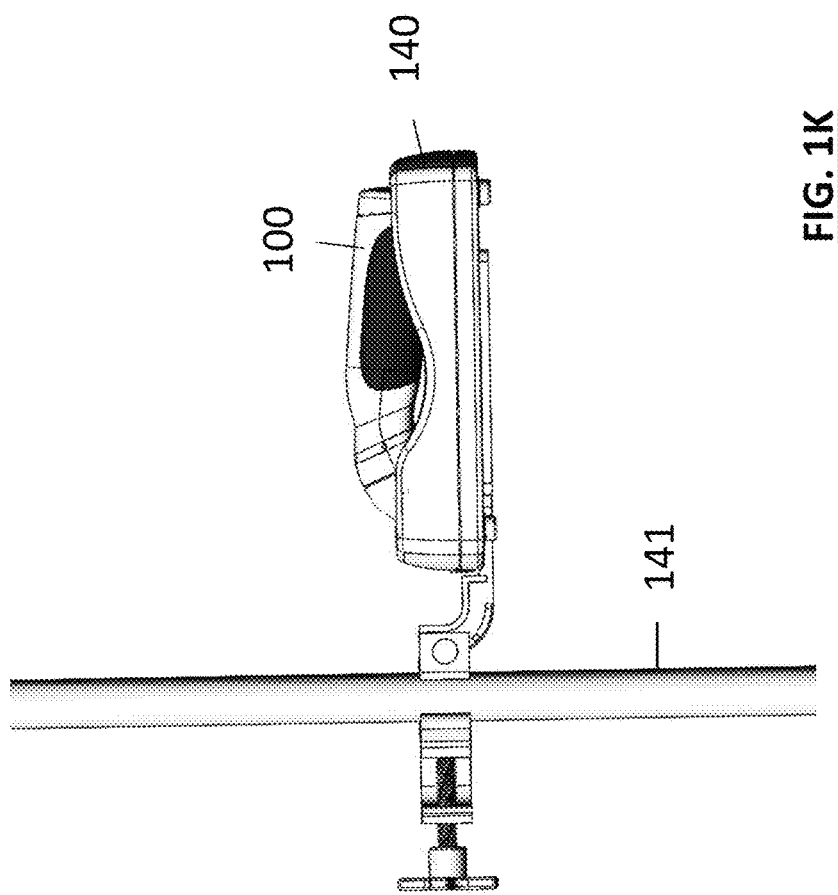
Figure 1J:
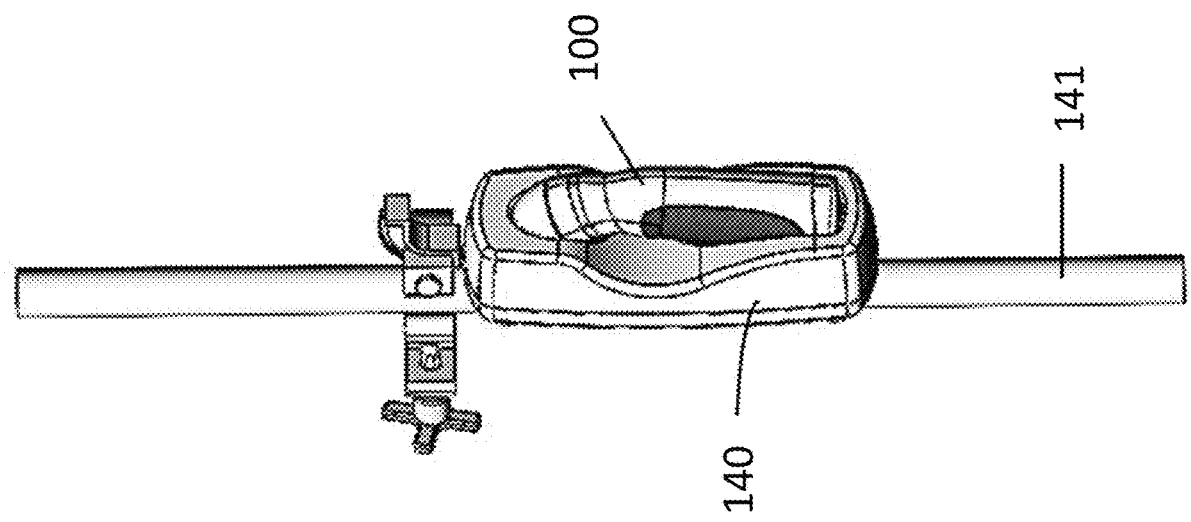

FIGS. 1J and 1K show an embodiment of a disinfection unit 100 positioned within charging base 140. The charging base 140 is mounted to an IV pole 141. FIG. 1J shows the disinfection unit 100 and charging base 140 aligned along the IV pole 141, while FIG. 1K shows the disinfection unit 100 and charging base 140 mounted perpendicular to the IV pole 141. The charging base can also be mounted at angles between about 0-90°.

Figure 1M:
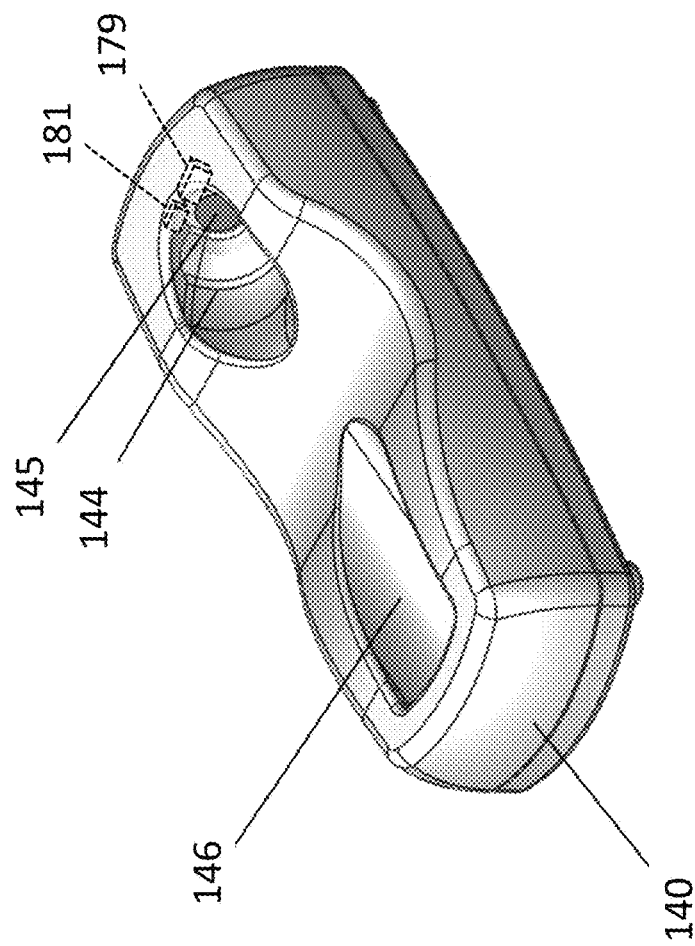
Figure 1L:
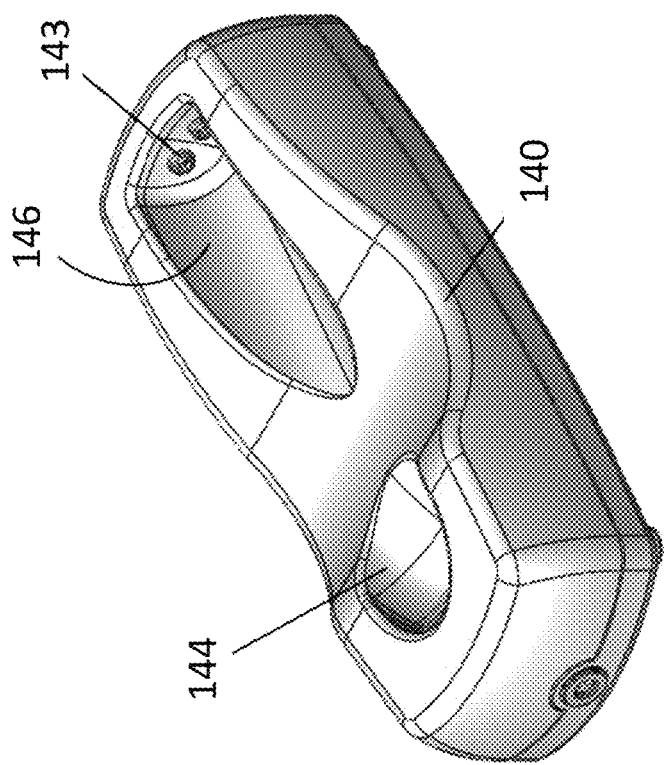

FIGS. 1L and 1M show perspective views of the charging base 140 without the disinfection unit positioned within it. As shown in FIGS. 1L and 1M, the base 140 comprises a depression 144 shaped to receive the head portion of the disinfection unit and a receptacle 146 shaped to receive the body portion of the disinfection unit 100. FIG. 1L shows charging contacts 143 configured to contact charging pins on the disinfection unit (not shown). FIG. 1M shows a disinfection window 145 that can comprise a UV transmissivity material (e.g., quartz). Behind the window 145 is a UV LED 179 (may be 2 or more LEDs) that can be used to disinfect the head portion and opening of the disinfection unit.

Figure 1O:
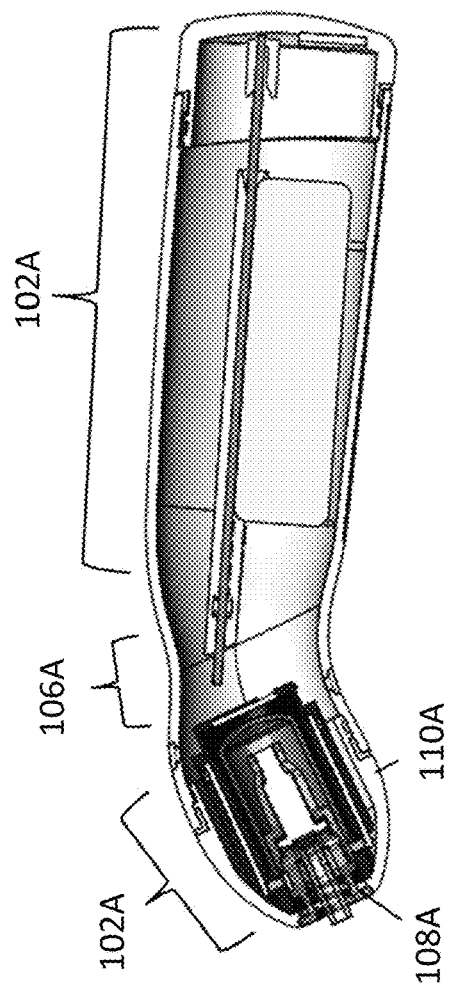
Figure 1N:
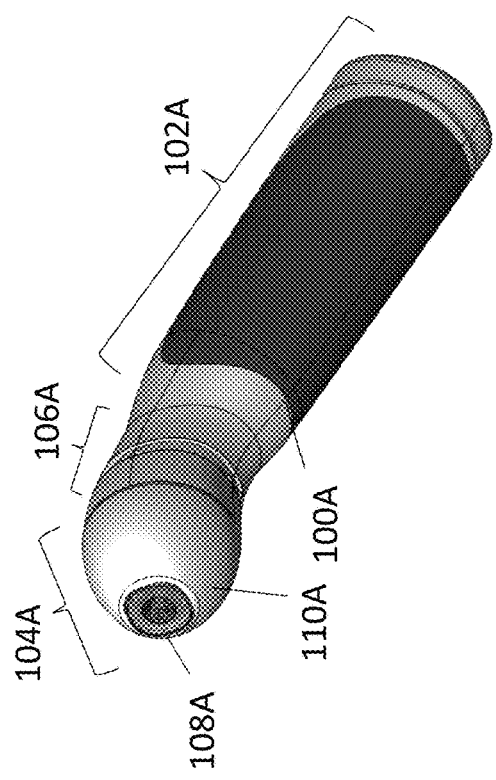

FIG. 1N shows a perspective view of another embodiment of a disinfecting unit 100A with an inserted connector. FIG. 1O shows a side view of the disinfection unit 100A with the inserted connector. The unit comprises a body portion 102A and a head portion 104A. The body portion comprises a generally rounded cross-sectional shape (e.g., ovular, circular, etc.), making the body portion 102A comfortable to grip in either a left or right handed grip. The body portion 102A can be gripped in the way one would grip a bicycle handle. The body portion 102A transitions to the head portion 104A at a neck portion 106A having a reduced diameter as compared to the body portion and the neck portion. Similar to the body portion 102A, the neck and head portions 106A, 104A have a generally rounded cross-sectional shape (e.g., ovular, circular, etc.) The head portion 104A is arranged at an angle as compared to the body portion 102A, with the angle occurring at or near the neck portion 106A. The angle can be about 20 to 40 degrees. In the embodiment shown, the angle is about 30 degrees. This angle can provide a comfortable orientation for a user to grip the body portion 102A and insert a component to be disinfected into the connector insertion opening 108A. The head portion 104A comprises a nose portion 110A near an end of the head portion 104A. The nose portion 110A extends from a midsection of the head portion 104A towards the connector insertion opening 108A. A diameter of the nose portion decreases as it extends towards the connector insertion opening 108A. The nose portion 110A can comprise a different material (e.g., aluminum) than the remainder of the disinfection unit. In other embodiments, the material of the nose portion can be the same as the remainder of the disinfection unit. In certain embodiment the device comprises commonly used plastics for molding including, but not limited to ABS (Acrylonitrile Butadiene Styrene), ABS/Polycarbonate blends, polypropylene, polycarbonate, and polyethylene. In some embodiments, the device can incorporate antimicrobial additives such as silver ions. A width of the nose portion can be about 25-60 mm. In some embodiments, a widest dimension of the nose portion is about 35 mm.

The connector insertion opening 108A can comprise a profile shaped to mate with a profile of a connector to be inserted. For example, the opening 108A comprises a generally square (e.g., square with rounded corners) shape, that can receive generally square shaped connectors. This non-circular configuration of both the opening 108A and the connectors can help ensure that the connector is properly rotated and oriented prior to insertion within the disinfection unit.

The head portion can comprise a disinfection progress indicator (e.g., like indicator 112). The indicator can comprise a series of lights spaced circumferentially around a portion of the disinfection unit. The indicator can be configured to change color to indicate the progress of the disinfection cycle. In some embodiments, the indicator is configured to sequentially illuminate the lights during the disinfection process to indicate progress of the disinfection cycle. In other embodiments the entire band could be configured to illuminate to indicate the start and end of the disinfection cycle. Circumferential illumination could provide status to the user regardless of hand piece orientation.

The indicator can also be configured to vary the intensity or frequency of the light to indicate progress of a disinfection cycle. Any combination of these light modulations are possible to indicate progress of the disinfection. Once all the lights are illuminated, the disinfection cycle is complete. In some embodiments, an audible alert can also be used. The disinfection progress lights can be positioned the entire circumference of the device. In some embodiments, the disinfection progress indicator can comprise lights positioned around a portion of the circumference of the device.

The disinfection unit can comprise a battery level indicator (e.g., similar to indicator 116). The indicator can change color and/or flash at varying frequencies to indicate a charge level of the battery. In some embodiments, the indicator can comprise a plurality of lights that sequentially illuminate to indicate the charge level of the battery. The indicator can also vary an intensity of light to indicate charge level. Any combination of this light modulation can be used to indicate a battery level. In some embodiments, an audible alert can also be used. In some embodiments, the circumferentially positioned light could be used to indicate battery level. The light could illuminate yellow light, and could be steady or flash. In some embodiments the frequency of the light can increase in frequency to indicate differences in the remaining battery charge. In some embodiments the color of the light could change to indicate differences in the remaining battery charge.

Figure 1P:
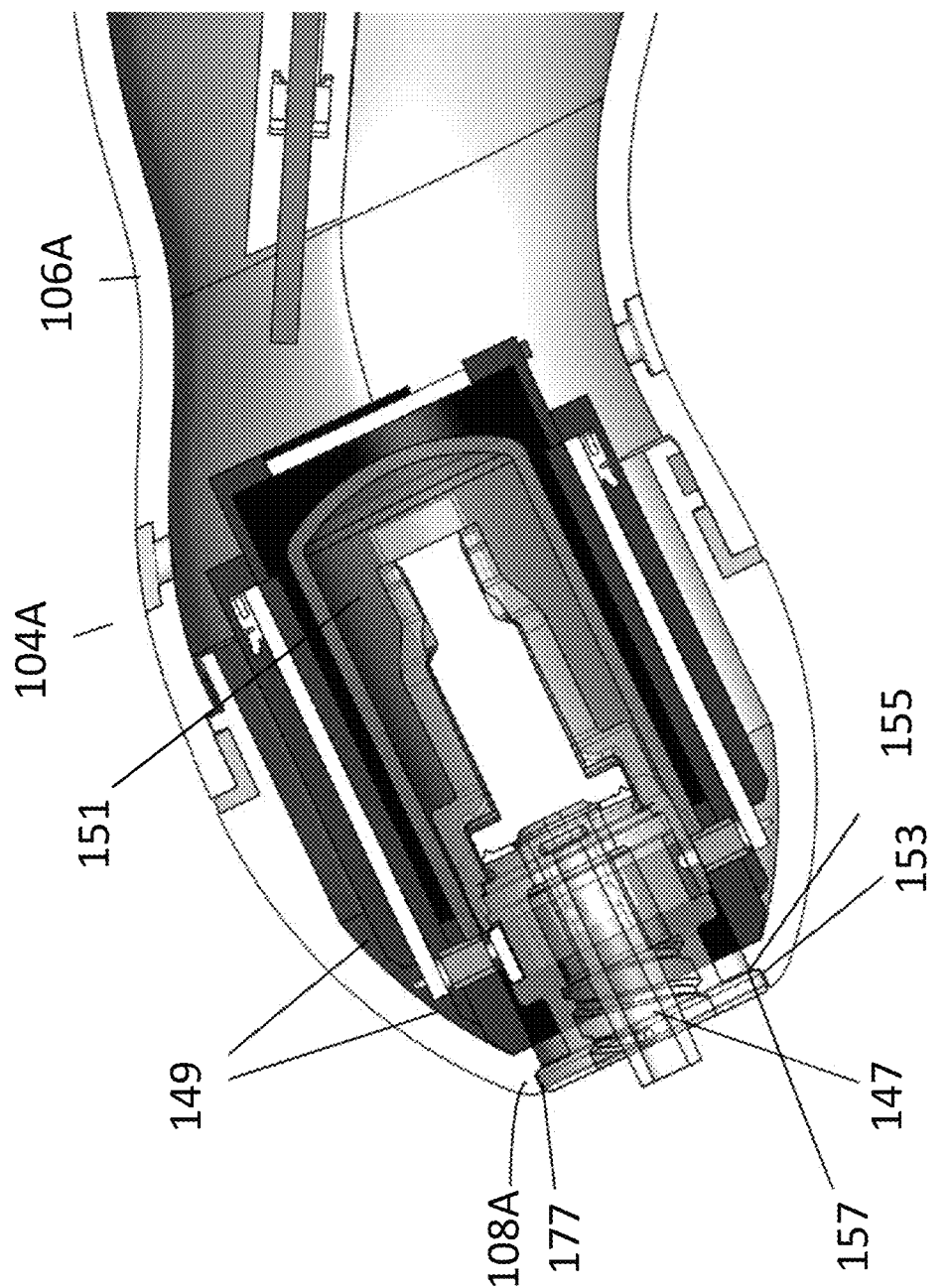

FIG. 1P shows a cross sectional detailed view of the head and neck portions 104A, 106A of the disinfection unit with an inserted connector 147 positioned within the opening 108A.

In certain embodiments, portions 149 of the system that are exposed to UVC light may be made out of materials that have particular benefits relative to UVC light. The head portion 104A comprises a UVC chamber 151 preferably fabricated from a material that is not physically affected by UVC exposure. The chamber 151 may be made of aluminum or other metals for example. The chamber may also be made out of Polyetherimide (such as Ultem). In certain embodiments the chamber material serves to isolate UVC light so that materials or components of the handheld unit are exposed to minimal UVC light, such as by using a UVC opaque material and including physical barriers to minimize UVC exposure except where desired. The material of the chamber may be selected to be variously UVC reflective or UVC absorptive to control light as desired within the chamber. Through selection of UVC transparent materials, elimination of shadows, and optimal placement of UVC LEDs, the system can disinfect in as fast as 1 second or even less.

In certain embodiments, the nose portion 110A comprises features configured to mate to corresponding features in the connector to help ensure the connector is properly oriented and fully inserted. For example, an outer portion 153 of the opening 108A may have a first diameter greater than an inner portion 155 of the opening. This change in diameter creates a shoulder 157 that can be used to seat a collar portion 177 of the connector 147 disposed in chamber 151.

Figure 1R:
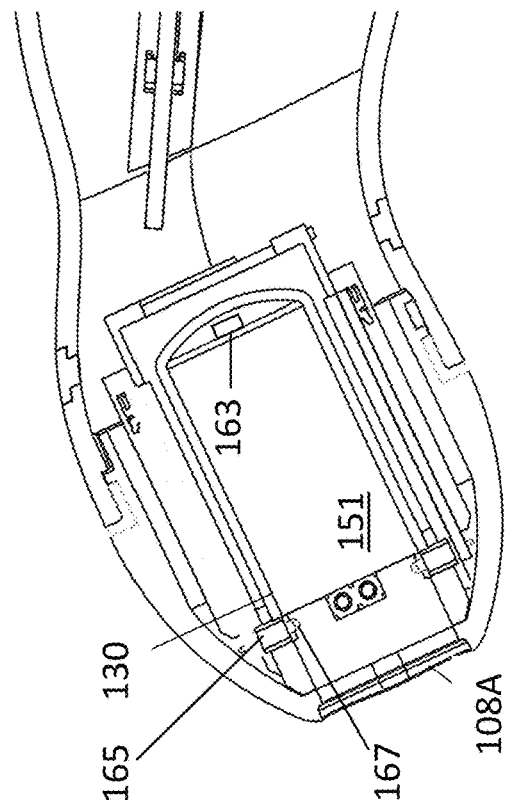
Figure 1Q:
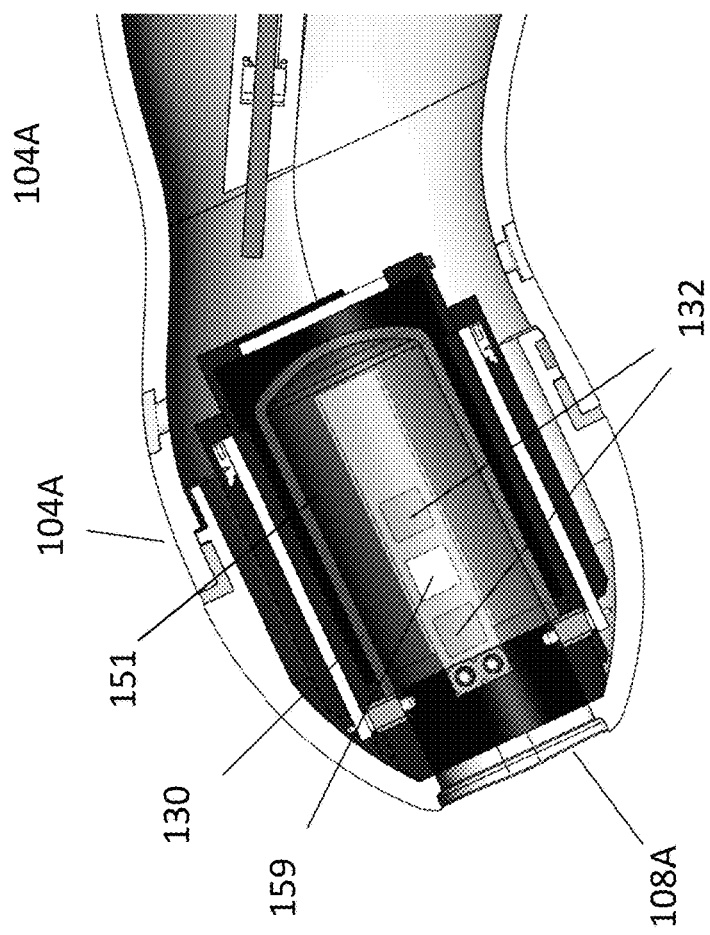

FIG. 1Q shows a cross section detailed view of the disinfection chamber 151 of the head portion 104A without the connector inserted. The disinfection chamber 151 comprises one or more light sensors 159, for example disposed between each set of LEDs 132. As described above, the light sensor can be used to verify light output from any of the LEDs, providing the system controller with a feedback signal that is compared to a threshold to determine the sufficiency of the irradiative power and intensity provided by the UVC LEDs for proper disinfection. The disinfection chamber 151 extends from the connector insertion opening 108A into the disinfection unit 100. In some embodiments, the chamber 151 comprises a generally cylindrical or barrel shape. The disinfection chamber may comprise a UV transmissive material (e.g., quartz) and serves to separate the connector insertion area from the LEDs and other internal components. In some embodiments, there are 8 LEDs 132 total. Pairs of LEDs can be positioned equidistantly around a circumference of the chamber at four positions along the circumference. Each pair is spaced along the length of the chamber and may be separated by an LED light sensor 159 disposed therebetween. This configuration ensures that a component inserted within the chamber 151 will receive UV energy sufficient for desired microbial reduction or disinfection. In certain embodiments, for example where the chamber 151 is configured to accommodate a substantially square cross sectioned connector as described below, the LEDs or pairs of LEDs 132 are disposed along the perimeter of the cross section such that they illuminate each of the four sides of the connector.

In certain embodiments, the disinfection unit 100 does not include an activation button. Instead, a disinfection cycle can be automatically triggered when the system senses, for example optically, magnetically or mechanically, insertion of a connector or other component to be disinfected within the head portion of the device. Triggering the system can initiate a disinfection cycle of a desired time frame (e.g., about 1 second, about 10 seconds, about 20 seconds, about 10-15 seconds, about 10-20 seconds, about 15-25 seconds, about 5-25 seconds, about 25-35 seconds, etc.). In some embodiments, the disinfection cycle is about 15 seconds. As described elsewhere herein, in some embodiments, the disinfection unit may comprise an activation control to allow manual initiation of a disinfection cycle.

FIG. 1R shows a sectional view of the head portion 104A taken from an end of the head portion with the connector inserted. In certain embodiments, an end LED 163 can be used for disinfection of an end portion of a component inserted and to be disinfected. The end of the component may comprise a flat surface or surfaces that may not be sufficiently illuminated by LEDs 132. Thus, the end LED can serve to illuminate such surfaces. Each LED can have an associated circuit board (now shown).

Figure 1T:
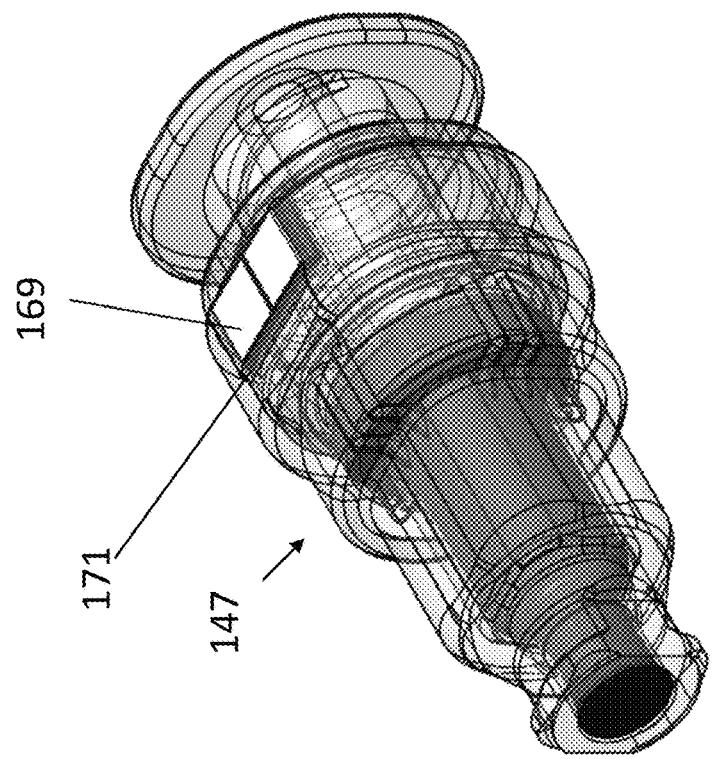
Figure 1S:
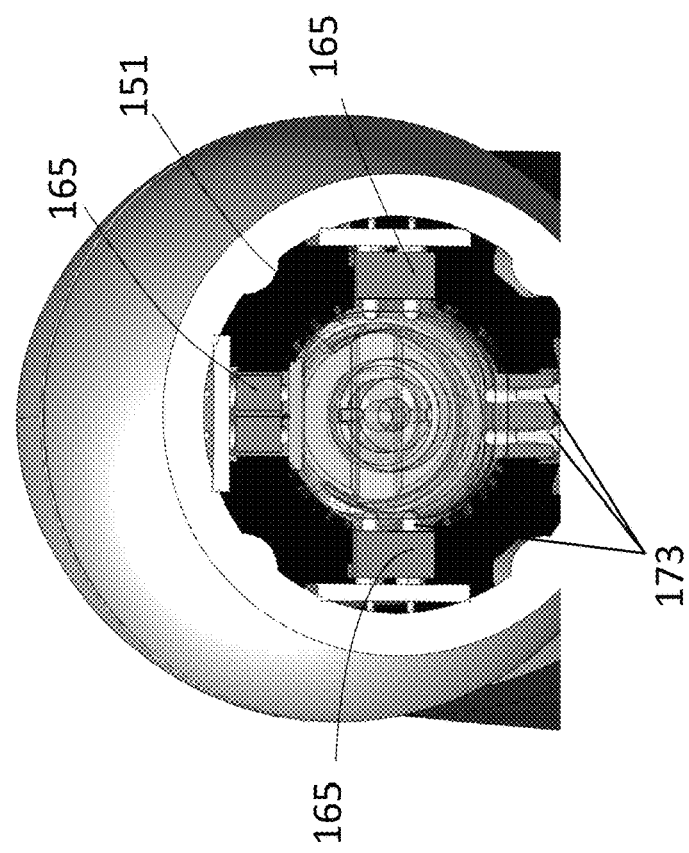

In some embodiments, the sensor that triggers the disinfection cycle can be an electrical contact switch 165. The switch may be integrated into the mechanical housing and mate with electrical contacts 167. When the connector 147 is properly inserted for disinfection, electrical contacts 167 mate with corresponding contacts 169 on the connector 147, as seen in FIG. 1T. FIG. 1T shows an example of a connector 147 as described above. Embodiments of connectors that can be used are described in U.S. Provisional Applications No. 62/822,658 filed Mar. 22, 2019, and 62/911,059 filed Oct. 4, 2019, entitled "Needleless Connector Valve for UV Disinfection", the disclosures of which are incorporated herein by reference in their entirety. The controller in the handpiece can detect the connection and initiate a disinfection cycle. As shown in greater detail in FIG. 1S, the electrical switch 165 and contacts 167 can for example use spring loaded "pogo" pins 173 that are spring biased towards the inserted connector 147 to ensure electrical connection with corresponding contacts 169. In alternative embodiments, a magnetic or optical connection, rather than the described electrical connection, is established for communication of information between the connector 147 and handpiece 100.

Mechanical contact may be desired for the precision of placement compared to a proximity sensor. In certain embodiments, in order to properly align the inserted connector 147 in the handpiece, it may be desirable to mechanically index the connector. In certain embodiments, this is achieved by creating a geometry, such as a square profile that only fits in one or more exact orientations. Such a square connector geometry is illustrated in FIG. 1T. In order to ease use, multiple sets of pogo pin contacts 173 may be used in an array for each surface (four surfaces in the FIG. 1T arrangement) of the profile to minimize the requirement for the user to select only one orientation. This may be also be achieved with multiple electrical connectors 169 on the connector, for example a pair on each of the four sides of the connector 147, all of which can be balanced against increased cost and complexity of the system and its components. As mentioned above, the chamber 151 may be shaped to accommodate the substantially square cross sectioned connector 147, in which case the LEDs 132 are disposed along the perimeter of the cross section such that they are able to illuminate each of the four sides of the connector.

In certain embodiments, for example in a test mode, when the handpiece 100 is in the charging station or base 140, each LED or LED set (132, 163, 179) can be turned on individually so that the light output can be verified using the corresponding light sensor. In certain embodiments an LED 179 (FIG. 1M) in the charging station used to disinfect the tip of the handpiece 100 can also be provided with a corresponding light sensor 181 to test and verify its output. Verification ensures the LEDs are performing within specification, and confirms that there is no obstruction, damage, or contamination within the UVC 151 chamber or elsewhere that could prevent proper disinfection.

In certain embodiments, when the unit 100 is charging in base 140, all of the LEDs (120, 132) in the head portion of the unit can also be configured to activate to disinfect the interior of the head portion of the unit. The unit 100 and base 140 can be configured to wirelessly charge the disinfection unit.

In certain embodiments, electrical contacts 169 or the like can be part of a security system. This may be as simple as a fixed resistor value that the handpiece 100 is programmed to recognize, or for example an IC chip 171 in the connector 147 that can provide any level of complex encryption and identification of the connector to the handpiece 100. The IC chip 171 can be used for identification of the connector 147 to prevent piracy or misuse, and could also be used to identify exactly the time that a connector is disinfected and provide other relevant information. The chip 171 may also be used as part of a time out feature that ensures a connector is not used outside its stated life. The chip can also be used to correlate a disinfection cycle to a component allowing various qualified and preprogrammed disinfection cycles to be used for each connector or connector family, for example. The chip 171 can be selected to support the sterilization cycle used for the connector such as e-beam, gamma sterilization, or eto.

Additional embodiments of hand held disinfecting units are described below. Unless described otherwise, the embodiments of disinfection units described herein have similar features to those described with embodiments described elsewhere herein. For example, each disinfection unit can comprise the sensor features, automatic/manual initiation of disinfection, LED configuration, etc. described with respect to other disinfection units.

Figure 2A:
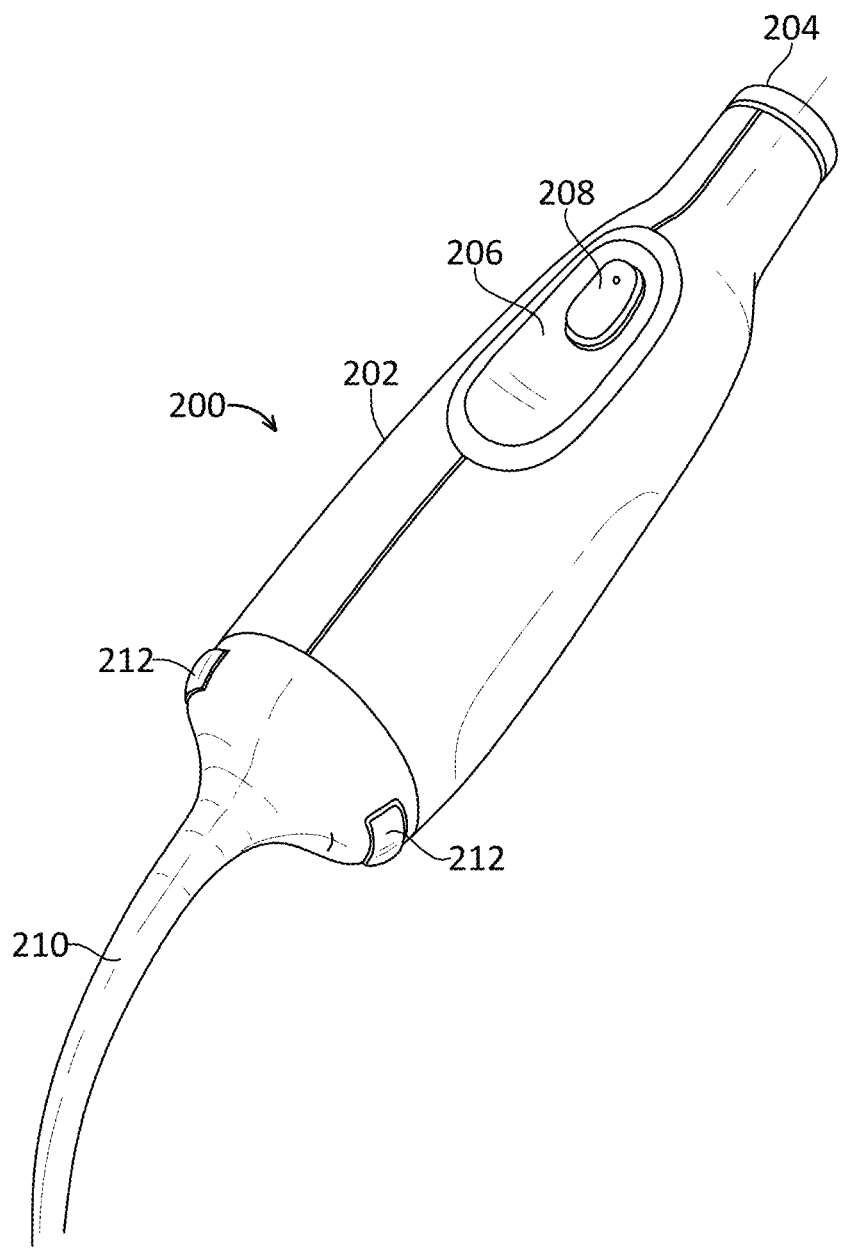
FIGS. 2A-C show various views of a hand held UV disinfecting unit in accordance with certain embodiments.

FIG. 2A illustrates an embodiment of a flashlight style disinfection unit 200 configured to disinfect one lumen or connector. Similar to the unit described above, the connector can be inserted into an aperture 204 at a distal end of the disinfection unit 200. This unit 200 does not have an angled head portion like the unit 100 described above. The unit 200 narrows to a neck portion terminating in the aperture 204. The unit 200 comprises a main body section 202. The main body section 202 comprises a recessed area 206 comprising a control button 208. The curves of the body 202 and the recessed section 206 can provide an ergonomic design for holding the body 202 within the user's hand and using the thumb to control the button 208. The unit 200 comprises a cable 210 configured to be attached to a proximal end of the main body section 202. The cable 210 can be used as a charging cable. The cable 210 can also be used for data transfer. The cable 210 can comprise release buttons 212 to facilitate quick release of the unit 200 from the cable 210. The unit 200 can comprise rechargeable batteries and a controller to allow for portability.

Figure 2B:
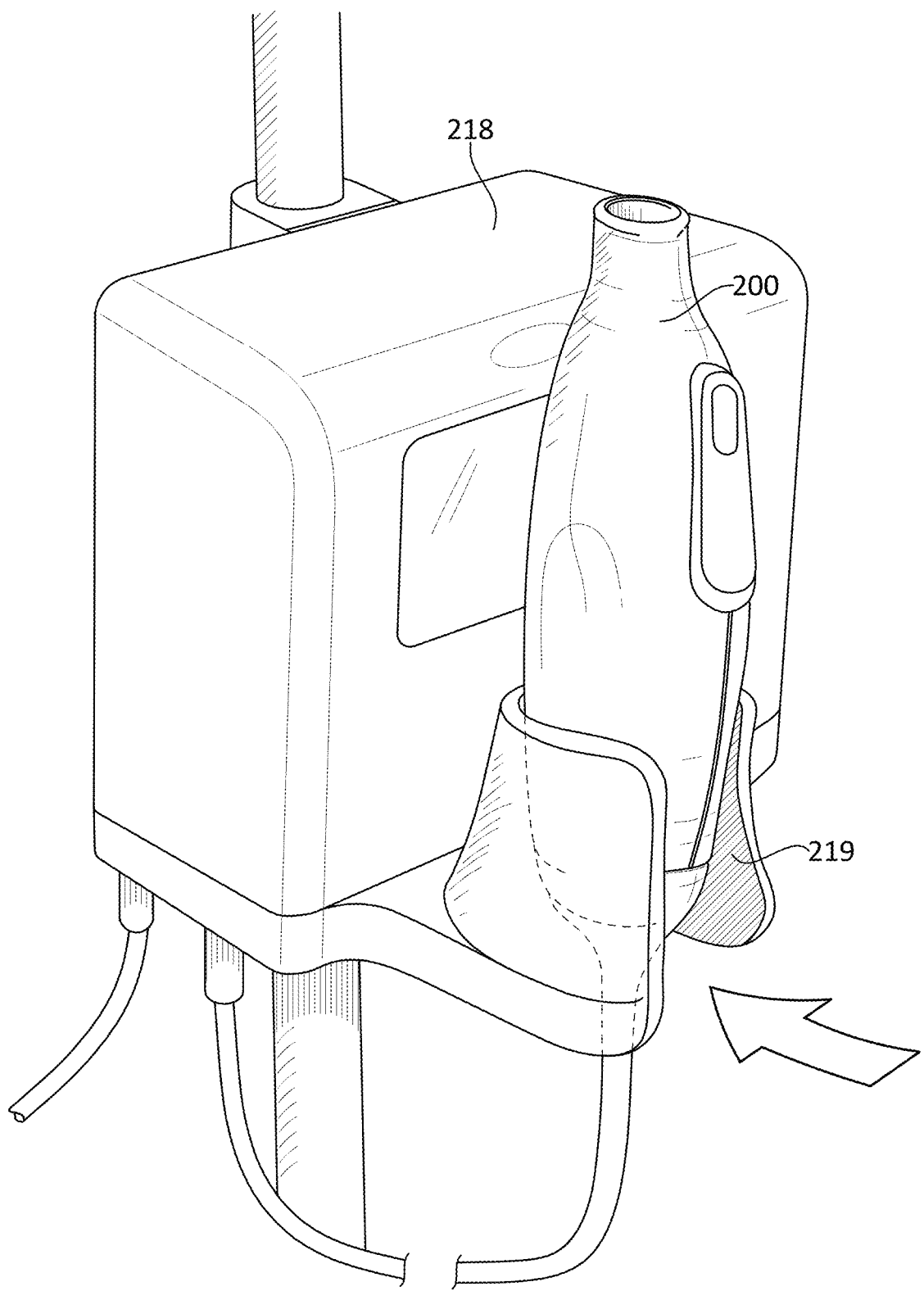

FIG. 2B shows the disinfecting unit 200 in a pole mounted power controller base 218. In the view of FIG. 2B the handheld UV disinfecting unit 200 is shown in the stowed position within a specifically configured receptacle 219 on the power controller base.

Figure 2C:
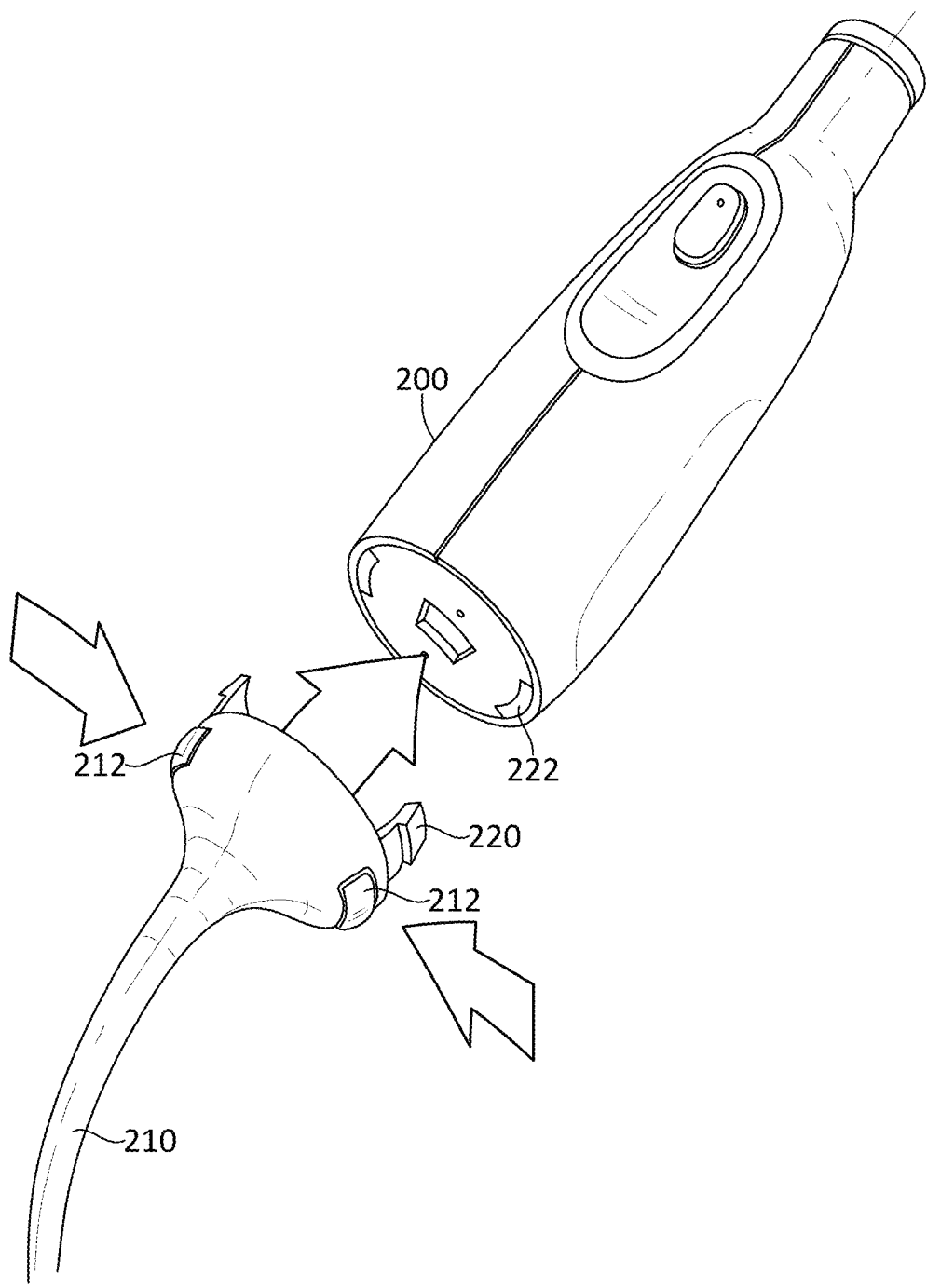

FIG. 2C depicts the disinfection unit 200 with the charging cable 210 released after the operation of a quick release which disengages tab 220 on the charging cable 210 from slots 222 within an end of the disinfection unit 200. Buttons 212 can be used to control the quick release of the unit 200 from the cable 210. To reengage the cable 210 with the unit, a user simply engages the tabs 220 with the slots 222. In the released configuration, the hand held disinfecting unit 100 contains rechargeable batteries which deliver the power for the UVC LED illumination.

Figure 2D:
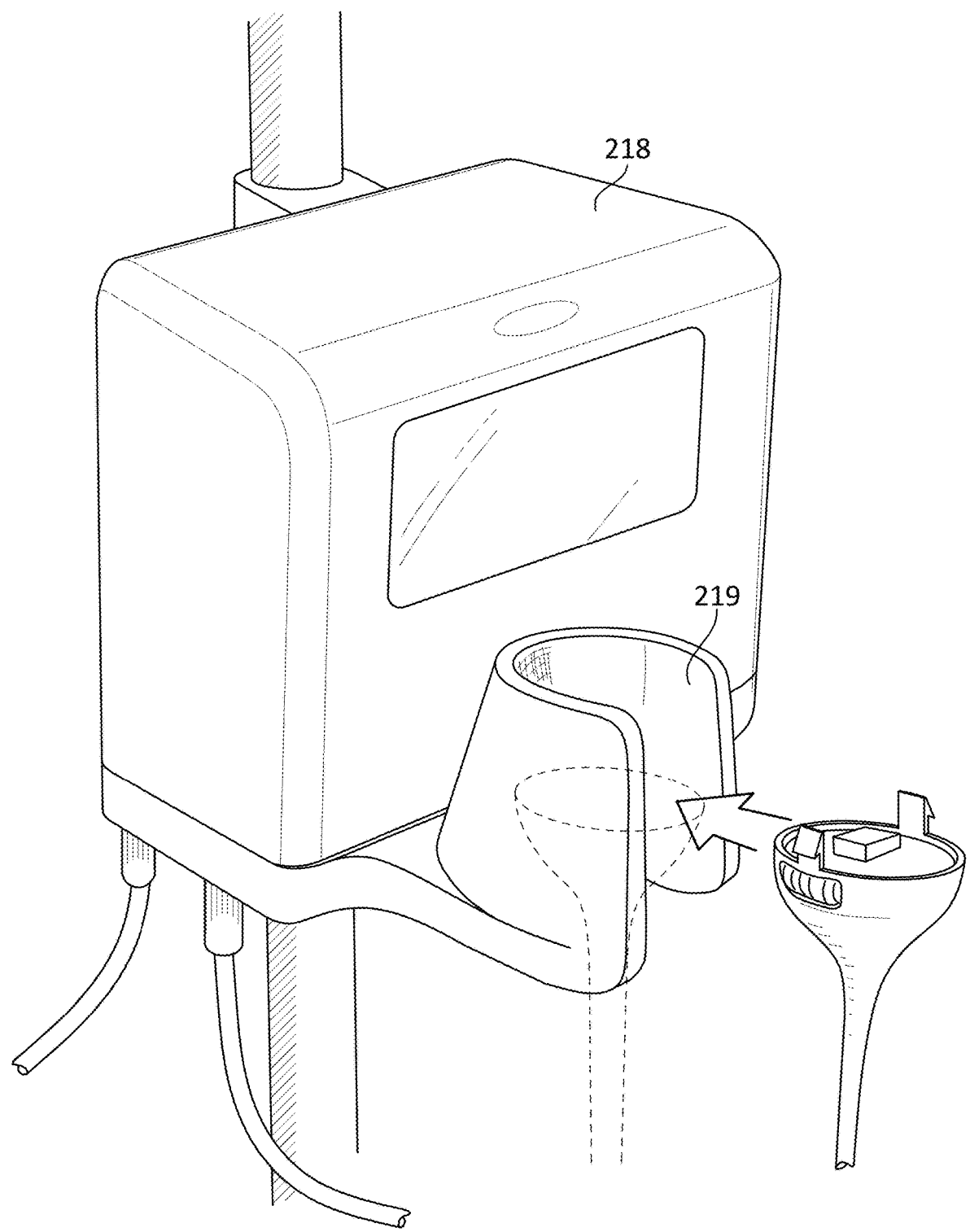
FIG. 2D is a perspective view of an embodiment of a power controller base that can be used with disinfection units.

FIG. 2D is a perspective view of the power controller base of FIG. 2B with the handheld disinfecting unit removed to illustrate the charging cord 210 interoperability with the specific receptacle 219 formed in the power controller base.

Figure 3A:
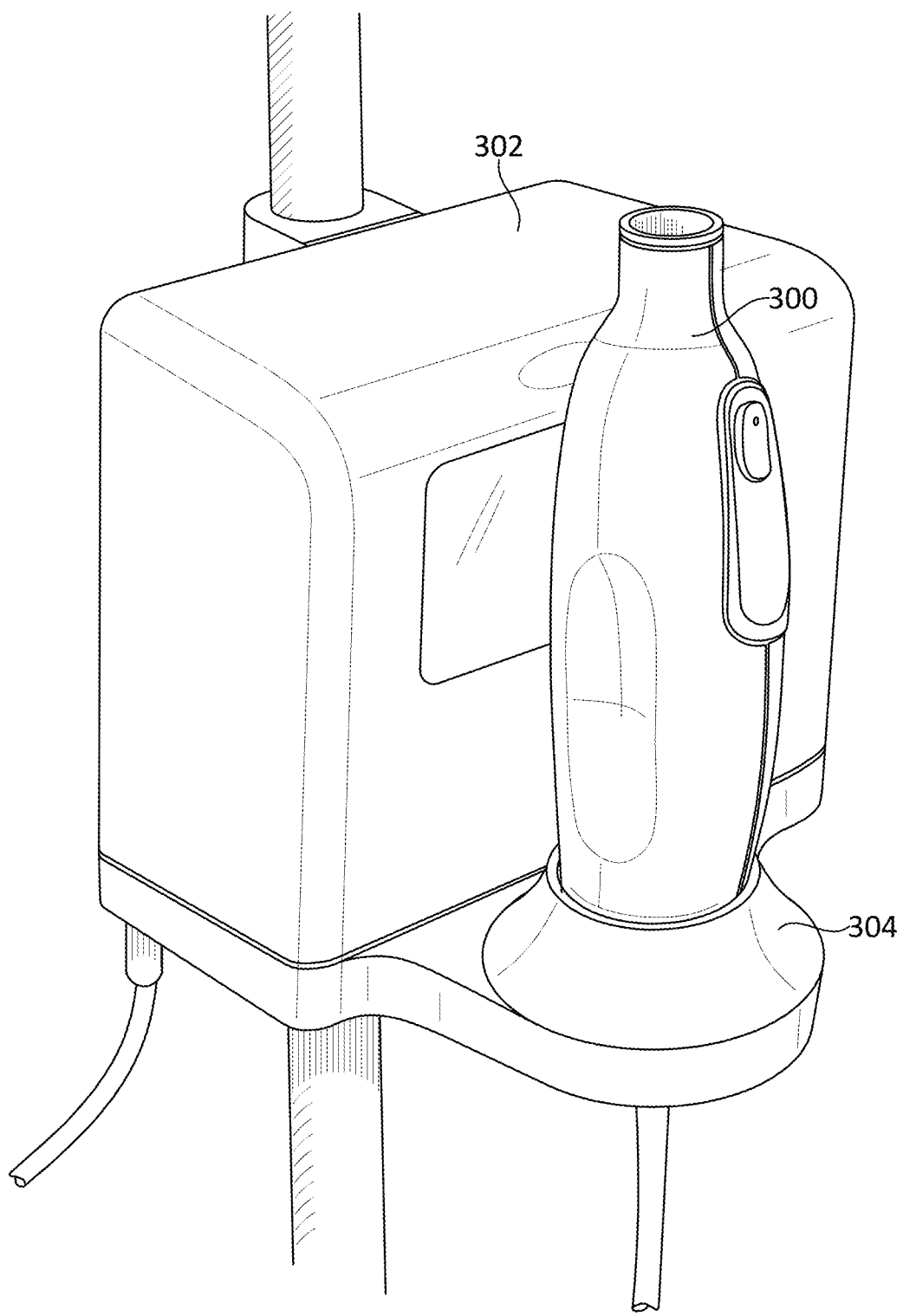
FIG. 3A is perspective view of alternative embodiment of a hand held UV disinfecting unit in a pole mounted power controller base.

FIG. 3A is perspective view of a hand held UV disinfecting unit 300, similar to unit 200 in a pole mounted power controller base 302, similar to that of FIG. 2B. The handheld UV disinfecting unit 300 is shown in the stowed position within a built in charging base 304 on the power controller base. In this configuration, the hand held UV disinfecting unit's rechargeable batteries are charged via induction coils within the disinfecting unit 300 and within the charging base 304 rather than through a charging cable. It is advantageous to use this kind of inductive charging configuration as that provides for smooth sealed surfaces that are easier to clean.

Figure 3B:
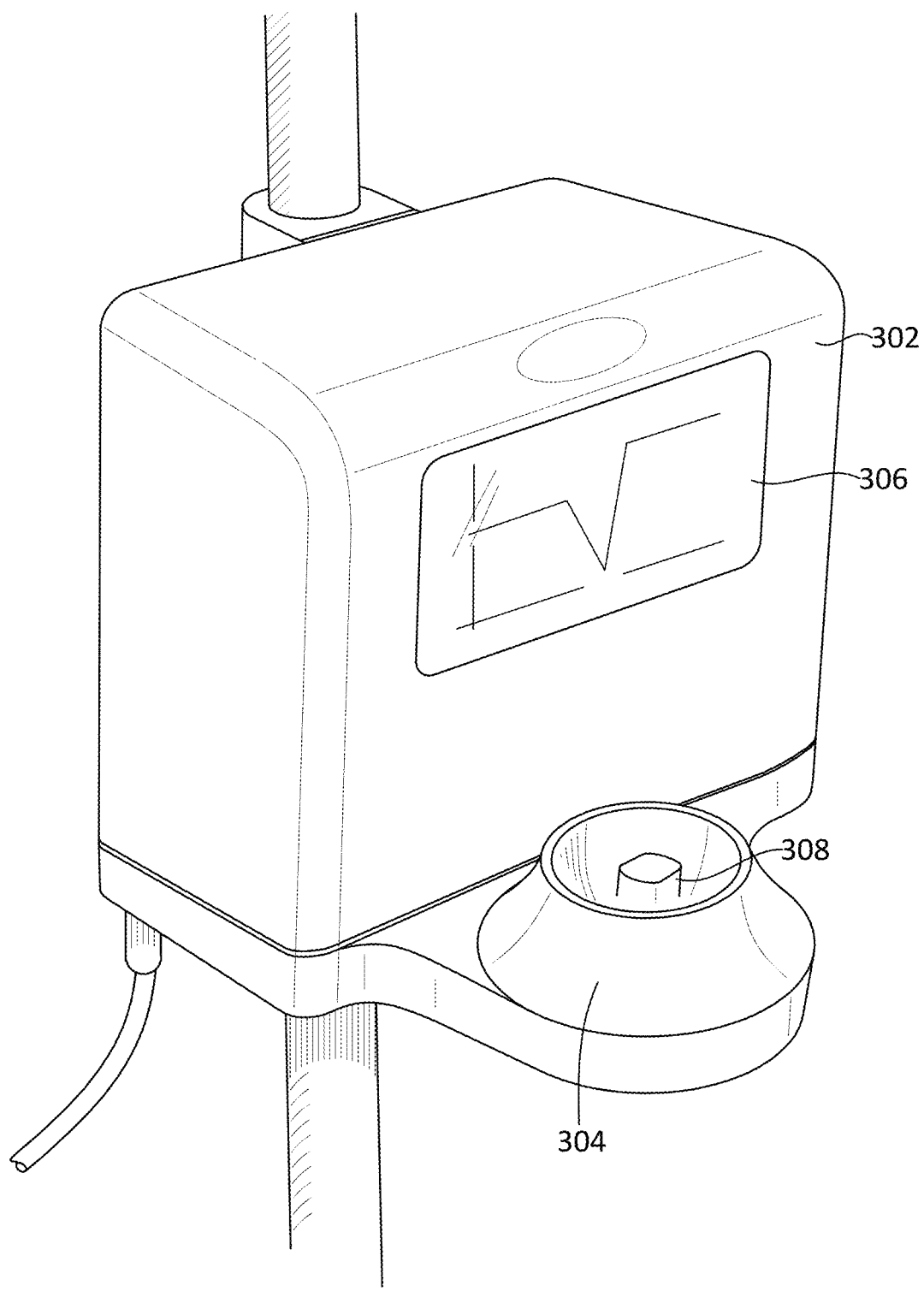
FIG. 3B is a perspective view of the power controller base of FIG. 3A with the handheld disinfecting unit.

FIG. 3B is a perspective view of the power controller base 302 of FIG. 3A with the handheld disinfecting unit removed to illustrate the charging base 304 and the specific alignment feature 308 (e.g., a protrusion) formed in the charging base 304 adapted and configured to mate with a corresponding alignment feature (e.g., an aperture or port) in the hand held disinfecting unit to ensure optimal inductive charging. The power controller base 302 can comprise a display 306 configured to show information about disinfection cycles, such as the last disinfection cycle. The display can also be configured to show daily or weekly disinfection cycles.

Figure 4A:
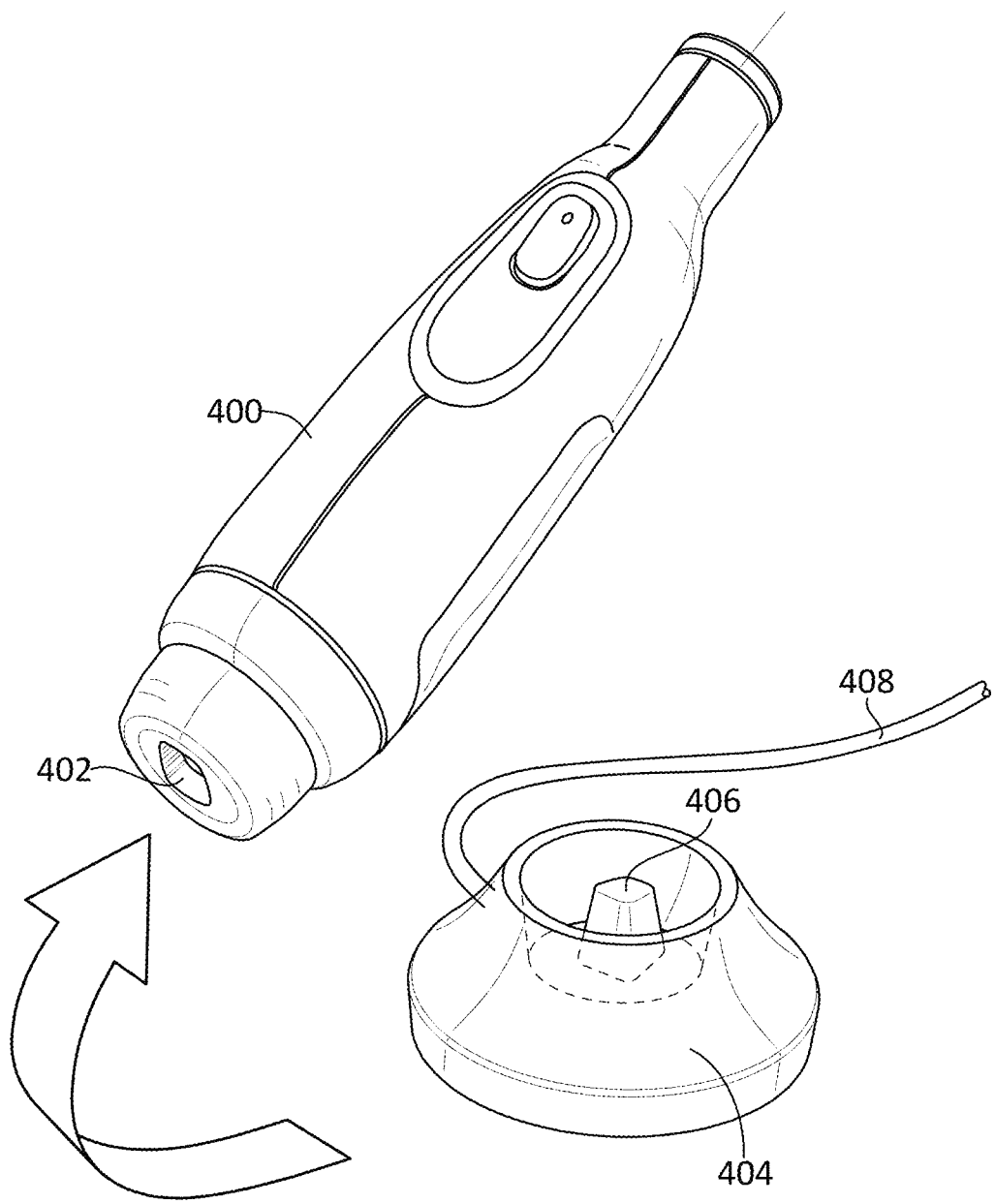
FIG. 4A is a perspective view of a disinfection unit and a charging base.

FIG. 4A is a perspective view of a charging base 402 and a disinfection unit 400, similar to units 200, 300. In this view, the handheld disinfecting unit 400 is removed and illustrates the charging base 404 and the specific alignment feature 406 (e.g., protrusion) adapted and configured to mate with a corresponding alignment feature 402 (e.g., an aperture) that is visible in the base of the hand held disinfecting unit. The charging base 404 can comprise a power cable 408 configured to connect to a power outlet.

Figure 4B:
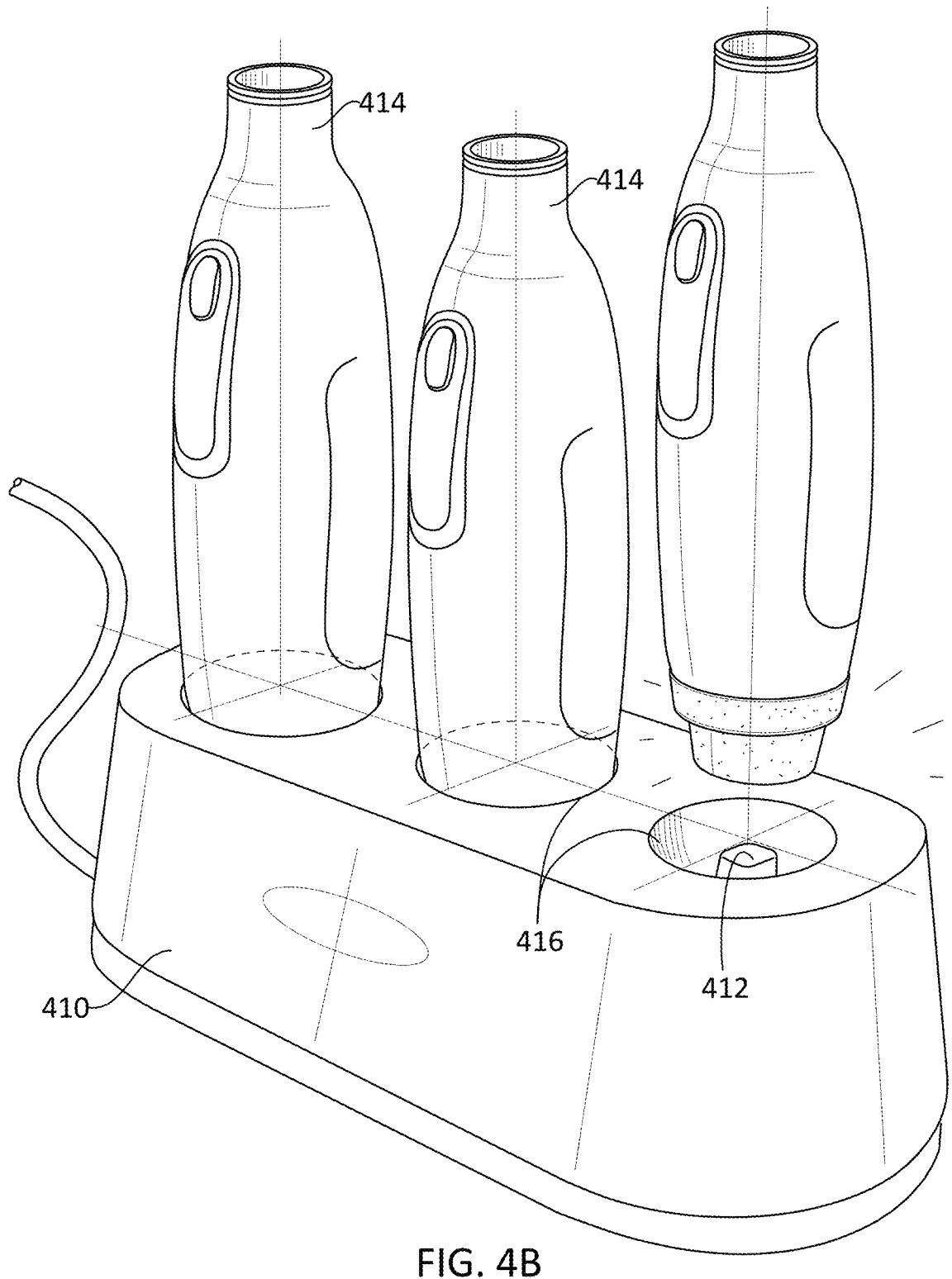
FIG. 4B is a perspective view of a multiple hand held unit charging base having docks to receive three hand held disinfecting units.

FIG. 4B is a perspective view of a multiple hand held unit charging base 410 having docks 416 to receive three hand held disinfecting units 414 using a complementary charging feature 412 between the charger dock and each one of the hand held disinfecting units. In this view, three hand held devices are shown with two docked into the multi-unit charging base and one raised above a docking port 416 making visible the correspondingly shaped base 418 of the hand held disinfecting unit and the alignment feature 412 on the dock.

Figure 5A:
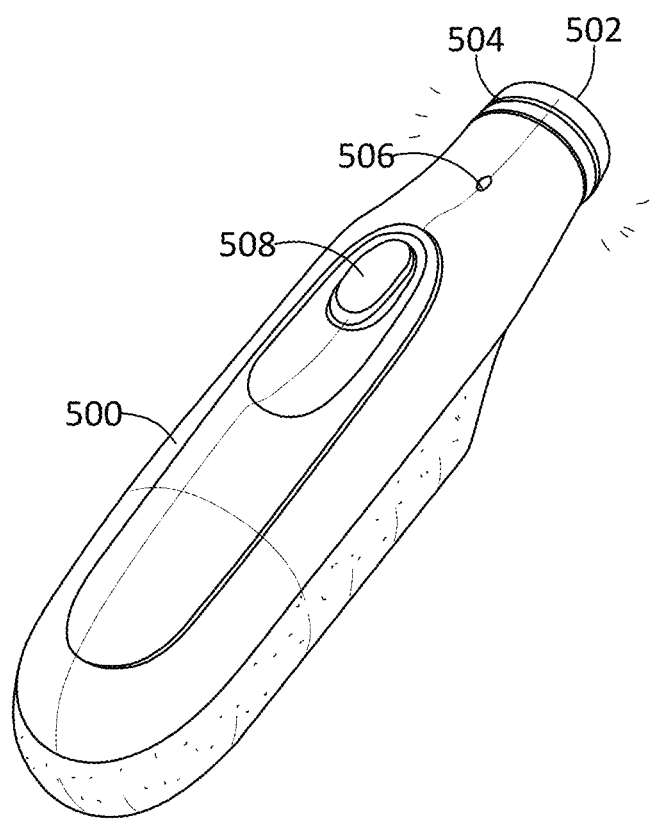
FIGS. 5A-C are perspective, top and side views respectively of another alternative hand held disinfecting unit.
Figures 5B, 5C:
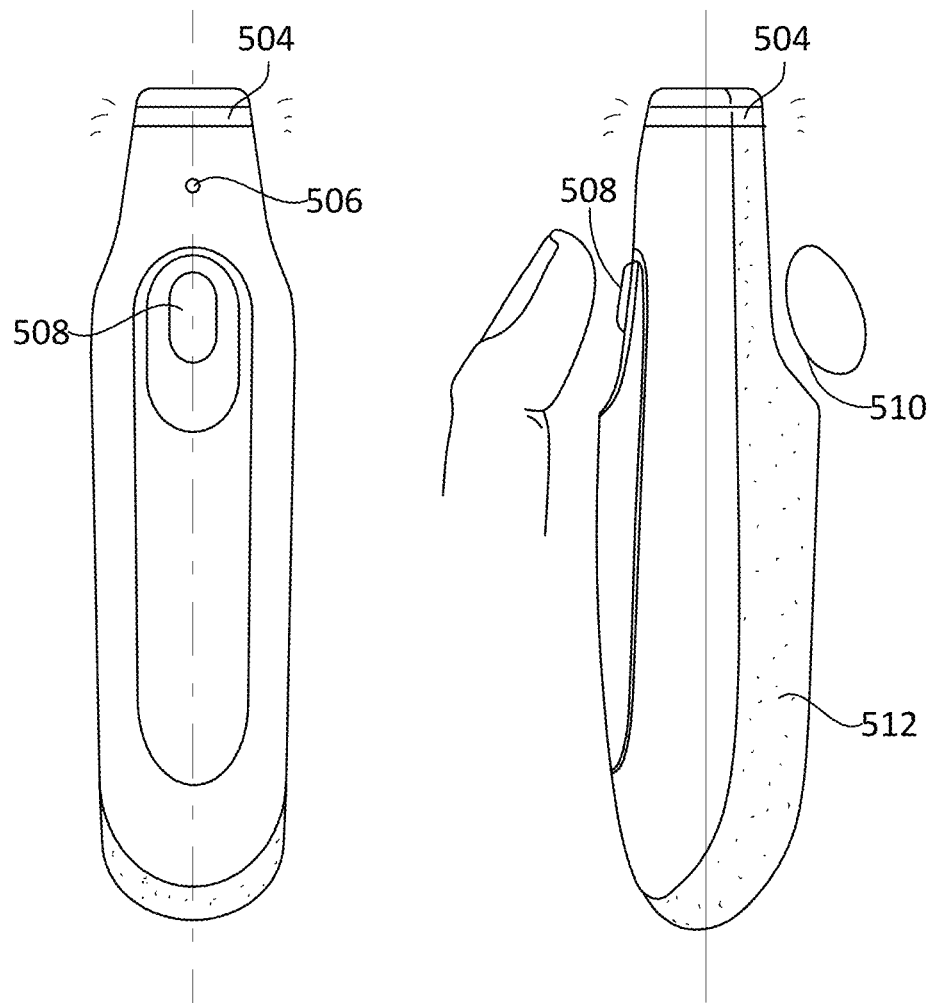

FIGS. 5A-C are perspective, top and side views, respectively, of another embodiment of a hand held disinfecting unit 500, similar to the disinfection units described above, having an aperture 502 adapted and configured to receive a selected portion or optionally all of a component to be disinfected. The disinfecting unit 500 includes an illuminating ring 504 at the opening of the aperture 502 that is configured to illuminate to indicate the delivery of disinfecting light. The ring 504 can also be used. The illuminating ring 504 is an indicator that can be seen from all directions around the aperture. The illuminating ring 504 can change intensity, can change color, and can change a pulsing rate or any combination of the three to indicate the progress of the delivery of disinfecting light. The unit 500 can also comprise a battery charging indicator 506 and a start cycle button 508. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figures 5D, 5E:
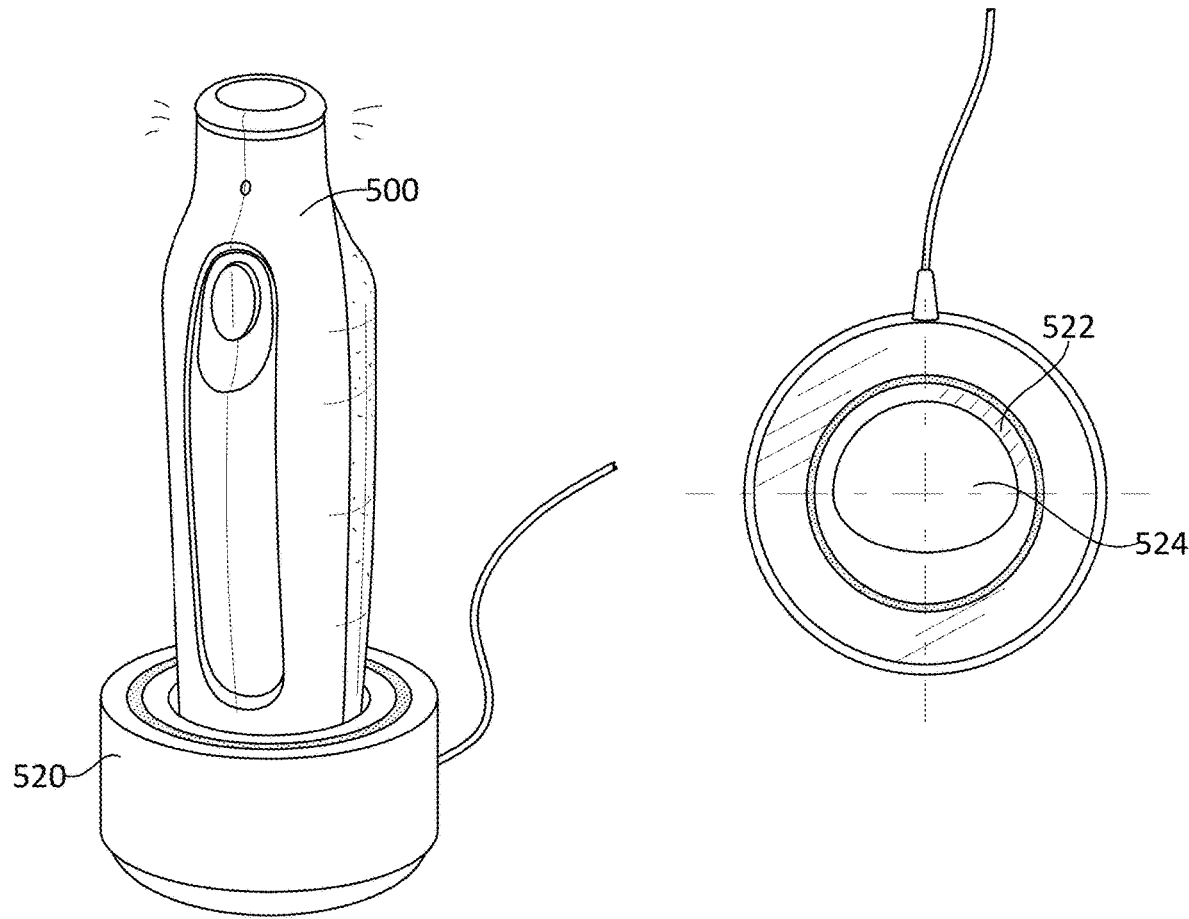
FIG. 5D is a perspective view of the handheld UV disinfecting unit of FIG. 5A shown in a stowed position within a specifically configured charging dock.
FIG. 5E is a top down view of the charging dock of FIG. 5D.

The disinfection unit 500 comprises a soft touch or overmolded grip area and a hook detail 510 for the index finger (FIG. 5C). The underside 512 of the unit 500 can comprise an overmolded rubber-like material for additional user comfort. A concave contour on the underside of the unit 500 provides a nesting feature for a user's index finger FIG. 5D is a perspective view of the handheld UV disinfecting unit 500 of FIG. 5A shown in a stowed position within a specifically configured charging dock 520. FIG. 5E is a top down view of the charging dock of FIG. 5A with the hand held disinfecting unit removed and the charging illumination ring 522 visible around the perimeter of the specifically configured charging receptacle 524 to couple the hand held disinfecting unit to the charging dock 520. The charging illumination ring 522 is an indicator that can be seen from all directions around the charging dock which may change intensity, color, or change at a pulsing or modulated rate or any combination of these characteristics so as to indicate visually to the user the charging progress of the hand held disinfecting unit.

Figure 5F:
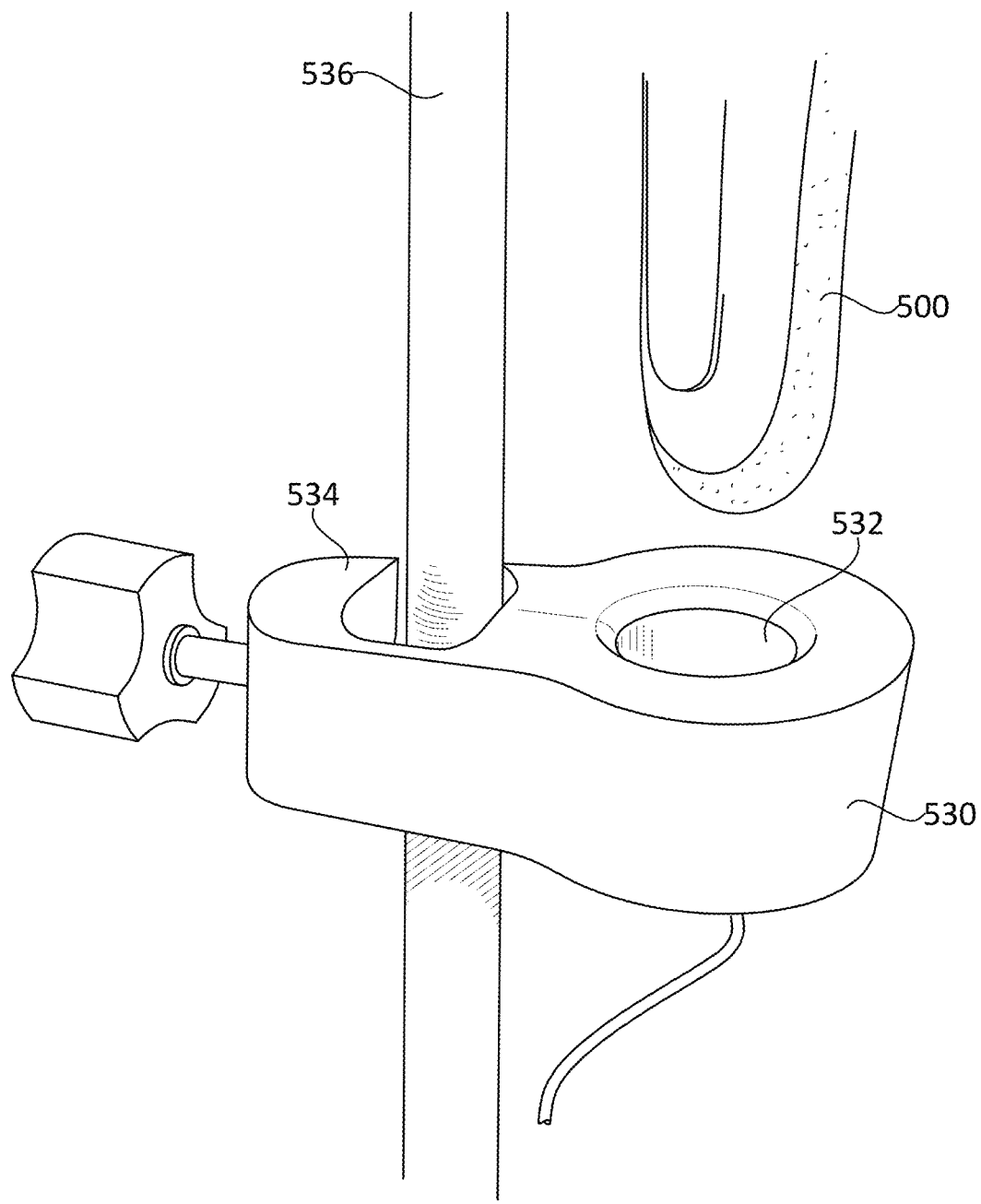
FIG. 5F is perspective view of the charging base of FIG. 5D adapted for use on a pole for use in a patient room.

FIG. 5F is a perspective view of the charging base 530 of FIG. 5D adapted for use on a pole for use in a patient operating, or procedure room. A mounting bracket 534 attached to the charging can be used to mount the base on the pole 536. A handheld disinfecting unit 500 as shown in FIGS. 5A-C is shown above the charging base 530 with an arrow indicating the direction to move the hand held unit 500 to engage the specifically configured charging receptacle 532 thereby coupling the hand held disinfecting unit to the charging dock.

Figure 6:
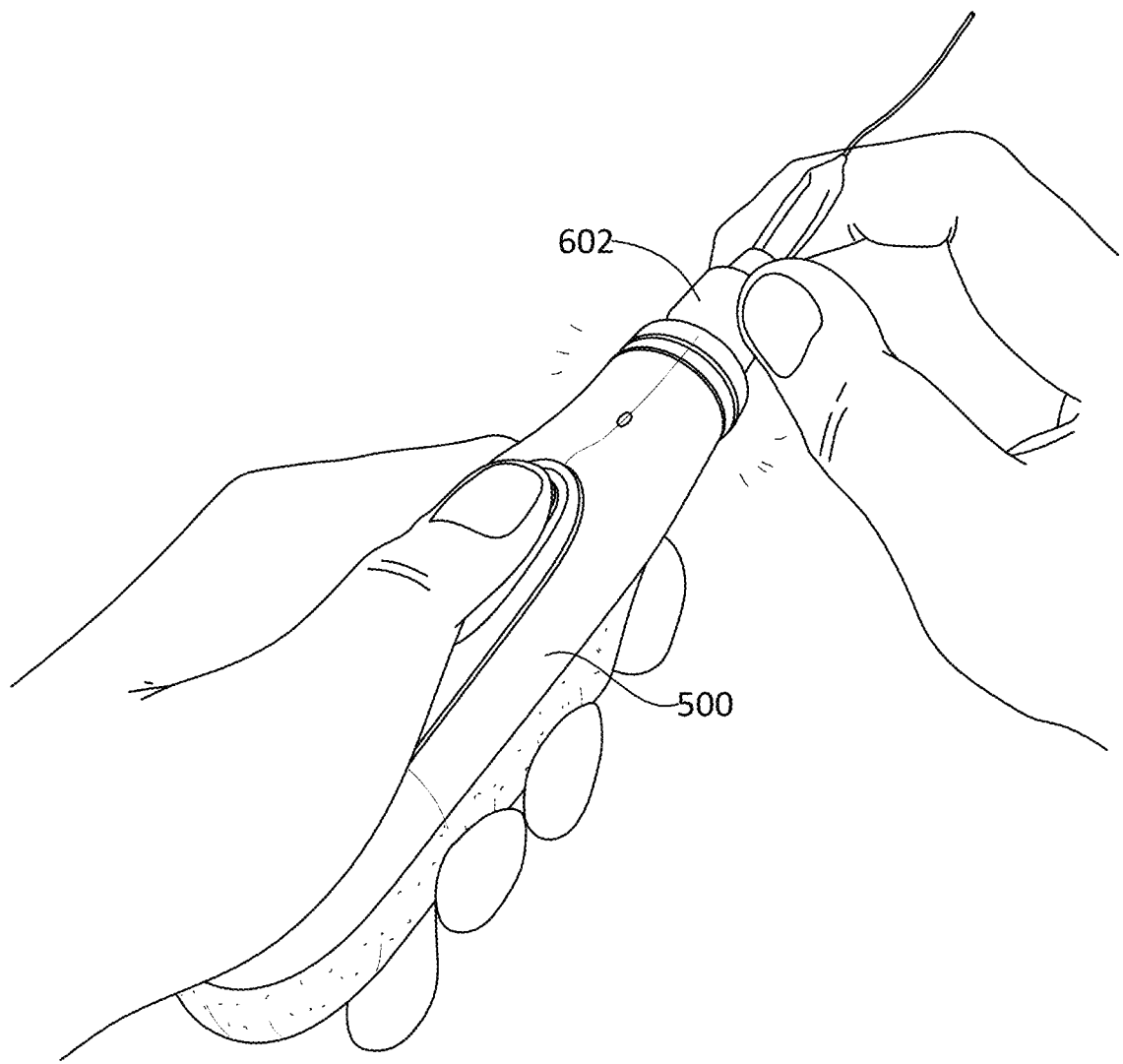
FIG. 6 is a perspective view of a connector or a component inserted within the a disinfecting unit.

FIG. 6 is a perspective view of a connector 602 or a component with the unit 500 slipped over all or a specifically selected portion of the connector 602. The connector is shown inserted within the portable disinfecting unit 500 of FIG. 5A in position to disinfect all or a specifically selected portion of the connector or component. FIG. 6 illustrates how a user would grip the disinfection unit 500 and place the connector 602 within the unit 500. FIG. 6 shows a user using a left hand to grip the unit 500 and a right hand to insert the connector 602, but the opposite is also possible with the same ergonomic feel and advantages.

Figures 7A, 7B:
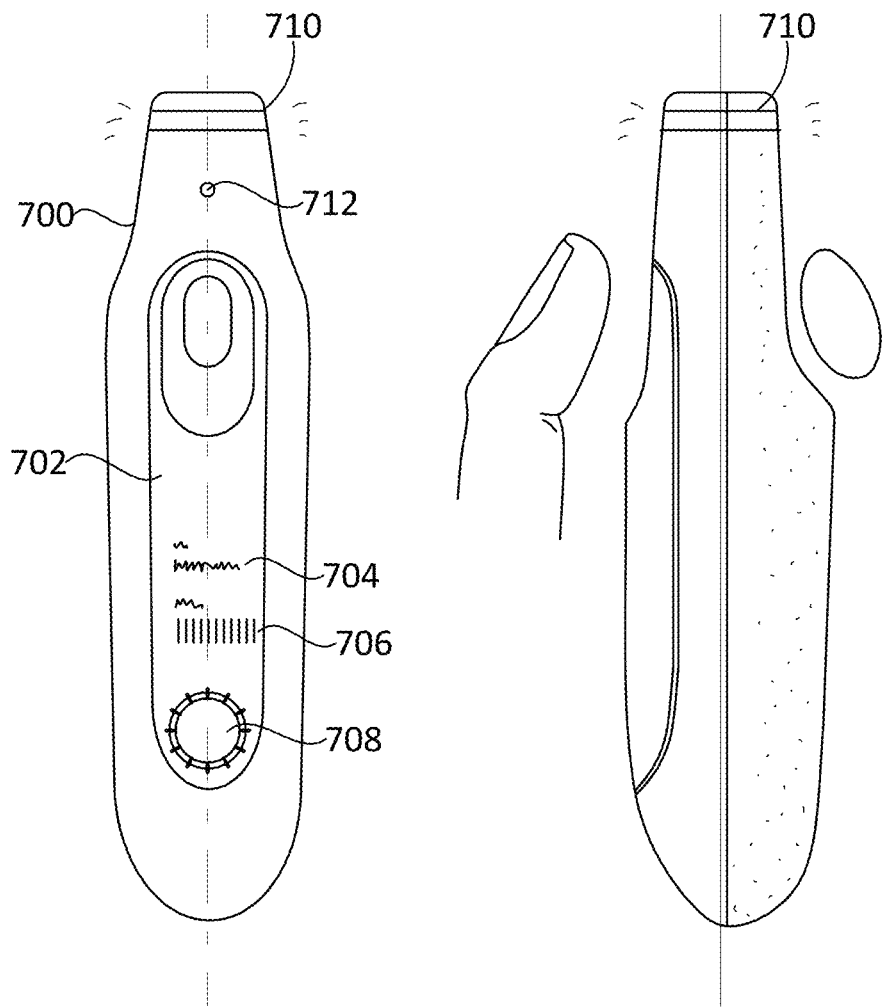
FIGS. 7A and 7B are top and side views respectively of another alternative embodiment of a hand held disinfecting unit.

FIGS. 7A and 7B are top and side views respectively of another embodiment of a hand held disinfecting unit 700 similar to that shown in FIGS. 5A-C having an aperture adapted and configured to receive a selected portion or optionally all of a component to be disinfected. As best seen in the top view of FIG. 7A the hand held disinfecting unit 700 is configured to include an editable electronic display 702. In the view shown in FIG. 7A, the display 702 is configured to show patient name 704, hospital ID 706, and frequency of use 708. The unit 700 and display 702 can comprise function indicators, status indicators (e.g., battery indicator 712), use indicators (e.g., progress ring 710) or patient information in a variety of different configurations. The display can be fully visible while the unit 700 is in a charging base. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 7C:
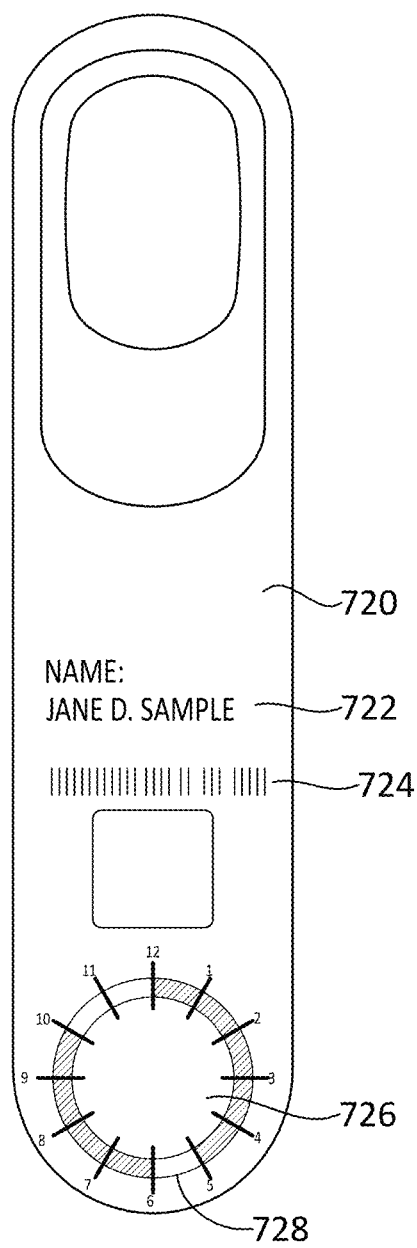
FIG. 7C is a detailed view of an editable electronic display.

FIG. 7C is a top view of an alternative an editable electronic display 720 configured to include function indicators, status indicators, use indicators or patient information in a variety of different configurations with this view showing a patient name 722, a hospital ID 724, and a frequency of use indicator 726. The frequency of use indicator can show use by the hour. If an hour field is not filled, as at hour 728, a cycle was not run.

Figure 8A:
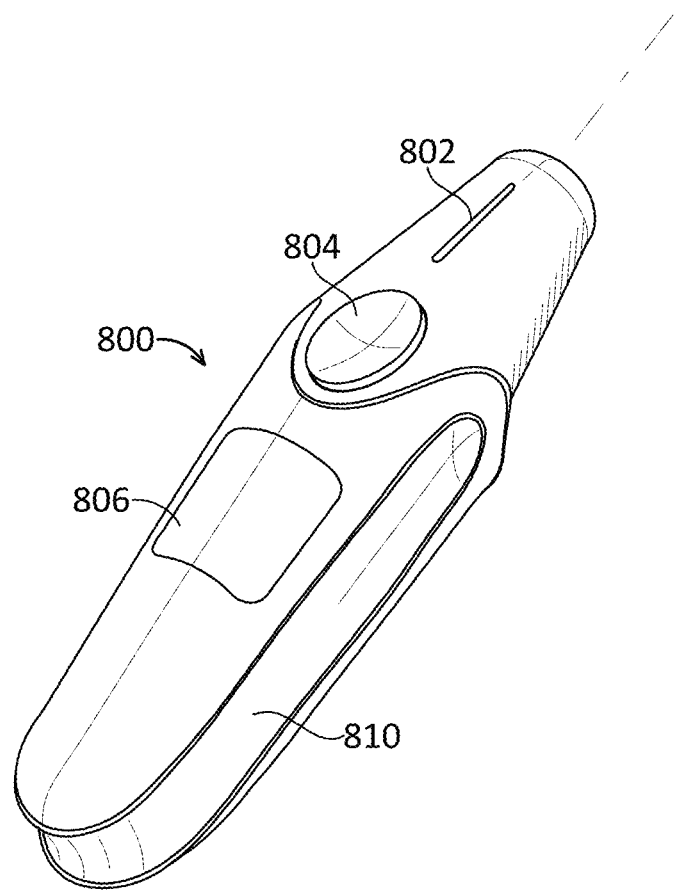
FIGS. 8A-C are perspective, top and side views respectively of an embodiment of a hand held disinfecting unit.
Figures 8B, 8C:
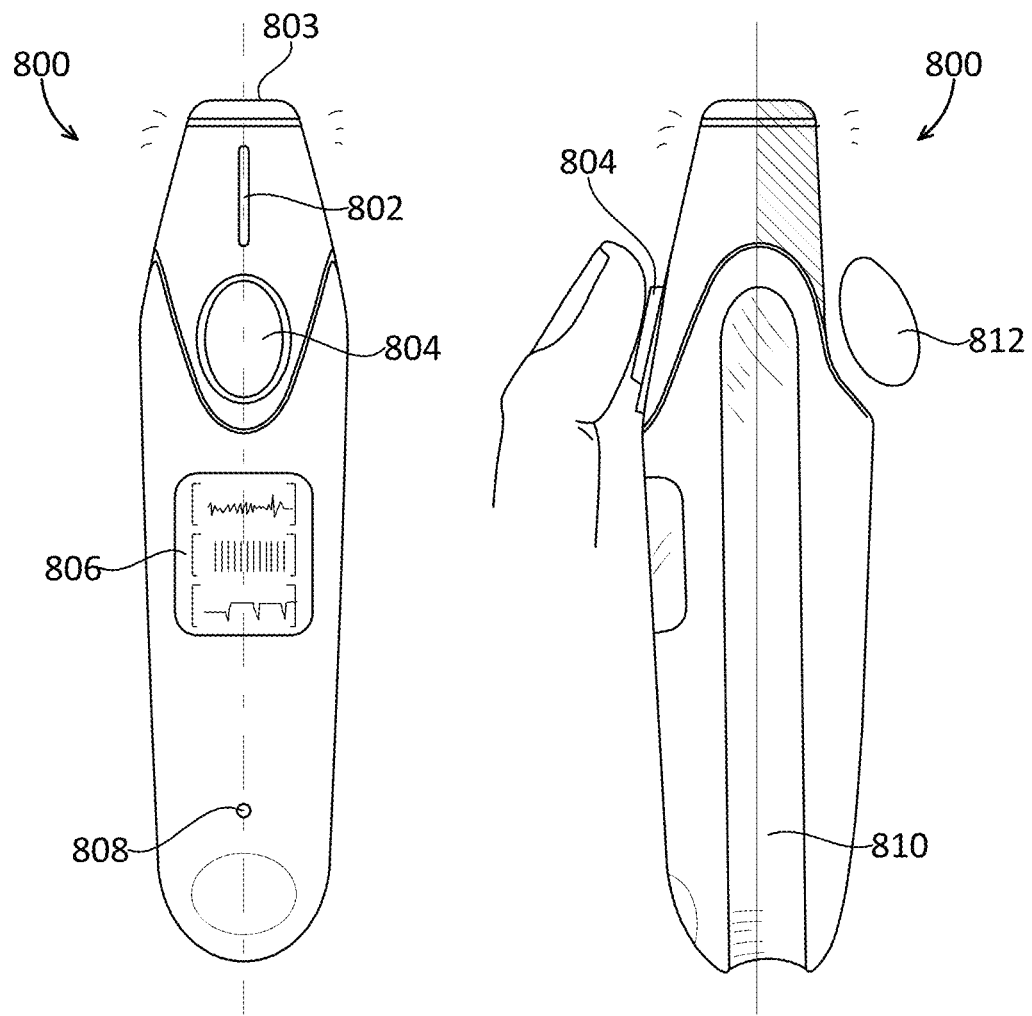

FIGS. 8A-C are perspective, top and side views respectively of another alternative hand held disinfecting unit 800 having an aperture 803 adapted and configured to slip over or receive a selected portion or optionally all of a component to be disinfected. The disinfection unit 800 comprises a body portion expanding in diameter towards a wide neck portion, and a head portion reducing in diameter from the neck portion towards the aperture 803. As best seen in the top view of FIG. 8B the hand held disinfecting unit is configured to include a progress status bar 802 and an editable electronic display 806 configurable into one or more of function indicators, status indicators, use indicators or patient information in a variety of different configurations including a patient name, a hospital ID, or a frequency of use indicator. The unit 700 comprises a battery charge indicator 808. The unit 800 comprises a soft grip recessed portion and button 804 for an ergonomic grip and a hook feature 812 for an index finger. A concave central band 810 extends along the sides and the bottom of the unit 800.

Figure 8D:
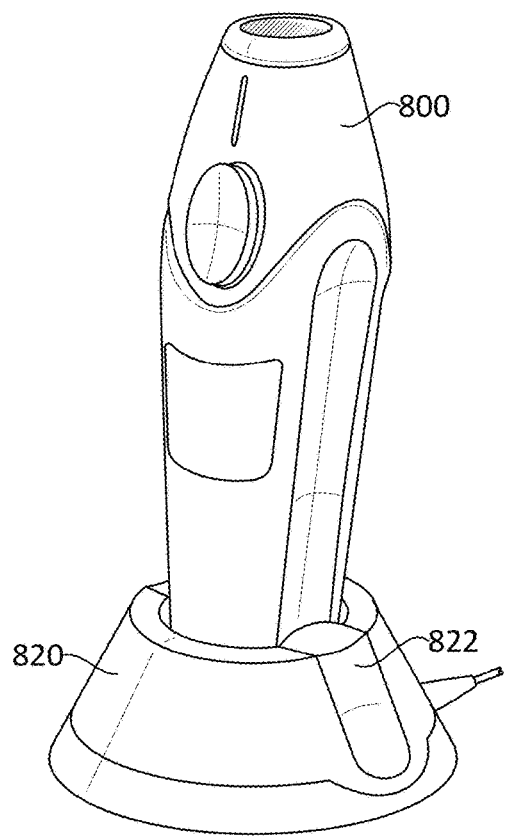
FIG. 8D is a perspective view of the handheld UV disinfecting unit of FIG. 8A shown in a stowed position within a specifically configured charging dock.
Figure 8E:
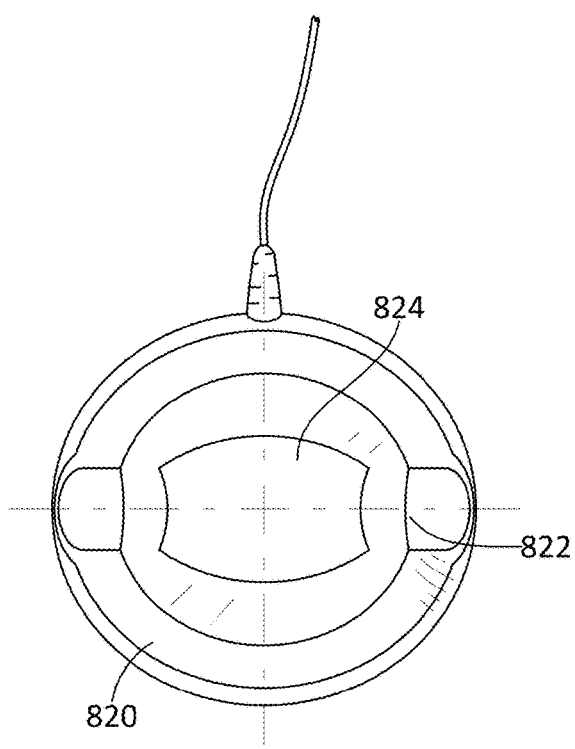
FIG. 8E is a top down view of the charging dock of FIG. 8D.

FIG. 8D is a perspective view of the handheld UV disinfecting unit 800 of FIG. 8A shown in a stowed position within a specifically configured charging dock 820. FIG. 8E is a top down view of the charging dock 820 of FIG. 8D with the hand held disinfecting unit removed to show the specifically configured charging receptacle 824 to couple the hand held disinfecting unit to the charging dock as well as visual and physical alignment features 822 configured to mate with the convex central band 810 on the unit.

Figure 8F:
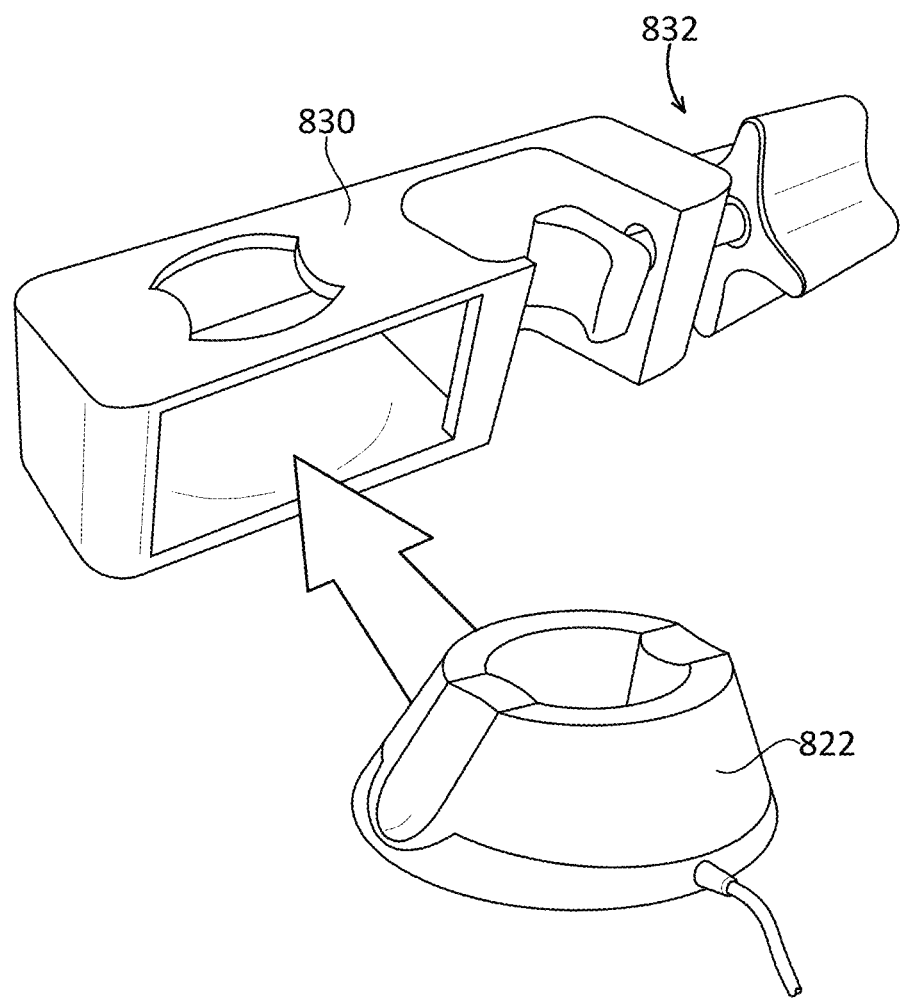
FIG. 8F is perspective view of the charging base of FIG. 8E being inserted into a base adapted for use on a pole for use in a patient room.
Figure 8G:
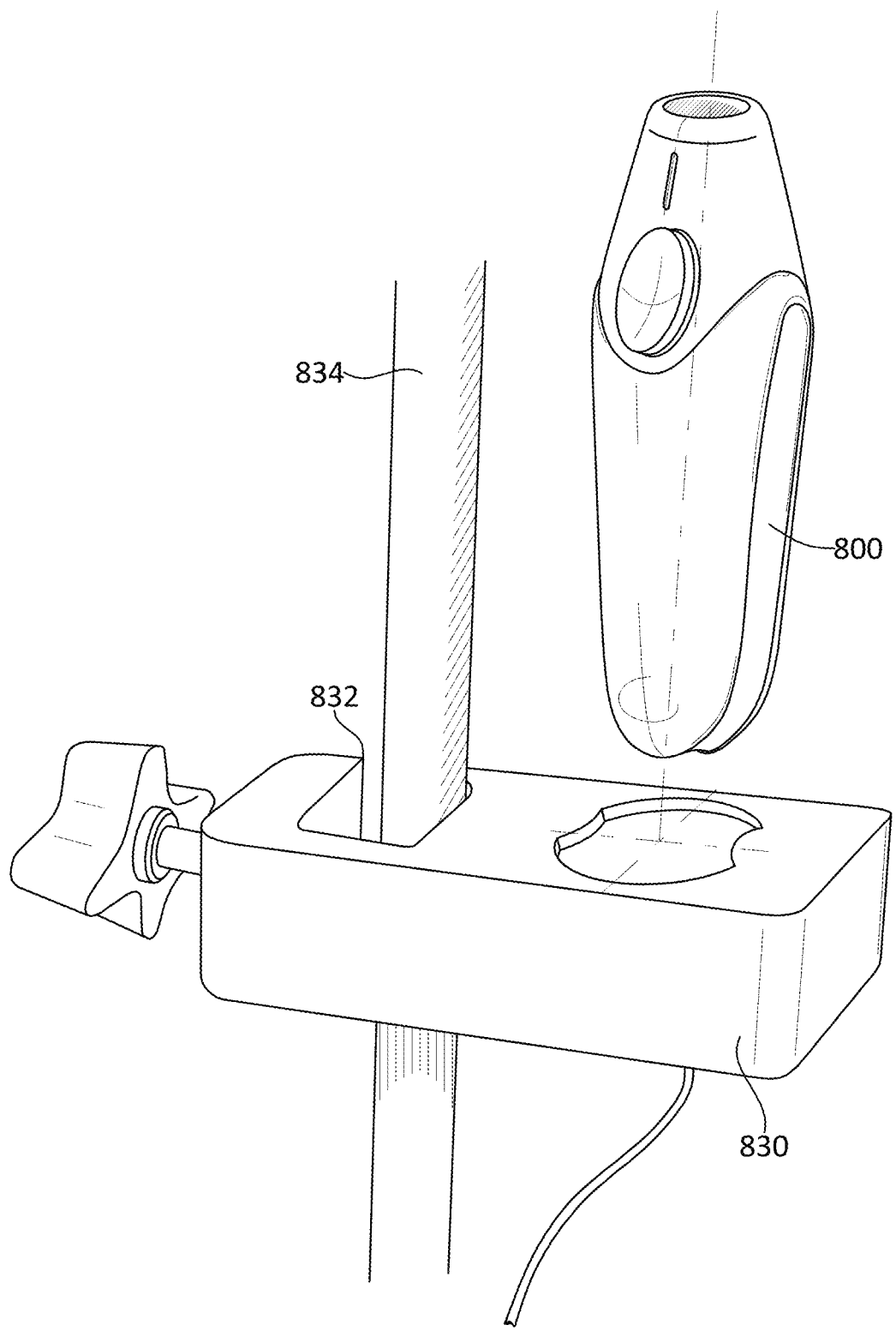
FIG. 8G illustrates the handheld disinfecting unit of FIG. 8A above the charging base.

FIG. 8F is a perspective view of the charging base 822 of FIG. 8E being inserted into a base 830 adapted for use on a pole for use in a patient room. The base 830 comprises a mounting bracket 832 configured for mounting base to a pole. FIG. 8G illustrates the base 830 mounted to an IV pole 834 using bracket 832 and with a handheld disinfecting unit 800 as shown in FIGS. 8A-C above the charging base 822.

Figure 9A:
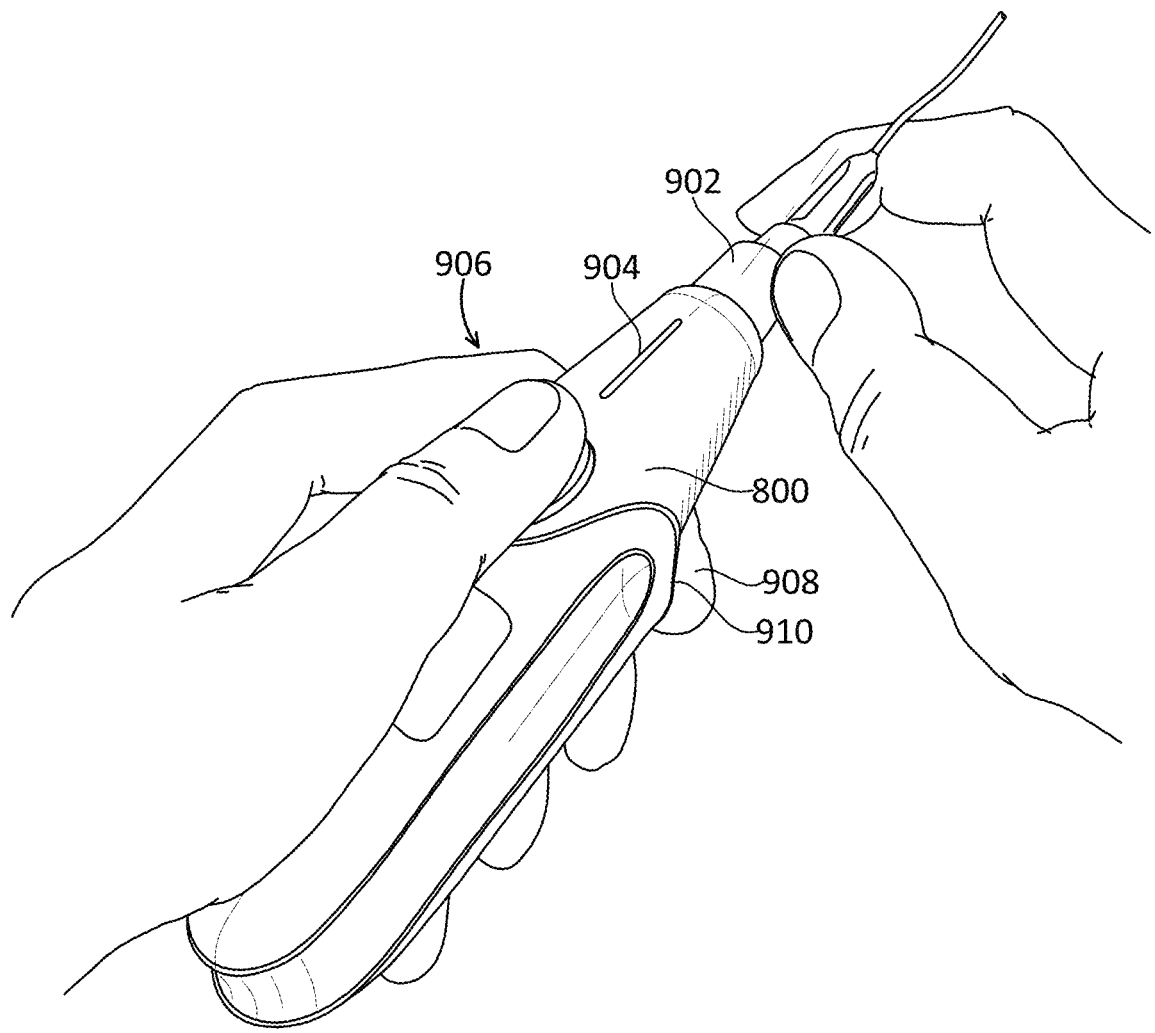
FIG. 9A shows a perspective view of a connector or a component inserted within the portable disinfecting unit of FIG. 8A.

FIG. 9A illustrates a perspective view of a connector 902 or a component inserted within the portable disinfecting unit 800 of FIG. 8B in position to disinfect all or a specifically selected portion of the connector or component. This view illustrates how the status indicator 904 near the aperture remains visible while a user grips the hand held disinfecting unit to permit thumb 906 activation of the disinfection function. The index feature 908 is shown in a nesting position on a recessed nest 910 of the unit 800. FIG. 9A shows a user holding the unit with the left hand and the connector with the right hand, but the opposite grip is also possible with the same ergonomic grip on the unit.

Figure 9B:
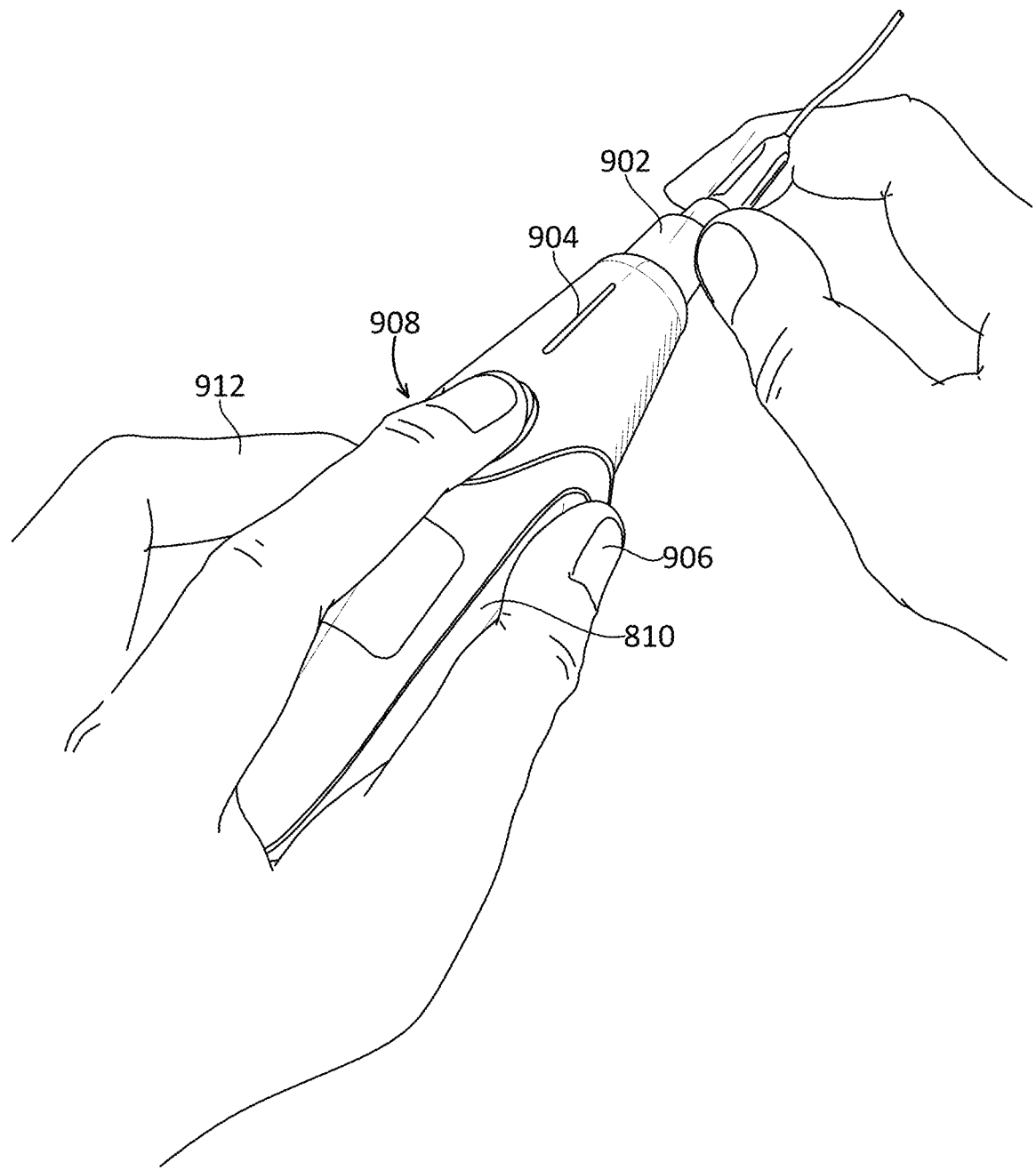
FIG. 9B shows a perspective view of a connector or a component inserted within the portable disinfecting unit of FIG. 8A in an alternative grip to that shown in FIG. 9A.

FIG. 9B illustrates a perspective view of a connector 902 or a component inserted within the portable disinfecting unit 800 of FIG. 8B in position to disinfect all or a specifically selected portion of the connector or component. FIG. 9B shows an alternative grip position nesting the thumb 906 and middle finger 912 in the concave band and using the index finger 908 for activation 810. This view illustrates how the status indicator 904 near the aperture remains visible while a user grips the hand held disinfecting unit to permit index finger activation of the disinfection function. FIG. 9B shows a user holding the unit with the left hand and the connector with the right hand, but the opposite grip is also possible with the same ergonomic grip on the unit.

Figure 10A:
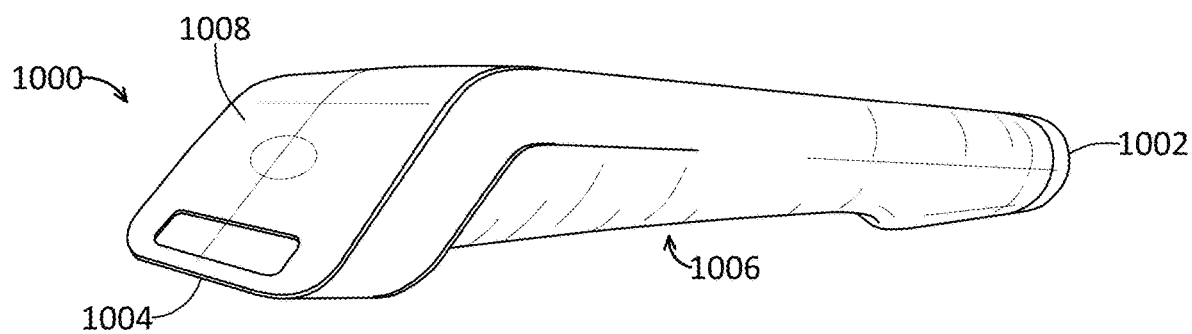
FIGS. 10A-C are perspective, top and side views respectively of another alternative embodiment of a hand held disinfecting unit
Figures 10B, 10C:
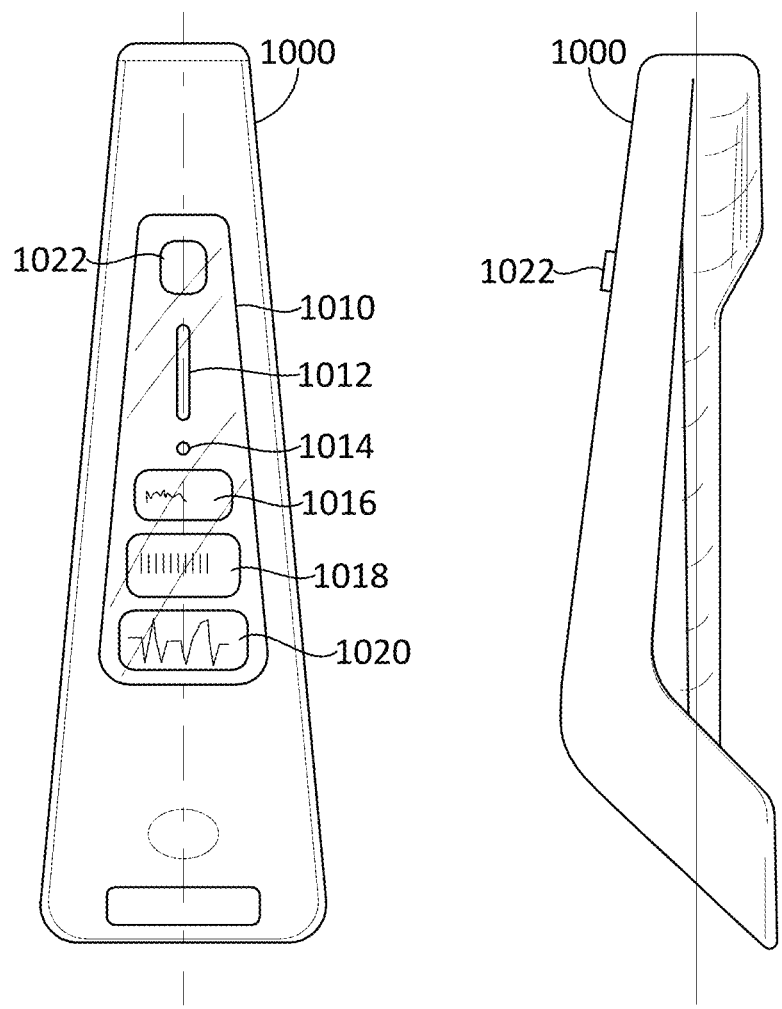

FIGS. 10A-C are perspective, top and side views respectively of another embodiment of a hand held disinfecting unit 1000 having an aperture 1002 adapted and configured to receive a selected portion or optionally all of a component to be disinfected. The unit 1000 can have a shape resembling a remote control, with an elongate body and a generally flat top surface. The top surface has a tapered shape, tapering towards the aperture 1002. The unit 1000 can be configured to be placed temporarily on a table surface, resting on flat surface 1004. The shape of that surface can prevent the handpiece from rolling off the table. A soft undercut 1006 under the unit 1000 can allow for easy pick up. The angled surface 1008 at the end of the device can be used for inductive charging in the base. The unit 1000 comprises progress status indicator or bar 1012, battery charge indicator 1014, and start button 1022. As best seen in the top view of FIG. 10B, the hand held disinfecting unit 1000 is configured to include an editable electronic display 1010 configurable into one or more of status indicators, use indicators or patient information in a variety of different configurations including a patient name 1016, a hospital ID 1018, or a frequency of use indicator 1020. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 10D:
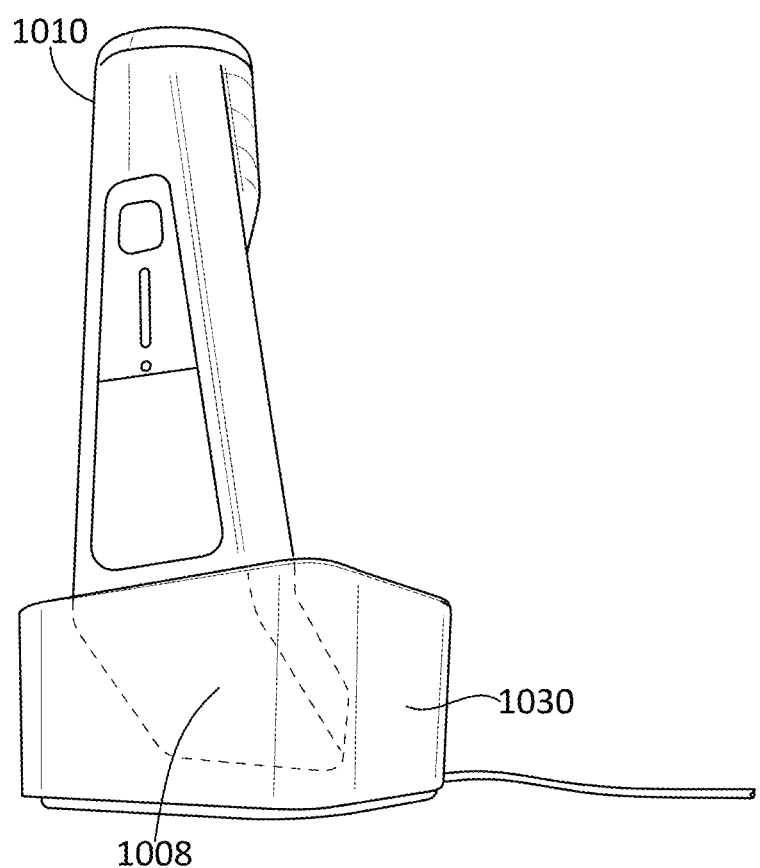
FIG. 10D is a perspective view of the handheld UV disinfecting unit of FIG. 10B shown in a stowed position within a specifically configured charging dock base.

FIG. 10D is a perspective view of the handheld UV disinfecting unit 1000 of FIG. 10B shown in a stowed position within a specifically configured charging dock base. The angled surface 1008 of the unit 1000 is configured to mate with a corresponding slot in the base 1030

Figure 10E:
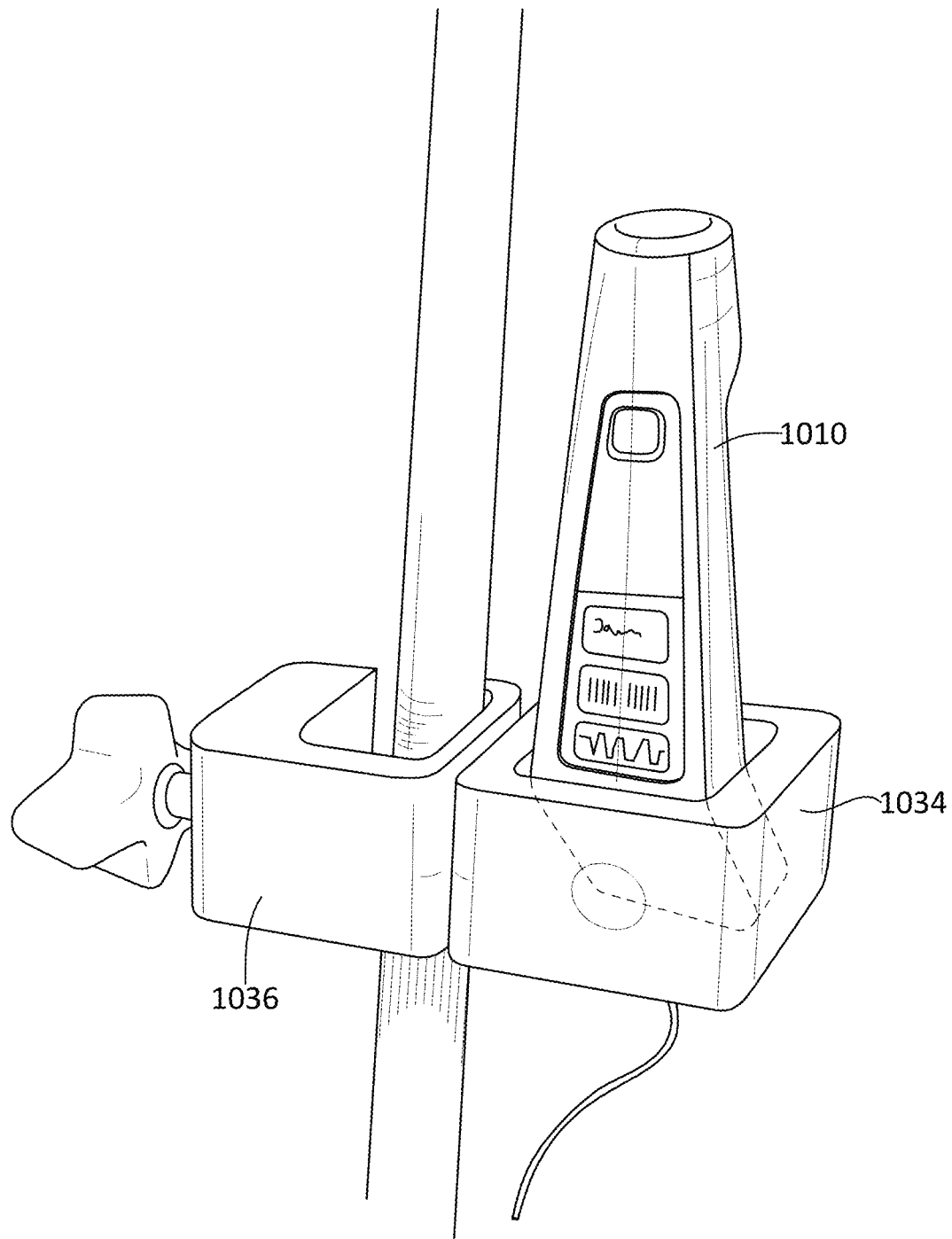
FIG. 10E is a perspective view of the handheld UV disinfecting unit of FIG. 10B shown in a stowed position within a specifically configured charging dock base adapted for use with a pole mount enabling use at patient bedside or hospital room.

FIG. 10E is a perspective view of the handheld UV disinfecting unit 1010 of FIG. 10B shown in a stowed position within a specifically configured charging dock base 1034 adapted for use with a pole mount 1036 enabling use at patient bedside or hospital room.

Figure 11A:
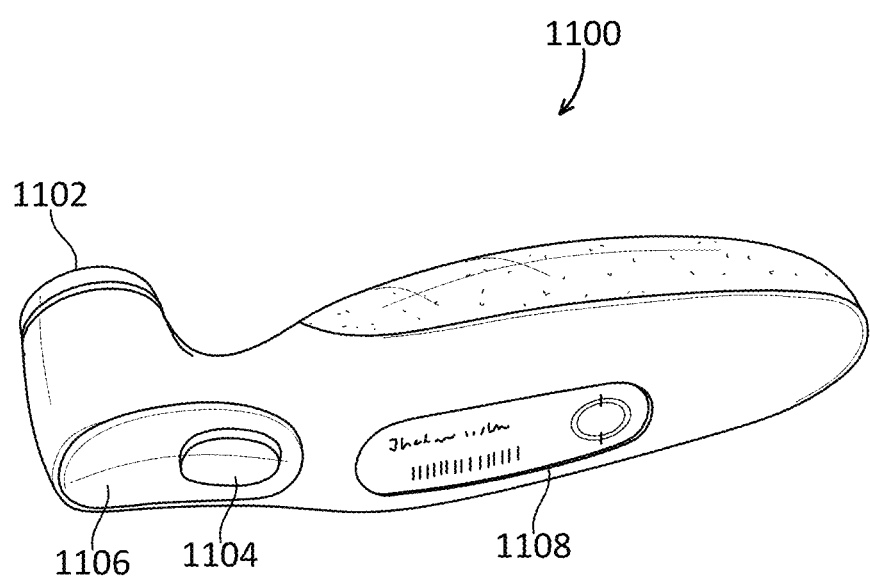
FIGS. 11A-D are perspective, bottom, side and top views respectively of another alternative embodiment of a hand held disinfecting unit
Figure 11B:
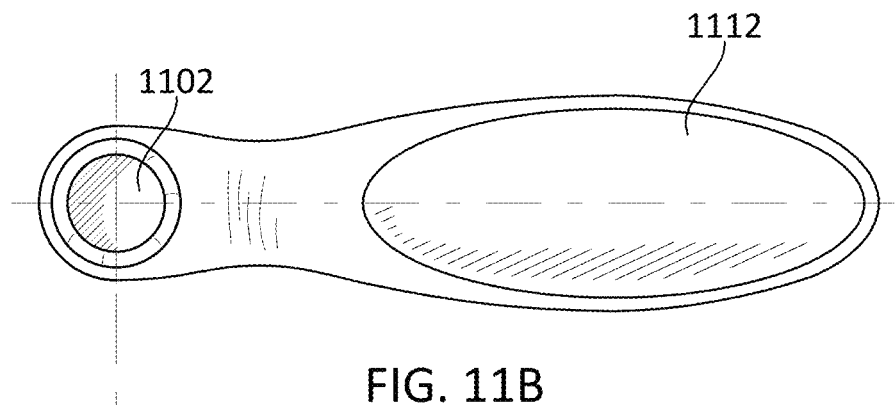
Figure 11C:
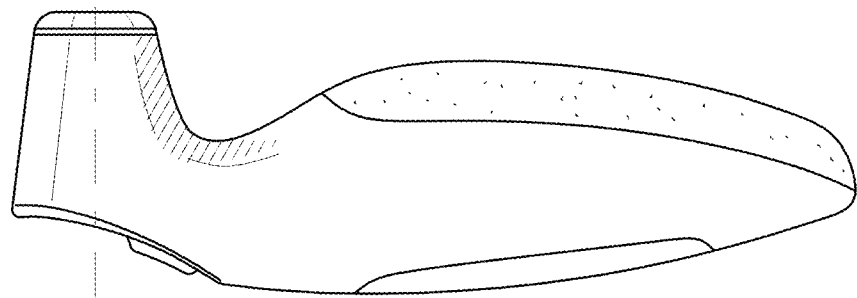
Figure 11D:
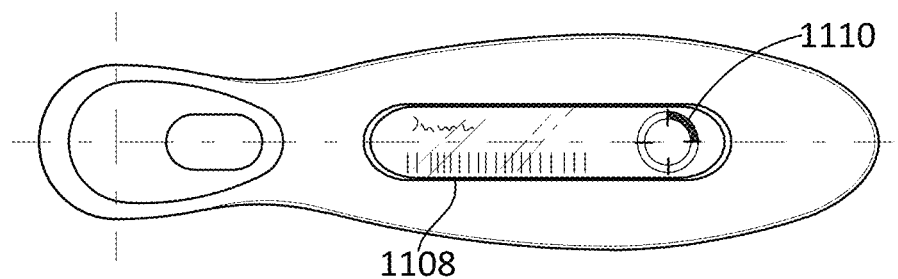

FIGS. 11A-D are perspective, bottom, side and top views respectively of another alternative hand held disinfecting unit 1100 having a body portion, a head portion, and an aperture 1102 adapted and configured to receive a selected portion or optionally all of a component to be disinfected. The body potion has a rounded cross section and increases in diameter from an end of the body portion to a midsection of the body portion and reduces in diameter from the midsection of the body portion to a neck portion of the disinfection unit 1100. The head portion and the aperture 1102 are configured to open at roughly a 90 degree angle relative to the hand held portion of the device. The device 1100 is configured to be used sideways like a bicycle grip. The unit includes a recessed grip area 1106 comprising start button 1104. The unit 1100 also comprises an editable display 1108. As shown in FIG. 11B, an underside of the unit 1100 comprises a soft grip area 1112. As best seen in the view of FIG. 11D the hand held disinfecting unit is configured to include a progress status light or an editable electronic display 1108 configurable into one or more of function indicators, status indicators, use indicators or patient information in a variety of different configurations including a patient name, a hospital ID, or a frequency of use indicator. The display 1108 can be configured to flip 180°, depending on whether the unit 1100 is being held in the user's right hand or left hand. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

FIG. 11E is a perspective view of the handheld UV disinfecting unit 1100 of FIG. 11A shown in a stowed position within a specifically configured charging dock 1120. FIG. 11F is a top down view of the charging dock of FIG. 11E with the hand held disinfecting unit removed showing the perimeter of the specifically configured (e.g., triangular shaped) charging receptacle 1122 to couple the hand held disinfecting unit to the charging dock.

Figure 11G:
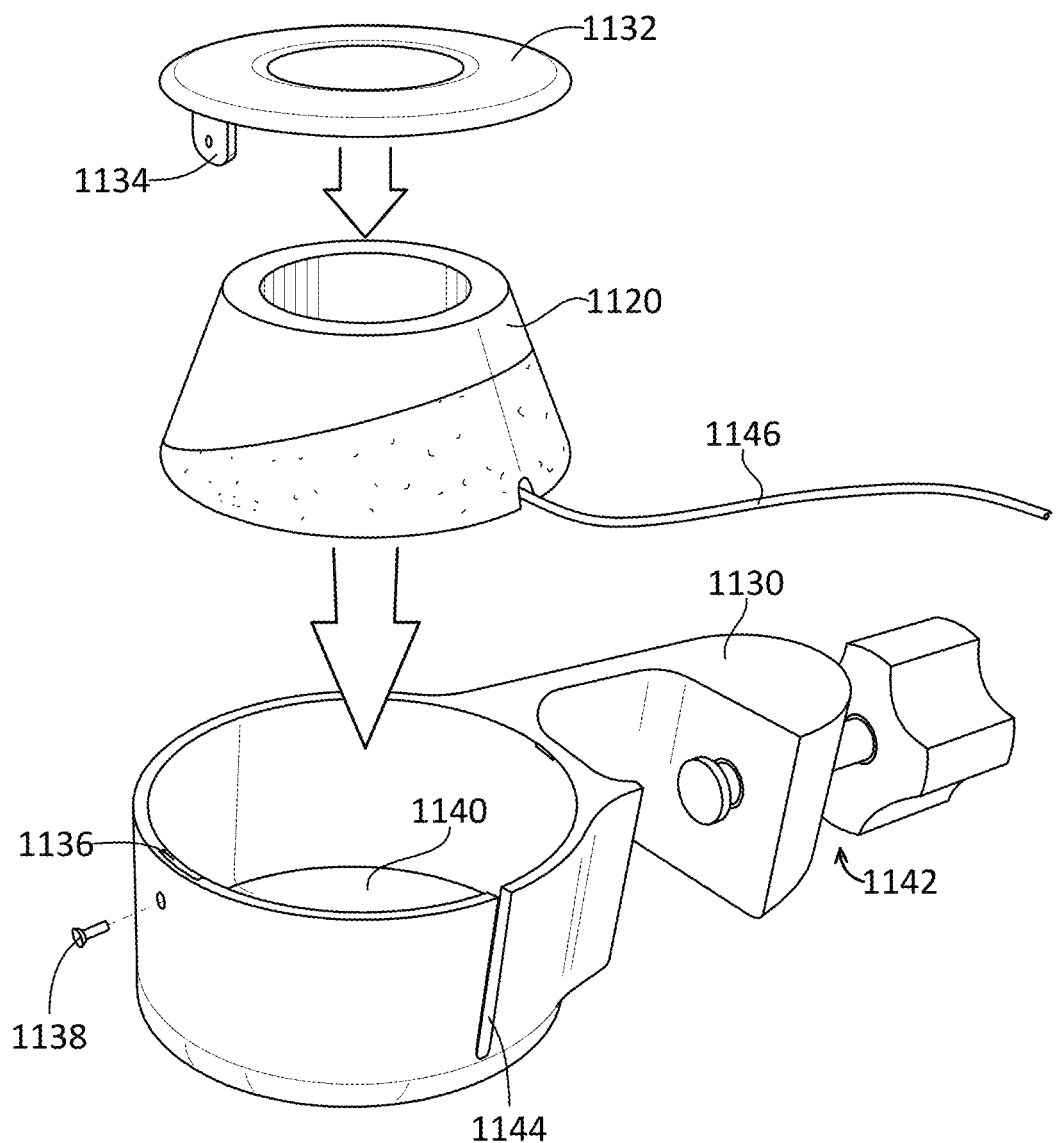
FIG. 11G is an exploded view of the components used to adapt the charging base of FIG. 11E for use on a pole.
Figure 11H:
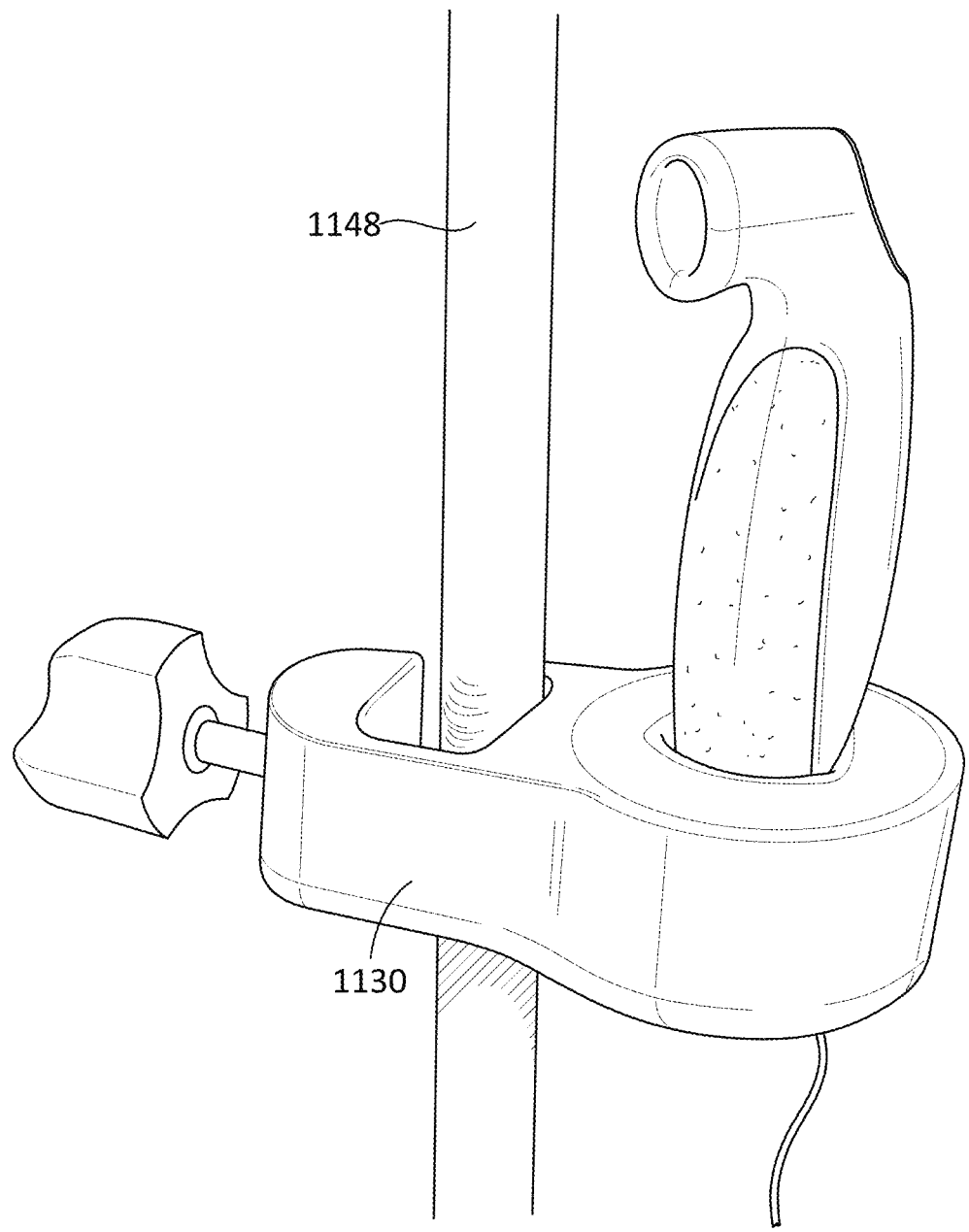
FIG. 11H is perspective view of the charging base of FIG. 11E modified as shown in FIG. 11G mounted on a pole with a handheld disinfecting unit as shown in FIG. 11A shown in a stowed configuration.

FIG. 11G is an exploded view of the components used to adapt the charging base of FIG. 11E for use on a pole. A mounting bracket 1130 comprises a bracket portion 1142 and a receptacle 1140 for receiving the charging base 1120. The receptacle 1140 includes a slot 1144 to allow the charging base cable 1146 to exit. A lid 1132 is configured to rest above the mounted charging base 1120 by engaging tab 1134 of lid 1132 with slot 1136 of the receptacle 1140 and engaging the two components with a screw 1138. FIG. 11H is a perspective view of the charging base of FIG. 11E modified using bracket 1130 as shown in FIG. 11G and mounted on a pole 1148 with a handheld disinfecting unit 1100 shown in a stowed configuration.

Figure 12:
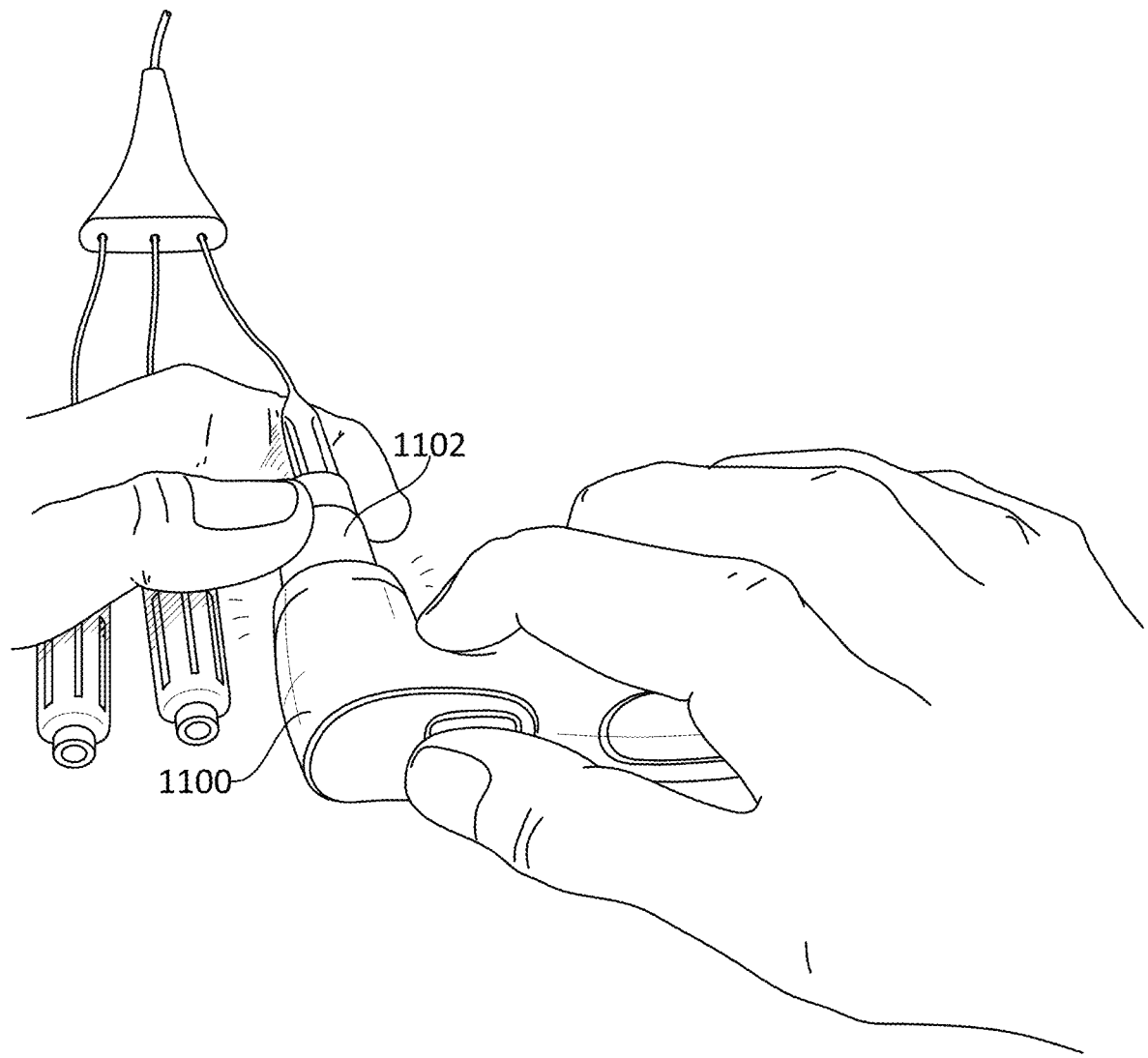
FIG. 12 is a perspective view of a connector or a component inserted within the portable disinfecting unit of FIG. 11A.

FIG. 12 is a perspective view of a connector or a component inserted within the portable disinfecting unit 1100 in position to disinfect all or a specifically selected portion of the connector 1102 or component. The aperture's 90 degree opening relative to the hand held portion of the device allows the user to hold the connector or component with an alternate grip during insertion as compared to a straight on or zero degree aperture opening.

Figure 13A:
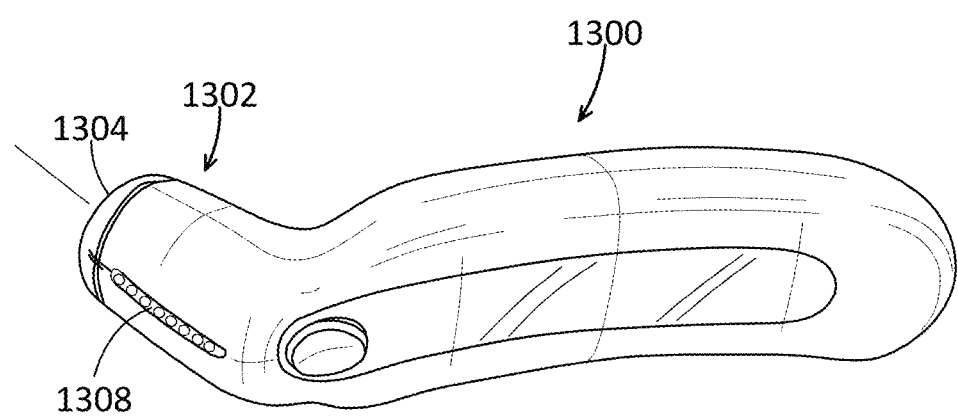
FIGS. 13A-C are perspective, side and top views respectively of an embodiment of a hand held disinfecting unit.
Figure 13B:
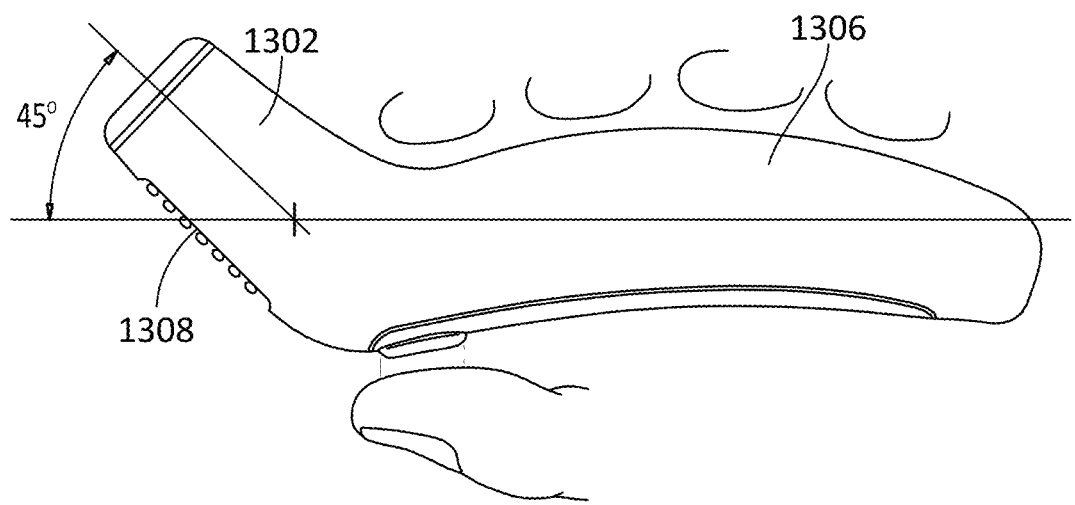
Figure 13C:
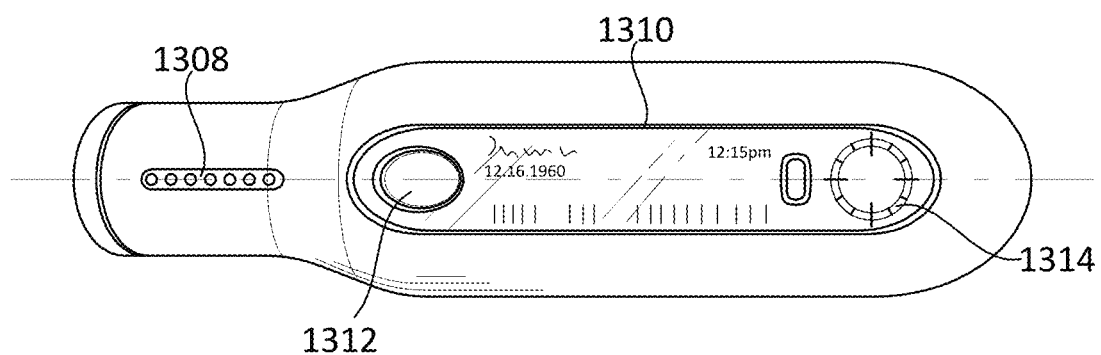

FIGS. 13A-C are perspective, side and top views respectively of a hand held disinfecting unit 1300 with a head 1302 angled between zero and 90 degrees containing an aperture 1304 adapted and configured to receive a selected portion or optionally all of a component to be disinfected. The unit 1300 comprises a control button 1312. As shown in FIG. 13B, the head can have an angle of about 45° relative to the body 1306. Other angles are also possible. The view of FIG. 13B also shows that top side of the body portion has a slide concave curve while the underside is convexly curved. As best seen in the view of FIG. 13C the hand held disinfecting unit 1300 is configured to include a variety of electronic progress, status, or lighting indications or an editable electronic display 1312 configurable into one or more of function indicators, status indicators, use indicators or patient information in a variety of different configurations including a patient name, a hospital ID, patient date of birth, date and time of last use, last several uses, indicator of last 24 hours, 12 hours, or 6 hours, or a differently configured frequency of use indicator 1314. The disinfection unit 1300 comprises a progress status bar 1308 that can comprise a number of lights (e.g., LEDs) configured to count down to show progress of a disinfection cycle. The unit 1100 can be configured to be held sideways (e.g., like a bicycle grip). The display 1310 can be configured to flip 180° depending on whether the unit is being held in the left or right hand.

Figure 13D:
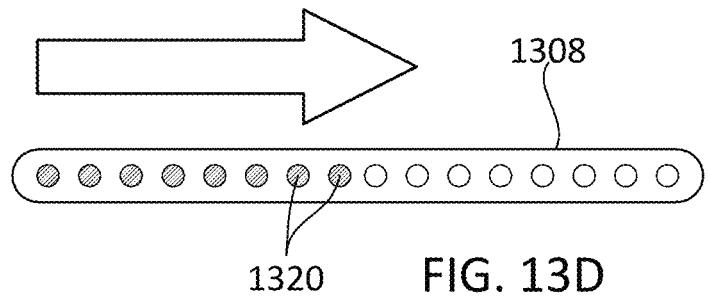
FIGS. 13D-F illustrate a variety of electronic progress, status, or lighting indications or an editable electronic display.
Figure 13E:
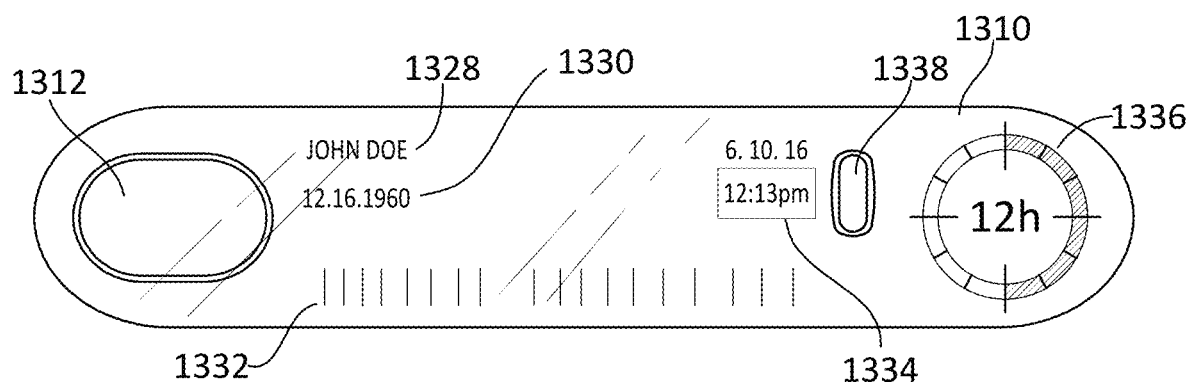
Figure 13F:
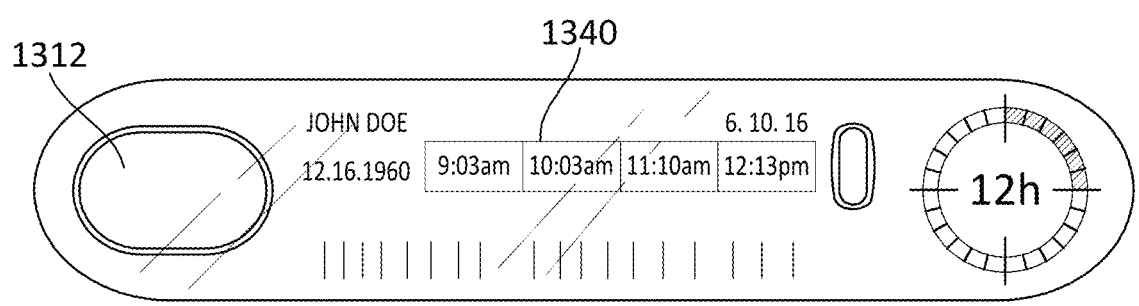
Figure 13G:
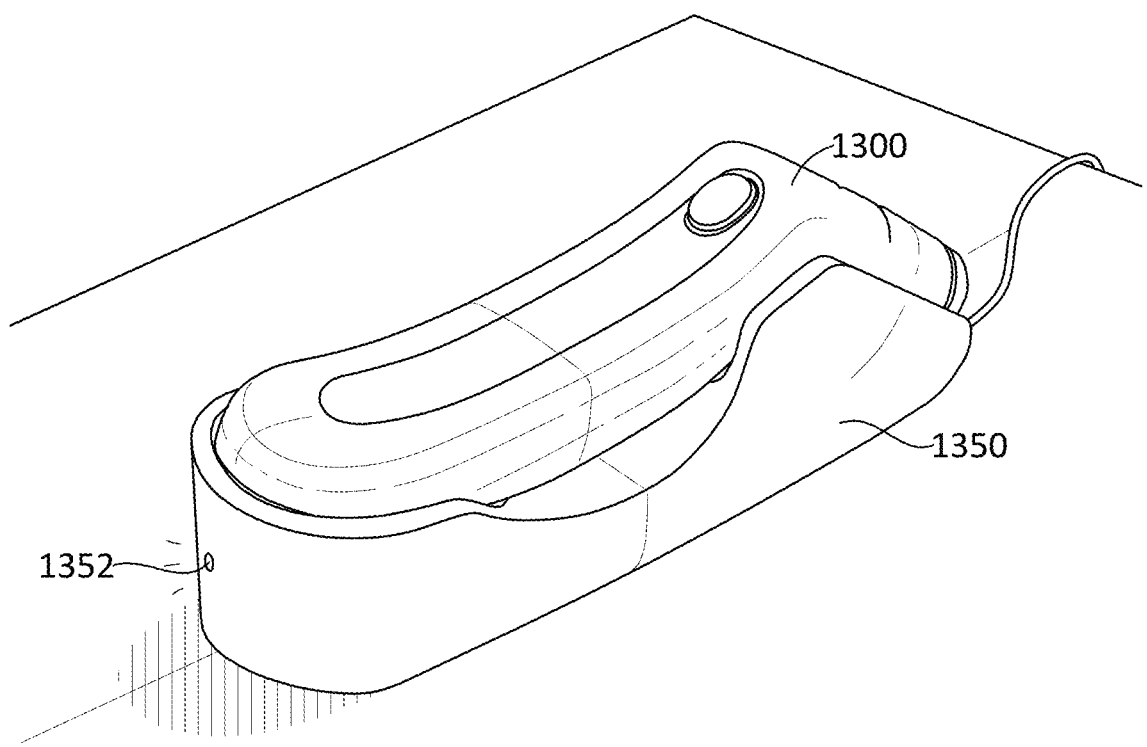
FIG. 13G is a perspective view of the handheld UV disinfecting unit of FIG. 13A shown in a stowed position within a specifically configured charging dock.

FIGS. 13D-F illustrate a variety of electronic progress, status, or lighting indications or an editable electronic display configurable into one or more of function indicators, status indicators, use indicators or patient information in a variety of different configurations including a patient name, a hospital ID, or a frequency of use indicator. FIG. 13D shows a progress indicator comprising a plurality of lights (e.g., LEDs) configured to sequentially illuminate during a disinfection cycle to count down time remaining in the cycle. FIG. 13E illustrates a blown up view of an example screen of the display 1310. As described above, the display can show the patient name 1328, patient date of birth 1330, patient ID number 1332, date and/or time of last use of the device 1334, and a circular indicator 1336 for showing the frequency of use. A button 1338 allows for toggling between showing the last 24 hours, the last 12 hours, and the last 6 hours of use. The control button 1312 can be positioned near or within the display. FIG. 13G shows another view of an example screen of display 1310. In FIG. 13G, the last several uses of the device are shown in section 1340.

FIG. 13G is a perspective view of the handheld UV disinfecting unit 1300 of FIG. 13A shown in a stowed position within a specifically configured charging dock 1350. The unit 1300 can be charged horizontally. An inductive charging surface can be below the unit 1300 in the dock. The dock can comprises a charging indicator light 1352.

Figure 13H:
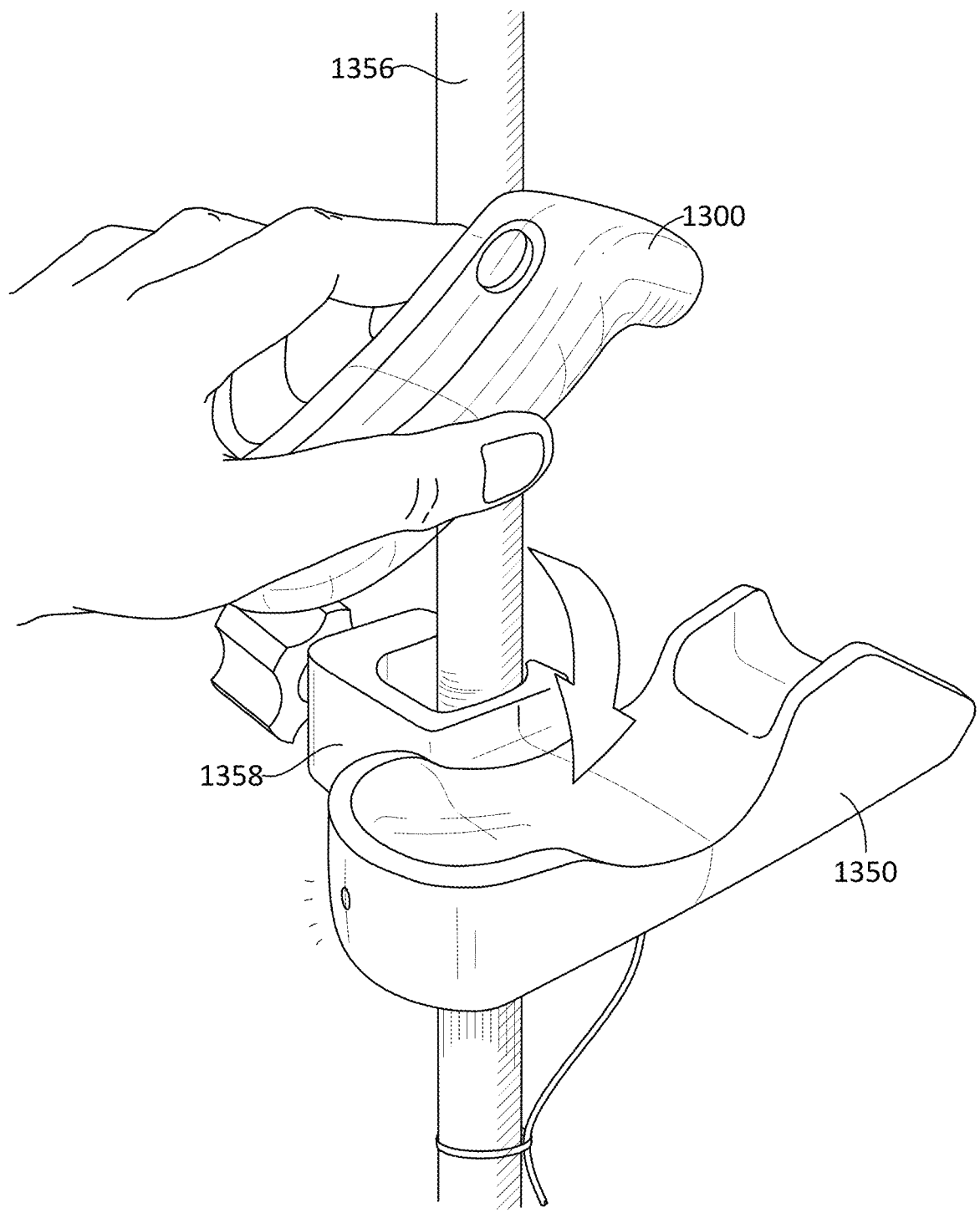
FIGS. 13H and 13I are perspective views of the charging base of FIG. 13E adapted to be mounted on a pole with a disinfecting unit of FIG. 13A shown above the base.
Figure 13I:
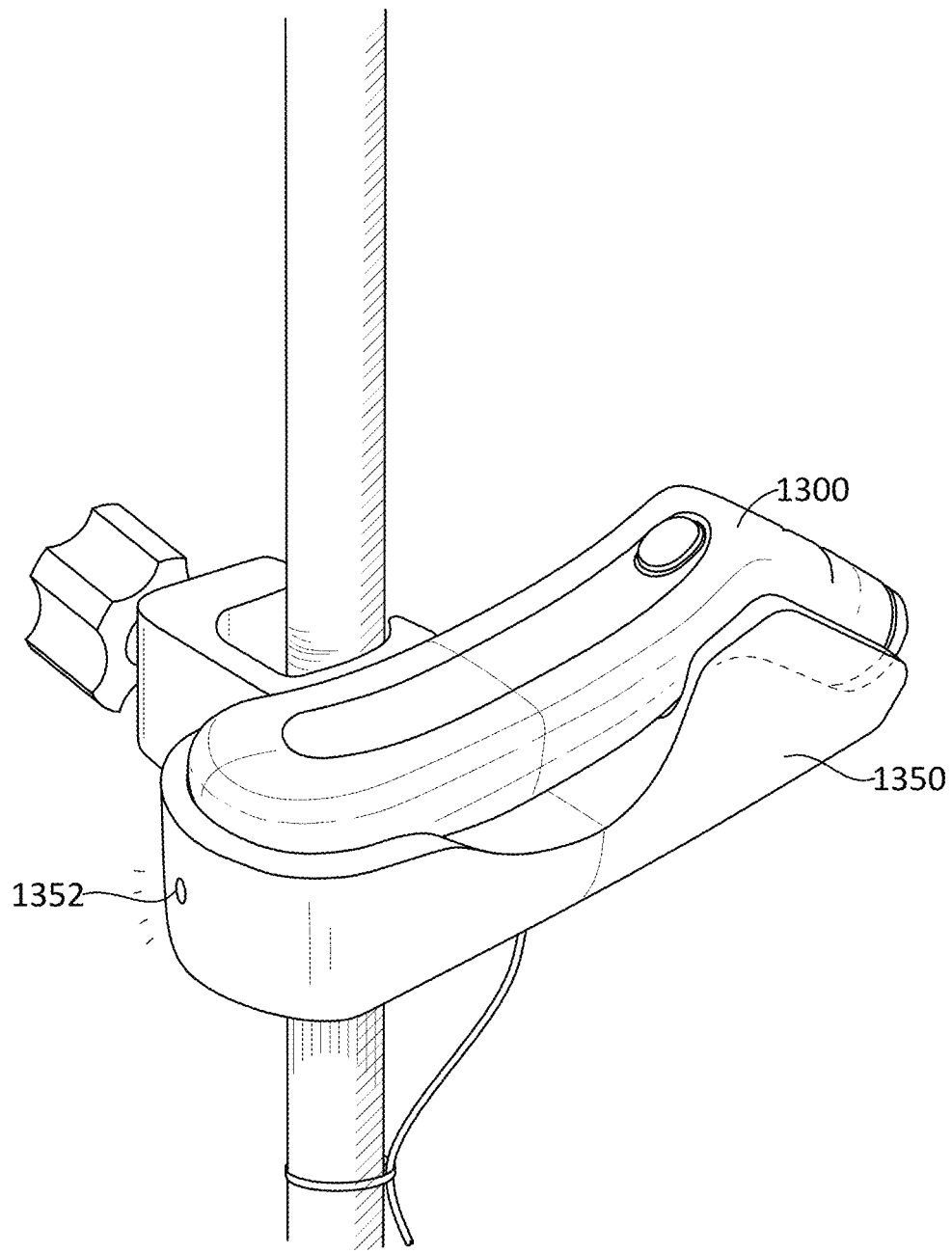

FIG. 13H is a perspective view of the charging base 1350 of FIG. 13E adapted to be mounted on a pole 1356 using bracket 1358. A disinfecting unit 1300 is shown above with an arrow indicating the direction of movement for engagement between the handheld disinfecting unit and the dock 1350 to place the hand held disinfecting unit into the stowed configuration as shown in FIG. 13I. In the stowed configuration, the charging indicator light 1352 is illuminated as long as the base 1350 has power. This horizontal stow position is advantageous over a vertical stow position for the pole mounted dock as many IV poles are full and crowded with infusion pumps and fluid pouches. This position also allows for easy pick up and placing of the unit 1300 on the base 1350.

Figure 14A:
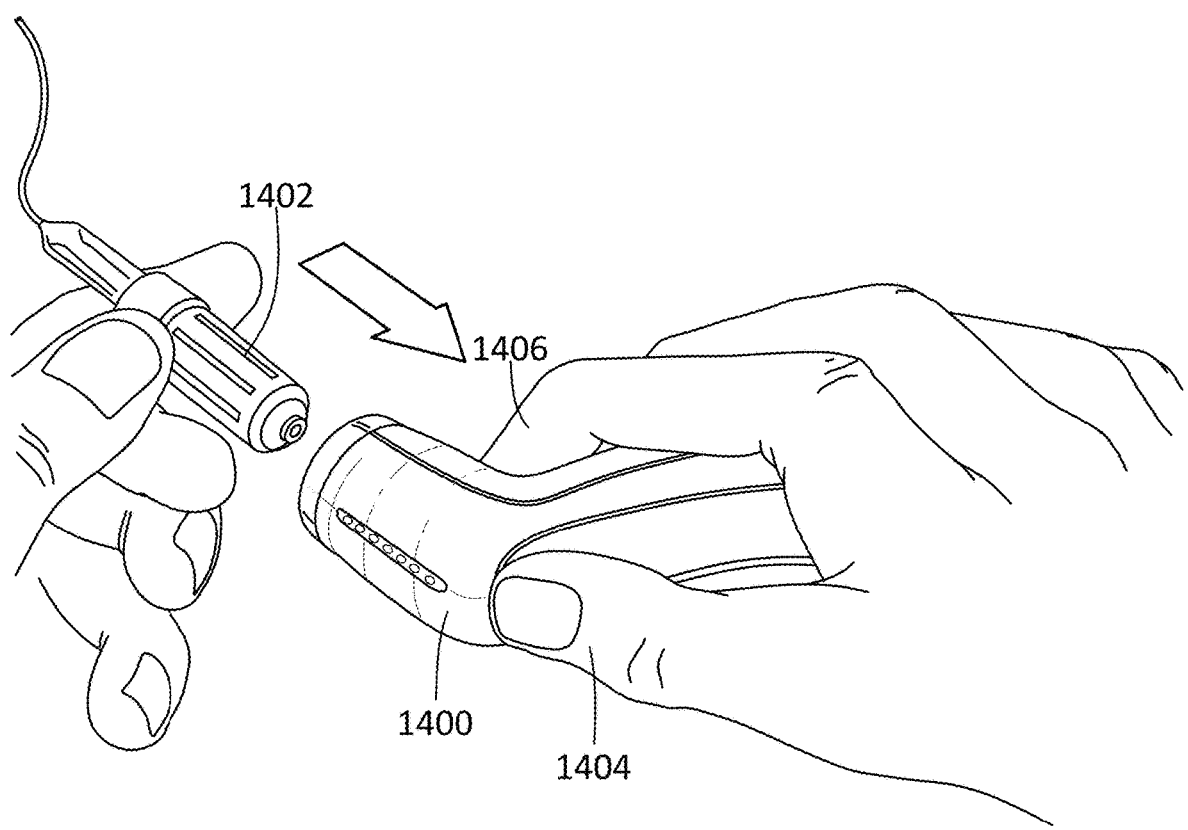
FIGS. 14A and 14B are two different perspective views of a connector or a component being advanced towards the portable disinfecting unit of FIG. 13A to disinfect all or a specifically selected portion of the connector or component.
Figure 14B:
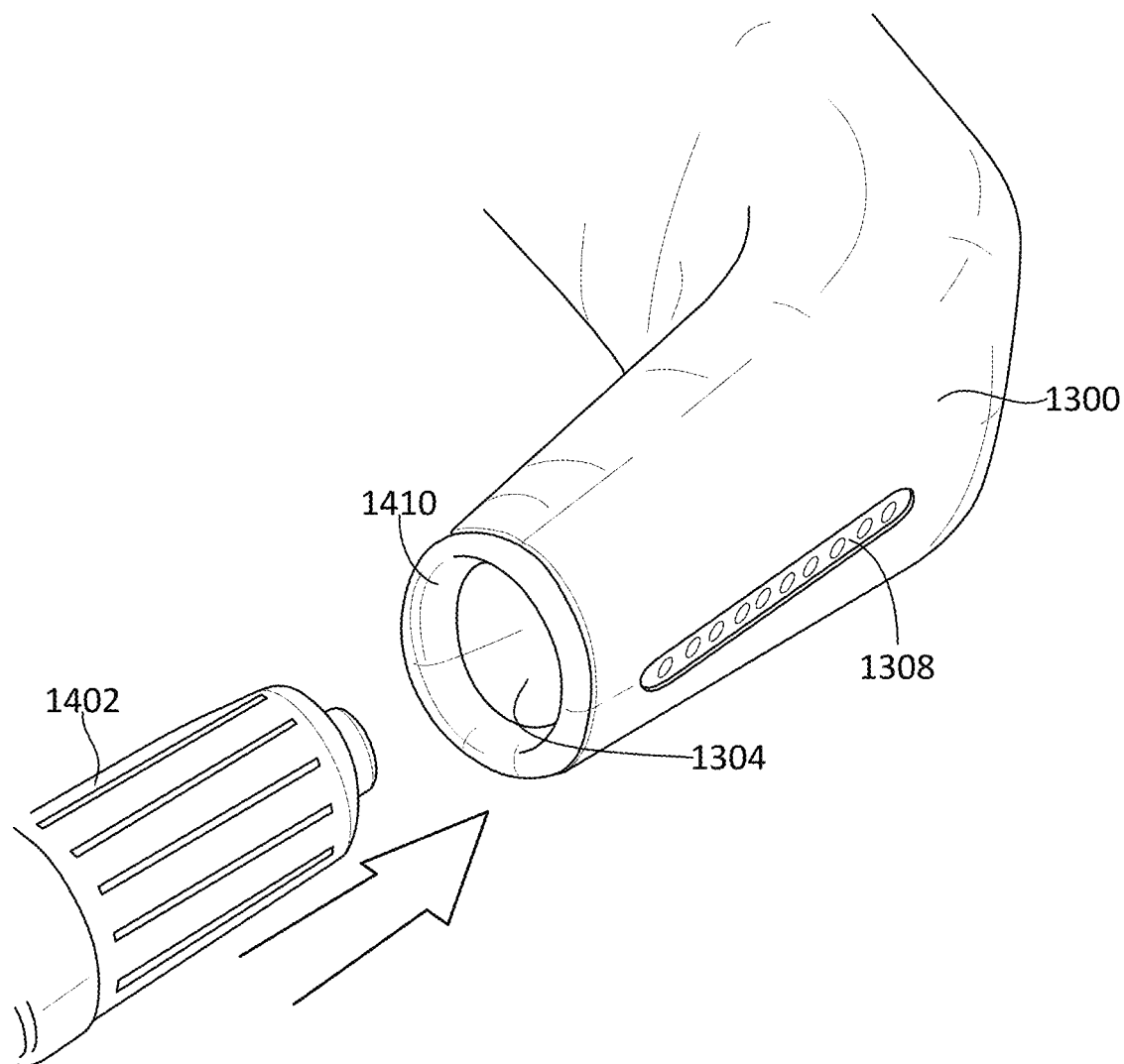
Figure 14C:
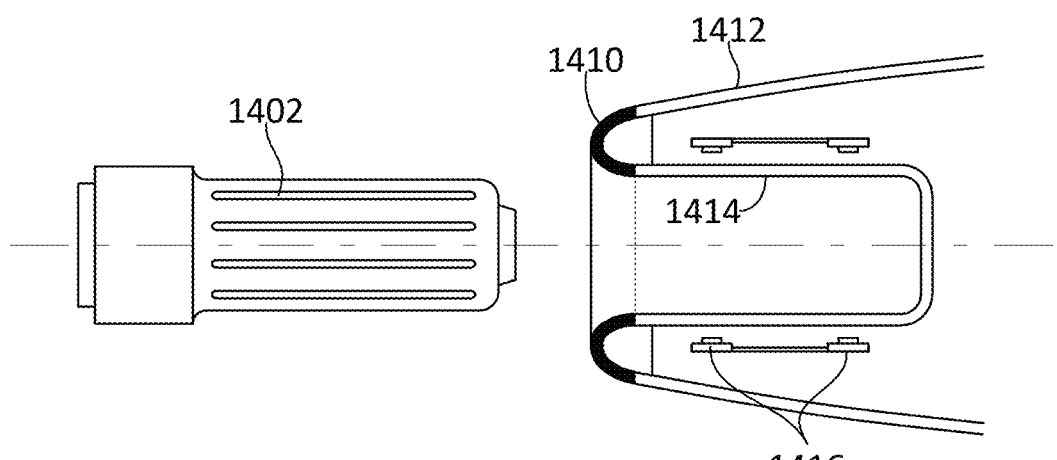
FIG. 14C is a section view of FIG. 14B showing the catheter or component in relation to a bullnose of the disinfecting.

FIGS. 14A and B are two different perspective views of a connector 1402 or a component being advanced towards and just prior to being inserted within the portable disinfecting unit 1300 of FIG. 13A to disinfect all or a specifically selected portion of the connector or component. As shown in FIG. 14A, the unit 1300 is shown in use sideways with the thumb 1404 in position on the control button and the index finger 1406 nested between the angled portion and main body of the unit. FIG. 14B shows the aperture 1304 of the unit 1300 in more detail. The aperture 1304 is surrounded by a rounded bullnose 1410, making the aperture easy to clear and rugged. FIG. 58C is a section view of FIG. 58B showing the catheter or component 1402 in relation to a bullnose (e.g., metal bullnose) 1410 of the disinfecting unit showing, the aperture, the easy to clean, solid smooth recess 1414, and a portion of LED bulbs 1416 used arranged around the aperture recess. The recess 1414 can comprise a UV transmissive material to allow transmission of UV energy from the LED bulbs to the connector 1402. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 15A:
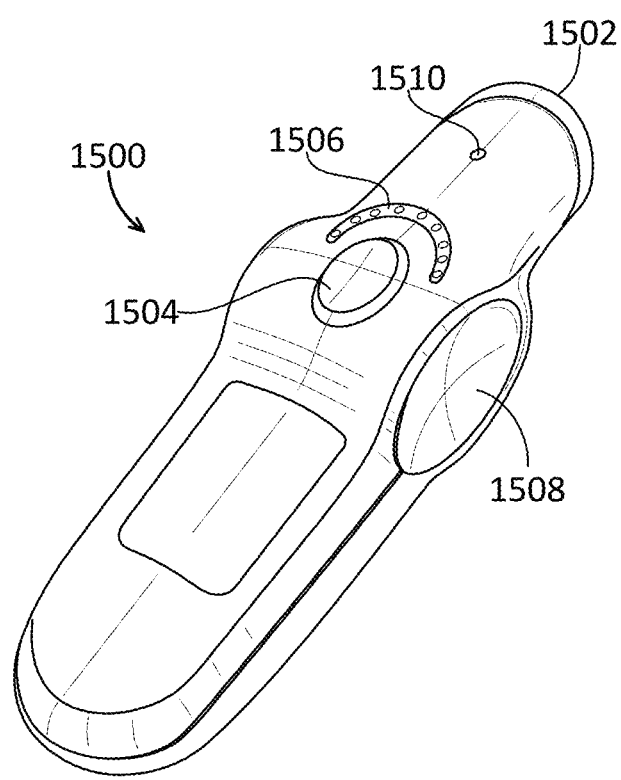
FIGS. 15A-C are perspective, side and top views respectively of an embodiment of a hand held disinfecting unit.
Figure 15B:
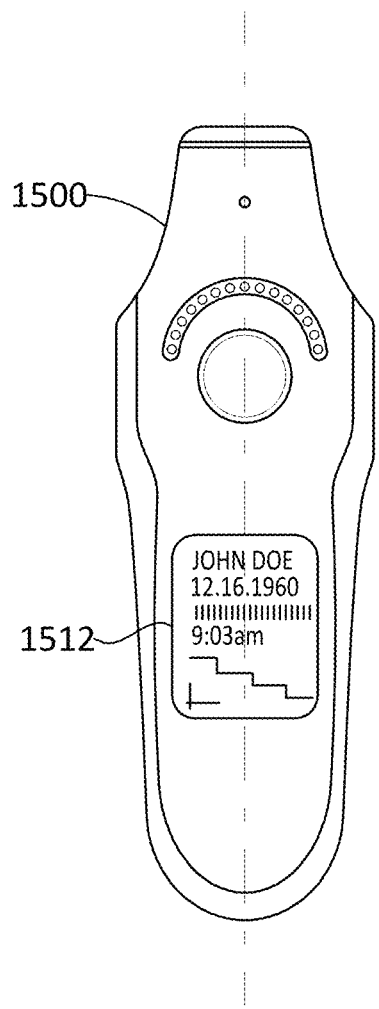
Figure 15C:
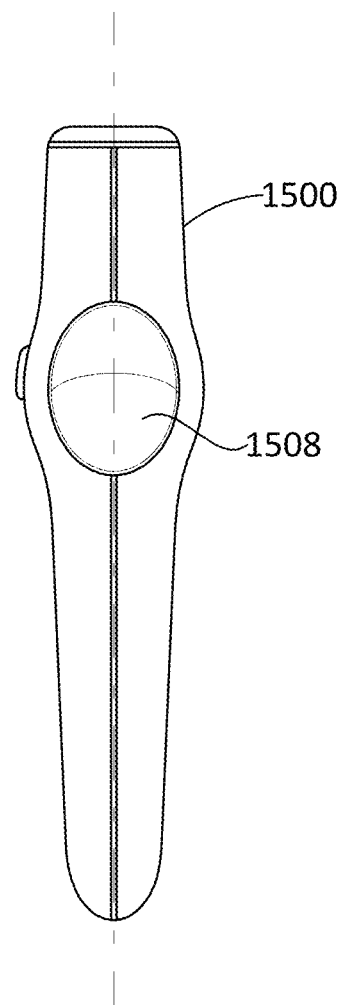

FIGS. 15A-C are perspective, side and top views, respectively, of a hand held disinfecting unit 1500 with an aperture 1502 adapted and configured to receive a selected portion or optionally all of a component to be disinfected. The unit 1500 comprises a control button 1504 operable by a finger (e.g., the thumb) and a curvilinear progress indicator 1506. The body portion widens around these features. The unit 1500 comprises concave side surfaces 1508 with two fingers (e.g., thumb and middle finger). The unit 1500 also comprises a battery indicator 1510. As best seen in the view of FIG. 15B, the hand held disinfecting unit is configured to include a variety of electronic progress, status, or lighting indications or an editable electronic display 1512 configurable into one or more of function indicators, status indicators, use indicators or patient information in a variety of different configurations including a patient name, a hospital ID, or a frequency of use indicator.

Figure 16A:
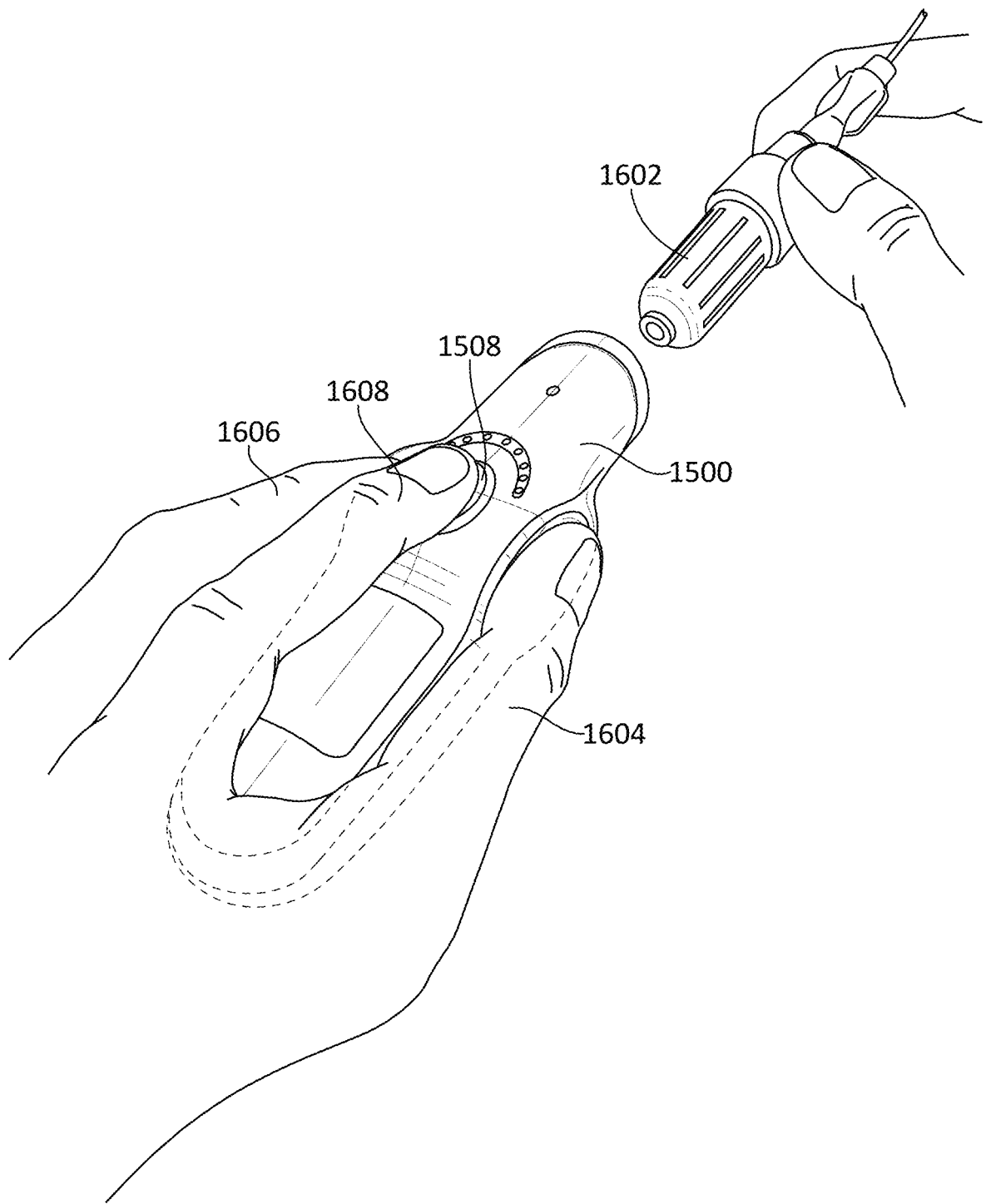

FIGS. 16A and 16B are perspective and top views, respectively, of a connector 1602 or a component being advanced towards and just prior to being inserted within the portable disinfecting unit 1500 of FIG. 15A to disinfect all or a specifically selected portion of the connector or component. The unit 500 is shown with the user's thumb 1604 and middle finger 1606 positioned within the side concave surfaces and the index finger 1608 positioned over the control button 1508 in FIG. 16A. FIG. 16B shows a detailed view of the progress status indicator 1506. The lights (e.g., LEDs) illuminate from left to right, filling in the shape of the indicator. At the end of the cycle, an audible alert can verify completion. The shape of the progress status indicator allows it to remain visible when a finger is positioned over the start button 1508. FIG. 16C is a top view of showing the connector 1602 or component inserted into the handheld disinfecting unit 1500 showing the differences in the status display as compared to FIG. 16B. In some embodiments, the start cycle button 1508 can also have an indicator. In some such embodiments, the start cycle indicator and the progress status indicator can have a same or similar configuration.

Figure 17A:
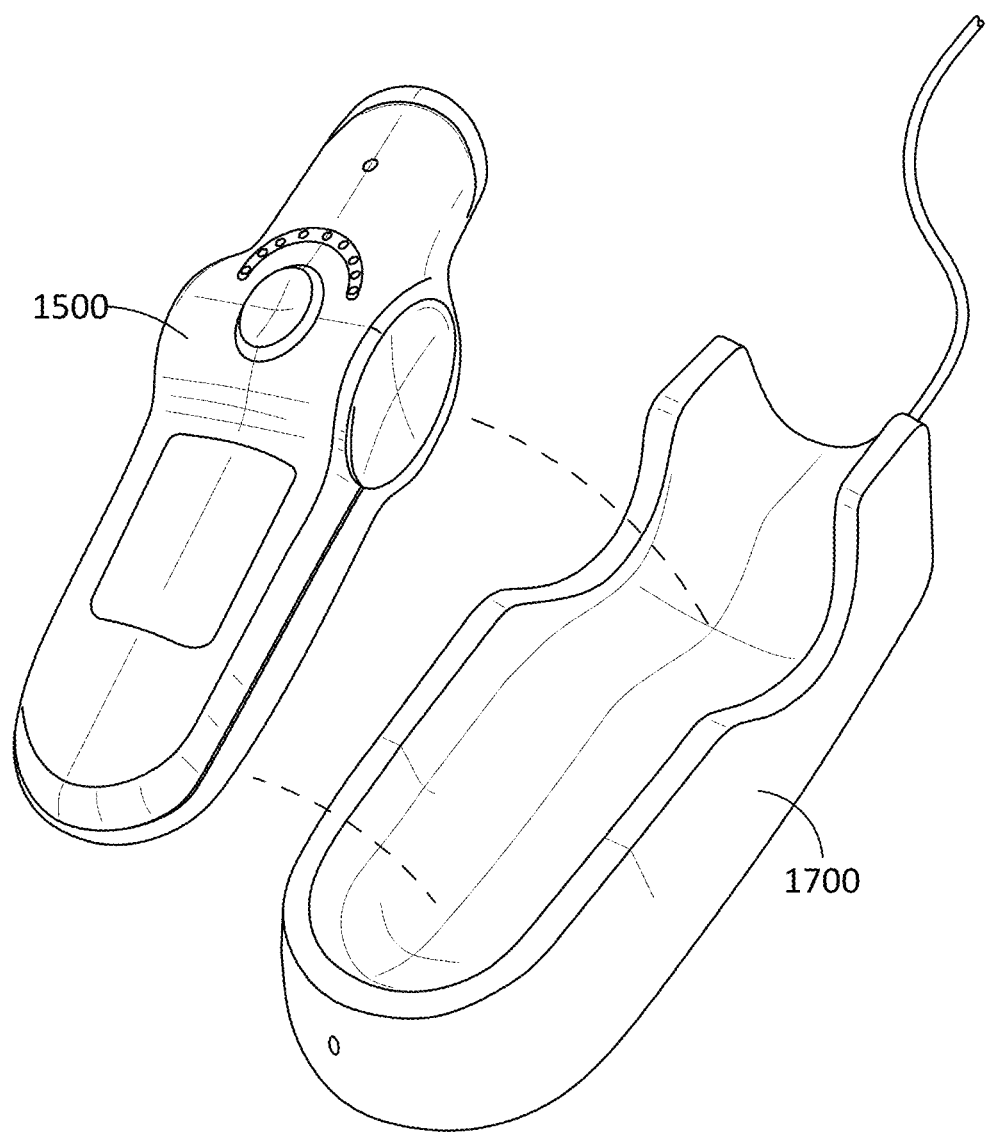
FIGS. 17A and 17B are perspective views of a charging base configured for specific engagement with a handheld disinfecting unit of FIG. 15A. A disinfecting unit of FIG. 15A is shown with the base.
Figure 17B:
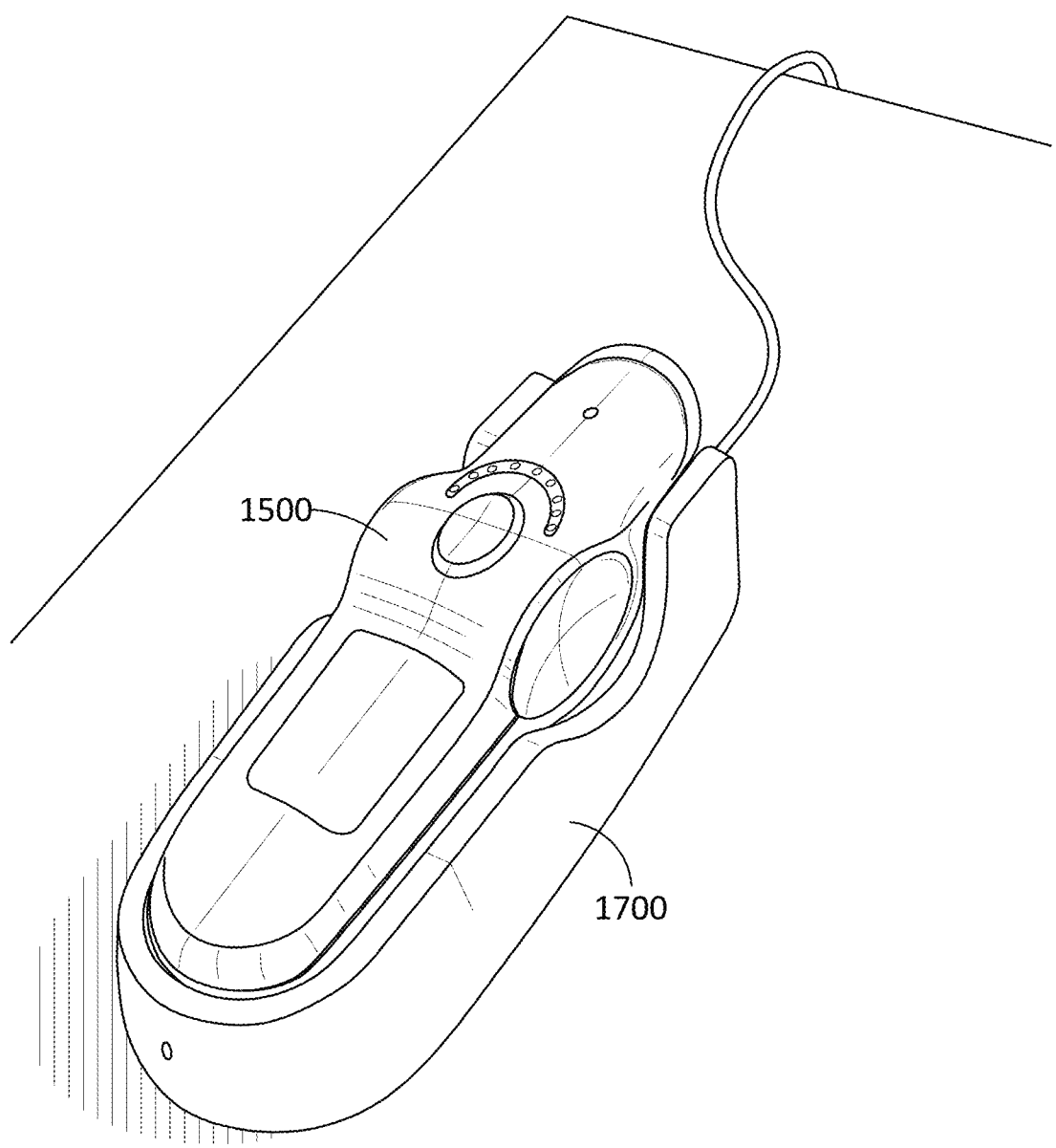

FIG. 17A is perspective view of a charging base 1700 configured for specific engagement with a handheld disinfecting unit 1500 of FIG. 15A. A disinfecting unit 1500 is shown above with an arrow indicating the direction of movement for engagement between the handheld disinfecting unit 1500 and the dock 1700 to place the hand held disinfecting unit into the stowed configuration as shown in FIG. 17B. The disinfection unit 1500 is placed horizontally within the charging dock 1700, which allows for easy pick up and placing of the unit 1500.

Figure 17C:
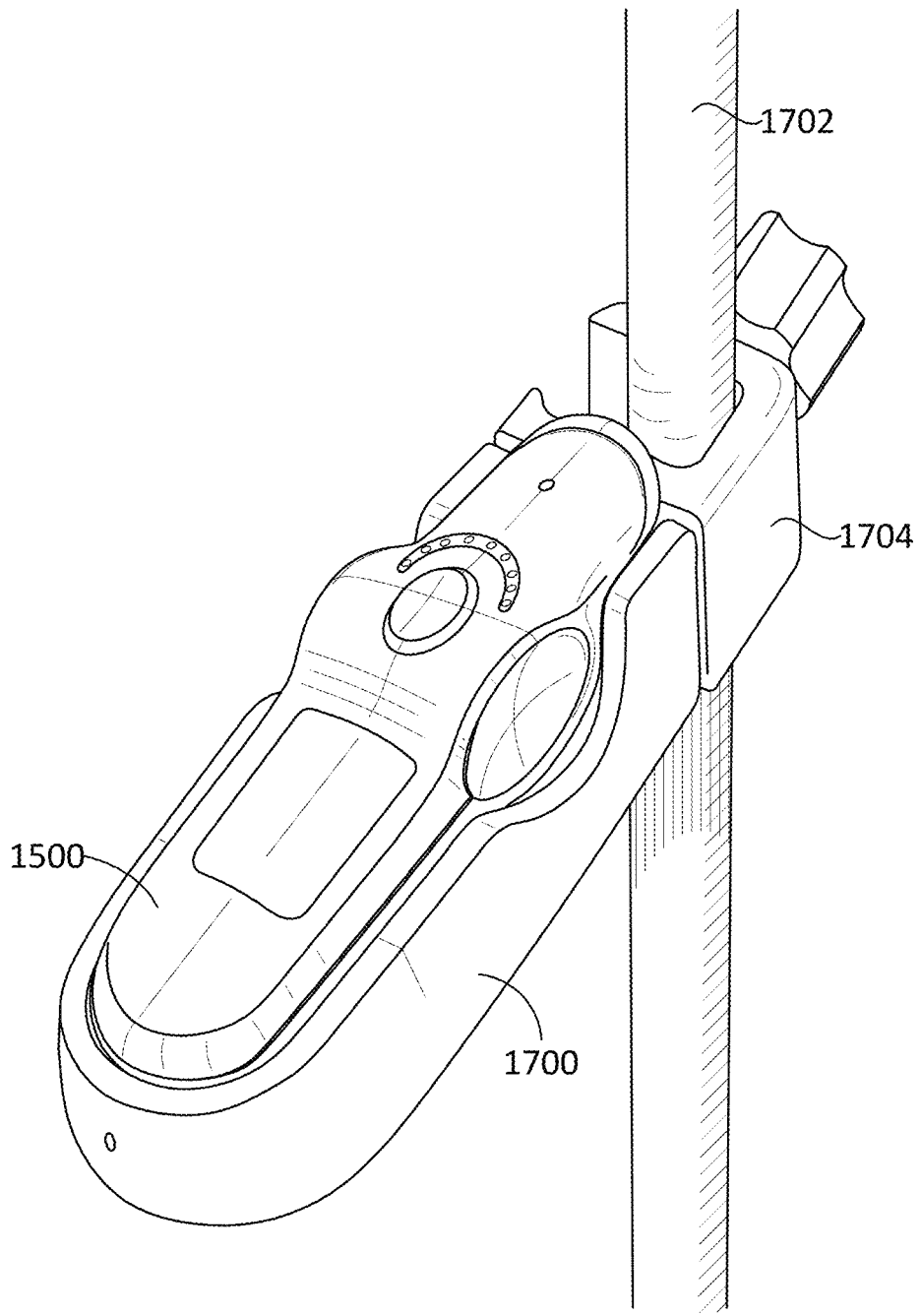
FIG. 17C is a perspective view of the handheld UV disinfecting unit of FIG. 15A shown in a stowed position within the specifically configured charging dock of FIG. 17A adapted for mounting on a pole.

FIG. 17C is a perspective view of the handheld UV disinfecting unit 1500 of FIG. 15A shown in a stowed position within the specifically configured charging dock 1700 of FIG. 17A adapted for mounting on a pole 1702 using mounting bracket 1704. This horizontal extended stow position presents the handheld UV disinfecting unit is a very accessible manner for the user to quick pick up for use. The dock 1700 is mounted on the pole with the aperture 1502 facing the pole, allowing for easy pick up for both left and right handed users.

As noted above, the disinfection units above may comprise any combination of features described with respect to other embodiments of disinfection units. For example, the embodiments of disinfection units shown in FIGS. 1A-17C may include one or more of the following features. The disinfection units can be configured to be handheld and have an aperture configured to slip over a connector or other component to be disinfected. The disinfection units can have an easy to clean, solid, smooth recess or aperture for insertion of connector or other component to be disinfected. The disinfection units can comprise a hand piece with smooth, easy to clean surfaces. The units can be battery powered and not include a power cord. They can be used with a charging cradle that sits on a counter, hospital bed, or IV pole with a connected power cord. The hand piece may be charged by lying flat horizontally using wireless inductive charging using no connector or charging pins/pads. There can be a start cycle button on hand piece. Some embodiments can have a progress status countdown (e.g., crescent shaped) with LEDs. The unit can be configured to produce an end and beginning of cycle audible sound in charging base. The units can comprise a battery charging indicator. The hand piece can be designed with and without an editable display screen (e.g., integral, flush.)

Figure 18:
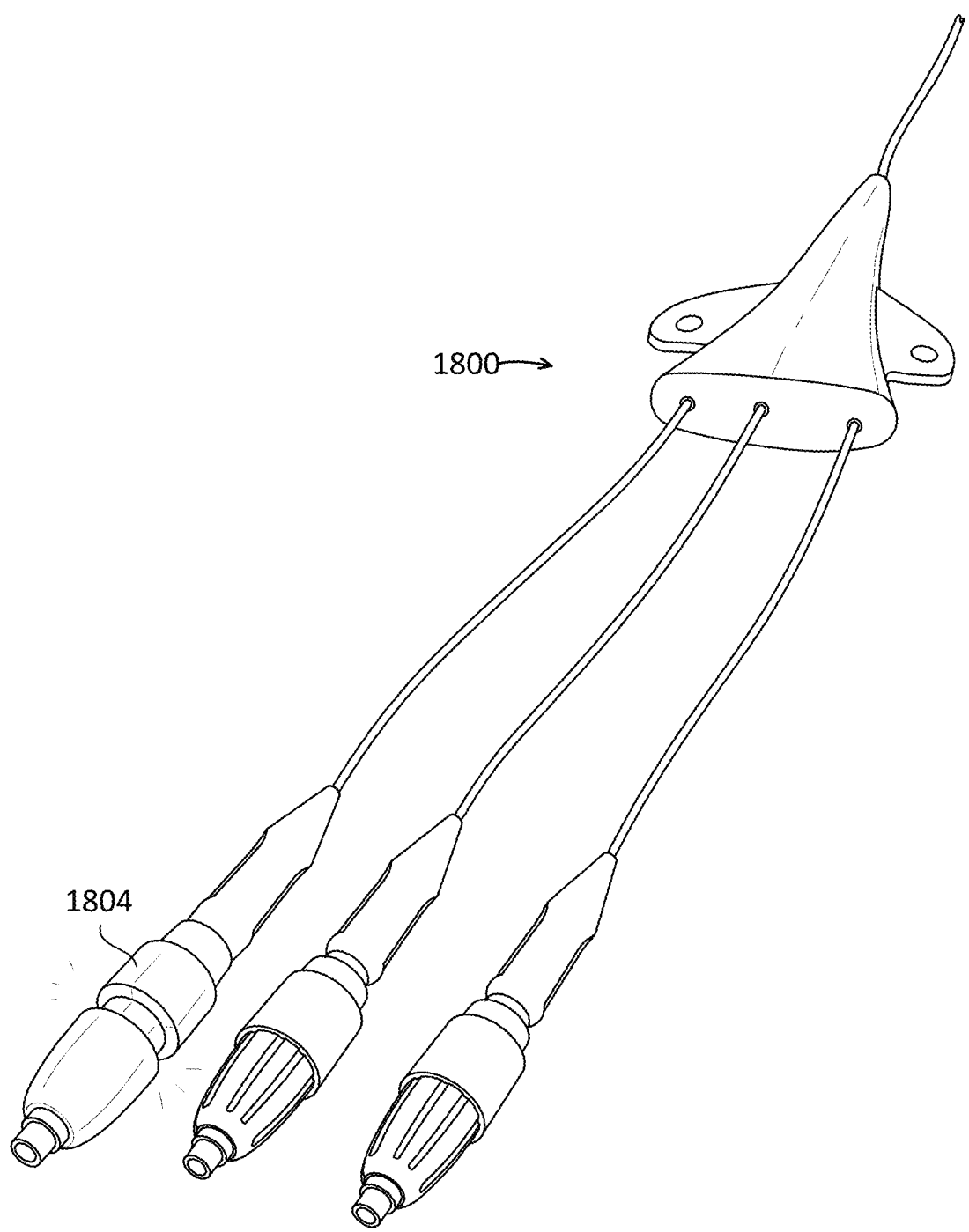
FIG. 18 is a perspective view of a catheter hub having three lines, one of the lines terminating in a universal adapter.

FIG. 18 is a perspective view of a catheter hub 1800 having three lines, one of the lines terminating in a universal adapter 1804 that can be used with any of the disinfection units described herein. The typical luer fittings of a CVC connection attach to the universal adapter 1804. The adapter 1804 comprises unique keyed features that prevent other adapters from fitting within a disinfection unit.

The catheter hub of FIG. 18 represents an exemplary device used as one of the first interventions that occurs when a patient is admitted into a hospital, namely the placement of an intravenous access line (IV). This percutaneously-placed IV line gives the caregivers a direct path to the patient's bloodstream via a peripheral vein for rapid administration of fluids, medication or for drawing blood samples. In more serious cases, where direct access to a high blood flow supply is needed, for example, in chemotherapy delivery, temporary kidney dialysis or heart monitoring catheterization, a Central Venous Catheter (CVC or Central Line) is inserted. FIG. 18 is intended to represent all such indwelling lines irrespective of insertion point or ultimate use with the patient. In typical fashion, this line is inserted percutaneously into a major branching vessel, frequently the subclavian vein, and then the distal segment of the catheter is directed into the superior vena cava. The resulting hub, lines (3 are shown in FIG. 18 although it can range from 1 to 5 hubs and lines) and connectors adapted as needed for disinfection according to one or more of the various disinfection techniques using one or more of the disinfection units described herein.

Both peripheral and central catheterization procedures create an open pathway or lumen from an external access site into the bloodstream. This intraluminal access site provides an attachment point for various therapeutic or diagnostic medical devices or components, including, but not limited to, stopcocks, needle-less access sites, IV bags, infusion pumps, drug delivery pumps, kidney dialysis equipment, thermal dilution catheters, and the like. In some alternatives, any of the listed or other such components used in conjunction with the access site may be adapted and configured for disinfection using one or more of the methods or systems of disinfection described herein.

Figure 19A:
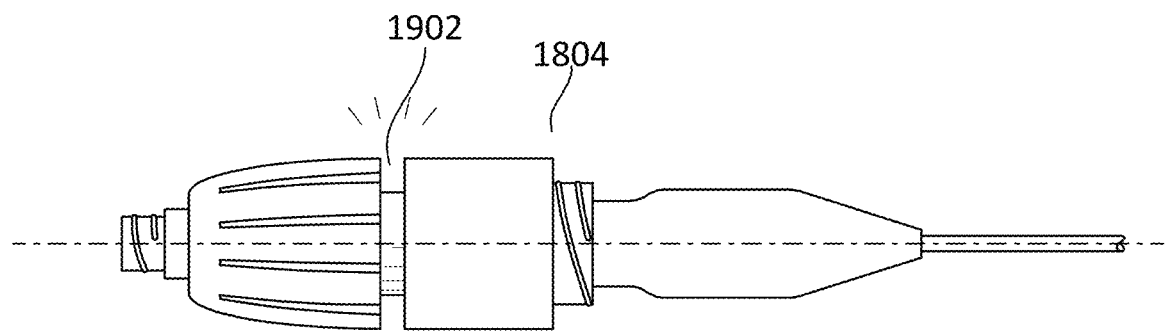
FIG. 19A is an enlarged and side view of one of the three universal adapters of FIG. 18.
Figure 19B:
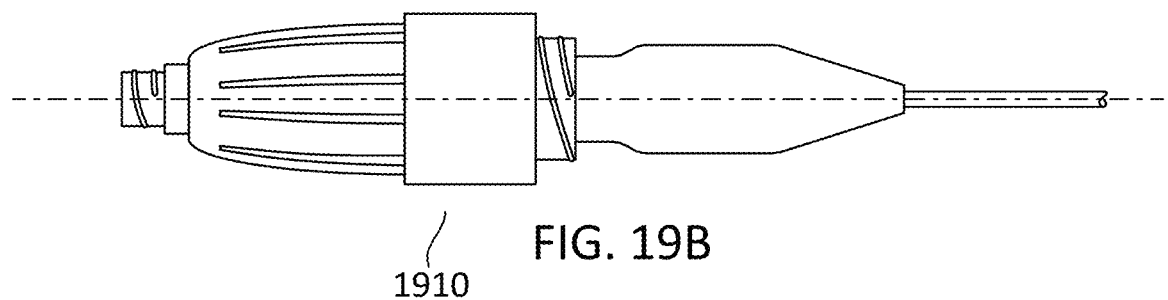
FIG. 19B is a needleless connector or adapter without a slot.

FIG. 19A is an enlarged and side view of the universal adapter 1804 of FIG. 18 with the adapter comprising a slot 1902 that is configured to be accepted by a disinfecting unit. The disinfecting unit would be incompatible with adapters not comprising such a slot. FIG. 19B is a needleless connector 1910 or adapter without a slot. The adapters are configured for use with one or more of the disinfection units or methods described herein including mechanical or electrical modifications or features to ensure that the adapter or a configured component are aligned and/or properly positioned with respect to a disinfecting unit.

Figure 20:
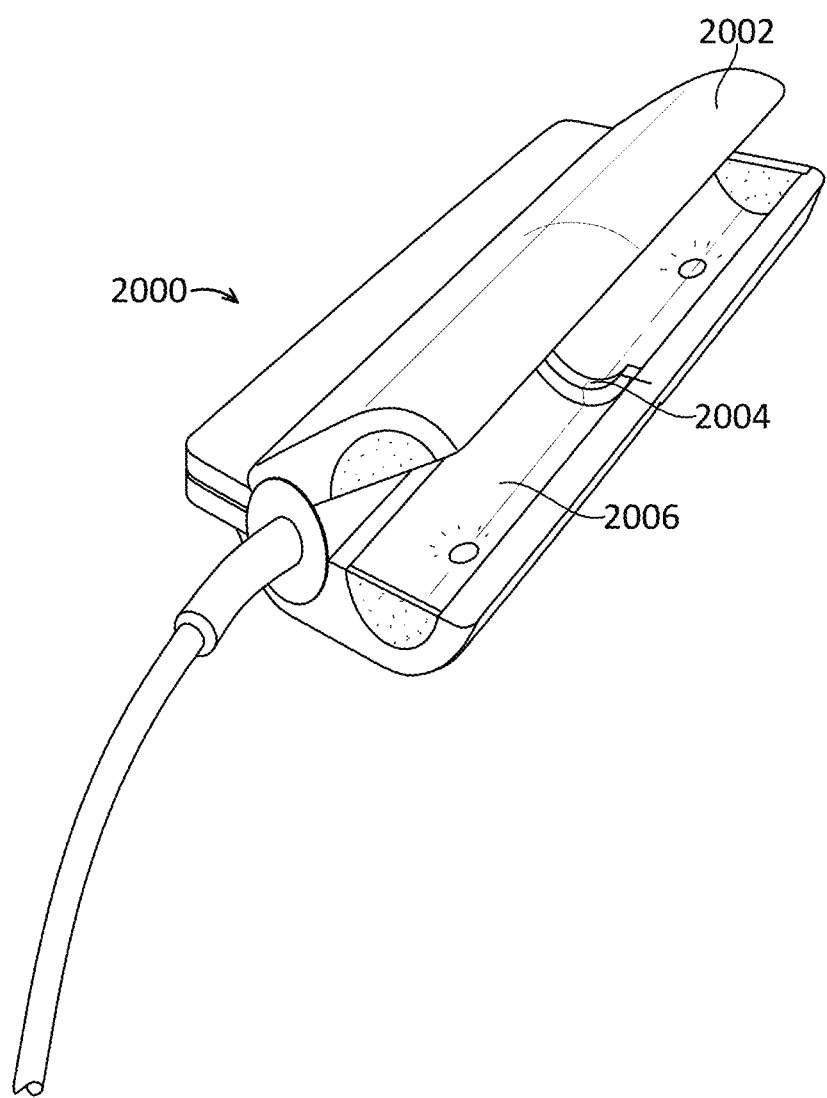
FIG. 20 is a perspective view of a UV LED disinfecting unit.

FIG. 20 is a perspective view of a UV LED disinfecting unit 2000 shown in the open position with a hinged lid 2002 and a raised rib 2004 that is configured to accept the slot 1902 of the universal adapter 1804. In this manner the disinfecting unit can be used on a universal adapter with a slot but cannot be used on a standard needless connector without a slot ensuring that the disinfecting unit is only used on adapters that are compatible with its UV light disinfecting function. The disinfection unit comprises a recessed portion 2006 configured to receive the connector to be disinfected. The use of a raised rib or other physical keying feature to ensure proper compatibility between the universal adapter and the disinfecting unit is not the only compatibility method possible. Alternately the universal adapter can include a visible marker, a magnetic marker, an RFID chip, or any other sensor that are well known that can be detected by an optical reader, magnetic sensor, RFID reader or any other sensor detector that is included in the UV light disinfection unit.

Figure 21:
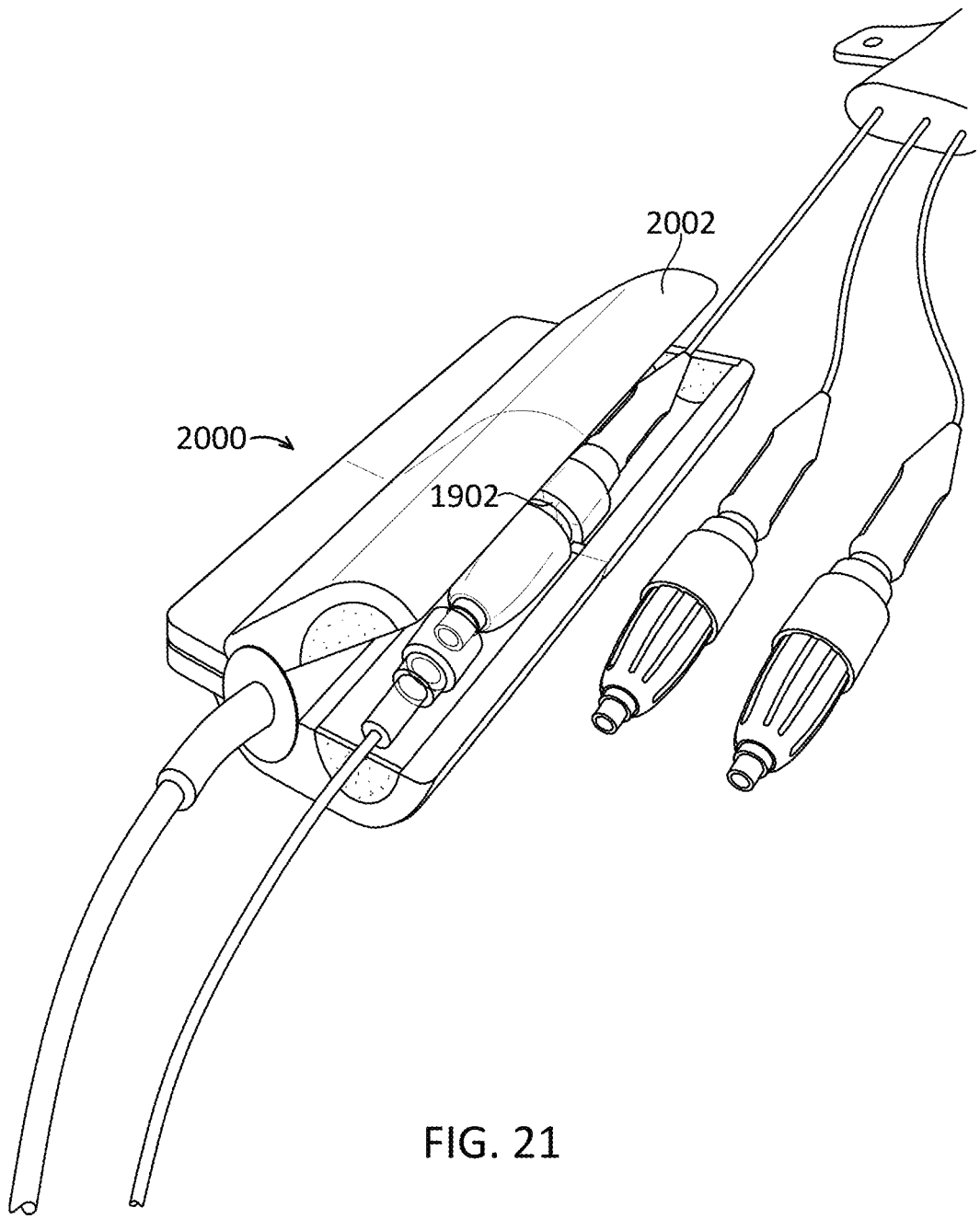
FIG. 21 is a perspective view of the UV LED disinfecting unit of FIG. 20 in the open position.

FIG. 21 is a perspective view of the UV LED disinfecting unit 2000 of FIG. 20 in the open position with the universal adapter 1804 of FIG. 18 positioned within the disinfecting unit where the raised rib of the disinfection unit has engaged one half of the slot 1902 on the universal adapter 1804. In addition the connecting hub of an infusion line (for fluid delivery, drug infusion, blood sampling, hemodialysis, or a similar therapy) is also connected to the proximal end of the universal adapter, and this hub can also be disinfected by the UV light disinfection device.

Figure 22:
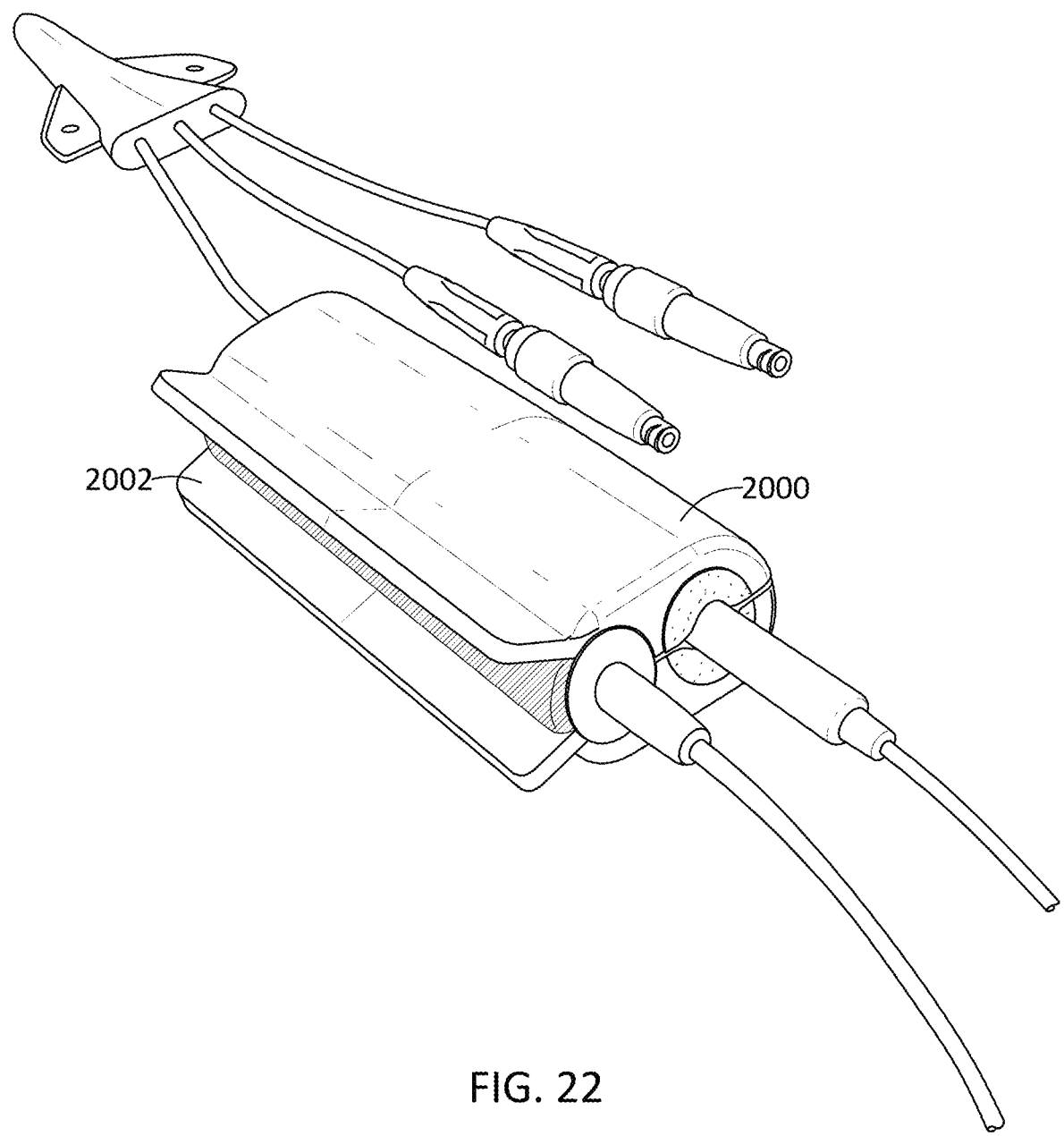
FIG. 22 is a perspective view of the UV LED disinfecting unit of FIG. 21 in the closed position.

FIG. 22 is a perspective view of a disinfecting unit 2200 in the closed position where the raised rib of the disinfection unit has engaged all of the slot on the universal adapter of FIG. 18, and the disinfection unit is ready to conduct a disinfecting cycle with the engaged universal adapter, the catheter hub and the infusion line hub. The disinfection unit 2200 comprises protruding portions 2202 on the top and bottom portions allowing for ease of opening and closing the unit. It is noted that if the universal adapter, the catheter hub or the infusion hub is comprised of a material that is relatively transparent to the UV disinfecting light then the UV light disinfecting device will be able to disinfect not only the exterior of the universal adapter, the catheter hub, or the infusion line hub but also the interior surfaces and spaces of these, as well. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 23:
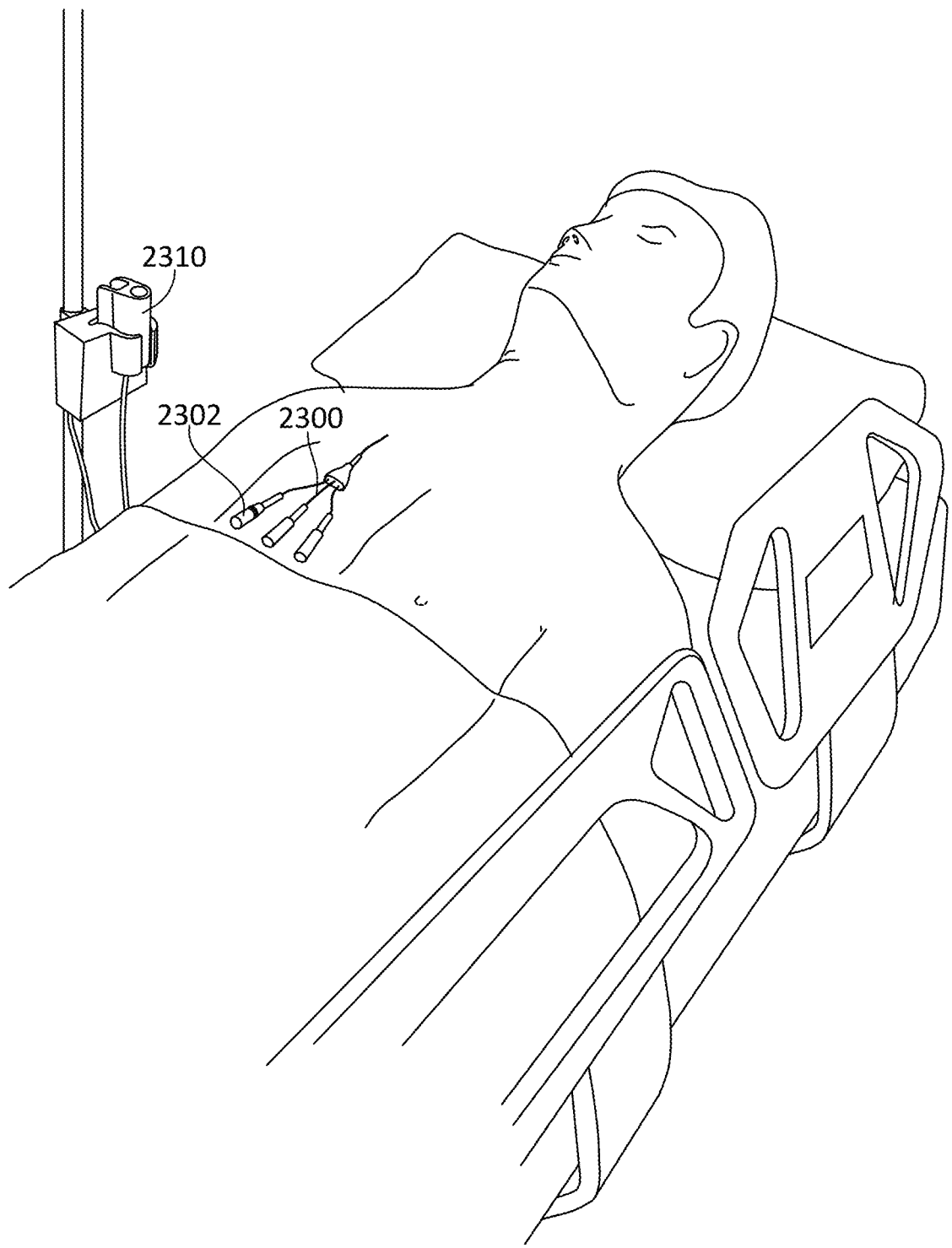
FIG. 23 is a perspective view of a patient having a catheter hub with a UV LED disinfecting unit in a stowed condition on a bedside holder.

FIG. 23 is a perspective view of a patient having a catheter hub 2300 and universal adapter 2302 as in FIG. 18 with the UV LED disinfecting unit 2310 of FIG. 20 in a stowed condition on a bedside holder which is located such that a care provider can easily access the UV LED disinfecting unit for use.

Figure 24:
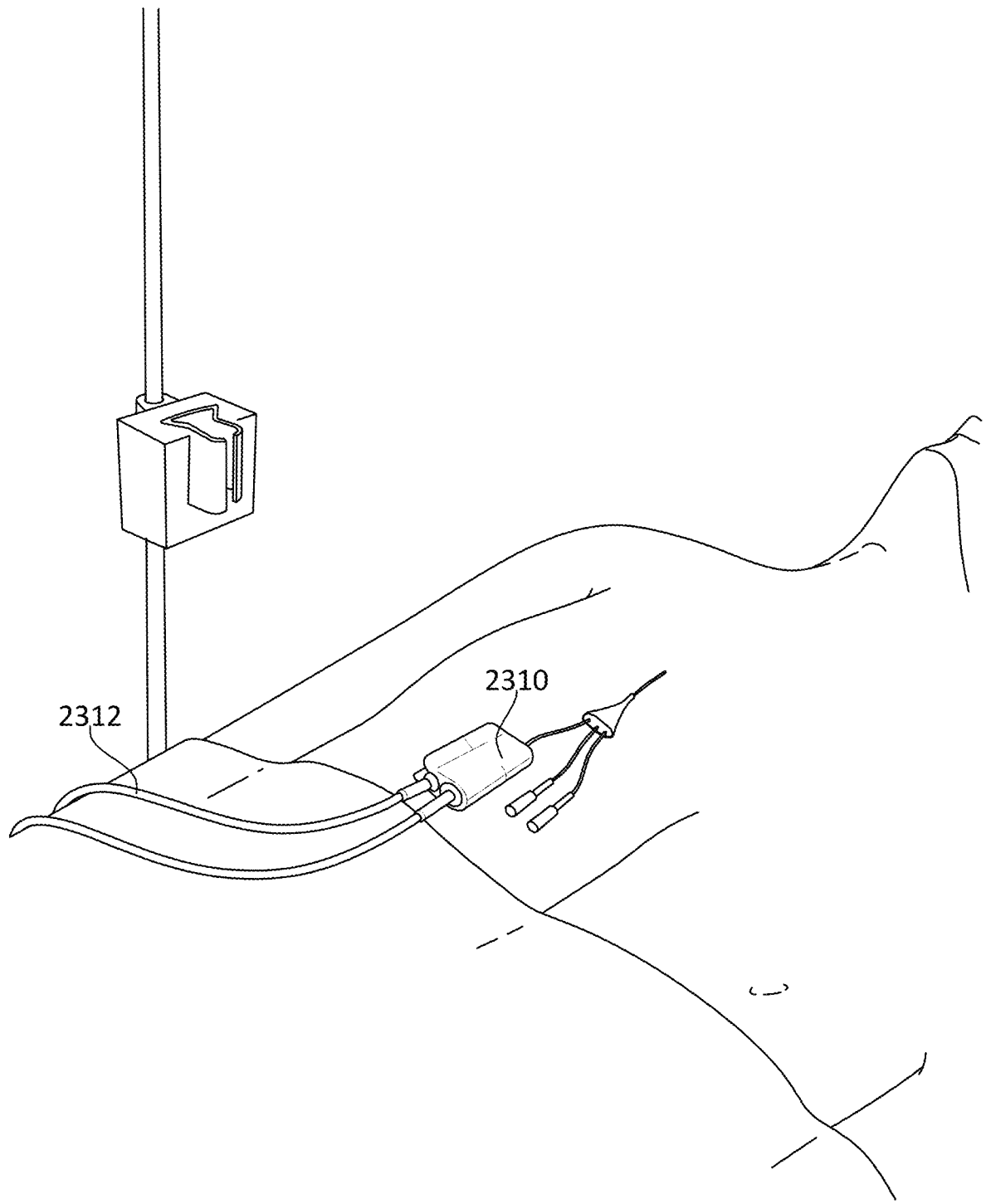
FIG. 24 is a perspective view of the patient in FIG. 23 with the UV LED disinfecting unit position to disinfect a universal adapter.

FIG. 24 is a perspective view of the patient in FIG. 23 with the UV LED disinfecting unit 2310 removed from the bedside holder and position to disinfect a universal adapter 2302 with an infusion line 2312 attached. As shown, the disinfection unit can rest on the patient during disinfection.

Figure 25:
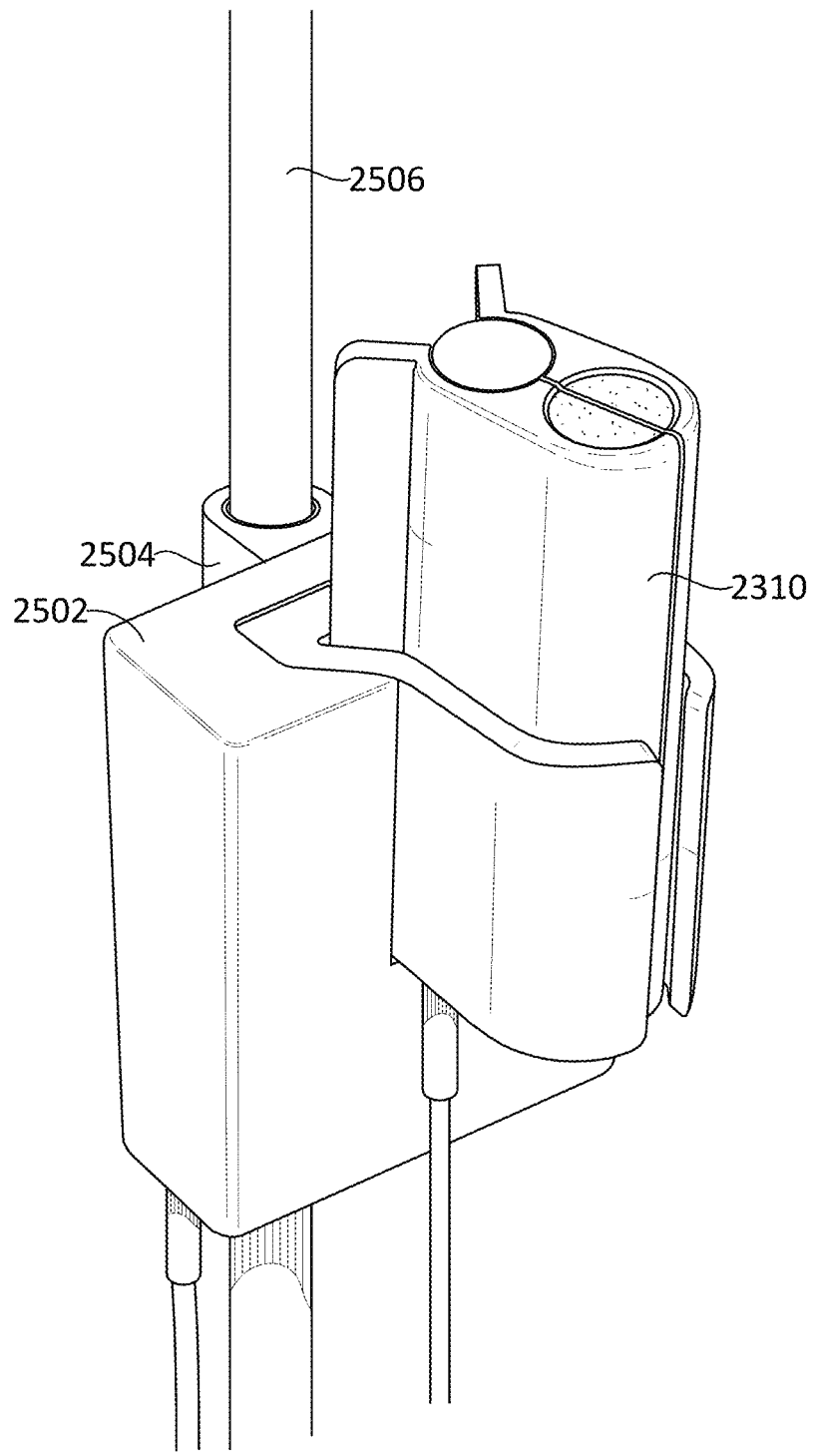
FIG. 25 is an enlarged view of FIG. 23 showing the UV LED disinfecting unit in the bedside holder.

FIG. 25 shows the disinfecting unit 2500 in the bedside holder 2502. The UV LED disinfecting unit 2310 is slideably held by a bracket 2504 contained on the bedside holder 2502 and the holder is mounted on an IV pole 2506.

Figure 26:
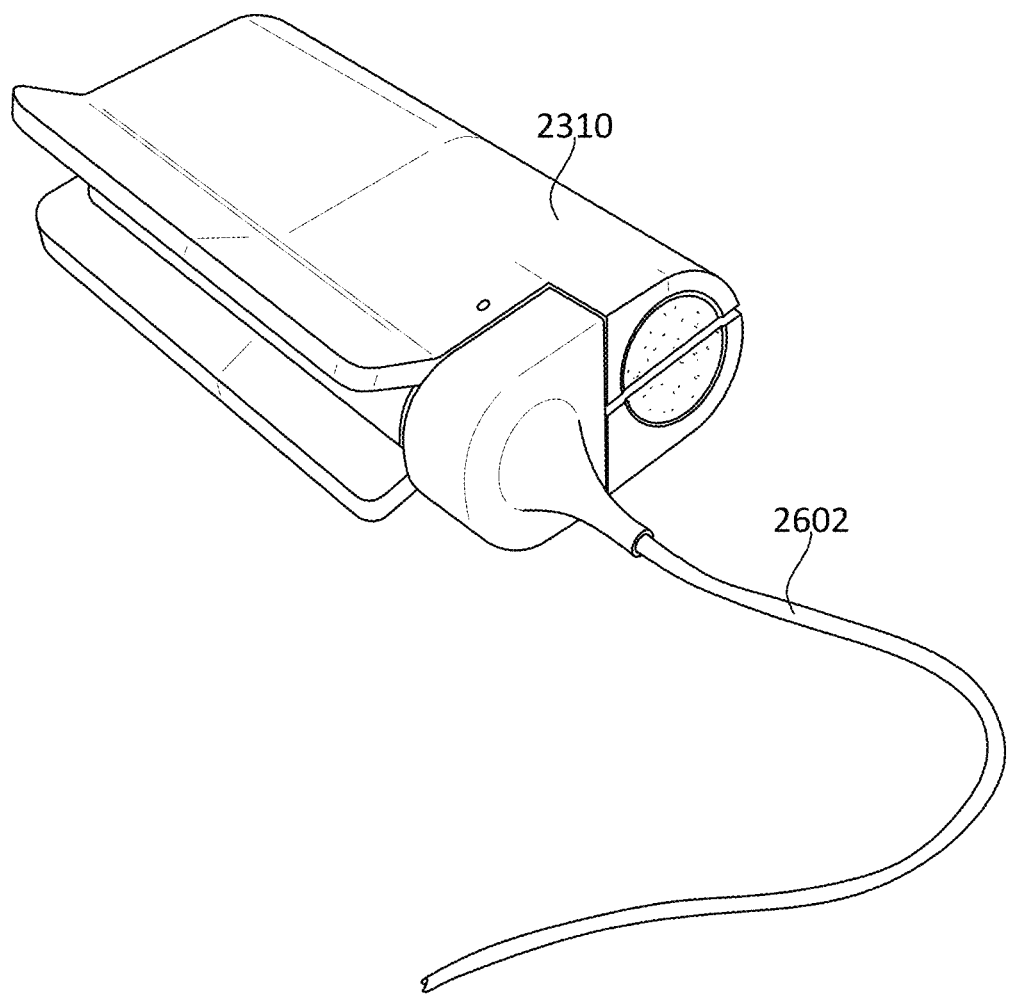
FIG. 26 is a perspective view of a UV LED disinfecting unit showing an embodiment of a charging plug and cable.

FIG. 26 is a perspective view of the UV LED disinfecting unit 2310 showing an embodiment of a charging plug and cable 2602.

Figure 27:
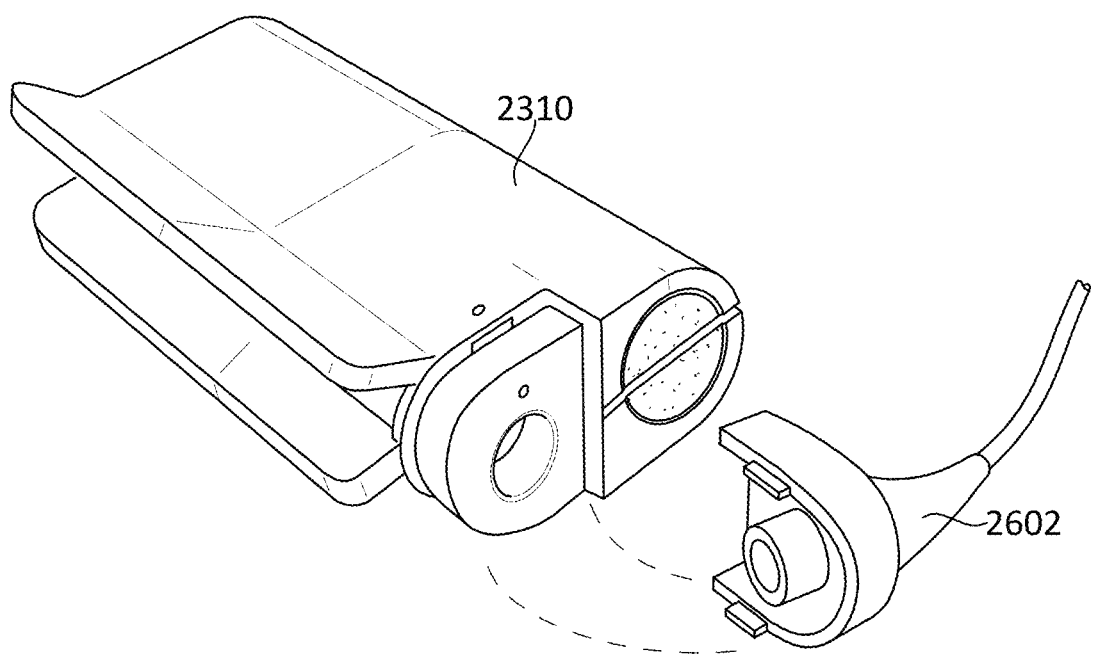
FIG. 27 is a perspective view of a UV LED disinfecting unit with the charging plug disconnected.

FIG. 27 is a perspective view of the UV LED disinfecting unit 2310 of FIG. 26 with the charging plug 2602 disconnected. Disconnecting the charging plug after rechargeable batteries contained in the UV LED disinfecting unit provides a non-tethered unit that can be more easily positioned over the universal adapter for disinfection. In addition, disconnecting the charging plug prior to using the UV LED disinfection device removes the charging cable from disinfection site and reduces the potential for contamination of the charging cable.

Figure 28:
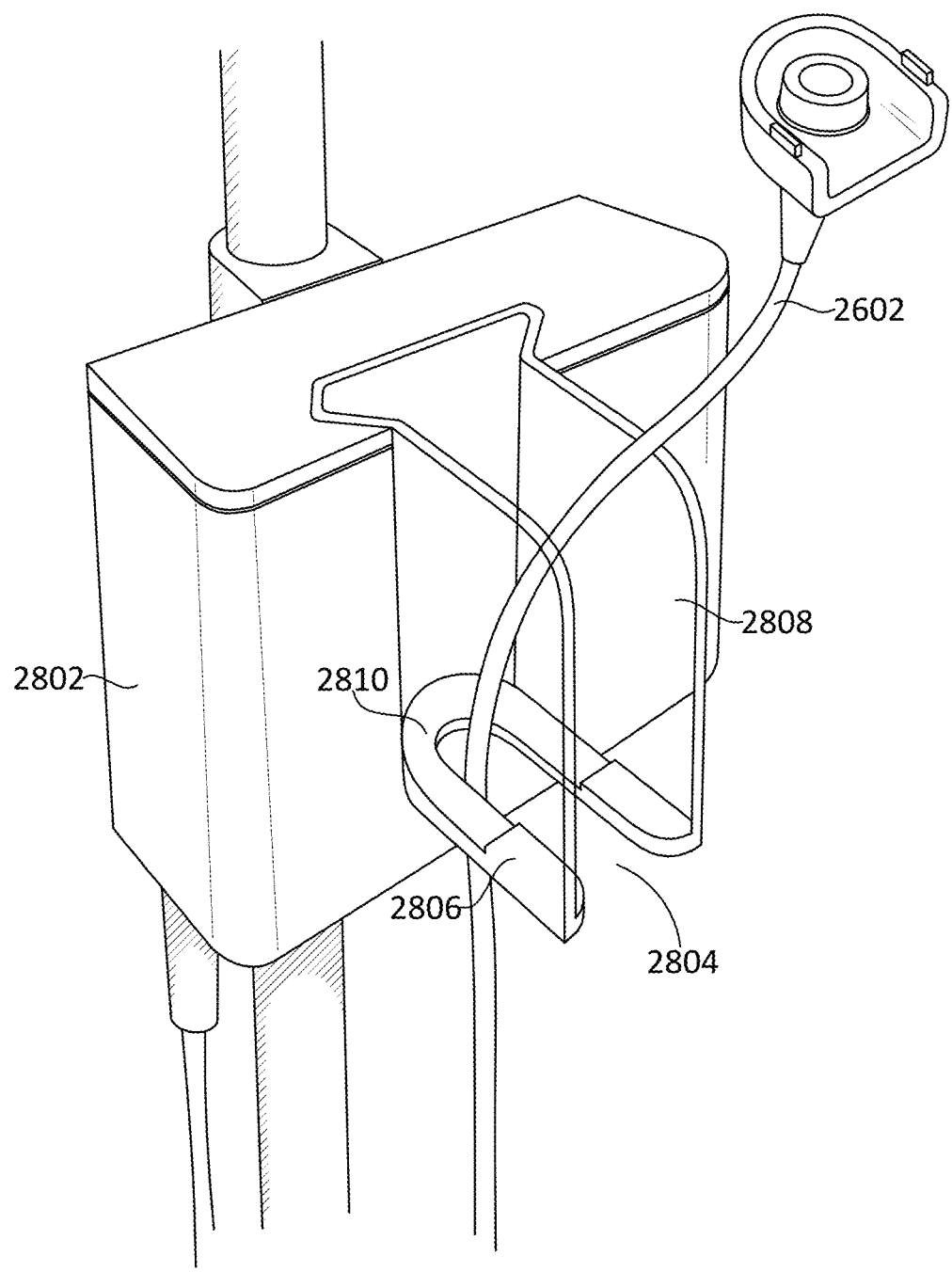
FIG. 28 is a perspective view of the charging plug and cable of FIGS. 26 and 27 in relation to a bedside power and control unit having a slot configured to retain the charging plug.

FIG. 28 is a perspective view of the charging plug and cable 2602 of FIGS. 26 and 27 in relation to a bedside power and control unit 2802 having a sleeve 2808 to receive the disinfection unit. The bottom surface 2810 of the sleeve comprises a slot 2804 configured to retain the charging plug. The bottom surface 2810 of the sleeve also has a step feature to prevent the charging plug from sliding forward.

Figure 29:
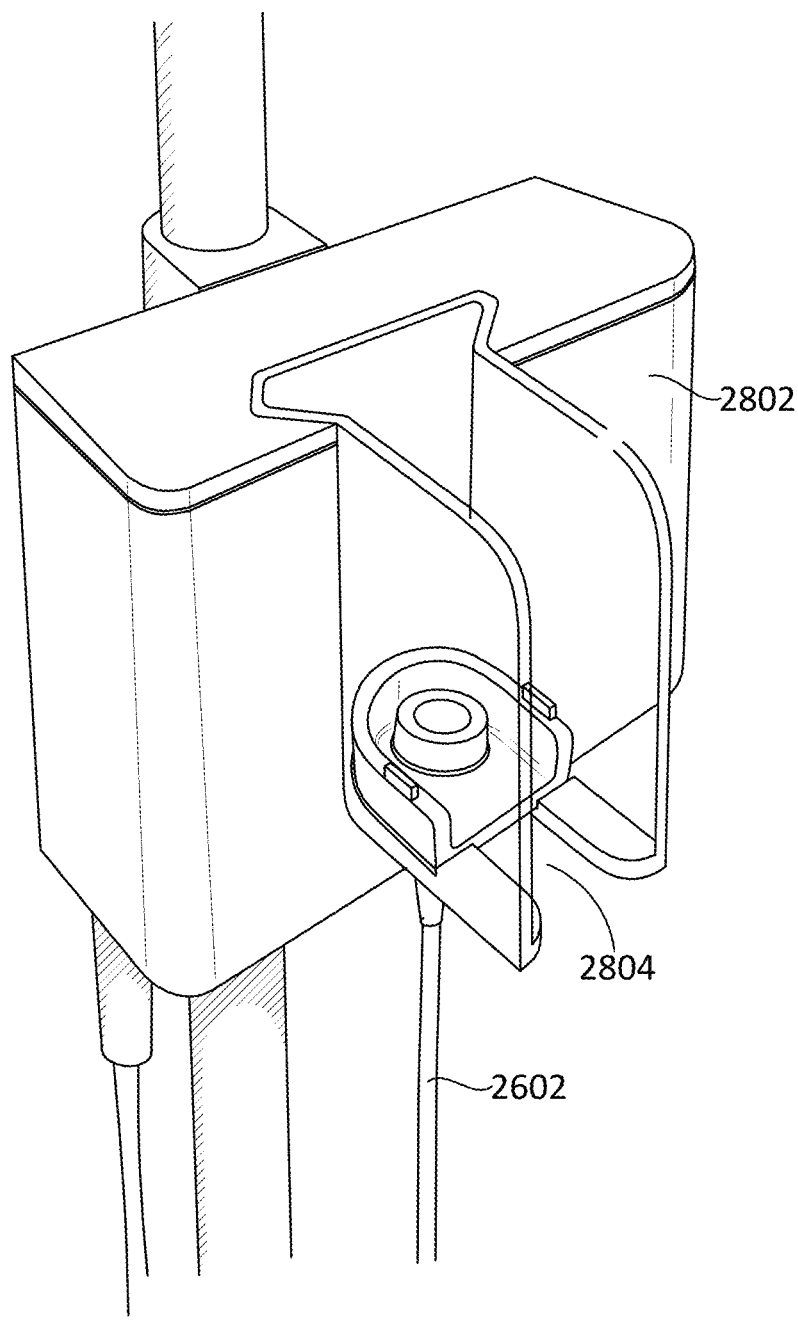
FIG. 29 is a perspective view of the charging plug and cable of FIG. 28 showing the charging plug retained in the slot of the bedside power and control unit.

FIG. 29 is a perspective view of the charging plug and cable of FIG. 28 showing the charging plug 2602 retained in the slot 2804 of the bedside power and control unit 2802. The charging plug and cable can stay in place when disconnected from the disinfection unit.

Figure 30:
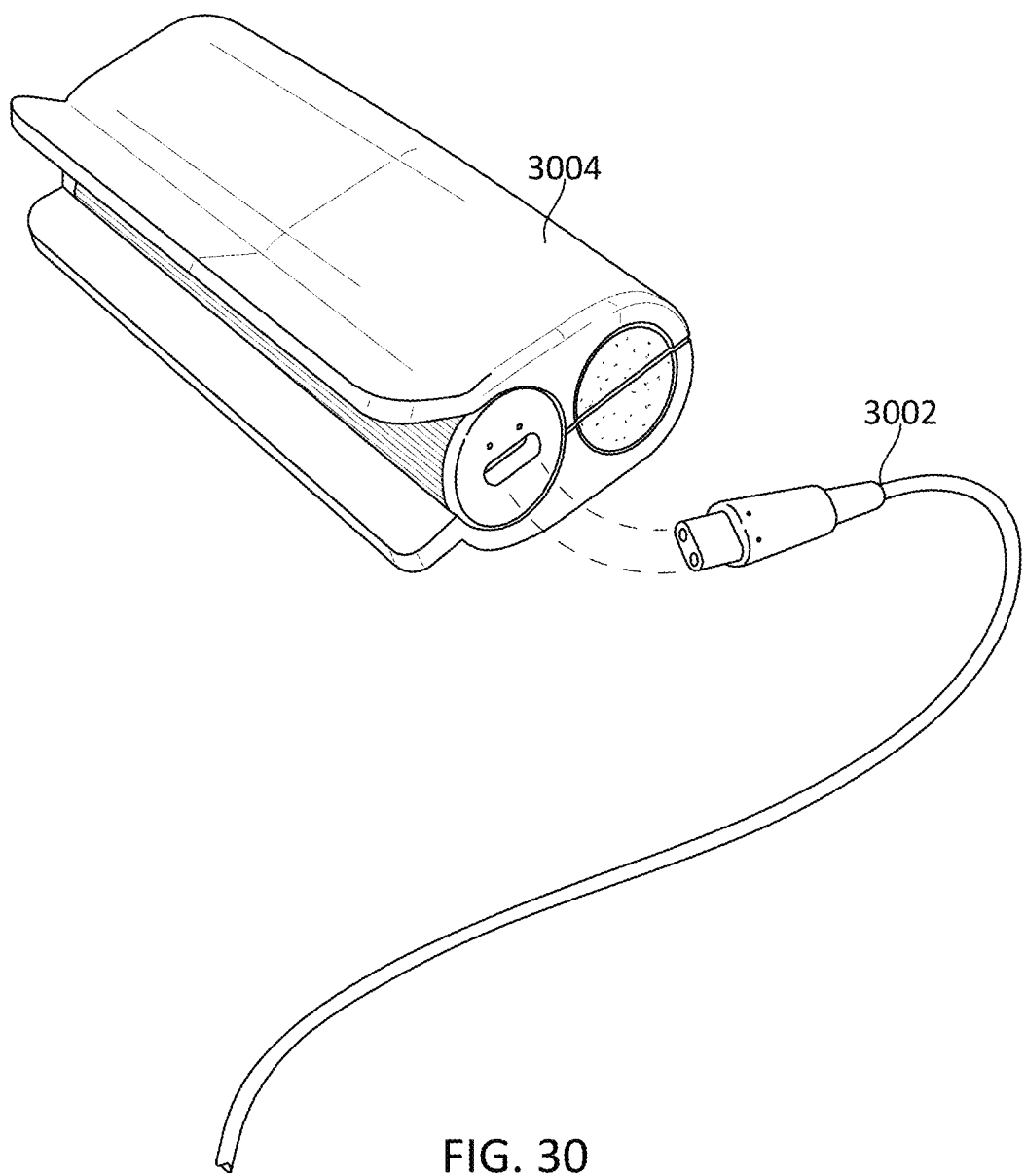
FIGS. 30 and 31 are perspective views respectively of another variation of a removable charging plug and cable in relation to a UV LED disinfecting unit and in relation to a bedside power and control unit.
Figure 31:
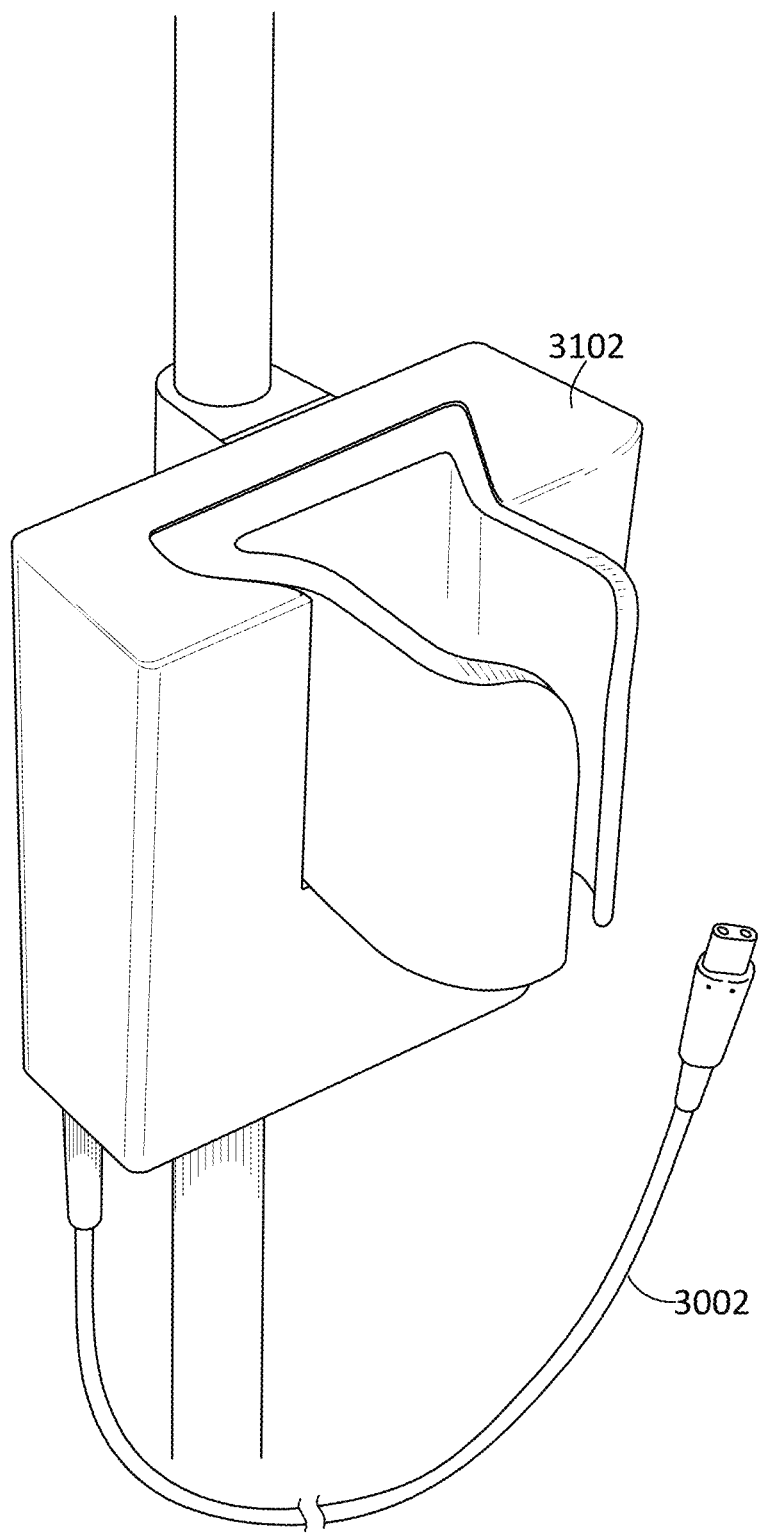

FIGS. 30 and 31 are perspective views respectively of a removable charging plug 3002 that is much smaller than the charging plug show. in FIGS. 27-29 and cable in relation to a UV LED disinfecting unit 3004 (FIG. 30) and in relation to a bedside power and control unit 3102 (FIG. 31).

Figure 32A:
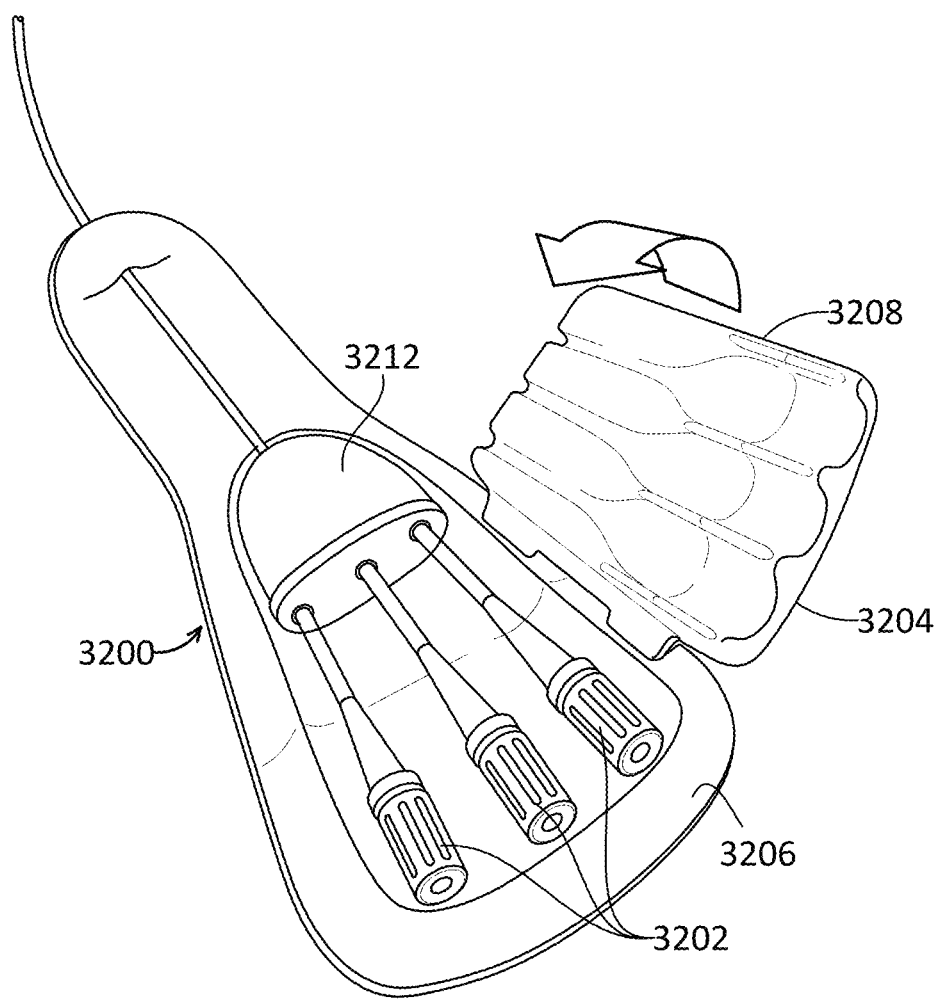
FIG. 32A is a perspective view of an embodiment of a disposable catheter hub and disinfecting unit assembly arranged on a patient worn adhesive patch.
Figure 32B:
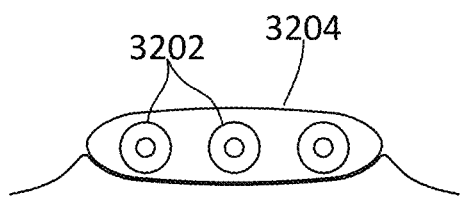
FIG. 32B is an end view of the disinfecting unit FIG. 32A with the lid and the closed position.

FIG. 32A is a perspective view of a disinfection assembly 3200 comprising a catheter hub 3212 with connected universal adapters 3202 and disinfecting unit assembly 3204 arranged on a disposable patient worn adhesive patch 3206. The catheter hub is connected to three universal adapters in an arrangement with a hinged lid 3208 containing a UV LED lighting arrangement 3210. FIG. 32B is an end view of the disinfecting unit FIG. 32A with the lid in the closed position. The assembly unit holds the catheter hub and universal adapters in a stable configuration so that the UV LED lights on the lid can be directed to each of the three catheter hub and universal adapter pairs without any one pair obstructing the light from reaching any other pair. In addition, the base underneath the catheter hub and universal adapter pairs can be configured with a reflective material to direct the UV light from the hinged lid to the underside of the catheter hub and universal adapter pairs. The base of the can also be adhesive backed so that the entire assembly can be securely fastened to the patient's skin. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 33A:
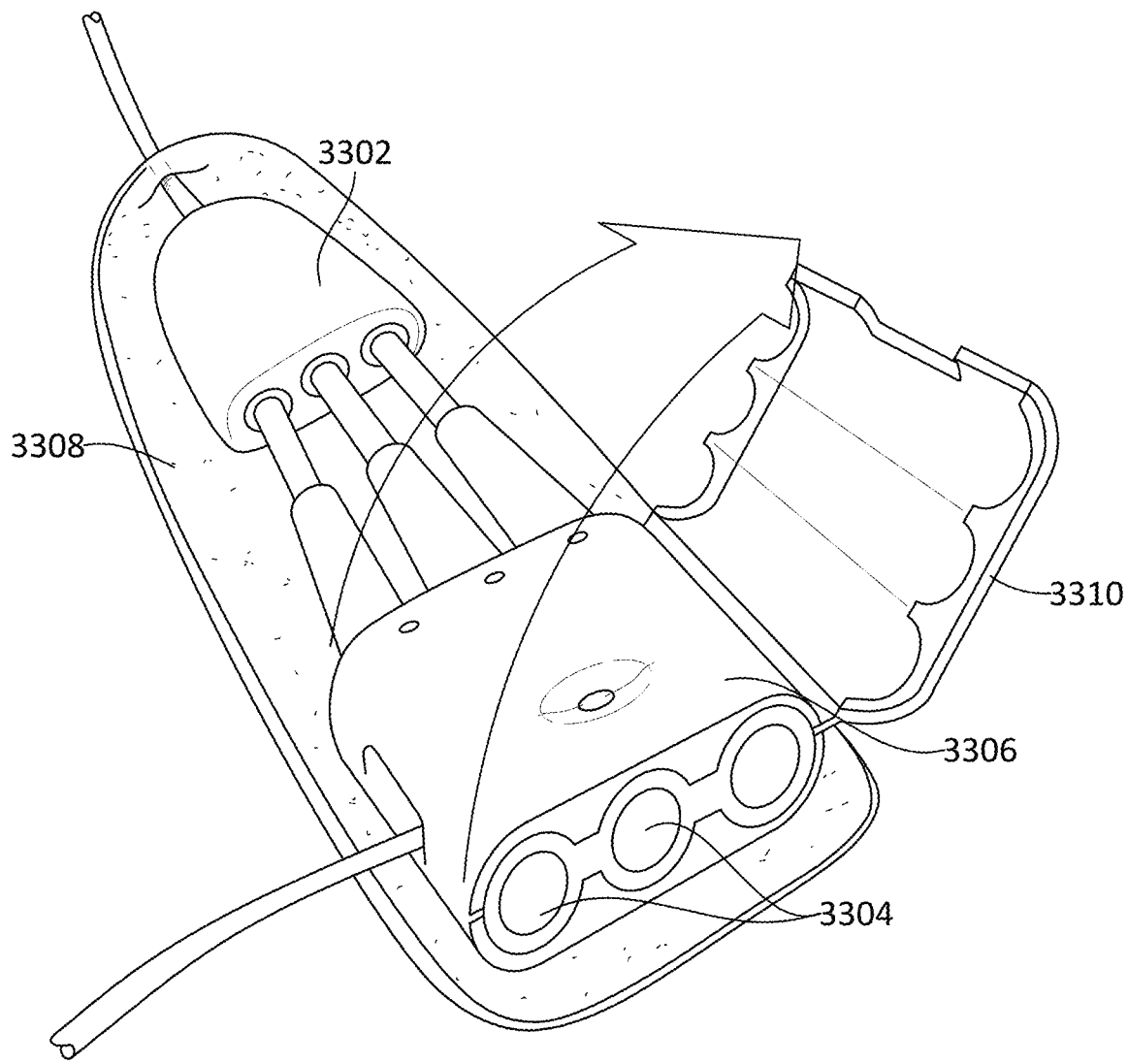
FIGS. 33A and 33B are perspective views of an embodiment of a disposable catheter hub and disinfecting unit assembly arranged on a patient worn adhesive patch.
Figure 33B:
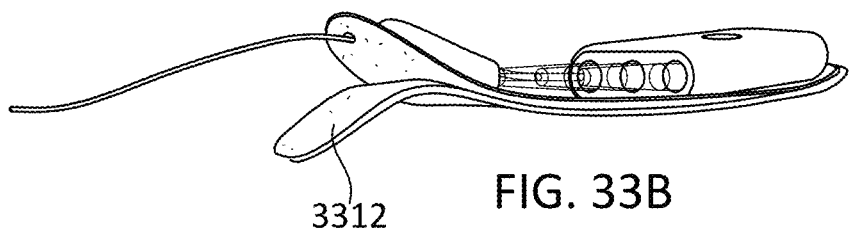

FIG. 33A is a perspective view of a catheter hub 3302, universal adapters 3304, and disinfecting unit assembly 3306 arranged on a patient worn adhesive patch 3308. The catheter hub is connected to three universal adapters in an arrangement with a hinged lid 3310 with both the lid and the base containing UV LED lighting arrangements. The lid is shown in the closed (FIG. 33B) and open (FIG. 33A) positions. FIG. 33B is a perspective view of the system of FIG. 33A showing a partially removed backing 3312 to expose the adhesive surface to join the unit to a patient.

Figure 34A:
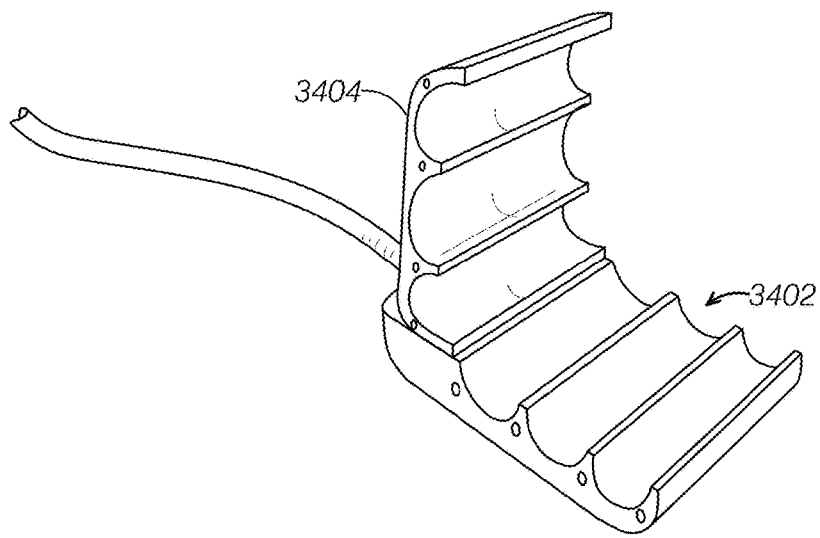
FIGS. 34A and 34B are perspective views of another variation of an embodiment of a UV LED disinfecting unit.
Figure 34B:
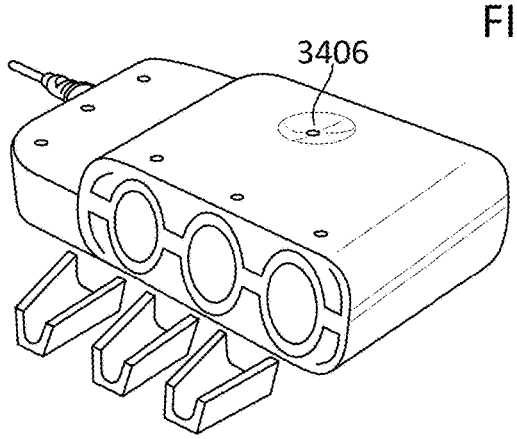
Figure 35A:
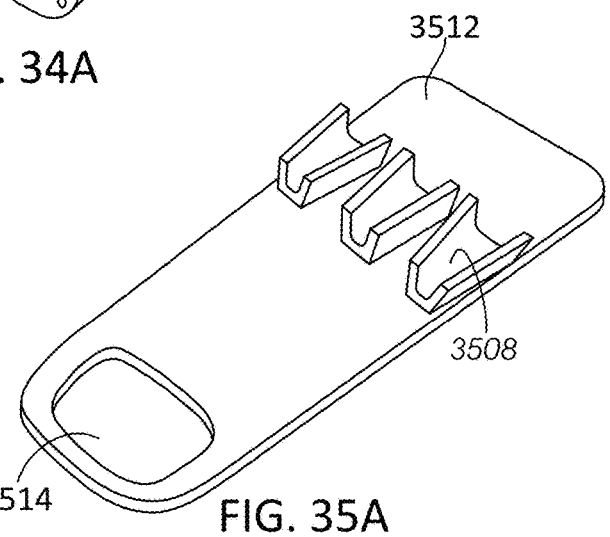
FIGS. 35A and 35B are a perspective view of a disposable manifold for use with a UV LED disinfecting unit.
Figure 35B:
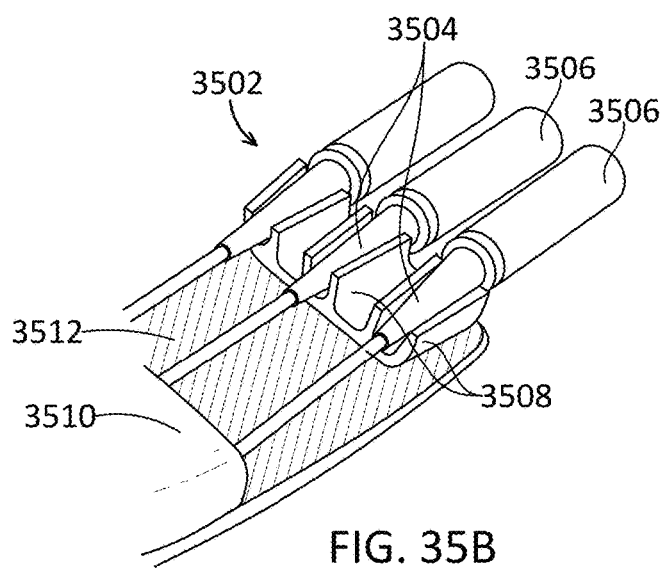

FIGS. 34A and 34B are perspective views of another variation of a UV LED disinfecting unit 3402 with a hinged lid 3404 shown in an open (FIG. 34A) and a closed (FIG. 34B) configuration. UV lights are positioned in the lid and the base of the unit. The unit 3400 can comprise an activation button 3406, shown in FIG. 34B FIG. 35A is a perspective view of a disposable carrier or manifold 3502 used to secure and align a CVC 3510 and one or more catheter hubs 3504 into an alignment for use with a UV LED disinfecting unit shown in FIGS. 34A and 34B. The manifold 3502 and CVC 3510 are configured to be worn by the patient on an adhesive patch 3512. The CVC 3510 is not actually adhered to the patch, but rests in an opening 3514 on the patch so that it is removable. FIG. 35B is a perspective view of the disposable carrier of FIG. 35A showing three catheter hubs 3504 with attached universal adapters 3506 held in position by the adapter engagement features 3508 of the carrier. This disposable carrier which just secures the catheter hubs is much smaller and thereby occupies a smaller footprint on the patient than the previously described version shown in FIGS. 32A-B and 33A-B.

Figure 36:
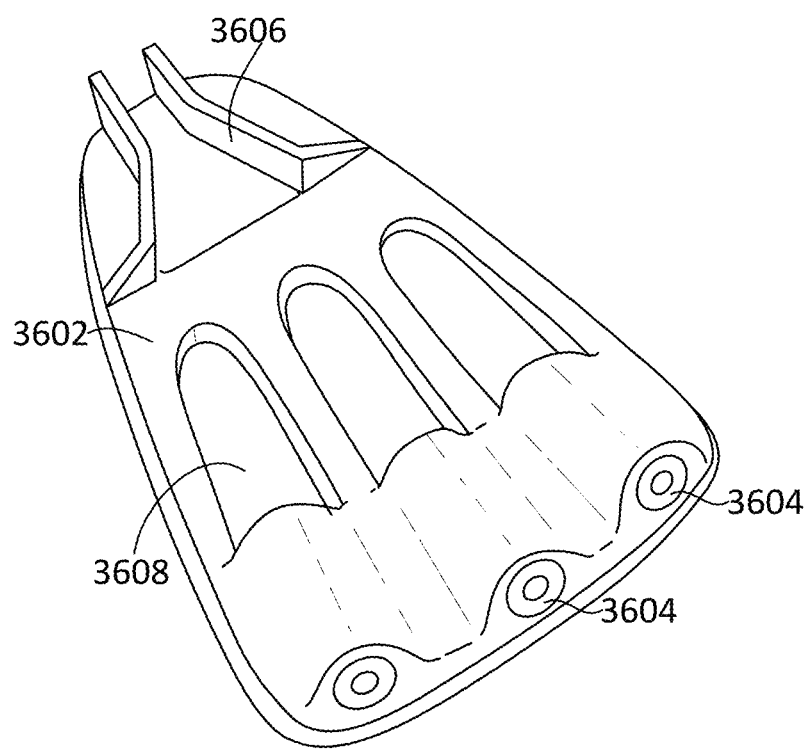
FIGS. 36 and 37 are a perspective views of an alternative embodiment of a manifold used with a UV LED disinfecting unit.
Figure 37:
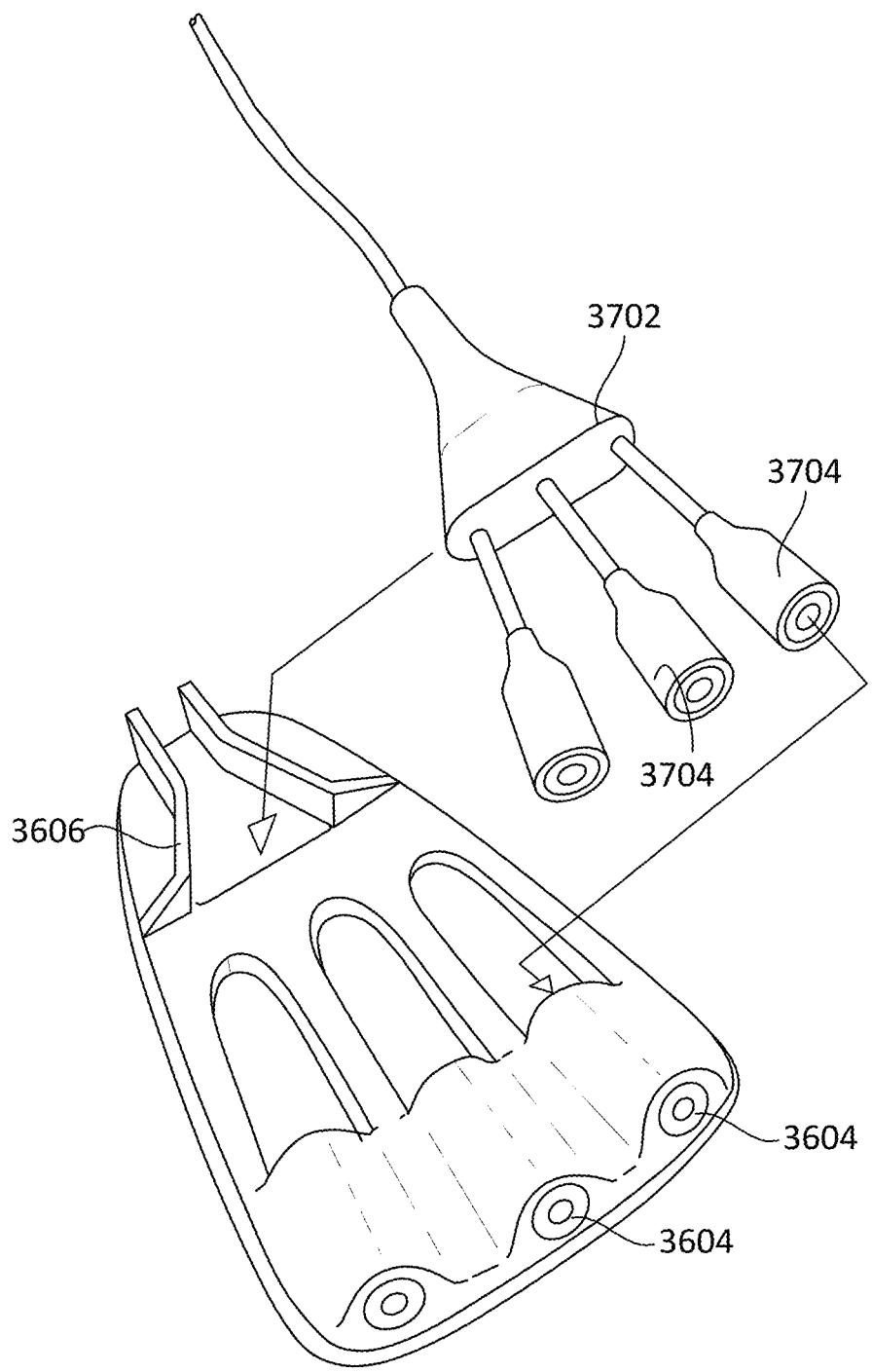

FIG. 36 is a perspective view of an alternative carrier or manifold 3602 used to secure one or more catheter hubs in position or use with a UV LED disinfecting unit. In this embodiment the universal adapters 3604 are integrated into the carrier 3602 or manifold to reduce the number of components and simplify the system. The carrier 3602 comprises snap in features 3606 to accommodate a CVC. The carrier 3602 comprises openings 3608 to accommodate three lumens. The depth of the openings 3608 allows for more finger clearance when inserting the catheter hubs. FIG. 37 is a perspective view of the manifold 3602 of FIG. 36 with arrows indicating movement of a catheter hub 3702 having three lines and connectors 3704 into engagement with the features of the manifold. The catheter hub 3702 is snapped into features 3606 and the connectors 3704 are attached to the adapters 3604.

Figure 38A:
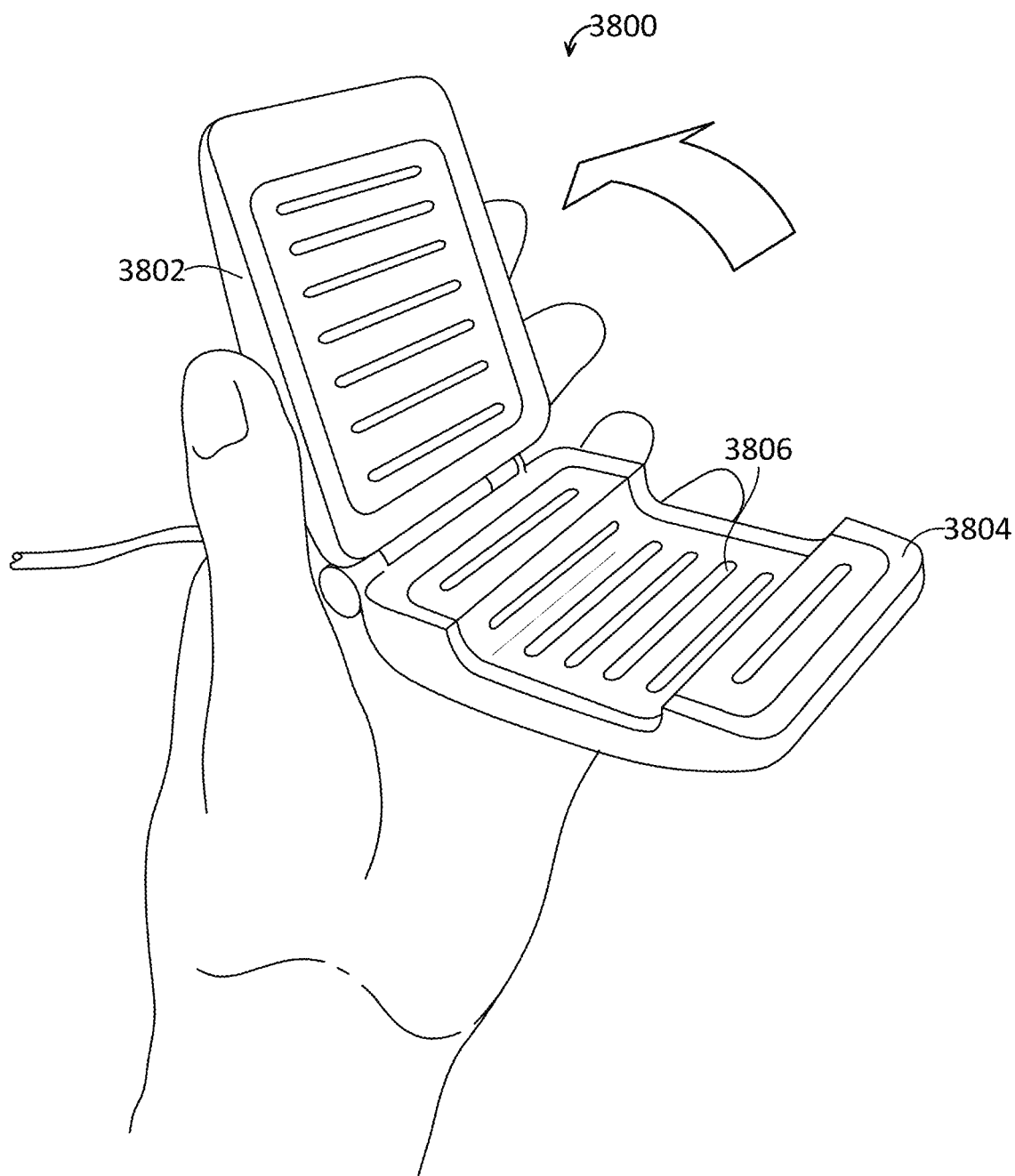
FIG. 38A-C are perspective views another embodiment of a UV LED disinfecting unit with a hinged lid.

FIG. 38A is a perspective view of another embodiment of a UV Light disinfecting unit 3800 with a hinged lid 3802. The UV Light disinfecting unit 3800 includes a base 3804 having a recessed portion 3806 adapted and configured to receive an adapter manifold. Although UV LEDs are a preferred source for UVC light in all of the UV light disinfecting devices described herein, the disinfecting unit can alternately be comprised of one or more UV lamps. The UV light disinfecting unit in FIG. 38A has UV lamps in both the base and lid portions. The UV lamps can be mercury vapor, xenon flash, or any other of a variety of lamps that produce light in the UVC wavelengths. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Figure 38B:
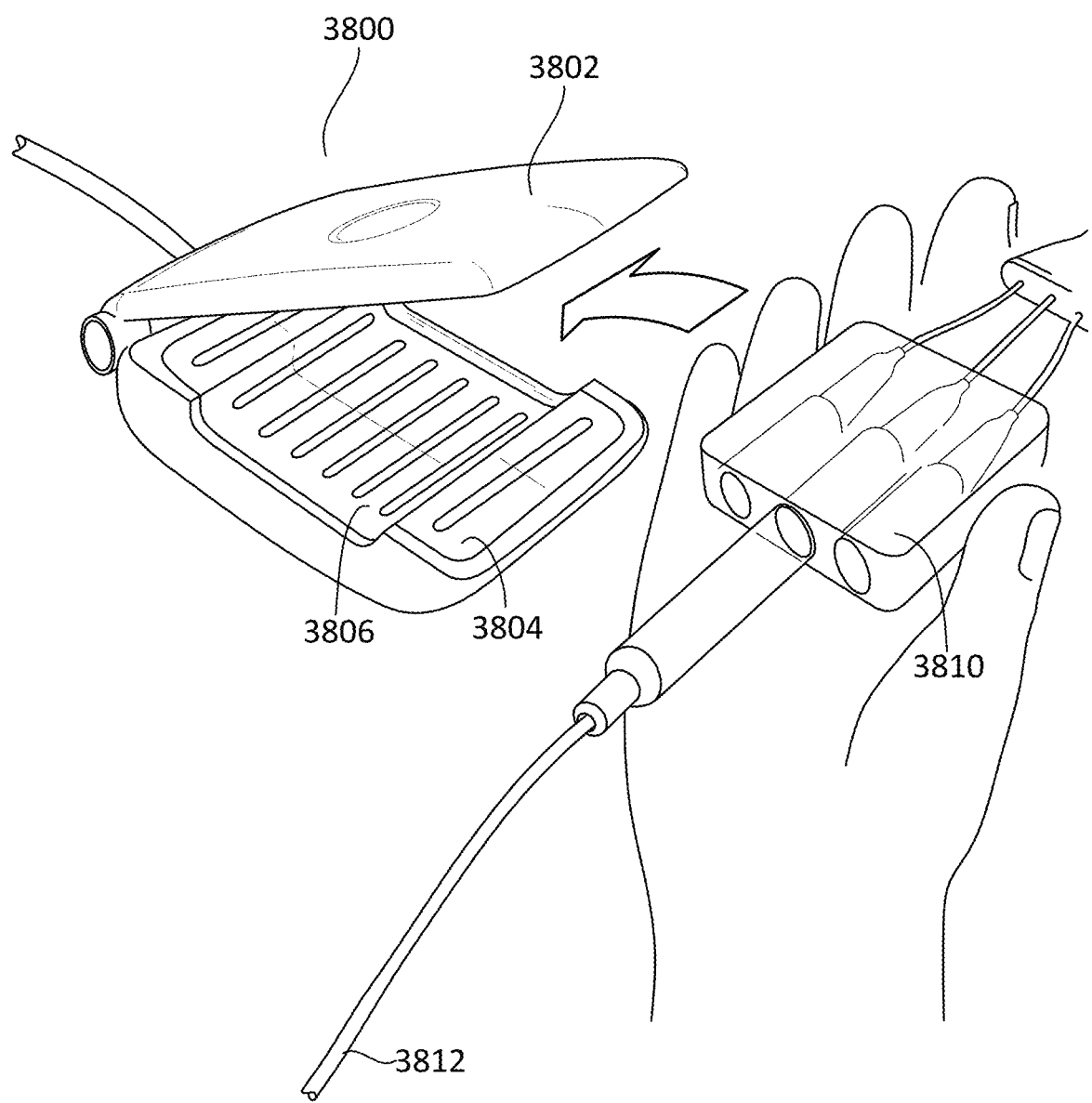

FIG. 38B is a perspective view of the UV LED disinfecting unit 3800 with a catheter hub and 3 port universal adapter manifold 3810 and one infusion line 3812 prior to placement within the recessed portion 3806 of the base 3804. The manifold 3810 can comprise a UV transmissive plastic to allow disinfection of the adapters contained within.

Figure 38C:
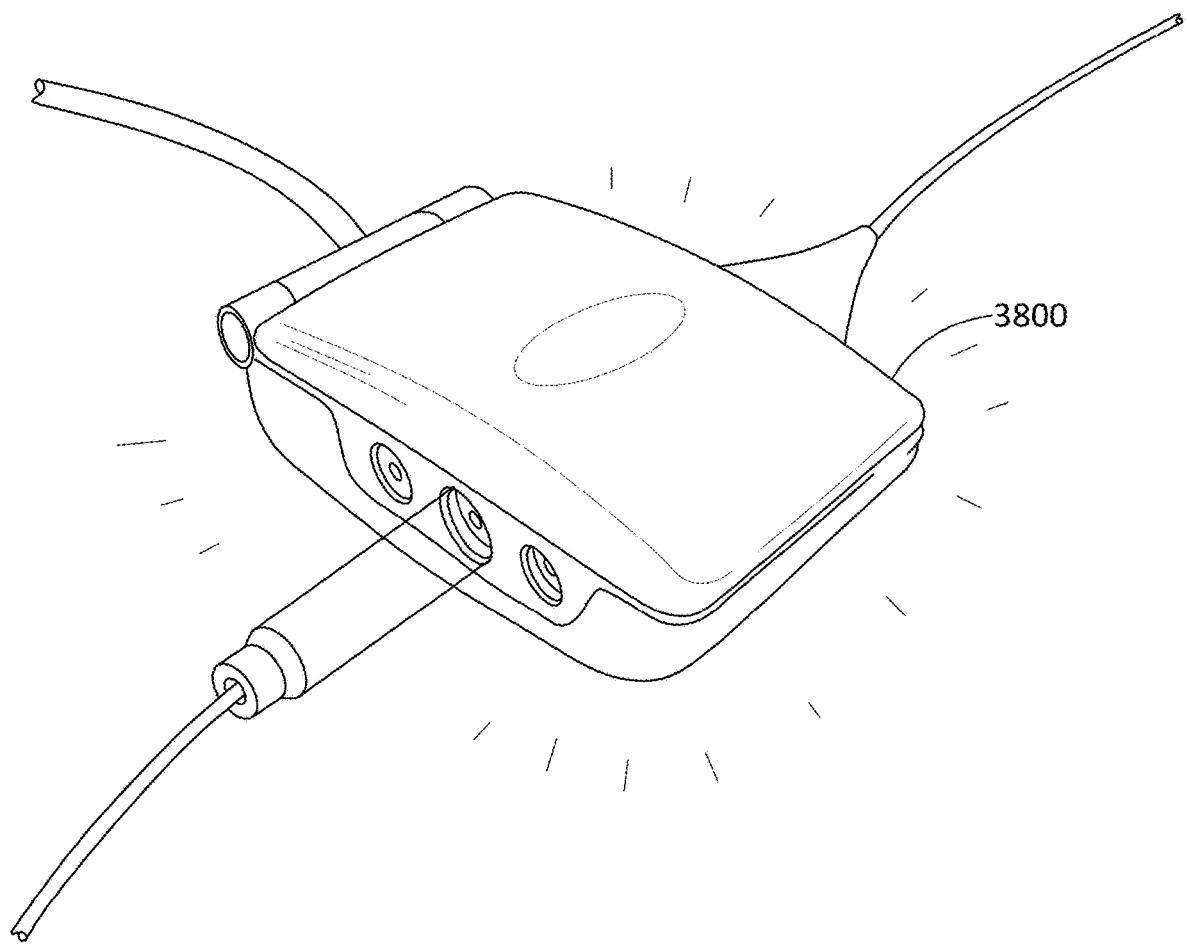

FIG. 38C is a perspective view of the UV LED disinfecting unit 3800 with the manifold 3810 positioned within the recessed portion of the base, the lid 3802 closed and the 3 port universal adapter manifold undergoing a disinfection cycle. The integration of two or more universal adapters into a single manifold can be advantageous as it allows the user to disinfect all ports together simultaneously rather than individually.

Figure 38D:
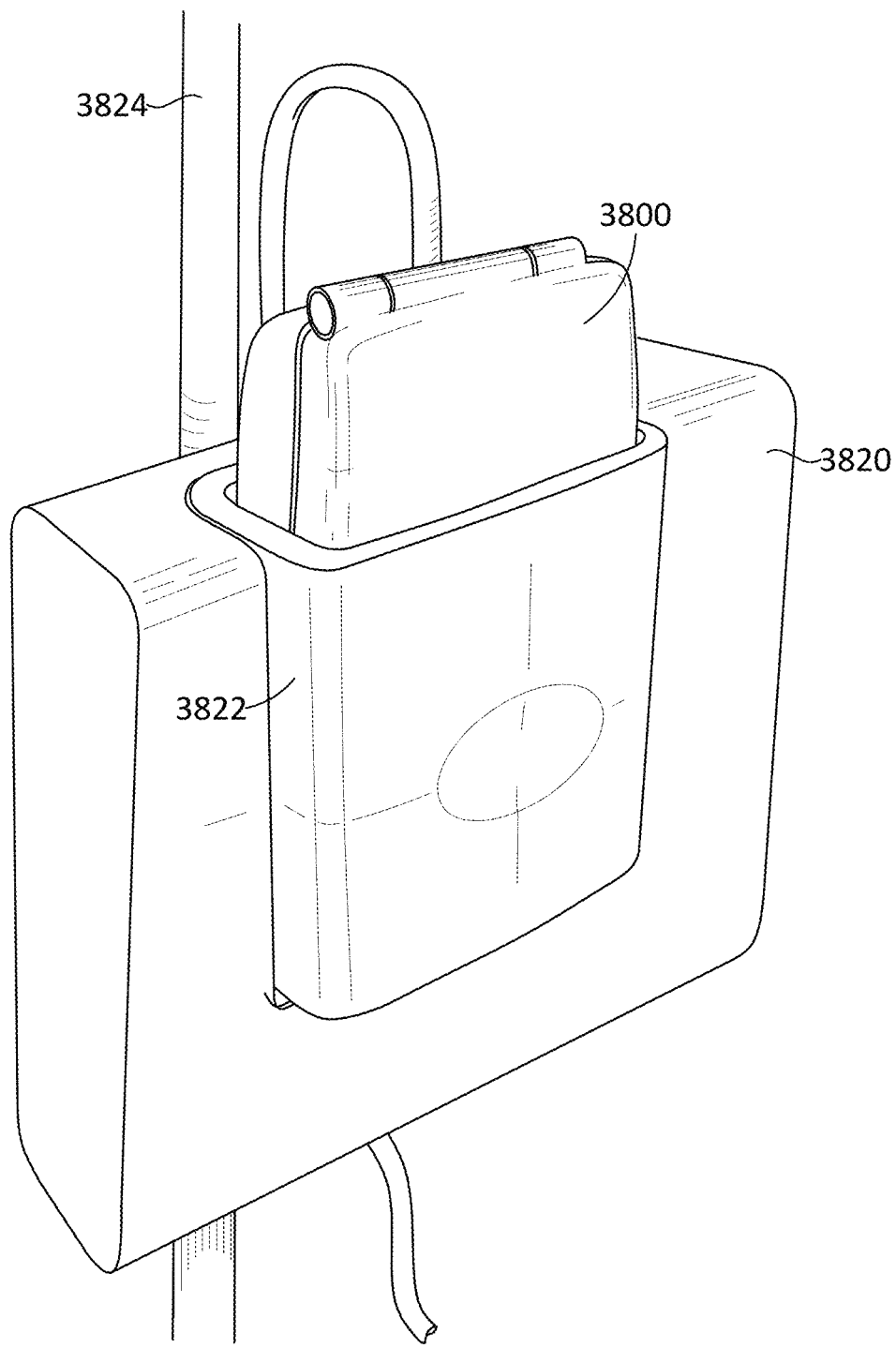
FIGS. 38D and 38E illustrate, respectively, the UV LED disinfecting unit of FIG. 21A within and removed from a bedside mounted power and control unit.
Figure 38E:
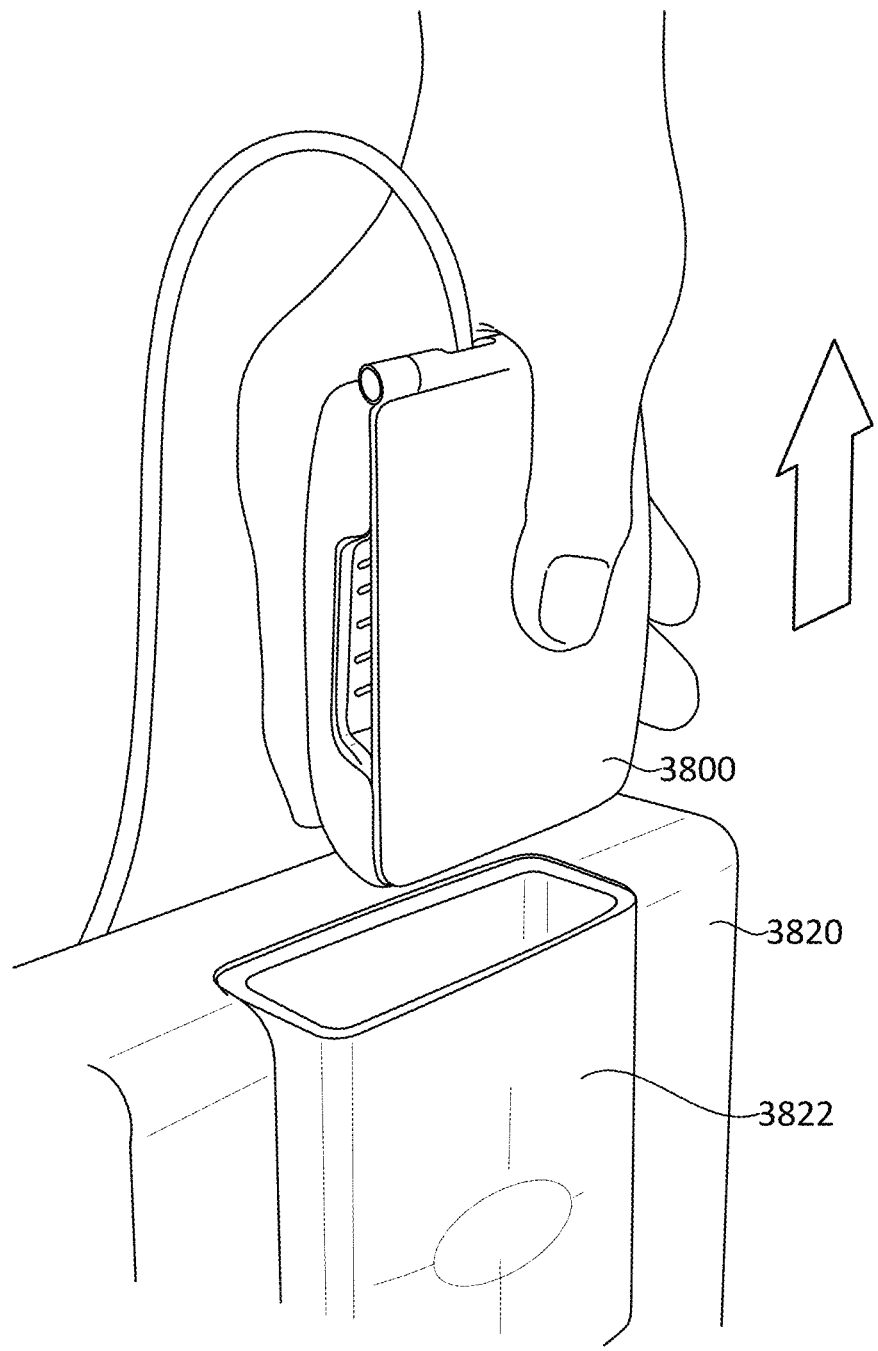

FIGS. 38D and E illustrate, respectively, the UV LED disinfecting unit 3800 within and removed from a bedside mounted power and control unit 3820. The power and control unit 3820 is mounted to an IV pole 3824 and includes a sleeve configured to receive the disinfection unit 3800. As shown in FIG. 38E, the disinfection unit 3800 can be removed from the charging base 3820 when it is time for a disinfection cycle.

Figure 39A:
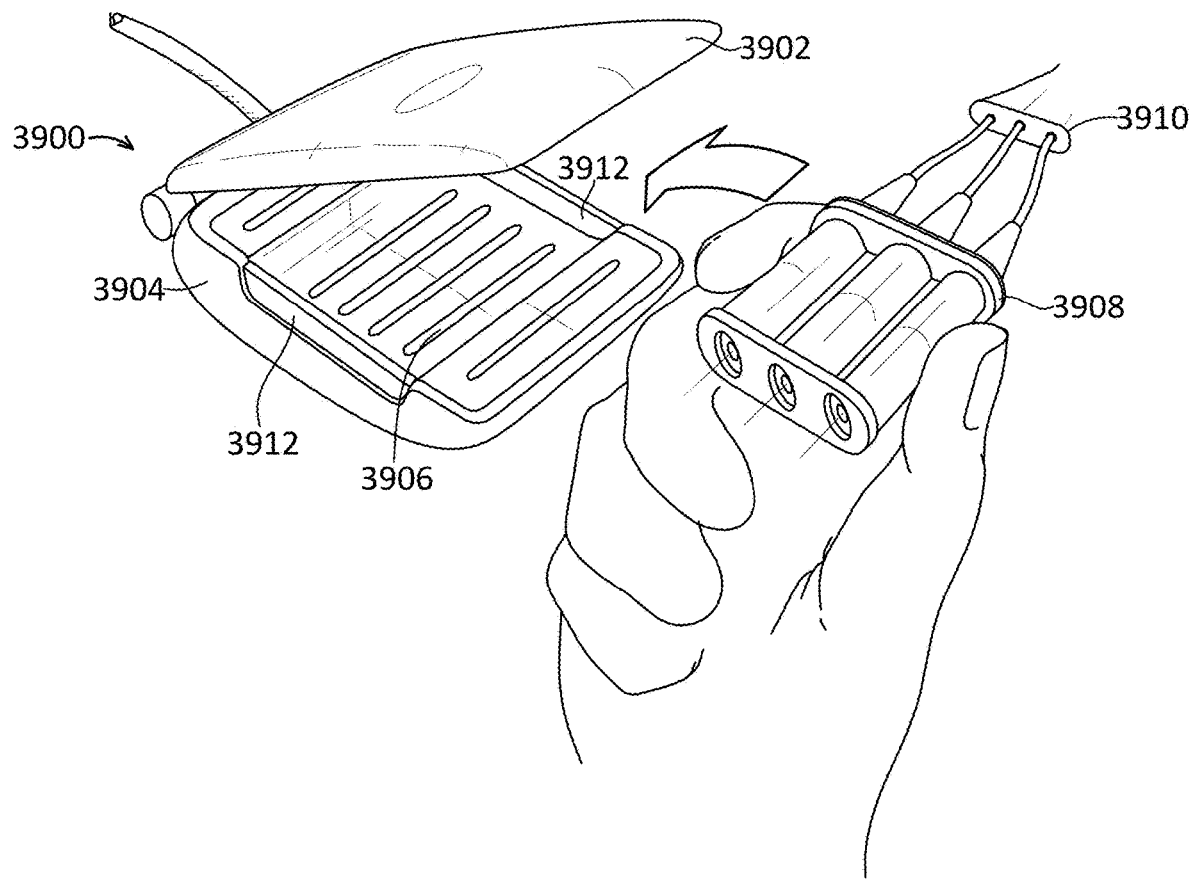
FIG. 39A is a perspective view of another embodiment of a UV LED disinfecting unit with a hinged lid and a manifold.

FIG. 39A is a perspective view of another embodiment of a UV LED disinfecting unit 3900 with a hinged lid 3902. The UV LED disinfecting unit 3900 includes a base 3904 having a recessed portion 3906 adapted and configured to receive an adapter manifold 3908. The view of FIG. 39A also includes a catheter hub 3910 and 3 port manifold 3908 prior to placement within the recessed portion 3906 of the base 3904. The manifold 3908 can comprise a UV transmissive material to allow for UV disinfection. The manifold can comprise flexible end caps 3912 (e.g., silicone end caps) to prevent UV light leakage. The manifold can be disposable. Luer fittings of catheter connections can be connected directly to the manifold. The 3 port manifold 3908 of this embodiment contains thinner walls as compared to the embodiment shown in FIG. 38B. The use of thinner walls can be advantages as the thinner the wall of UV transparent material that the UV light is directed towards the higher the amount of UV light can penetrate the wall.

Figure 39B:
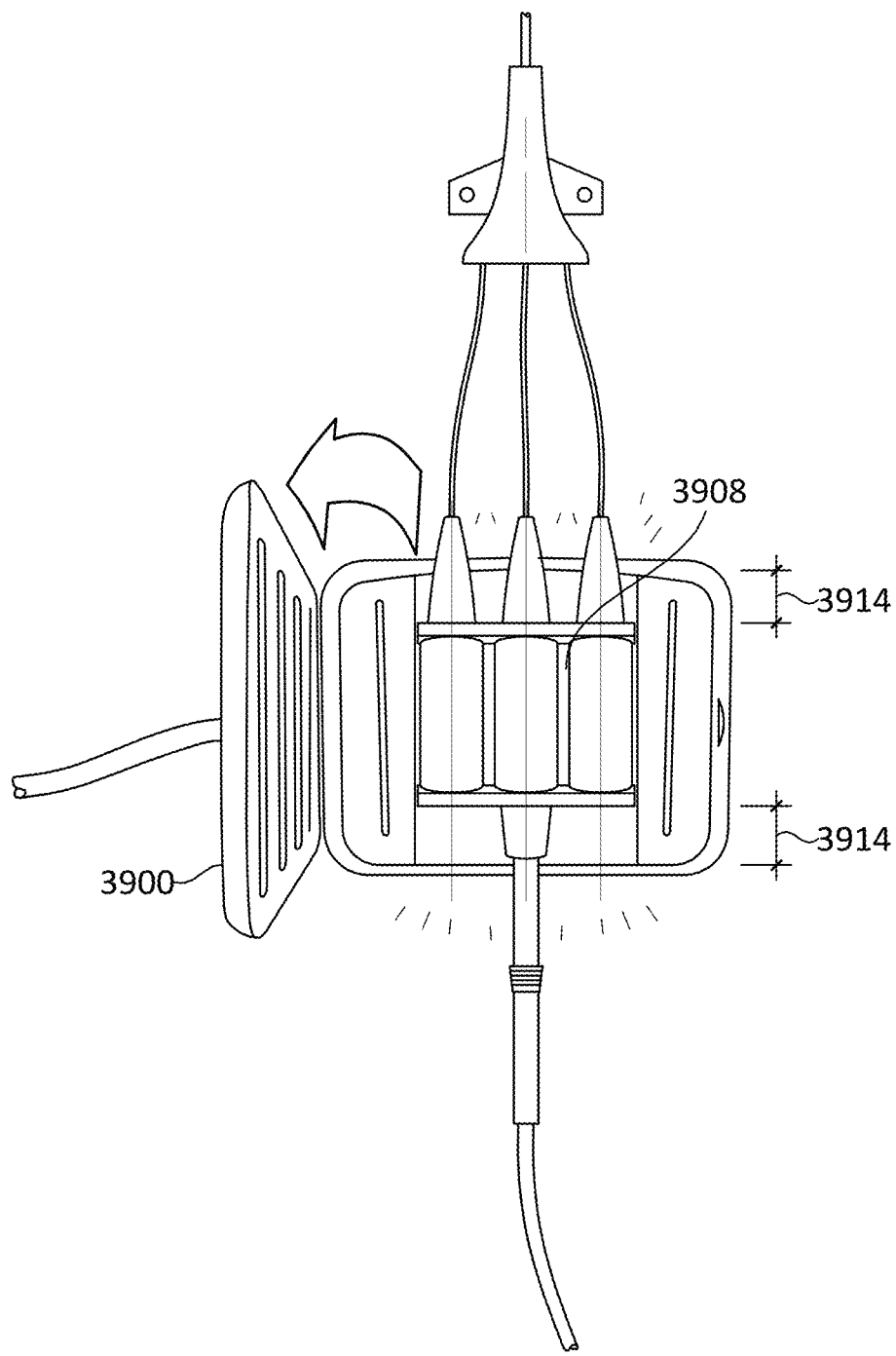
FIGS. 39B and 39C are various views of the UV LED disinfecting unit of FIG. 39A and the manifold of FIG. 39A.
Figure 39C:
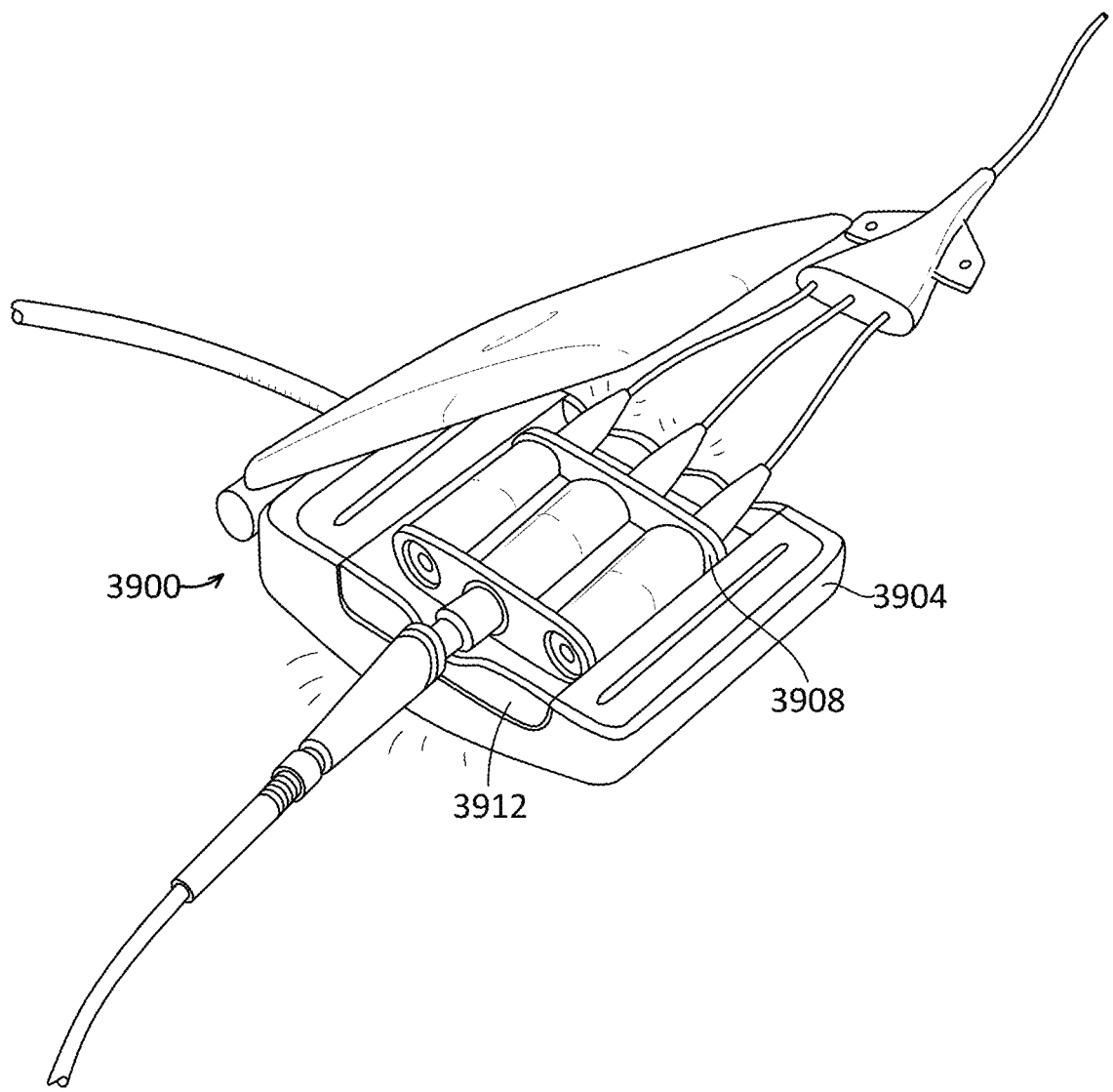
Figure 39D:
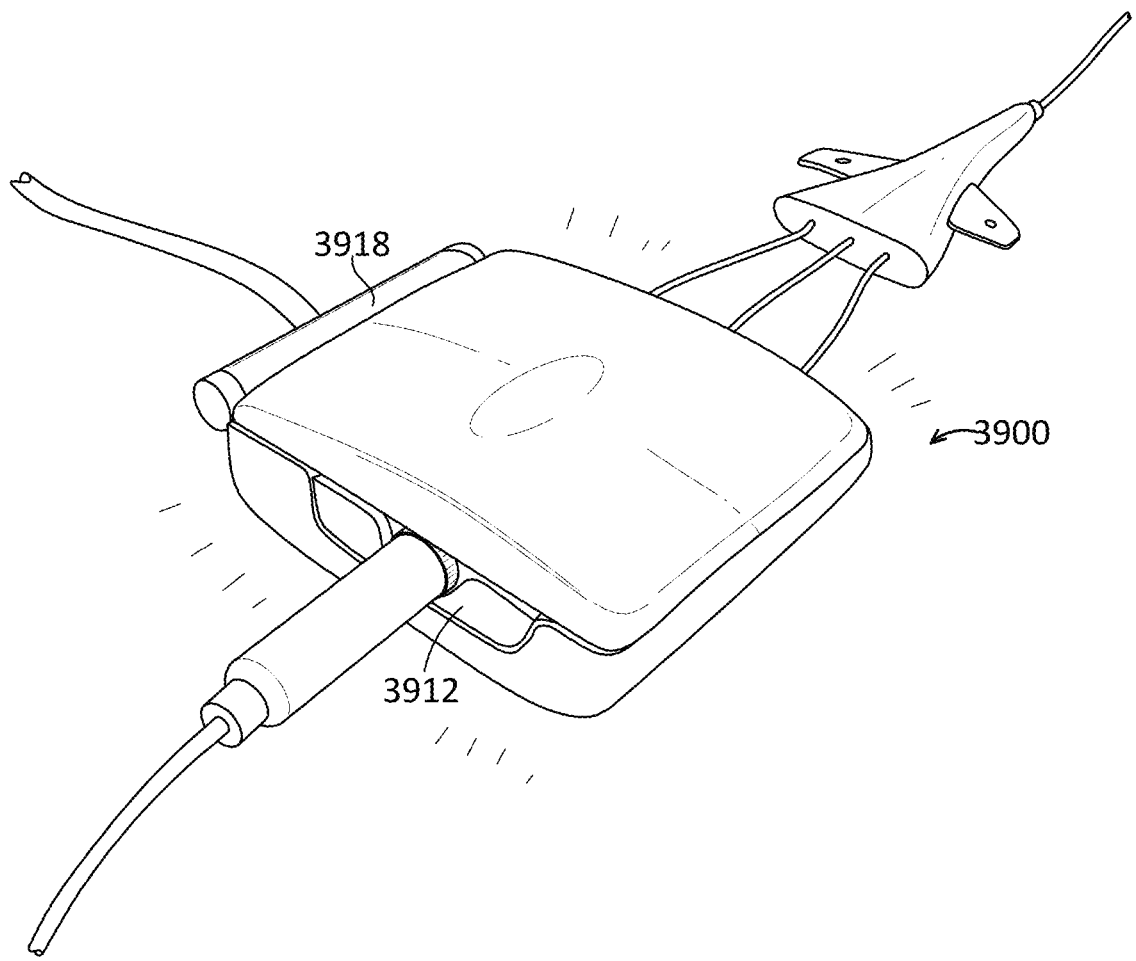
FIG. 39D is a perspective view of the UV LED disinfecting unit of FIG. 39A with the manifold positioned within the recessed portion of the base, the lid closed and the adapters within the manifold undergoing a disinfection cycle.

FIGS. 39B and C are various views of the UV LED disinfecting unit 3900 with the manifold 3908 positioned within the recess of the base 3904. Extra space 3914 is provided for UV lighting within the unit 3900 on either side of the manifold 3908. FIG. 39D is a perspective view of the UV LED disinfecting unit 3900 with the manifold 3908 positioned within the recessed portion of the base, the lid closed and the adapters within the manifold undergoing a disinfection cycle. The lid can have a spring loaded hinge 3918 to help keep the lid down and manifold in place. The recess of the base is advantages as it provides a volume to contain the 3 port manifold and isolate that volume and manifold from the exterior of the UV LED disinfecting unit. This isolated volume can be subject to very high levels of UV light for disinfection while that UV light is blocked from exiting the UV disinfecting unit. It can be important to block the UV light from the exterior as UV light in the 100 nm to 290 nm spectrum is known to cause harm to human skin and corneas. The top, bottom and sides for the recess ae formed by hard surfaces of the UV light disinfecting unit. The front and back portion of the recess can comprise compliant walls or endcaps 3912 of the UV disinfecting unit made by a silicone or elastomeric polymer membrane or foam which can seal around the catheter hubs or the catheter lumens as well as the infusion line hub or lumen. Alternately the front and back portion of the recess can be formed by hard surfaces with apertures that are configured to closely fit around the catheter hub, lumen, infusion hub, or lumen.

Figure 40A:
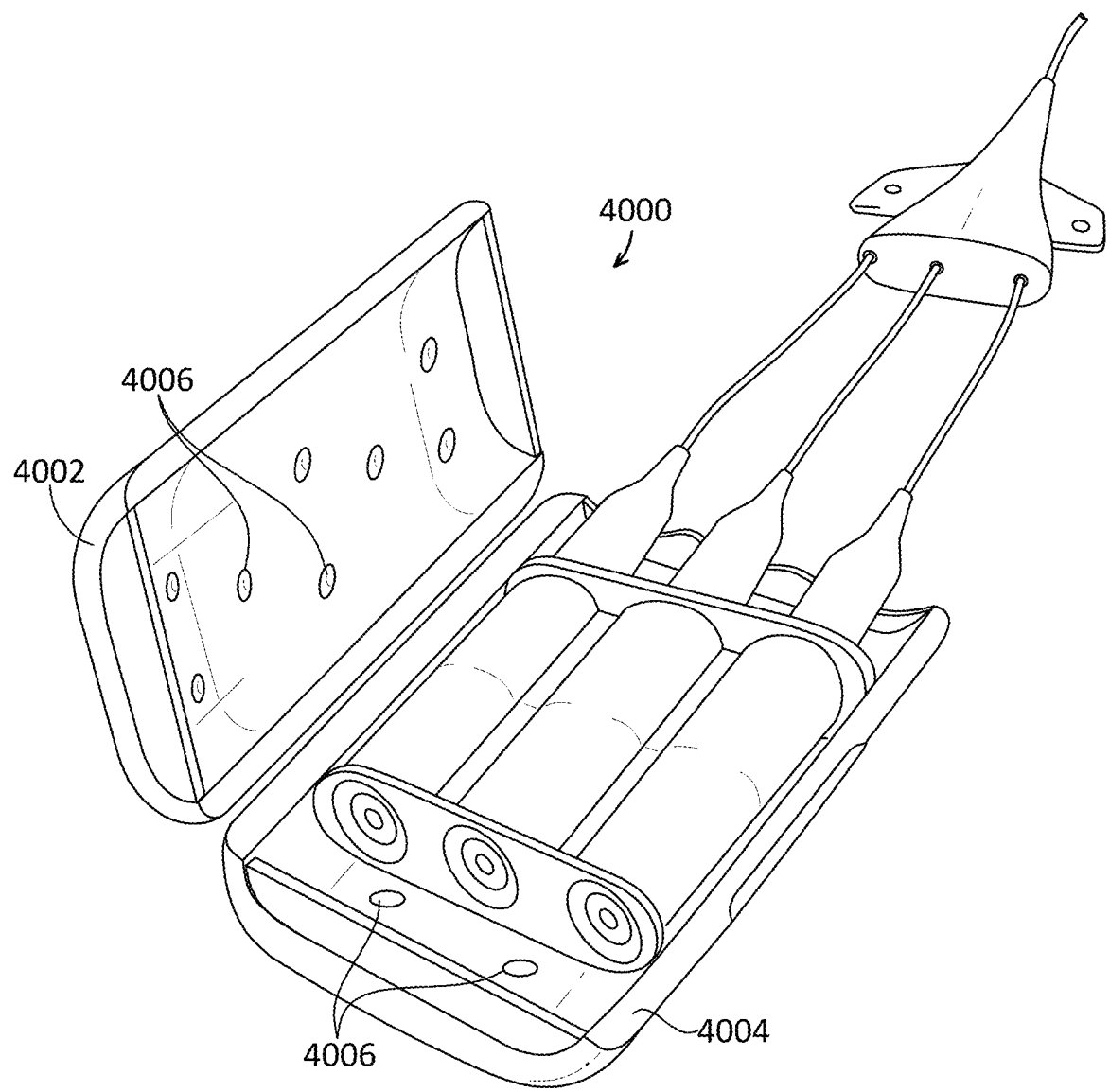
FIG. 40A is a perspective view of another embodiment of a UV LED disinfecting unit with a hinged lid in the open position and configured to receive an adapter manifold shown in the perspective view of FIG. 40B.

FIG. 40A is a perspective view of another embodiment of a UV LED disinfecting unit 4000 with a hinged lid 4002 and base 4004 in the open position. The UV LED disinfecting unit 4000 includes a lid and base lighting unit with a recessed portion adapted and configured to receive an adapter manifold 4010 shown in the perspective view of FIG. 40B. This embodiment is comprised of multiple LEDs 4006 contained in both the lid and base portions. As described above, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

The manifold 4010 is configured to connect 3 lumens 4012 to luer fittings 4016 of a catheter hub 4014. The manifold 4010 can comprise a UV transmissive material. The manifold 4010 can comprise a symmetrical profile, meaning it can be placed either way within the disinfection unit 4000.

Figure 40D:
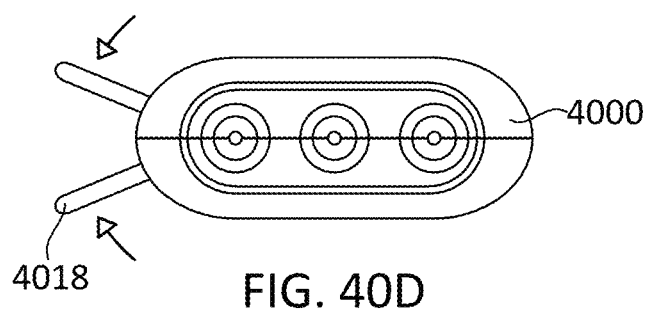
FIG. 40D is an end view of the UV LED disinfecting unit of FIG. 40C.
Figure 40B:
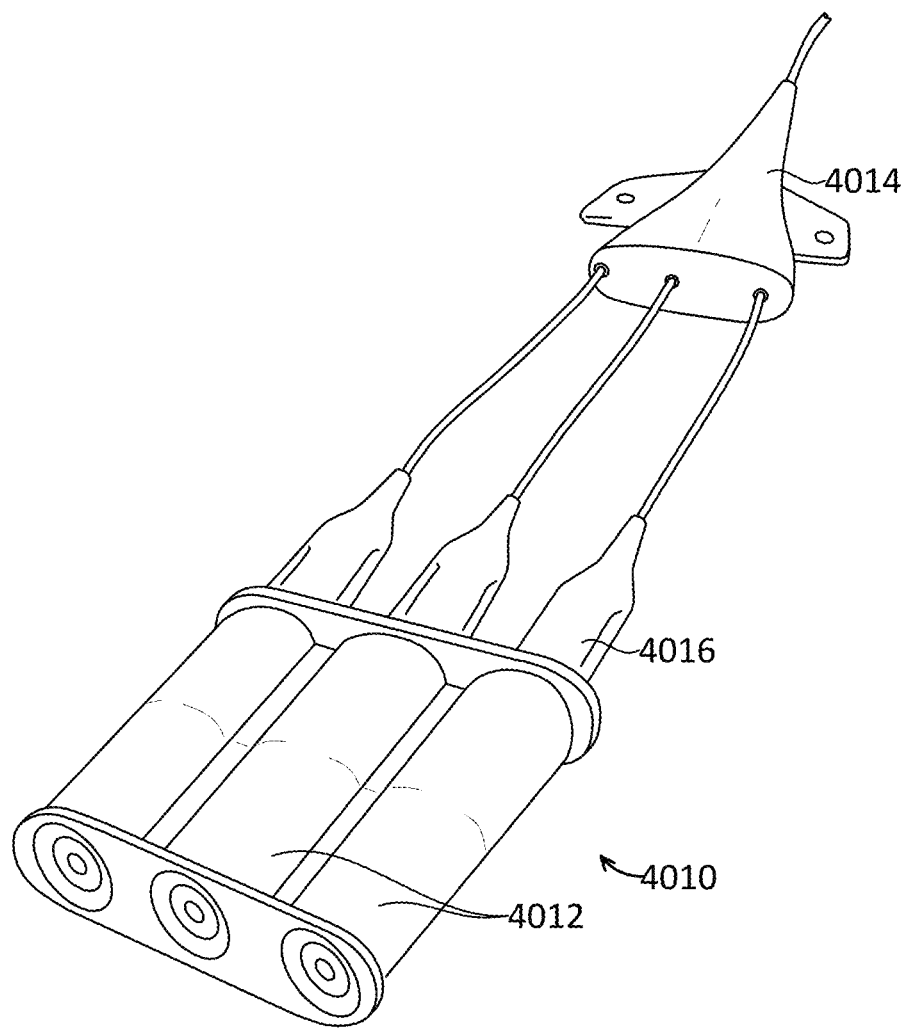
FIG. 40C is a perspective view of the UV LED disinfecting unit of FIG. 40A undergoing a disinfection cycle.
Figure 40C:
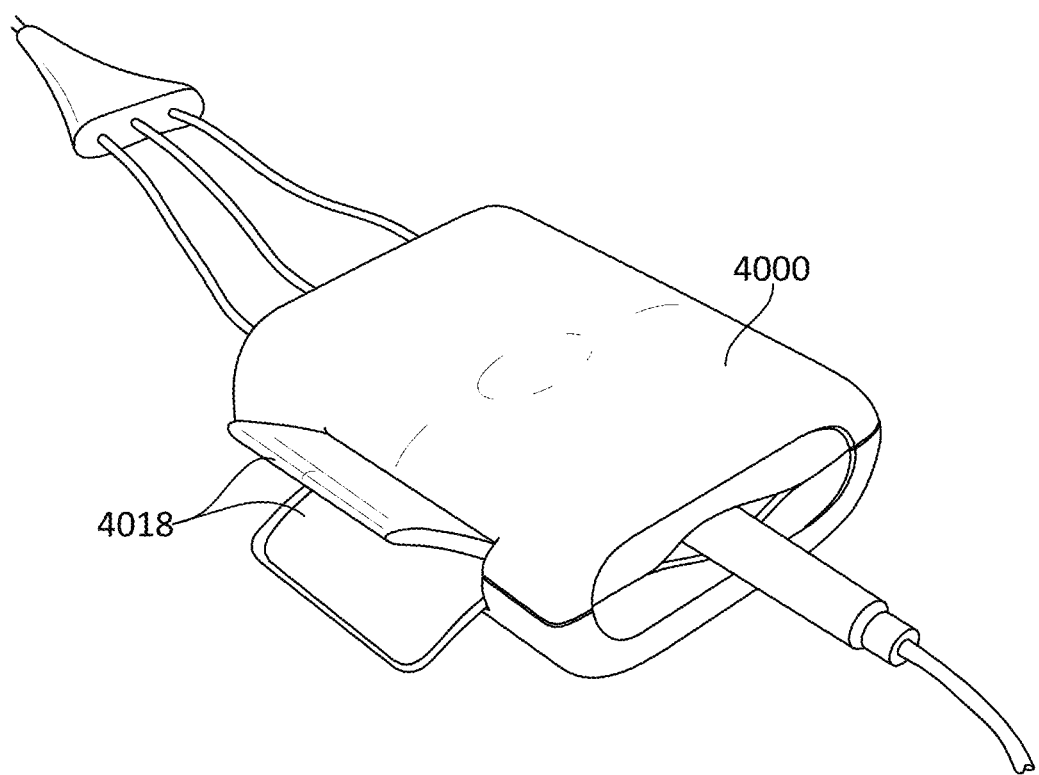

FIG. 40C is a perspective view of the UV LED disinfecting unit 4000 with the manifold 4010 positioned within the unit, the lid closed and the adapter manifold undergoing a disinfection cycle. This embodiment includes projecting wings 4018 on both the base and lid of the disinfecting unit that allow the user to easily squeeze to open the unit. FIG. 40D is an end view of the UV LED disinfecting unit 4000.

Figure 41A:
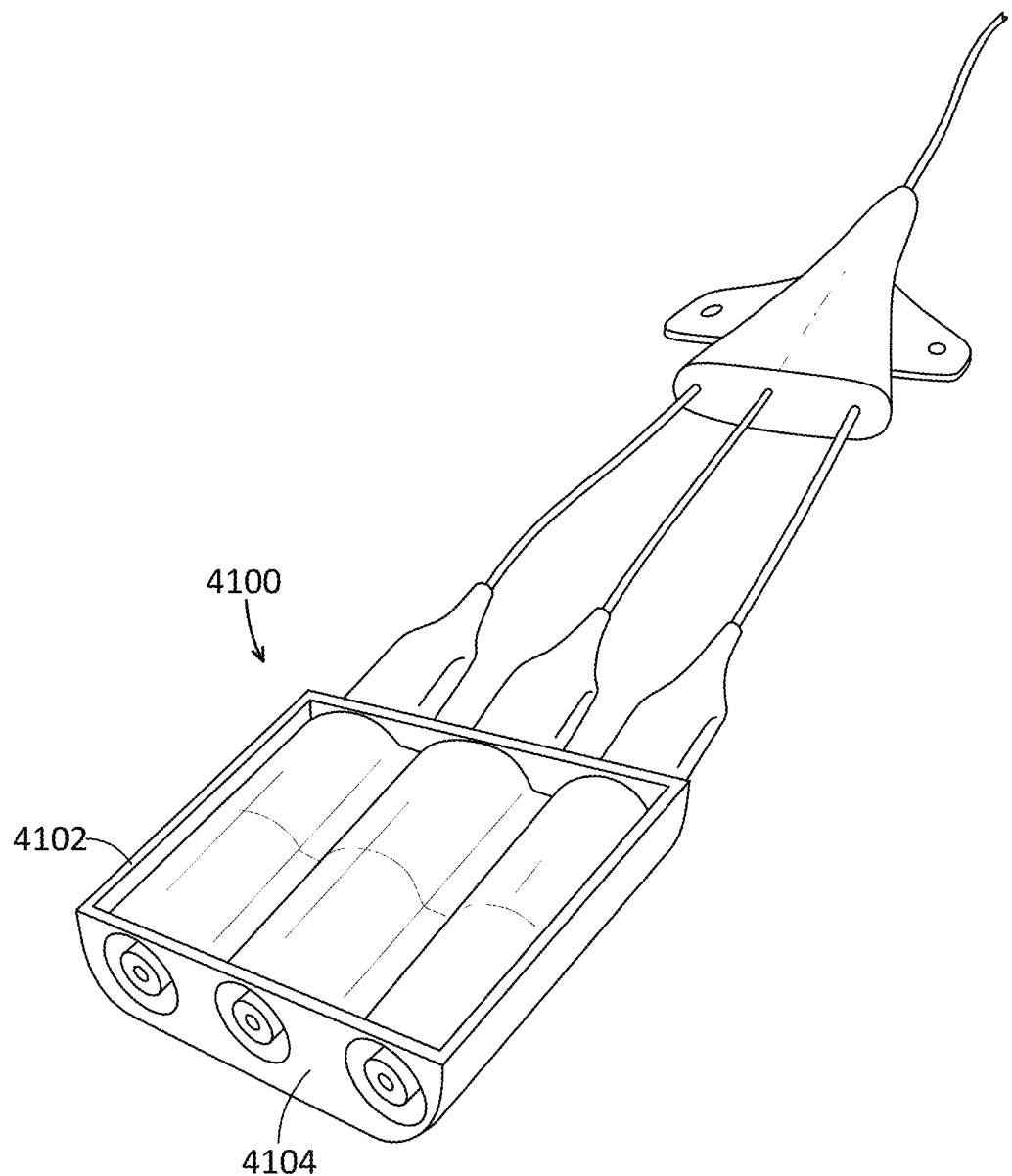
FIG. 41A is a perspective view of an embodiment of a three port manifold and catheter hub.

FIG. 41A is a perspective view of a three port manifold and catheter hub having raised endcaps 4014 that extend all along the manifold to create side wall features 4102 configured for use with a UV LED disinfecting system.

Figure 41B:
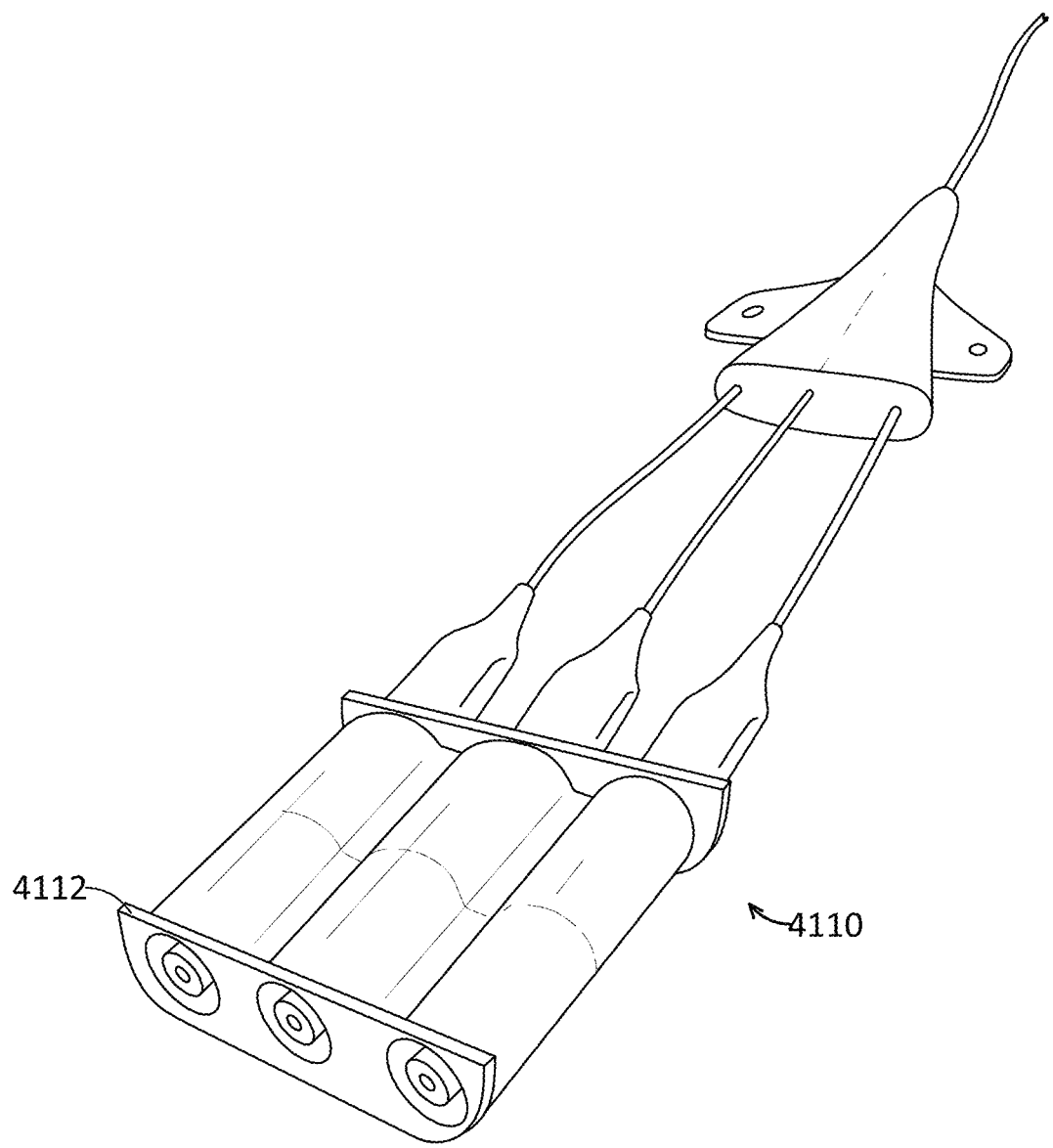
FIGS. 41B and 41C show various views of a three port manifold and catheter hub.
Figure 41C:
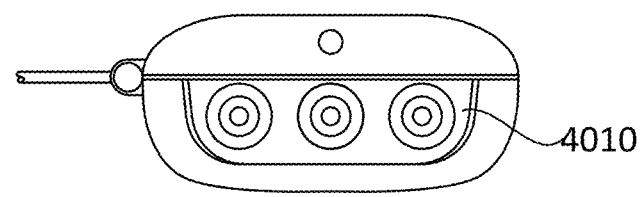

FIG. 41B is a perspective view of a three port manifold and catheter hub having no sidewalls and raised end wall features 4112 configured for use with a UV LED disinfecting system. This shape can offer directionality and a more secure fit within the disinfection device. FIG. 41C is an end view of the manifold 4110 positioned within a UV LED disinfecting unit with the lid closed and the adapters within the manifold ready to undergo a disinfection cycle.

Figure 42A:
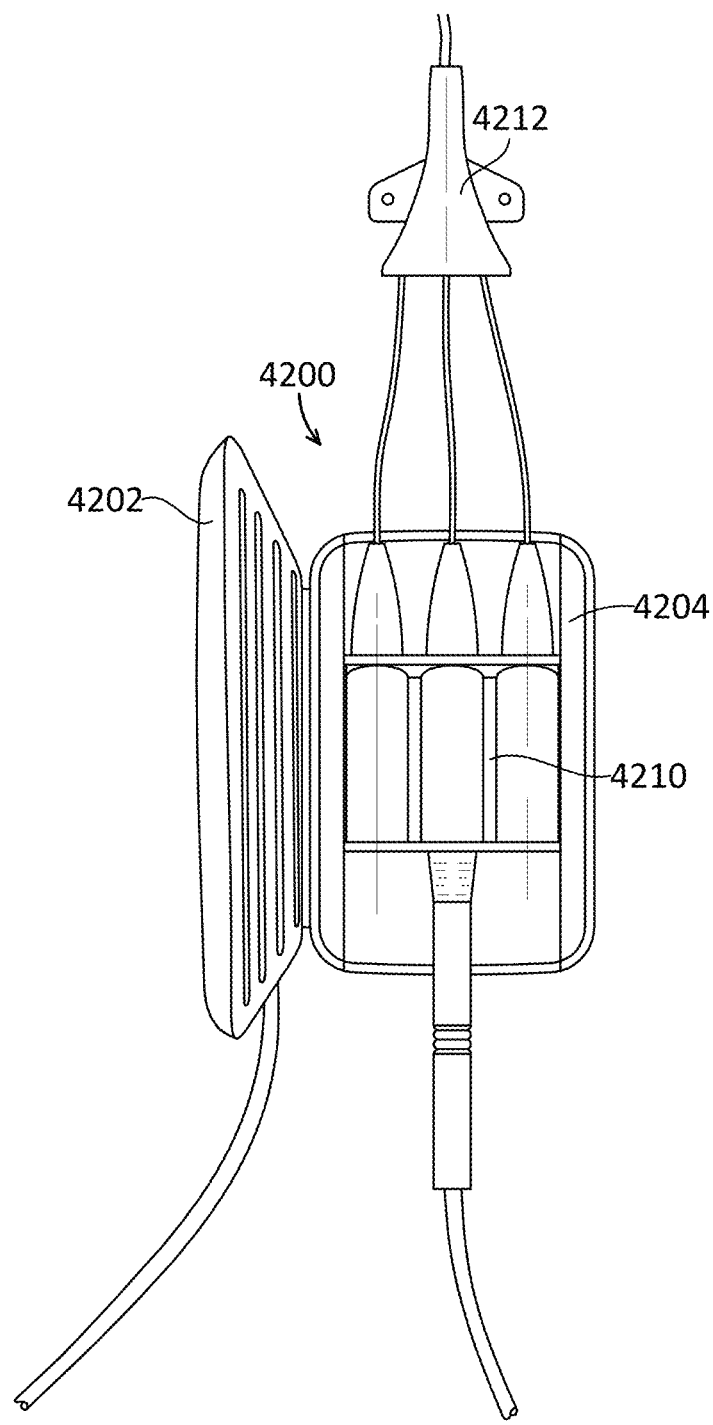
FIGS. 42A and 42B show various views of an embodiment of a UV LED disinfecting unit with a 3 port manifold placed within the unit.

FIG. 42A is a top down view of another embodiment of a UV LED disinfecting unit 4200 with a hinged lid 4202 and a base 4204 in the open configuration. The UV LED disinfecting unit 4200 includes a base 4204 having a recessed portion adapted and configured to receive an adapter manifold 4210. The view of FIG. 42A also includes a catheter hub 4212 and 3 port manifold 4210 placed within the recessed portion of the base. The UV LED disinfecting unit of this embodiment is longer than the previously described embodiments such that this UV LED disinfecting device can direct light to the entire length of the catheter hub and to a larger portion or in some cases the entire length or the infusion line hub as well.

Figure 42B:
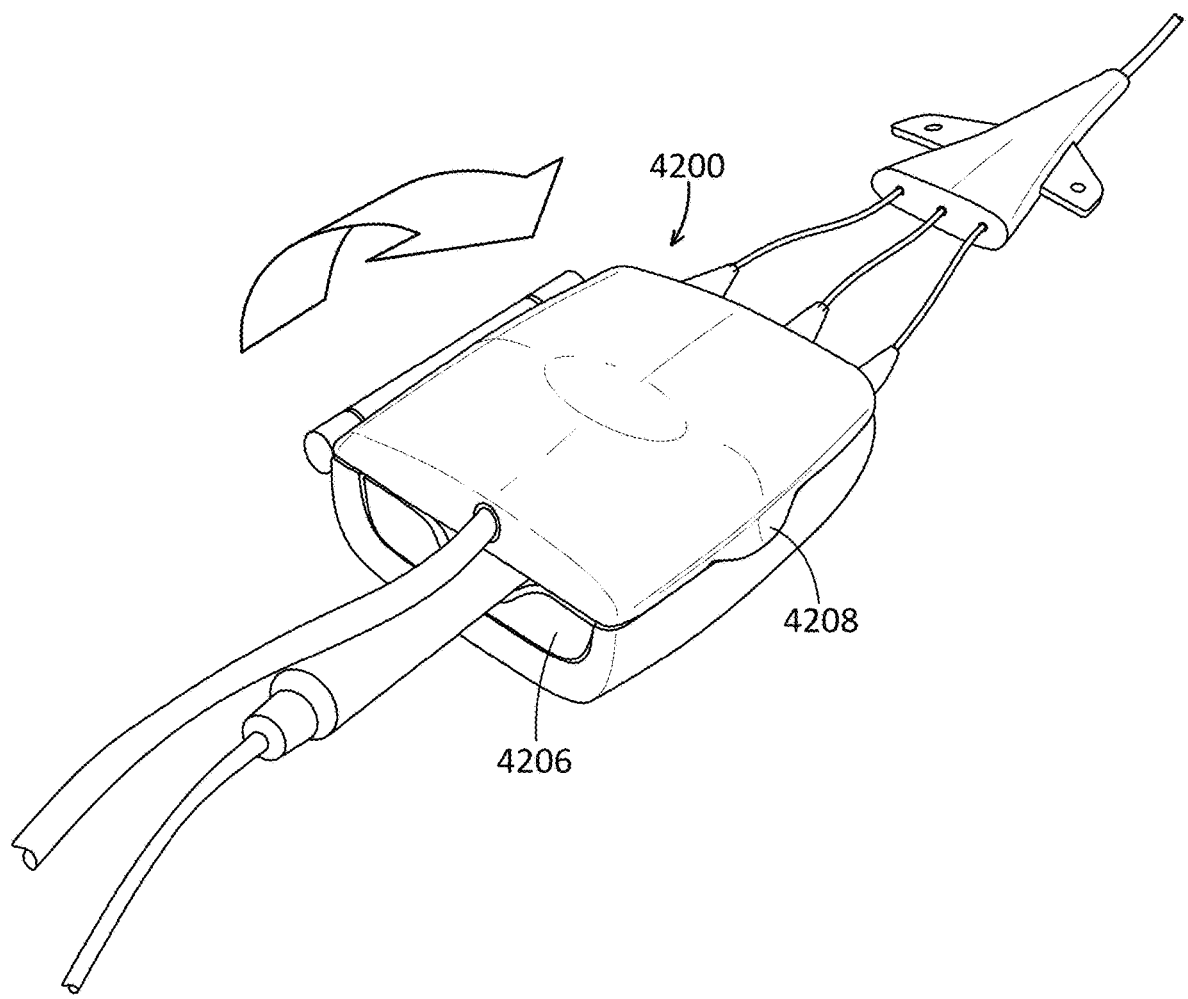

FIG. 42B is a perspective view of the disinfecting unit 4200 and manifold 4210 with the UV LED disinfecting unit lid closed and the manifold within ready to undergo a disinfection cycle. The manifold 4210 can comprise UV transmissive or transparent material. The unit 4200 comprises flexible endcaps 4206 that can prevent UV light leakage. A finger indent 4208 in the base 4204 can help with ease of opening and closing the unit 4200

FIGS. 43A-D are various views of a catheter hub 4302 and 3 port manifold 4304, a hinged lid UV LED disinfecting unit 4300. FIGS. 43E-H illustrate the steps of disinfecting a catheter hub and 3 port manifold. As shown in FIG. 43E, the IV pole is next to the patient bed. FIG. 43F shows the disinfection unit 4300 in a holster 4312 on a power supply unit 4314 on the IV pole 4316. FIG. 43G shows the unit 4300 being slid out of the holster 4312. FIG. 43H shows the unit 4300 resting on the patient with the manifold and attached catheter hub inside. FIG. 26I illustrates delivery of a fluid via the three port manifold after use of a bedside mounted UV LED disinfecting unit 4300.

The embodiments devices described herein (e.g., in FIGS. 32A-43I) may also be configured to have one or more of the following features. They can have a power supply (e.g., 120 VAC powered Power Supply). Some embodiments have a disposable Single Manifold Adapter to connect 1-5 CVC Luer fittings to a single Manifold Adapter made of UV transparent plastic. In some embodiments, the device provides additional space for UV lighting in front and rear of Manifold. The device can comprise flexible material (e.g. silicone, polymer elastomers, polymer foams, etc.) end-caps to prevent UV light leakage. The manifold adapter can be placed into the lower housing. The lid can close and disinfection may begin. The device can be used "as needed" and returned to charging base. A longer and narrow form-factor of the device is possible. In some embodiments, the power cord exit point is in-line with syringes/infusion lines. It can be perpendicular to syringes/infusion lines. The use of EV lamps rather than UVC LEDs, etc. These characteristics and features may be applied to other embodiments.

Figure 44A:
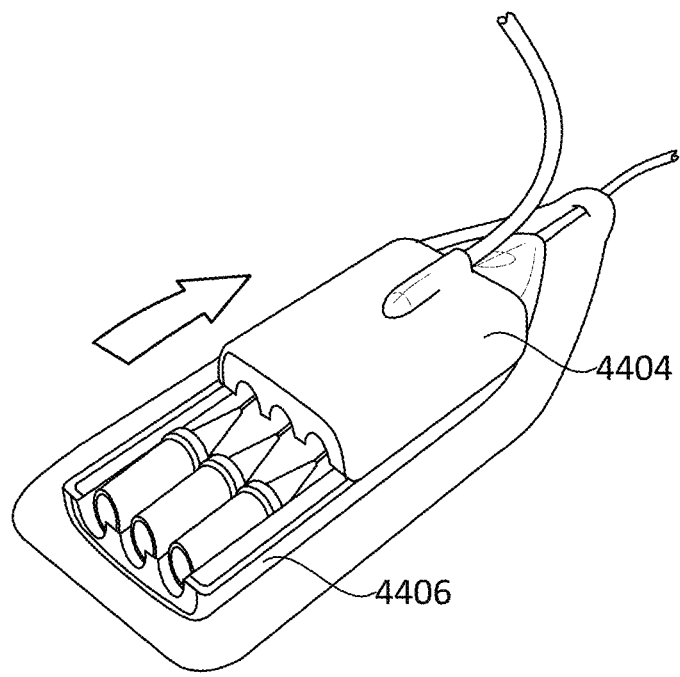
FIGS. 44A and 44B are perspective views of embodiments of a disposable catheter hub and disinfecting unit assembly arranged on a patient worn adhesive patch.
Figure 44B:
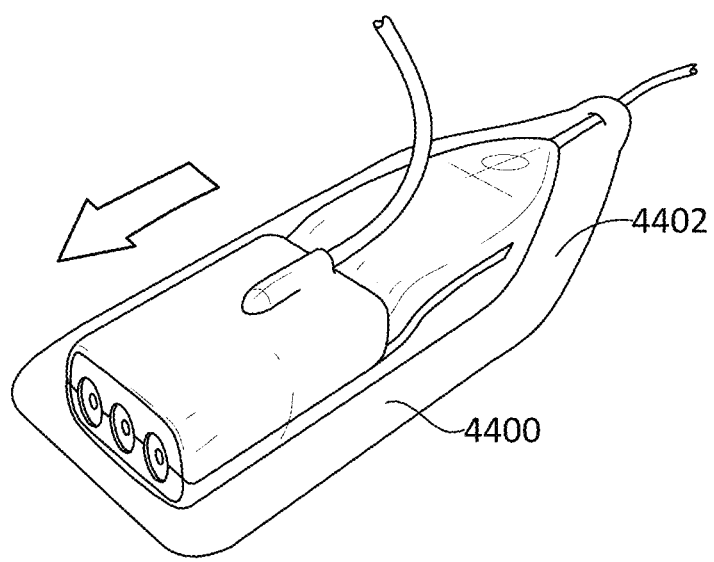

FIGS. 44A and 44B are perspective views of a disposable catheter hub and disinfecting unit assembly 4400 arranged on a patient worn adhesive patch 4402. The catheter hub is connected to three universal adapters in an arrangement with a sliding lid containing a UV LED lighting arrangement. FIG. 44A illustrates the sliding lid 4404 in an open position and FIG. 44B illustrates the sliding lid 4404 in a closed/disinfection position. The base 4406 of the disposable catheter hub and disinfecting unit assembly can also contain UV LEDs or its upper surface can be reflective to redirect the UV light from the sliding lid. The disposable catheter and disinfecting unit assembly can be configured to start UV light delivery for disinfecting automatically when the lid is slide closed. It can also be configured to stop UV light delivery automatically when the lid is slide open.

Figure 45A:
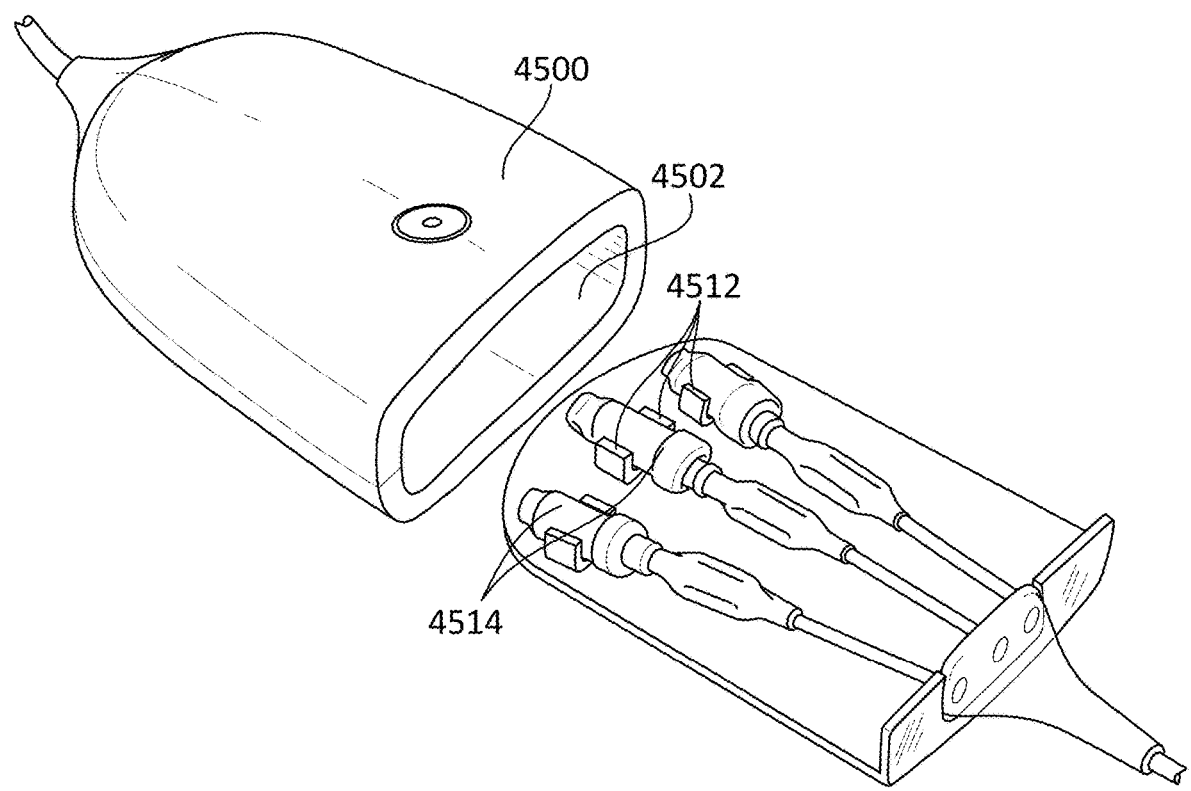
FIGS. 45A-45C show various views of embodiments of a disposable catheter hub and adapter mounts and a UV LED disinfecting unit.
Figure 45B:
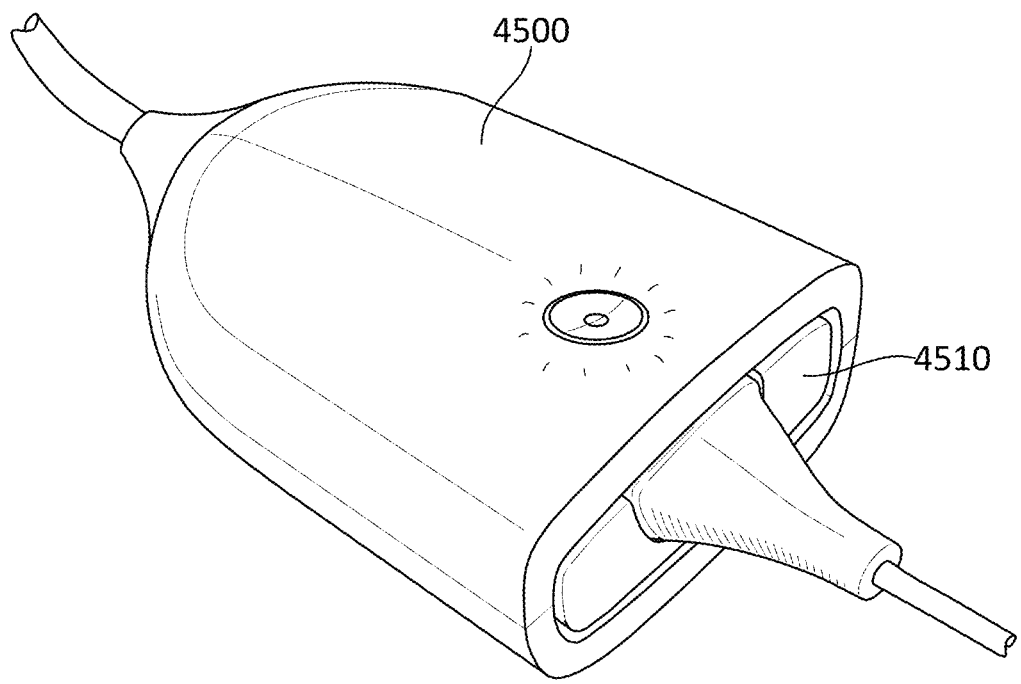
Figure 45C:
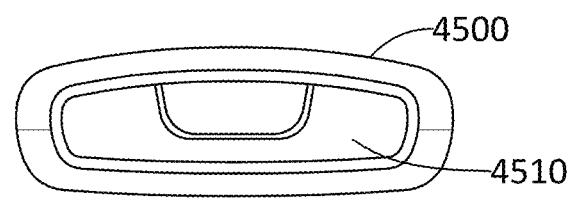

FIG. 45A is a perspective view of a disposable catheter hub and adapter mount and a UV LED disinfecting unit 4500. In this view the disposable catheter hub mount 4510 is positioned just prior to insertion into the disinfecting unit. The catheter hub mount 4510 comprises a tray like configuration and can be made of UV transmissive material. The mount 4510 has snap in features 4512 to hold the adapters 4514 in place. The disinfecting unit 4500 includes an interior geometry and end features adapted and configured to be releaseably coupled to corresponding features on the catheter hub and mount. The catheter hub and mount has a slot 4502 configured to accept the catheter hub. FIG. 45B is a perspective view of the disinfecting unit 4500 and mount 4510 with the mount 4510 inserted within and undergoing disinfection within the disinfecting unit 4500. FIG. 45C is an end view of the configuration in FIG. 45B. The unit 4500 can be configured to fully enclose a catheter hub positioned in the mount 4510.

Figure 46A:
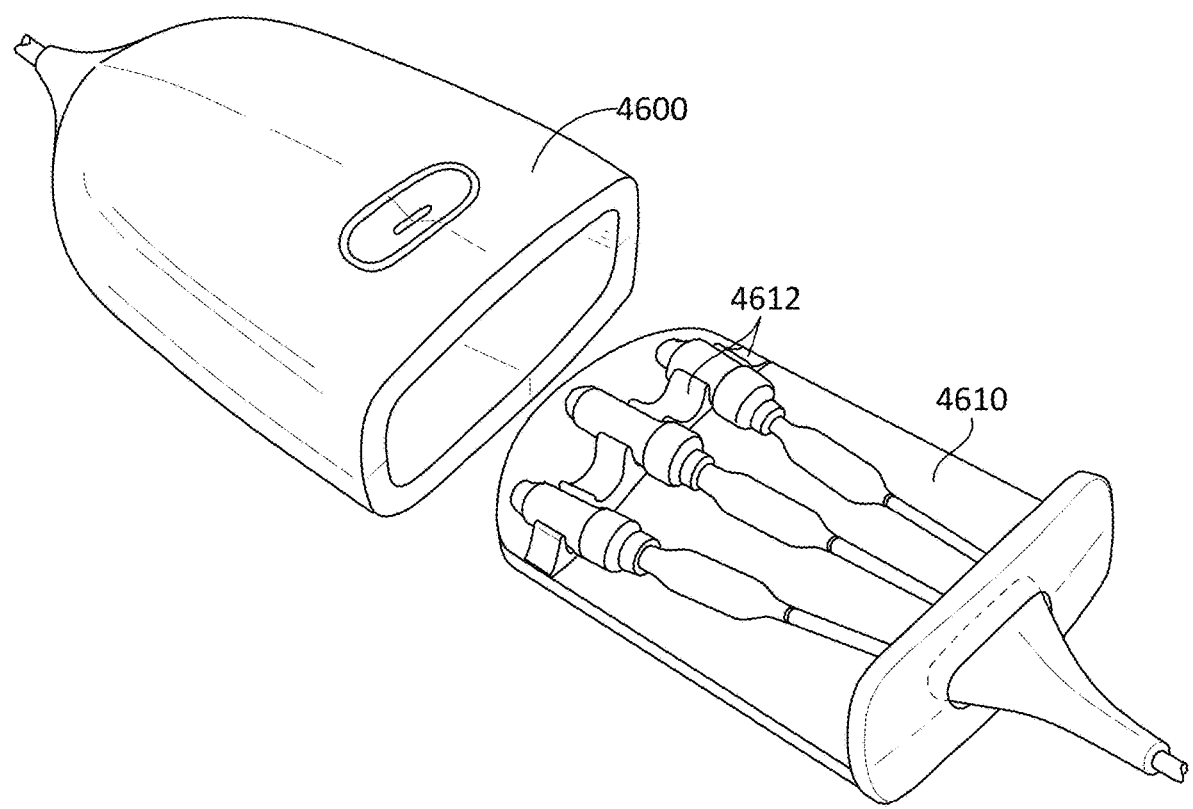
FIGS. 46A-46D show various views of embodiments of a disposable catheter hub and adapter mounts and a UV LED disinfecting unit.
Figure 46B:
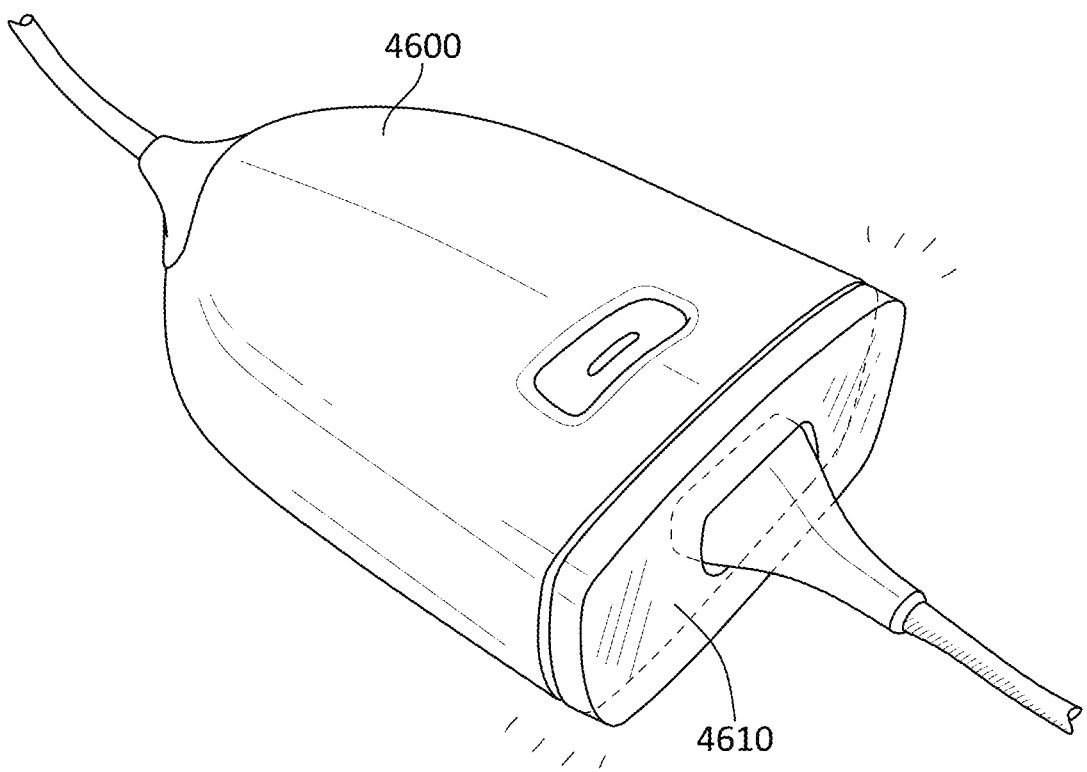
Figure 46C:
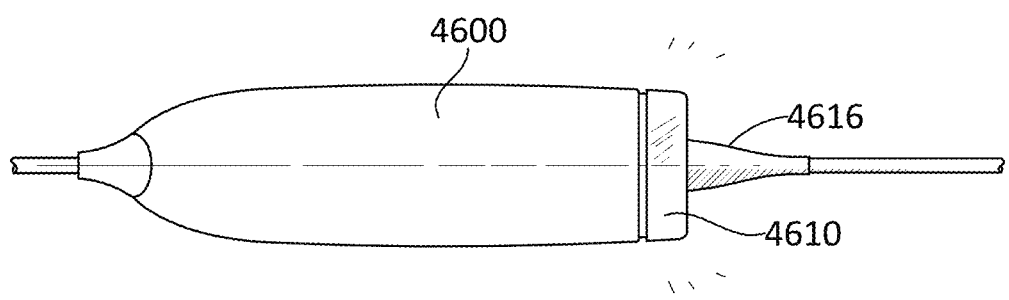
Figure 46D:
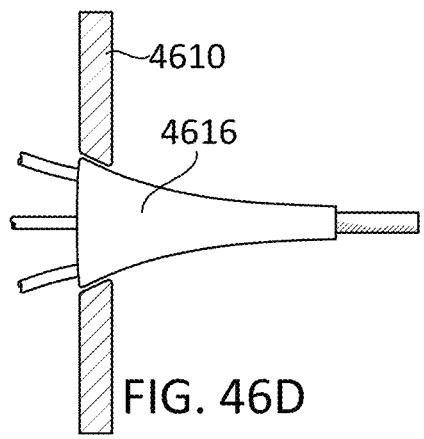

FIG. 46A is a perspective view of a disposable catheter hub manifold 4610 having adapter mounts 4612 and a UV LED disinfecting unit 4600. In this view the disposable catheter hub mount 4610 is positioned just prior to insertion into the disinfecting unit 4600. The disinfecting unit 4600 includes an interior geometry and end features adapted and configured to be releaseably coupled to corresponding features on the catheter hub and mount. FIG. 46B is a perspective view of the disinfecting unit 4600 and manifold 4610 with the manifold 4610 inserted within and undergoing disinfection within the disinfecting unit 4600. FIG. 46C is a side view of the configuration in FIG. 46B. FIG. 46D is an enlarged view of the CVC hub 4616 in relation to the sidewall of the manifold 4610 wherein the CVC hub 4616 is positioned through an aperture in the manifold 4610.

Figure 47A:
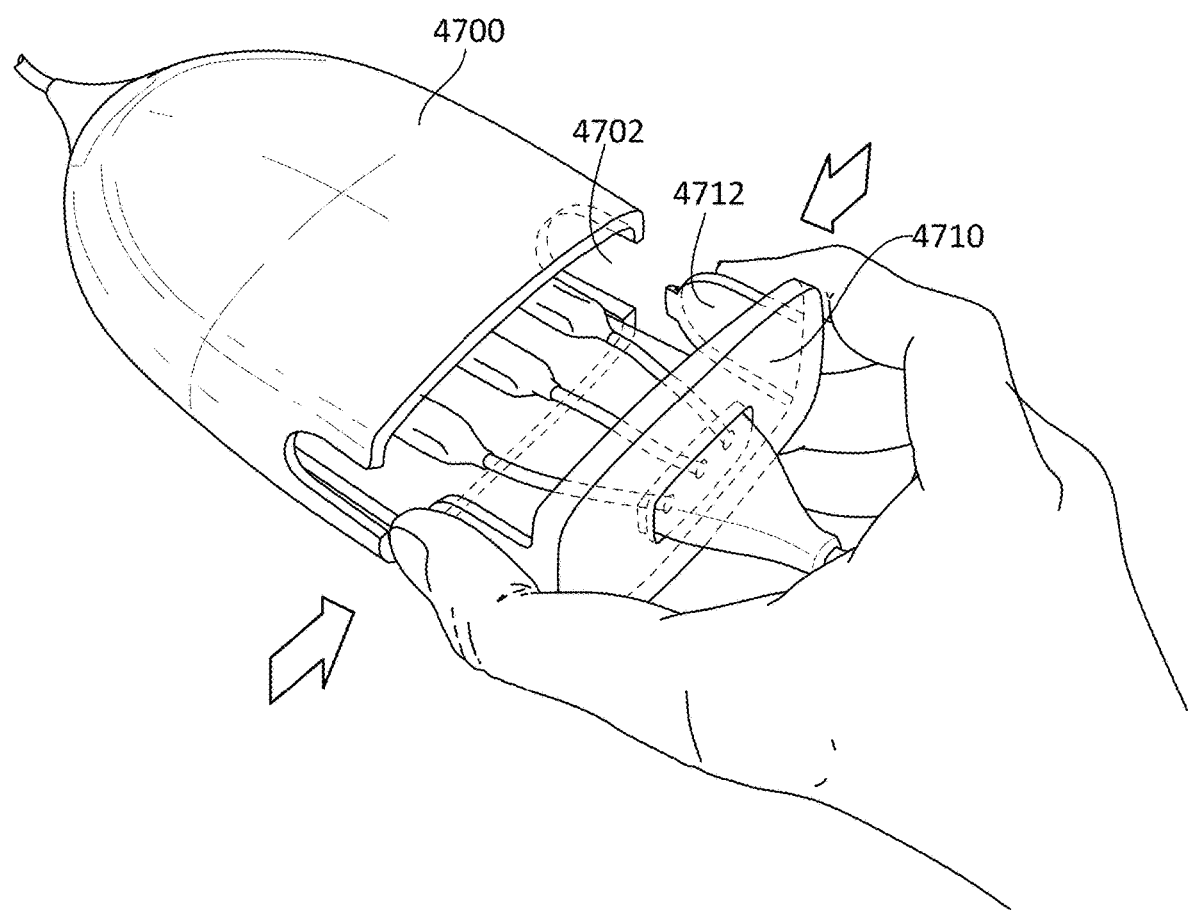
FIGS. 47A and 47B show perspective views of embodiments of a disposable catheter hub and adapter mounts and a UV LED disinfecting unit.
Figure 47B:
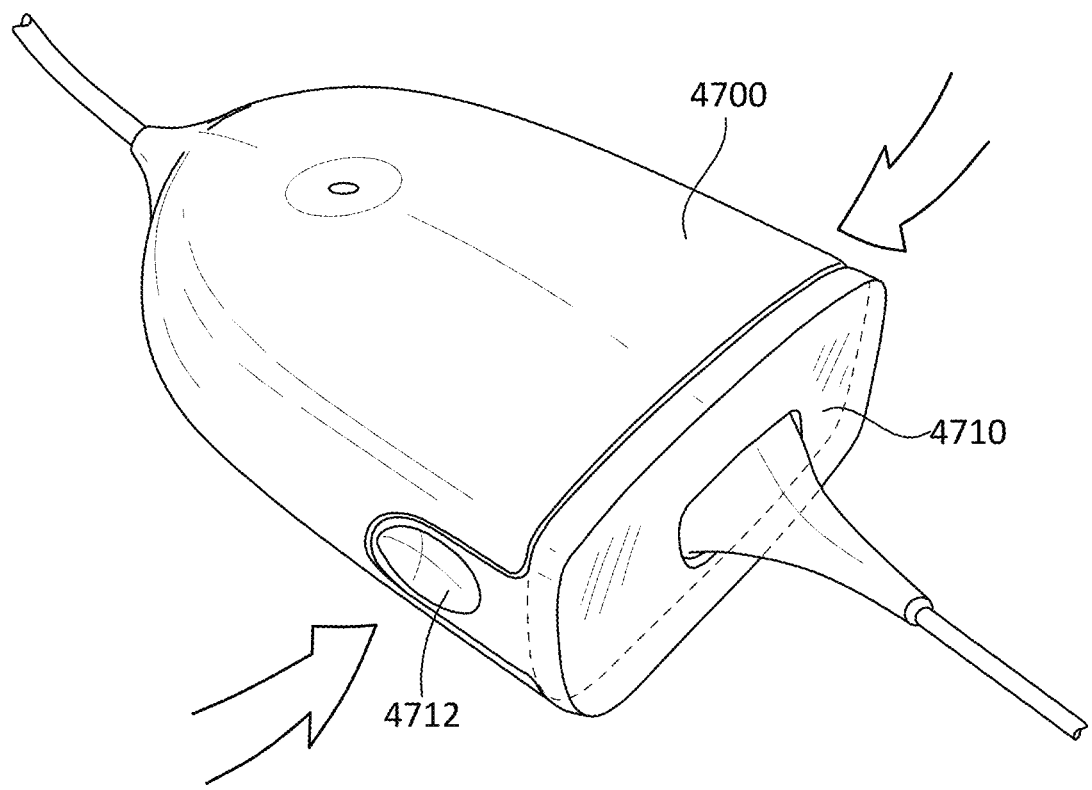

FIG. 47A is a perspective view of a catheter hub and adapter manifold 4710 and a UV LED disinfecting unit 4700. In this view the catheter hub manifold 4710 is positioned just prior to insertion into the disinfecting unit and includes retention detents 4712 to engage with complementary features 4702 in the sidewalls of the disinfecting unit. The disinfecting unit 4700 includes an interior geometry and end features adapted and configured to be releaseably coupled to corresponding features on the catheter hub and mount. FIG. 47B is a perspective view of the disinfecting unit 4700 and manifold 4710 with the manifold inserted within and ready for disinfection within the disinfecting unit 4700. The detents 4712 can be pressed to release the manifold 4710 from the unit 4700

Figure 48A:
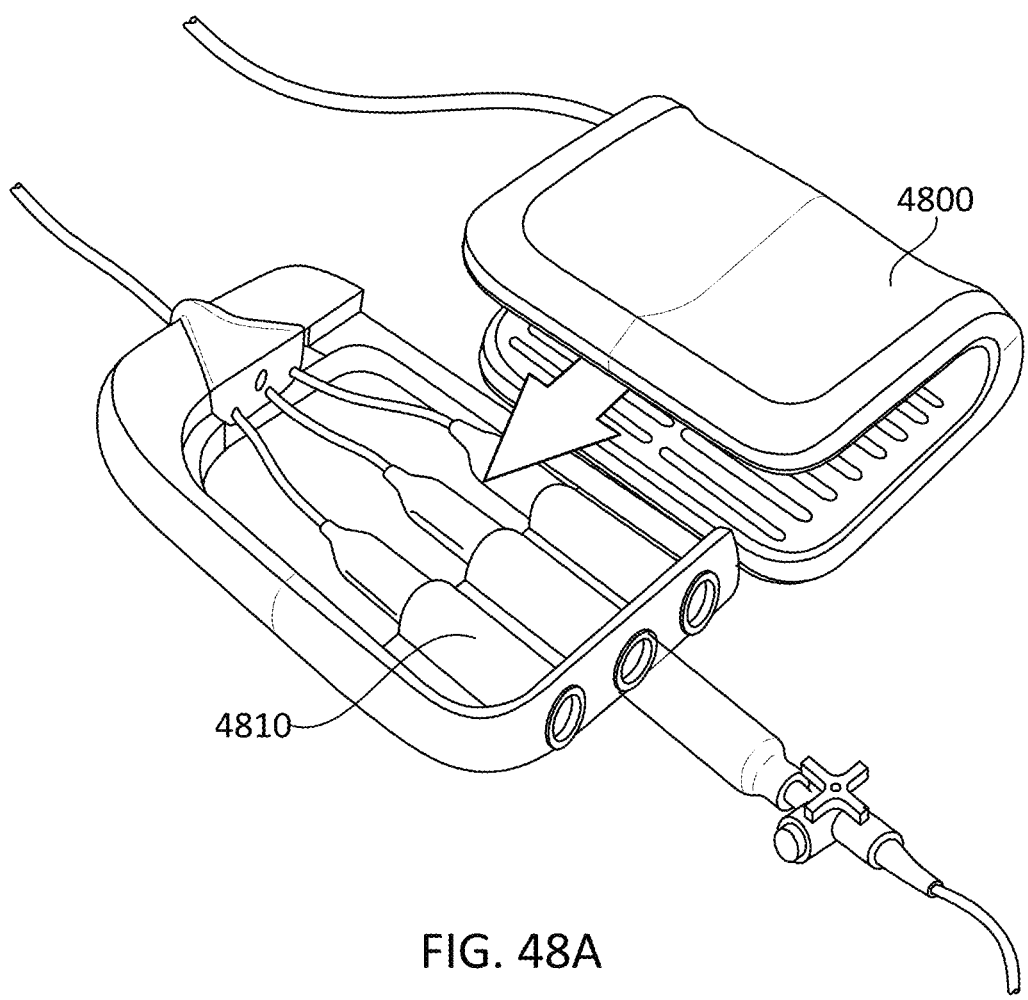
FIGS. 48A-D show various views of embodiments of a disposable catheter hub and transparent manifold adapter adapted and configured to releasably couple to a C-shaped UV LED disinfecting unit.
Figure 48B:
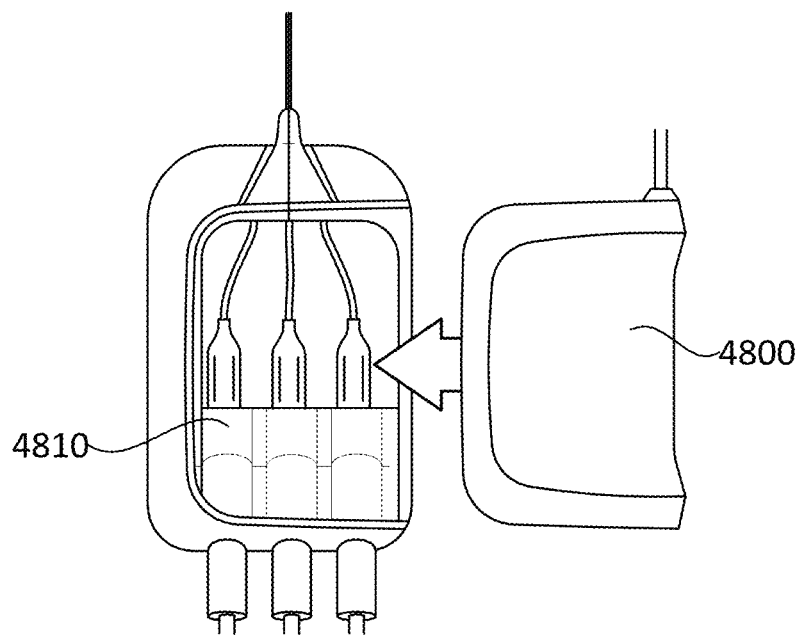
Figure 48C:
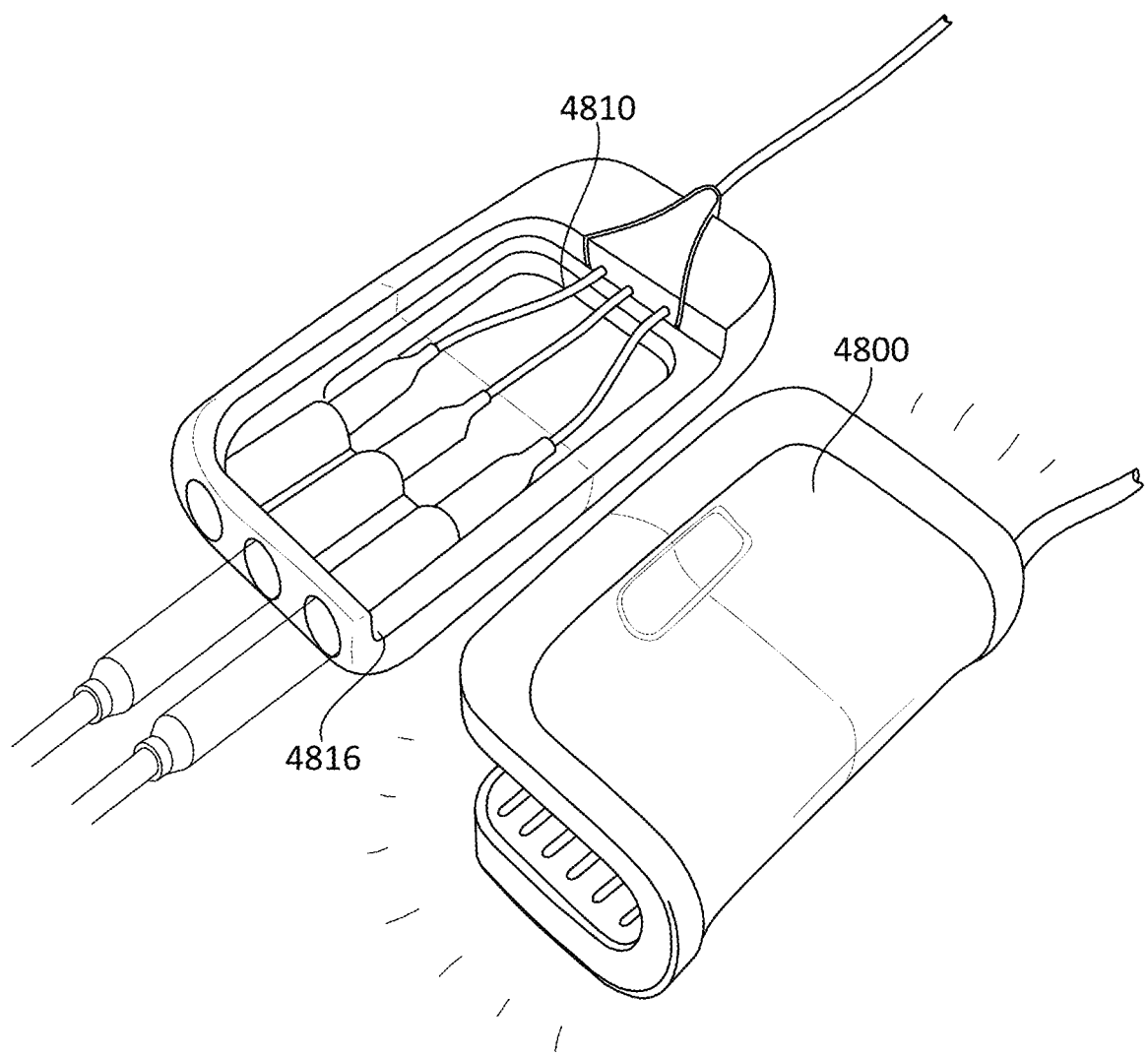
Figure 48D:
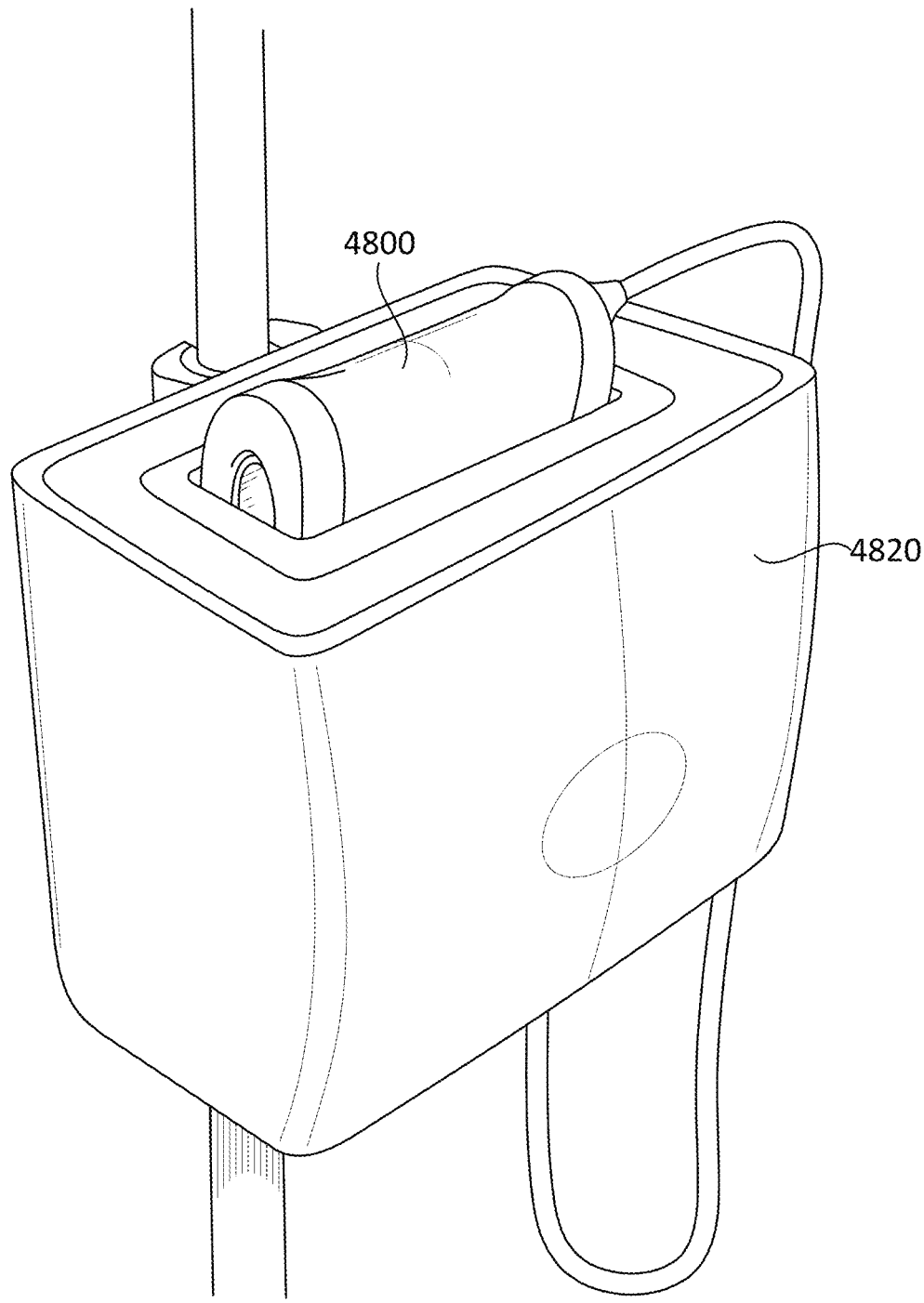

FIG. 48A is a perspective view of a disposable catheter hub and transparent manifold adapter 4810 adapted and configured to releasably couple to a C-shaped UV LED disinfecting unit 4800. In this view the disinfecting unit 4800 is positioned just prior to sliding across and into position placing the lighting array over, alongside and below the catheter hub and manifold 4810 during use. The disinfecting unit 4800 includes an interior geometry and features adapted and configured to slide along and be releaseably coupled to corresponding features on the catheter hub and mount. The disinfecting unit 4800 can have a non-slip exterior. FIG. 48B is a top view of the catheter hub and disinfecting unit of FIG. 48A. FIG. 48C shows how the disinfecting unit 4800 slides over a molded in track 4816 of the manifold 4810 that mates with a feature on the C-shaped disinfecting lumen to help ensure proper alignment of the two. FIG. 48D is a perspective view of the disinfecting unit 4800 in position within a pole mounted power and control unit 4820.

Figure 49A:
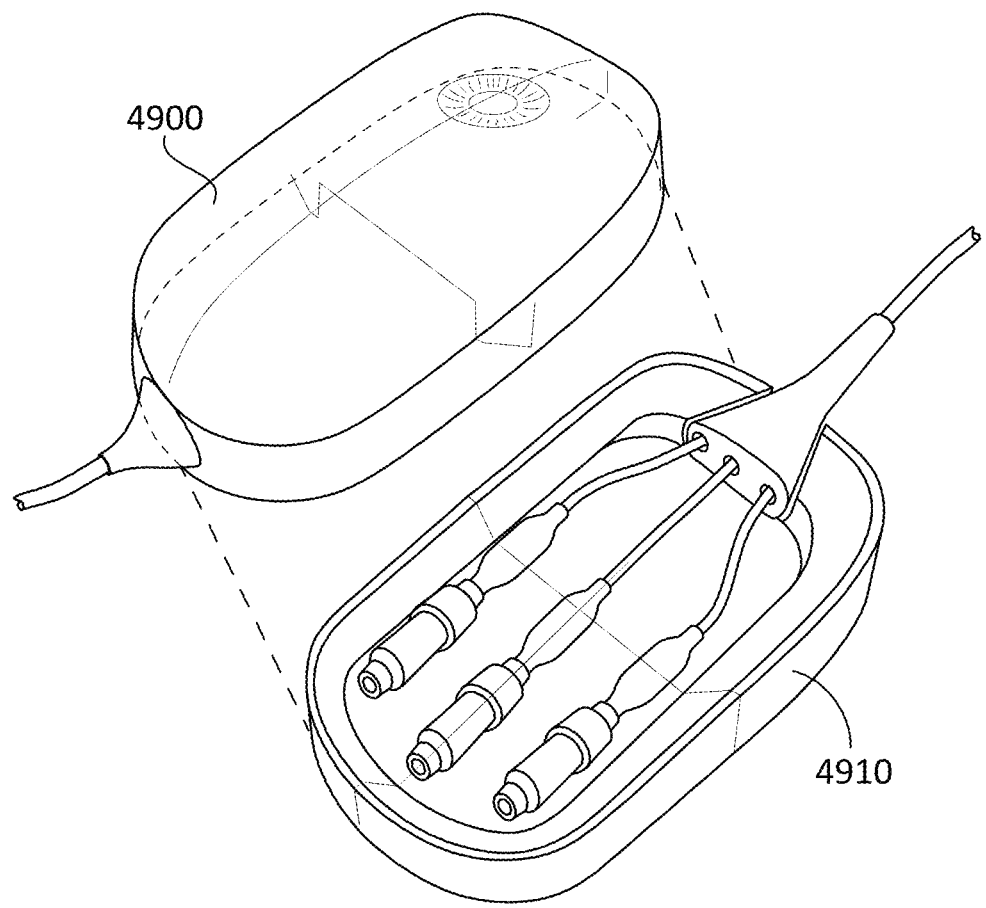
FIGS. 49A-49C show various views of embodiments of a disposable catheter hub with adapter mounts in a manifold tray and a hand held UV LED disinfecting unit adapted and configured to releaseably engage with the manifold tray.
Figure 49B:
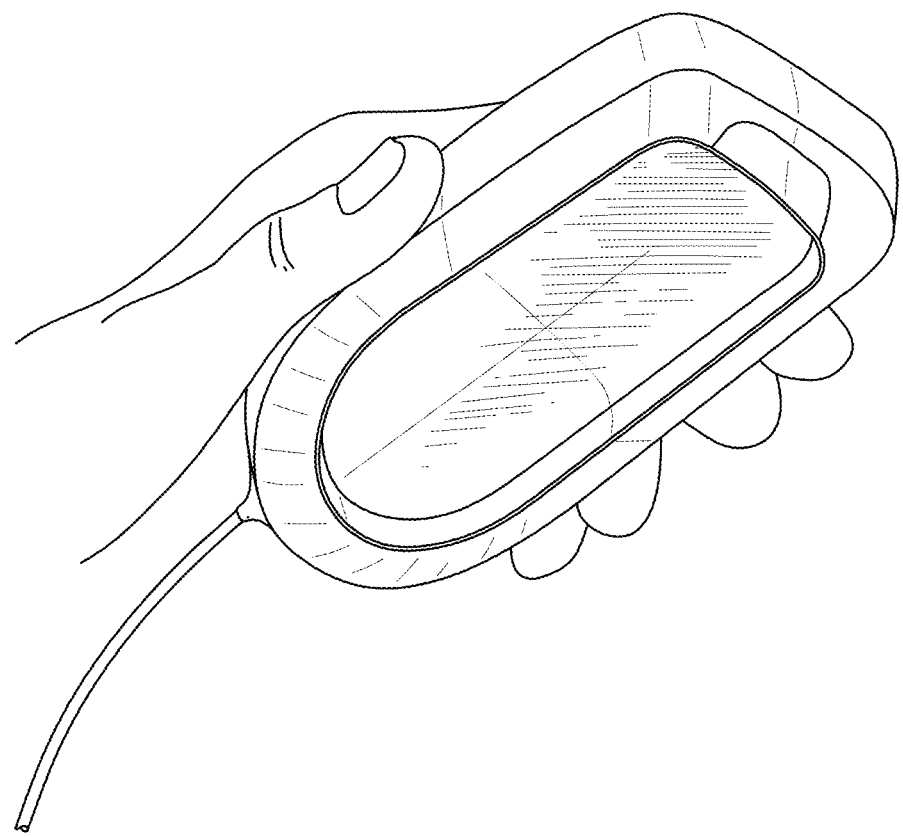
Figure 49C:
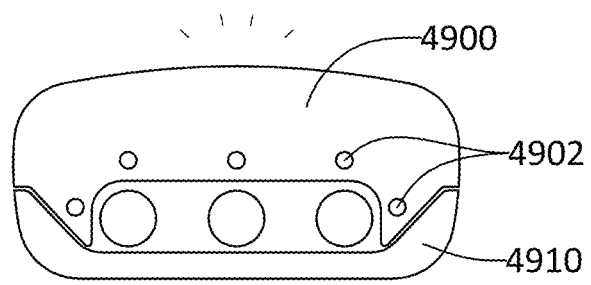

FIG. 49A is a perspective view of a catheter hub with adapter mount in a manifold tray 4910. Also shown in this view is a hand held UV LED disinfecting unit 4900 adapted and configured to releaseably engage with the manifold tray 4910. In this view, the disinfecting unit is positioned over the manifold with dashed lines indicating the direction for engaging with the manifold. The manifold 4910 may also include one or more retention features in addition to or in combination with sidewall or edge geometry to engage with complementary features in the disinfecting unit. FIG. 49B is a bottom up perspective view of the disinfecting unit illustrating the interior geometry and features adapted and configured to be releaseably coupled to corresponding features on the manifold tray 4910. The unit 4900 may comprise a large bevel to allow for a secure and consistent overlap of the UV device 4900 and tray 4910. FIG. 49C is an section view of the disinfecting unit 4900 coupled to the manifold tray 4910 showing engaged sidewall geometry and an arrangement of UV LED lights 4902 within the disinfecting unit 4900.

Figure 50A:
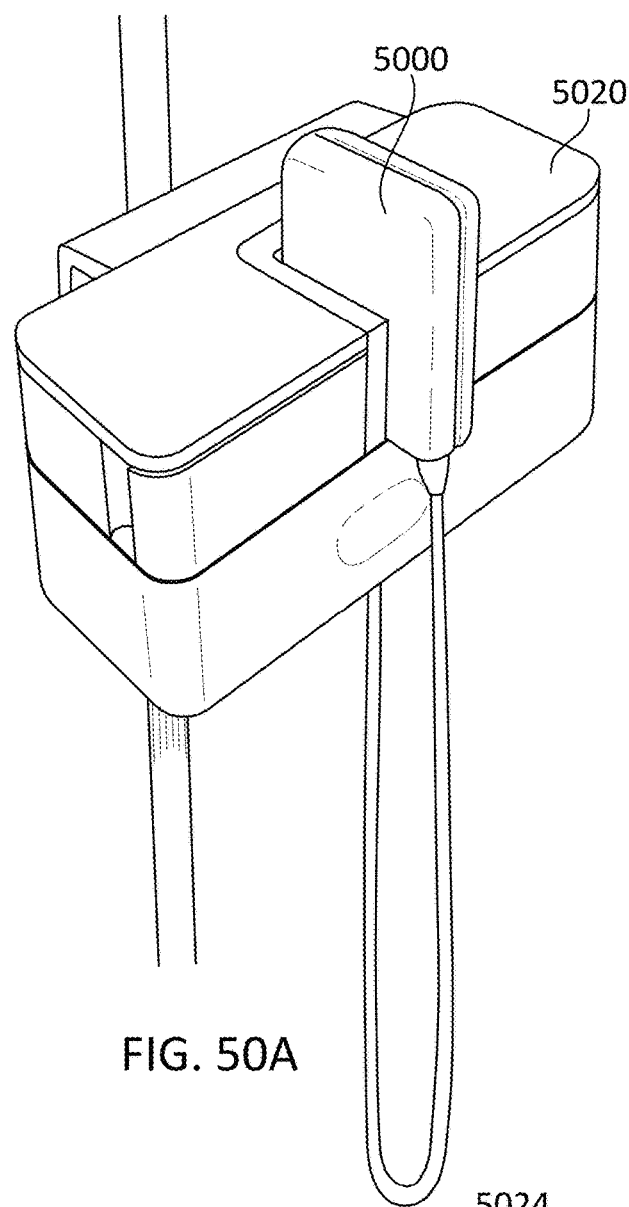
FIG. 50A shows an embodiment of a handheld UV disinfecting unit in a stowed configuration on a pole mounted power and control unit.

FIG. 50A is a handheld UV disinfecting unit 5000 in a stowed configuration on a pole mounted power and control unit 5020. FIG. 50B illustrates a perspective view of additional or alternative details of storage and charging configurations for the UV power and control console of FIG. 33A wherein the UV power and control module has storage areas 5022 that can also be used to store additional universal adapters, catheter hub and adapter mounts, adhesive mounts, etc. The console 5020 also has a holster 5024 with charging contacts for storing and charging the unit 5000.

Figure 50C:
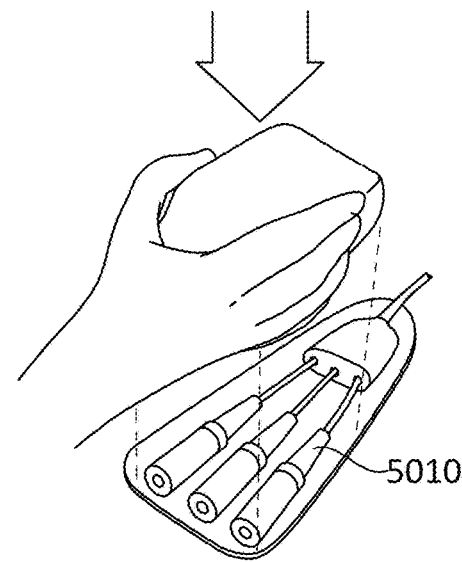
FIG. 50C is a perspective view of the handheld UV disinfecting unit of FIG. 50A in position above a catheter hub and manifold configured to receive the handheld UV disinfecting unit.
Figure 50B:
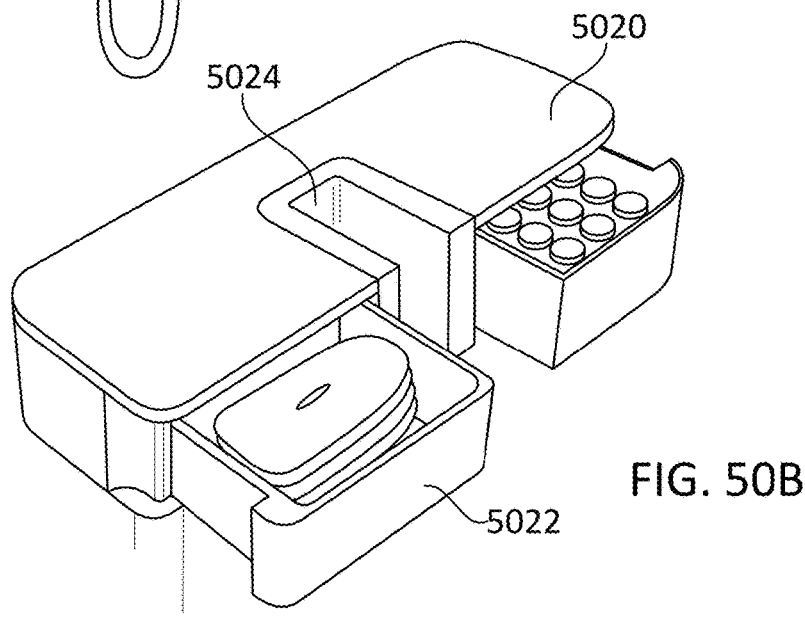
FIG. 50B illustrates a perspective view of additional or alternative details of storage and charging configurations for the UV power and control console of FIG. 50A.

FIG. 50C is a perspective view of the handheld UV disinfecting unit 5000 in position above a catheter hub and manifold 5010 configured to receive the handheld UV disinfecting unit 5000.

Figure 51C:
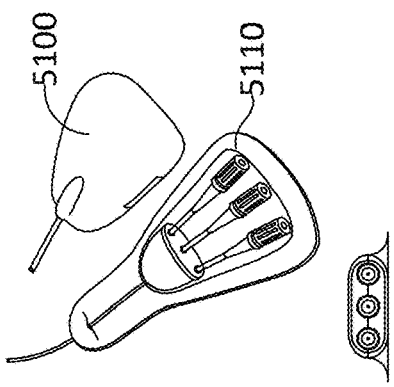
FIG. 51C is a perspective view of the handheld UV disinfecting unit of FIGS. 51A and 51B in position above a catheter hub and manifold configured to receive the handheld UV disinfecting unit.
Figure 51D:
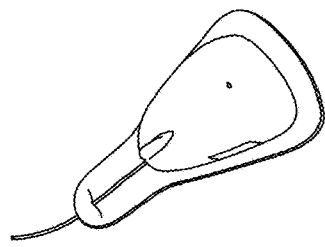
FIG. 51D is a close up perspective view of the handheld disinfecting unit in use as shown in FIG. 51A.
Figure 51B:
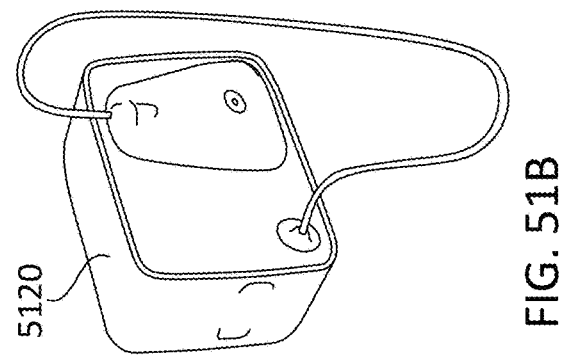
FIG. 51B shows a close up view of the disinfection control and power module of FIG. 51A with the handheld UV disinfecting unit in a stowed configuration.
Figure 51A:
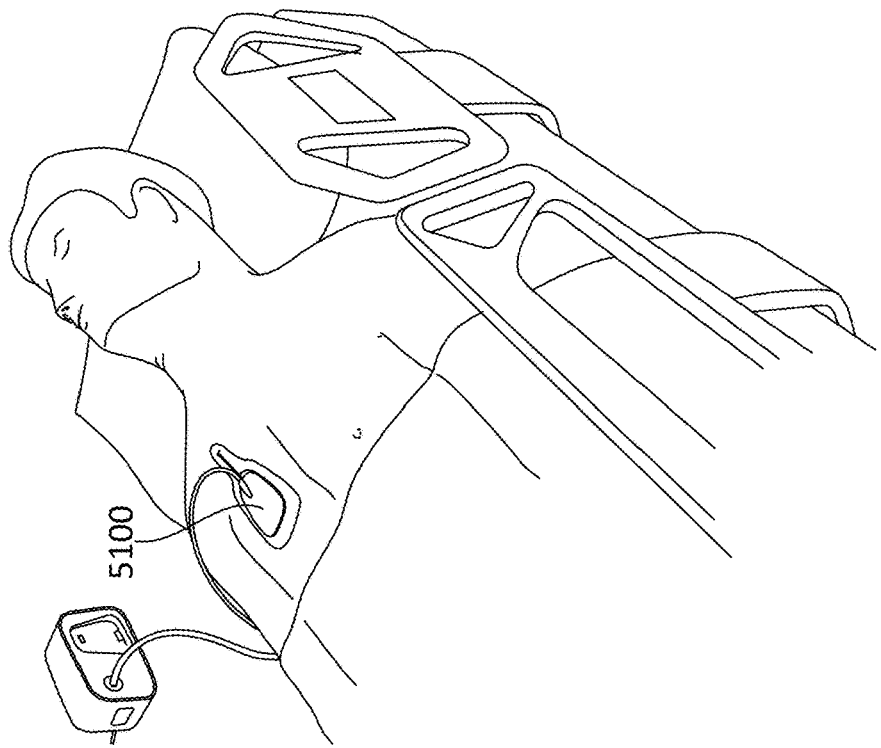
FIG. 51A is a perspective view of a handheld UV disinfecting unit in use on a patient having a catheter hub and manifold configured to receive the handheld UV disinfecting unit.

FIG. 51A is a perspective view of a handheld UV disinfecting unit 5100 in use on a patient having a catheter hub and manifold configured to receive the handheld UV disinfecting unit. FIG. 51B is a close up view of the disinfection control and power module 5120 of FIG. 51A with the handheld UV disinfecting unit in a stowed configuration. FIG. 51C is a perspective view of the handheld UV disinfecting unit 5100 in position above a catheter hub and manifold mount 5110 configured to receive the handheld UV disinfecting unit 5100. FIG. 51D is a close of perspective view of the handheld disinfecting unit 5100 in use as shown in FIG. 51A.

Figure 52C:
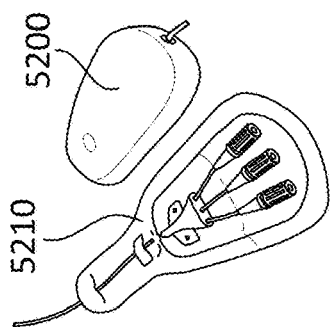
FIG. 52C is a perspective view of the handheld UV disinfecting unit of FIGS. 52A and 52B in position above a catheter hub and manifold configured to receive the handheld UV disinfecting unit.
Figure 52D:
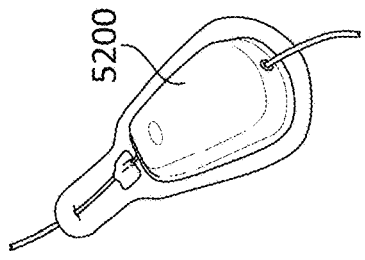
FIG. 52D is a close up perspective view of the handheld disinfecting unit in use as shown in FIG. 35A.
Figure 52B:
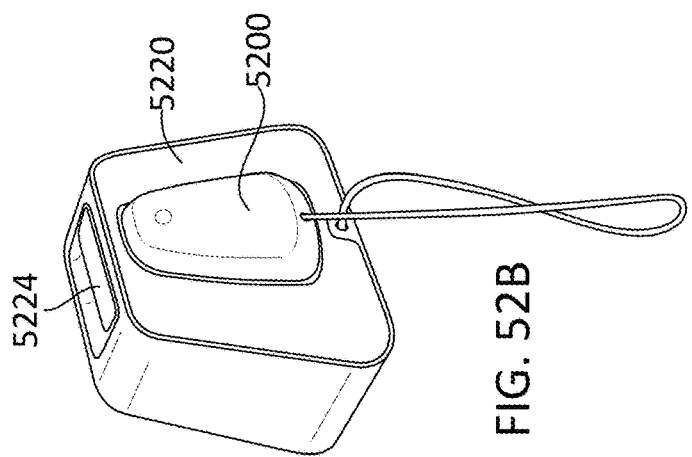
FIG. 52B shows a close up view of the disinfection control and power module of FIG. 52A with the handheld UV disinfecting unit in a stowed configuration.
Figure 52A:
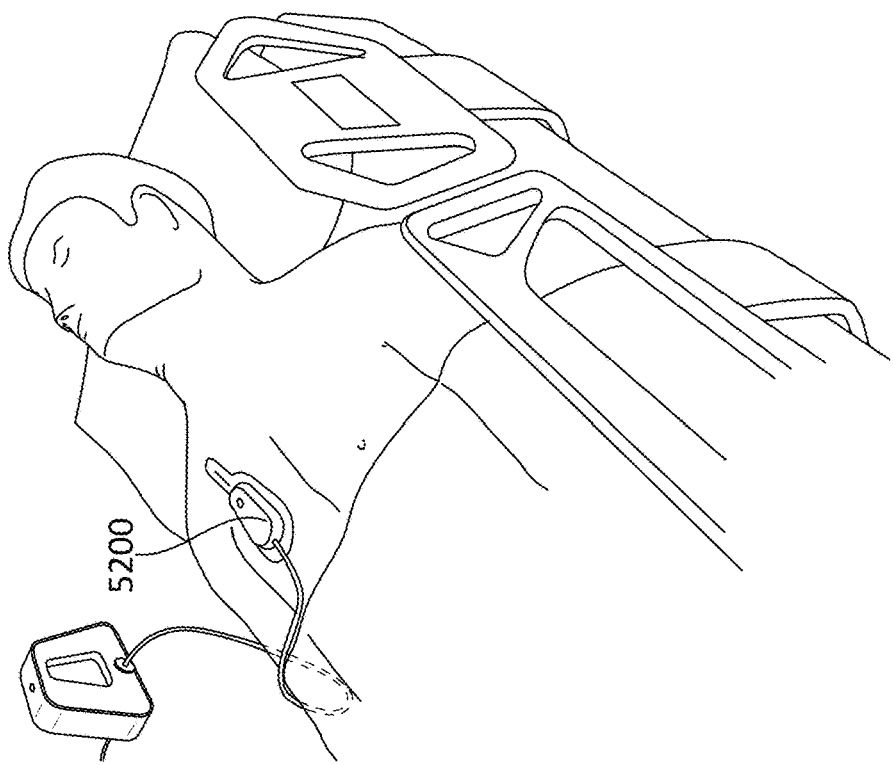
FIG. 52A is a perspective view of an embodiment of a handheld UV disinfecting unit in use on a patient having a catheter hub and manifold configured to receive the handheld UV disinfecting unit.

FIG. 52A is a perspective view of a handheld UV disinfecting unit 5200 in use on a patient having a catheter hub and manifold mount configured to receive the handheld UV disinfecting unit 5200. FIG. 52B is a close up view of the disinfection control and power module 5220 of FIG. 52A with the handheld UV disinfecting unit in a stowed configuration. The module 5220 has a handle 5224 for easy on handle repositioning. FIG. 52C is a perspective view of the handheld UV disinfecting unit 5200 in position above a catheter hub and manifold 5210 configured to receive the handheld UV disinfecting unit. FIG. 52D is a close of perspective view of the handheld disinfecting unit 5200 in use as shown in FIG. 35A.

Figure 53D:
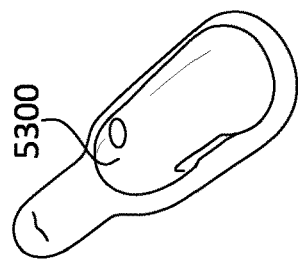
FIGS. 53D and 53E are close up of perspective views of the handheld disinfecting unit of FIG. 53A in position on the catheter hub and during activation for use.
Figure 53E:
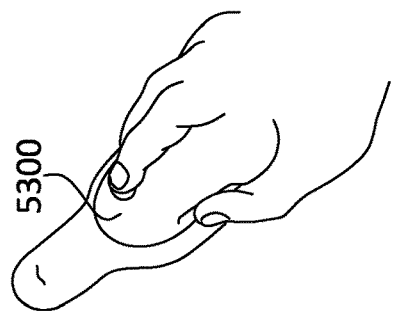
Figure 53B:
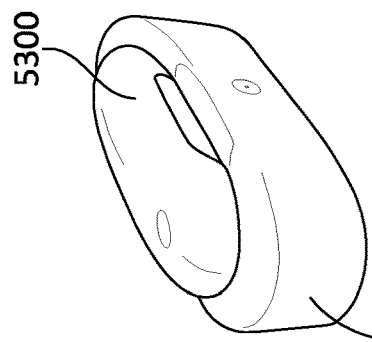
FIG. 53B shows a close up view of the disinfection control and power module of FIG. 53A with the handheld UV disinfecting unit in a stowed and charging configuration.
Figure 53C:
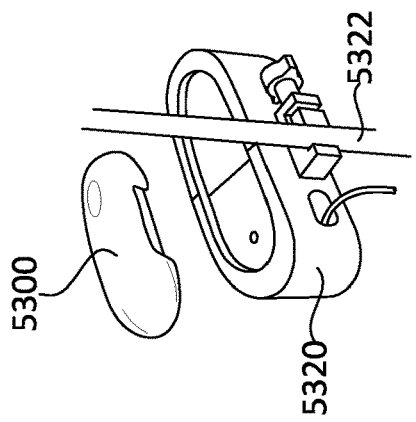
FIG. 53C is a perspective view of the handheld UV disinfecting unit of FIGS. 53A and 53B in position above a power charging and control unit mounted on a pole to enable alternative bedside use.
Figure 53A:
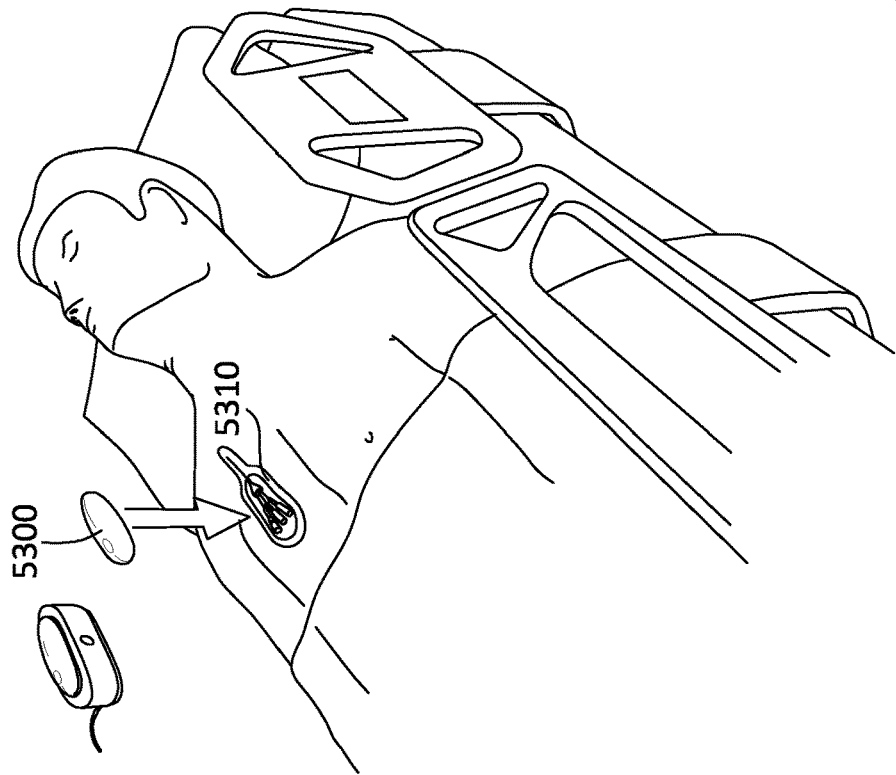
FIG. 53A is a perspective view of an embodiment of a wireless handheld UV disinfecting unit for use on a patient having a catheter hub and manifold configured to receive the handheld UV disinfecting unit.

FIG. 53A is a perspective view of a rechargeable battery powered wireless handheld UV disinfecting unit 5300 with arrows indicating direction for use on a patient having a catheter hub and manifold mount 5310 configured to receive the handheld UV disinfecting unit. FIG. 53B shows a close up view of the recharging module 5320 of FIG. 53A with the handheld UV disinfecting unit 5300 in a stowed configuration. FIG. 53C is a perspective view of the handheld UV disinfecting unit 5300 in position above a recharging module 5320 mounted on a pole 5322 to enable alternative bedside use. FIGS. 53D and E are close up of perspective views of the handheld disinfecting unit 5300 in position on the catheter hub and during activation for use (FIG. 53E).

Figure 54A:
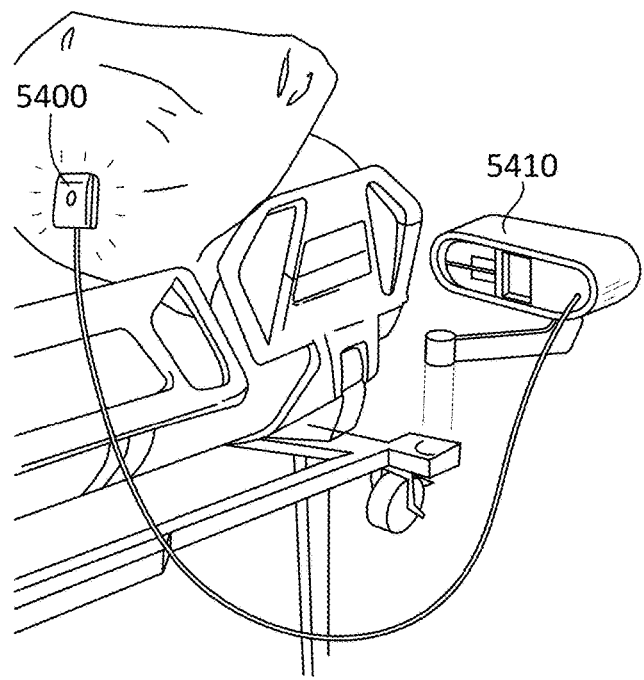
FIGS. 54A and 54B are perspective views of another embodiment of a handheld UV disinfecting unit having a hospital bed mounted control and power unit.
Figure 54B:
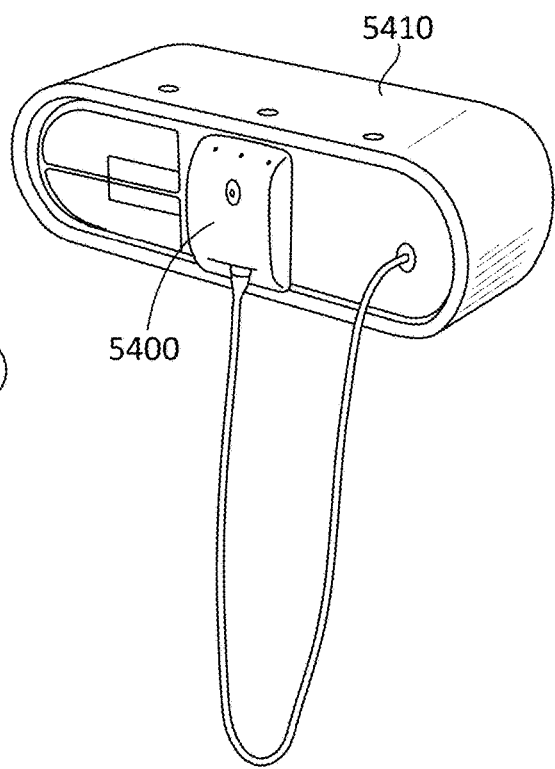

FIG. 54A is a perspective view of another handheld UV disinfecting unit 5400 having a hospital bed mounted control and power unit 5410 on a pole mounted to the side of the bed. FIG. 54B shows a close up view of the disinfection control and power module 5410 with the handheld UV disinfecting unit 5400 in a stowed configuration.

Figure 55A:
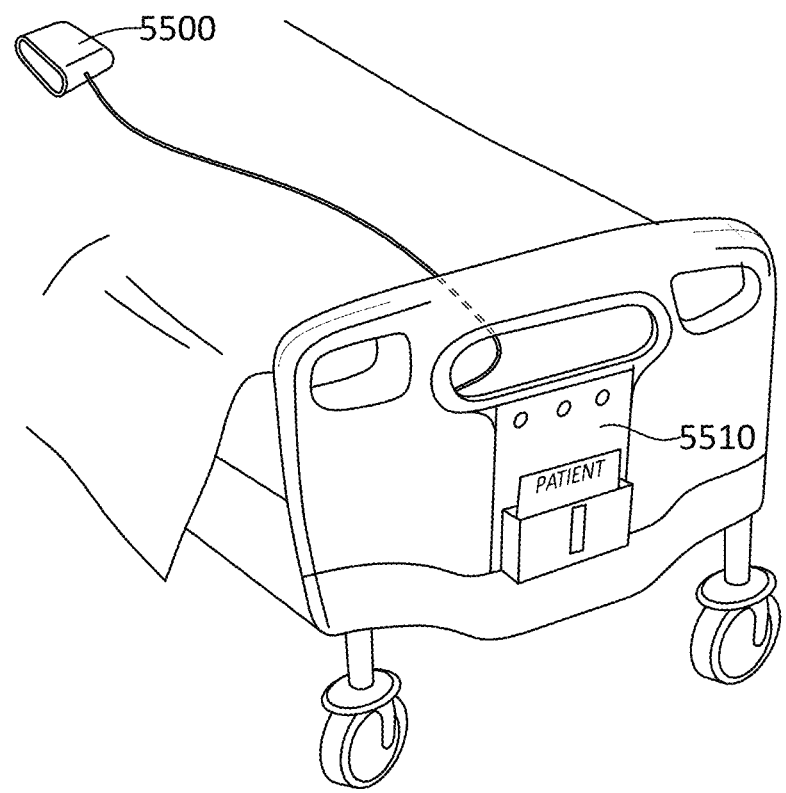
FIGS. 55A and 55B are perspective views of another embodiment of a UV disinfecting unit having an integrated hospital bed mounted display and control and power unit.
Figure 55B:
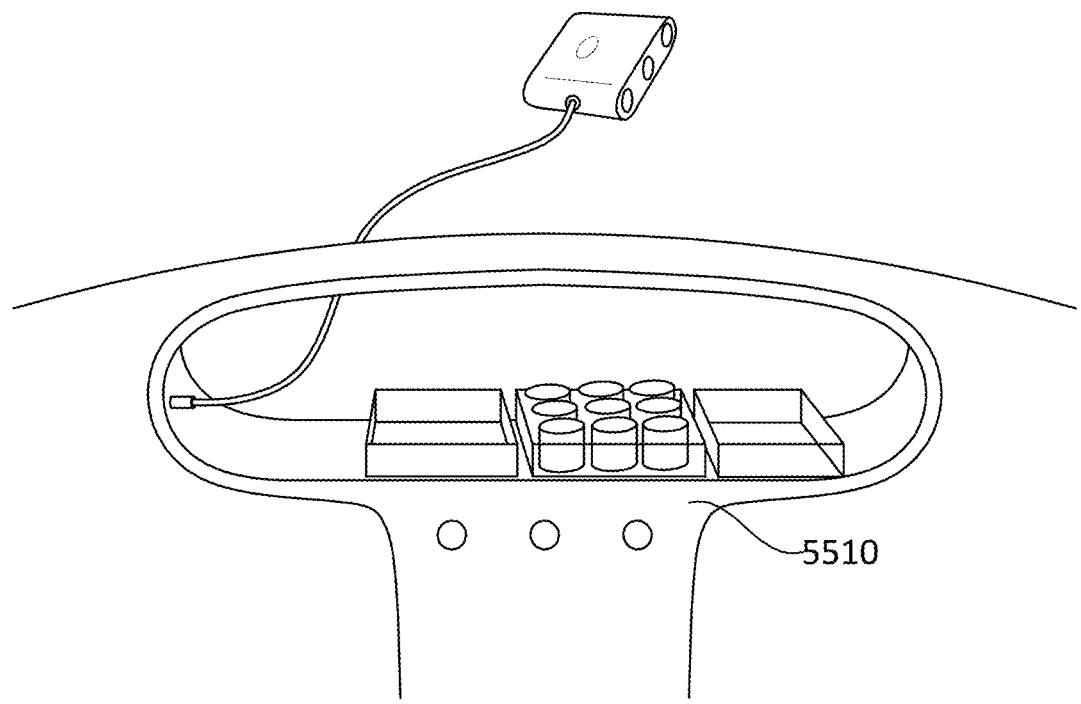

FIG. 55A is a perspective view of another UV disinfecting unit 5500 having an integrated hospital bed mounted display and control and power unit 5510. FIG. 55B shows close up view of the disinfection control and power module 5510 and indications for the UV disinfecting unit.

Figure 56:
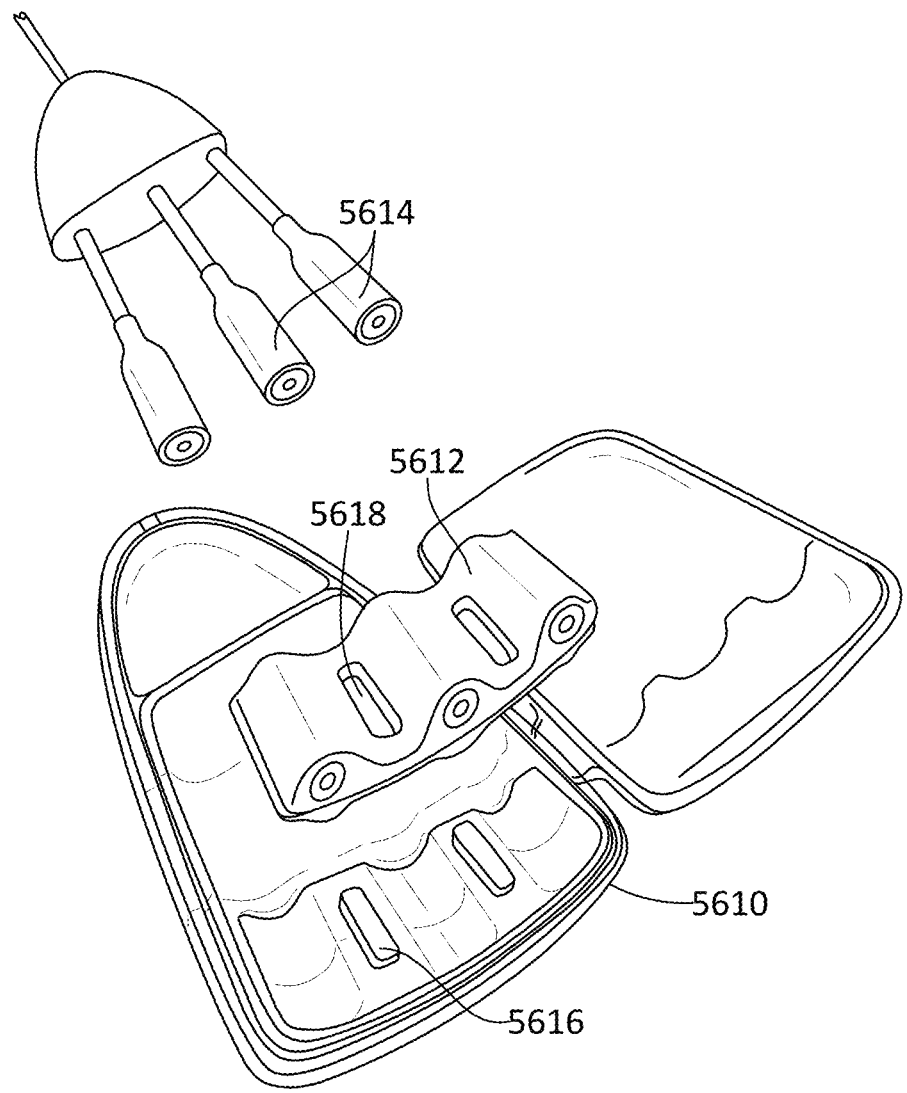
FIGS. 56-58 is a perspective view of embodiments of a hinged mounting base configured to receive a manifold adapter configured to secure three lumens.

FIG. 56 is perspective view of a hinged mounting base 5610 configured to receive a manifold adapter 5612 configured to secure three catheter hub lumens 5614. The lid is shown in the open configuration and before the three lumens 5614 are coupled to the manifold adapter 5612. Tabs 5616 on the mounting base 5610 are configured to interact with slots on the adapter 5618 to hold the adapter in place.

Figure 57:
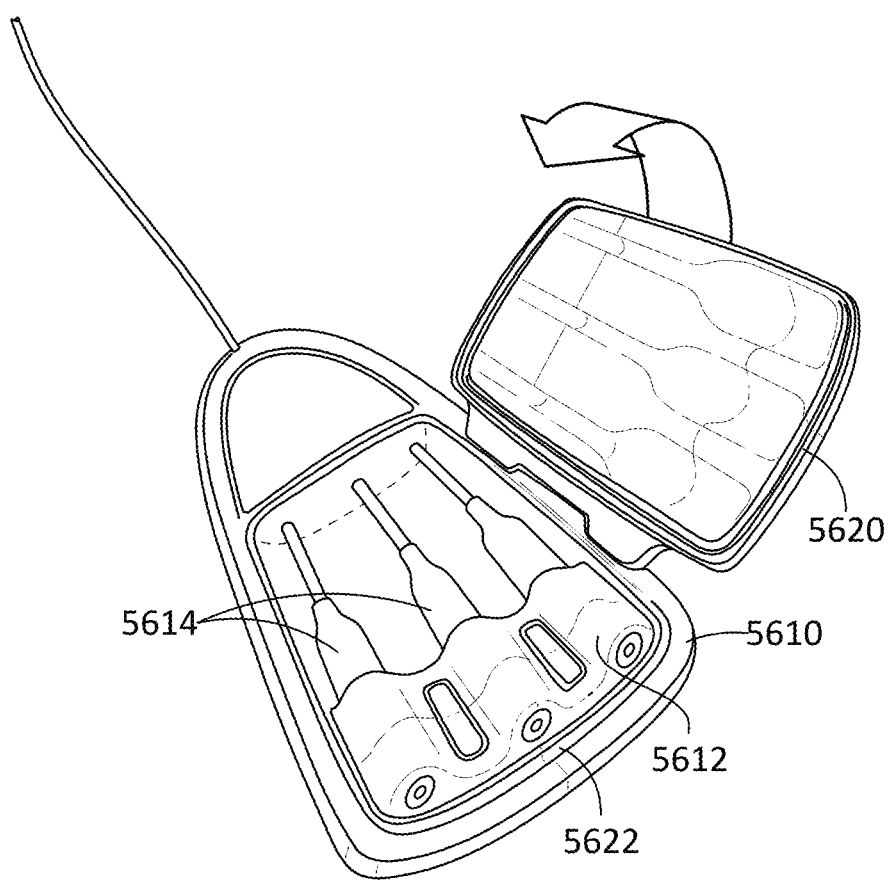
Figure 58:
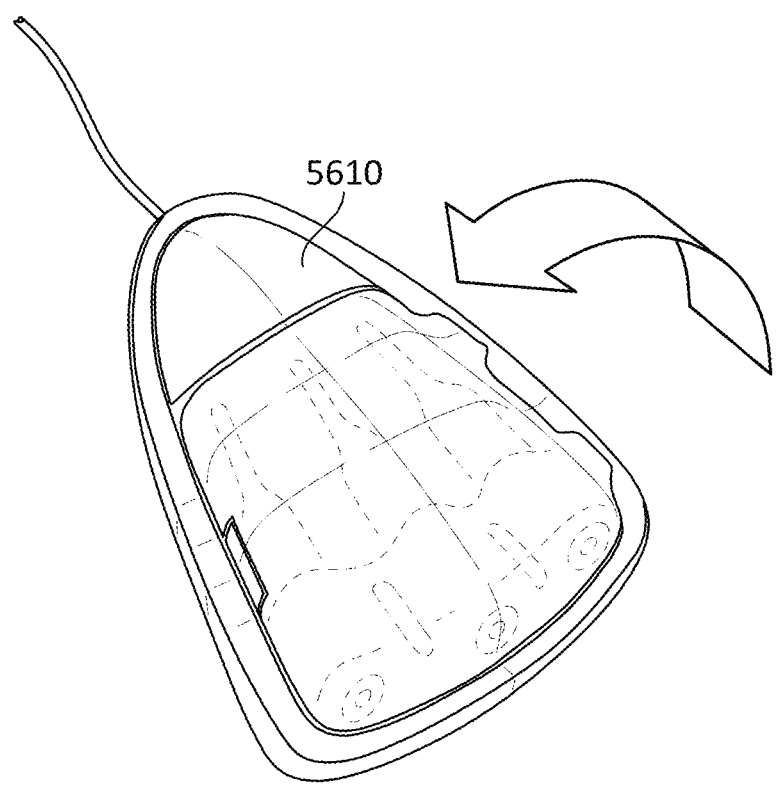
Figure 59:
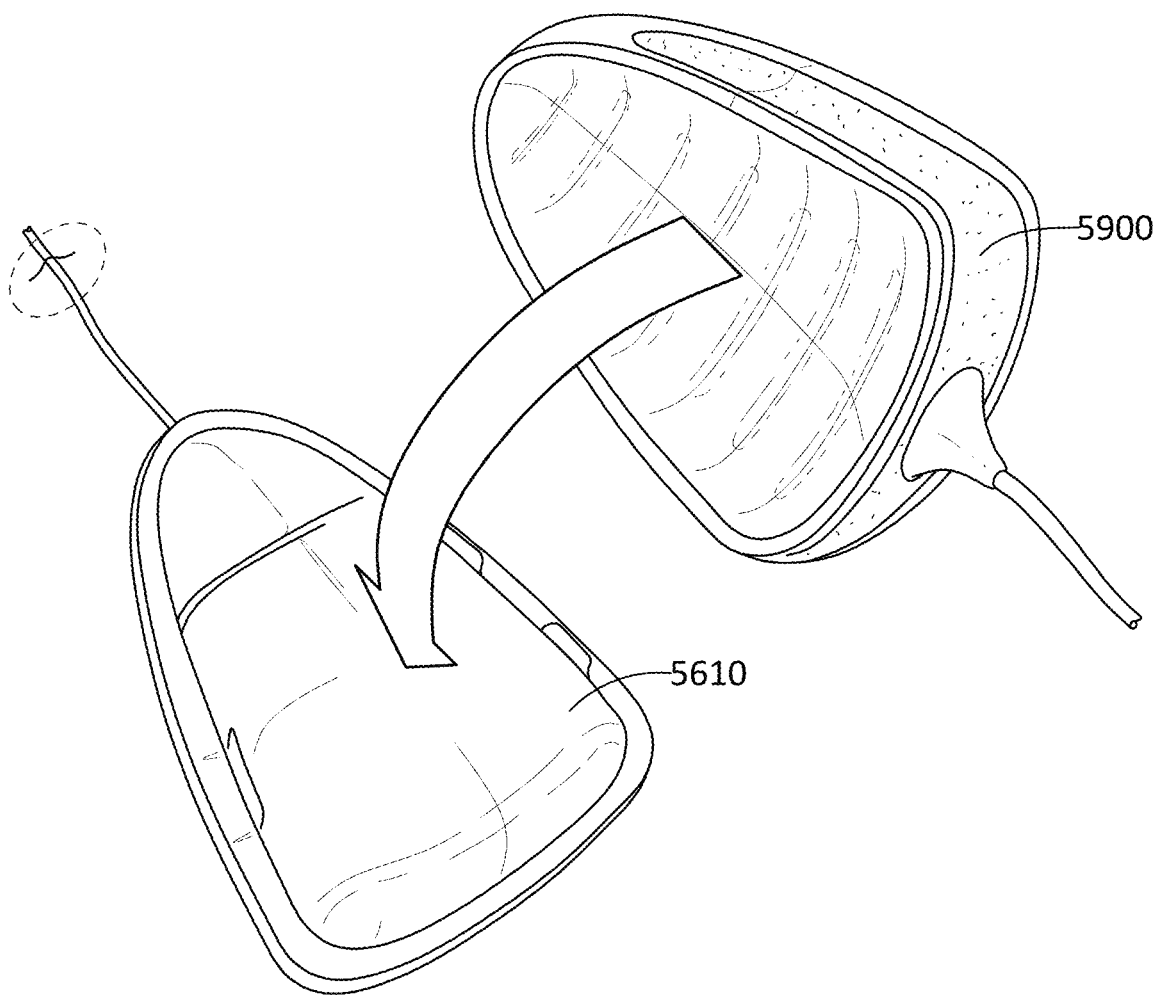
FIG. 59 is a perspective view of an embodiment of a hand held disinfecting unit adapted and configured to engage with the lid and base of the manifold of FIG. 56.

FIG. 57 is a perspective view of the hinged mounting base 5610 with the catheter hub lumens 5614 within the manifold and the manifold 5612 secured into the mounting base 5610. The lid of the mounting base 5610 comprises gaskets 5620 that are received by a recess 5622 in the base portion. FIG. 58 is a perspective view of the hinged mounting base 5610 with the lid closed. FIG. 59 is a perspective view of a hand held disinfecting unit 5900 adapted and configured to engage with the lid and base of the manifold 5610. The hinged mounting base 5610 is completely enclosed to provided protection to the catheter hub lumens and the manifold adapter from contamination due to dirt, body fluids, touch contamination, etc. By completely enclosing the catheter lumen hubs and manifold adapter with a UVC transparent material, the hinge mounting base allows UV light disinfection of the hubs and adapter without opening the mounting base. The disinfection unit 5900 can have a non slip rubber overmold and a concave interior to conform to the convex exterior of the mounting base 5610.

Figure 60:
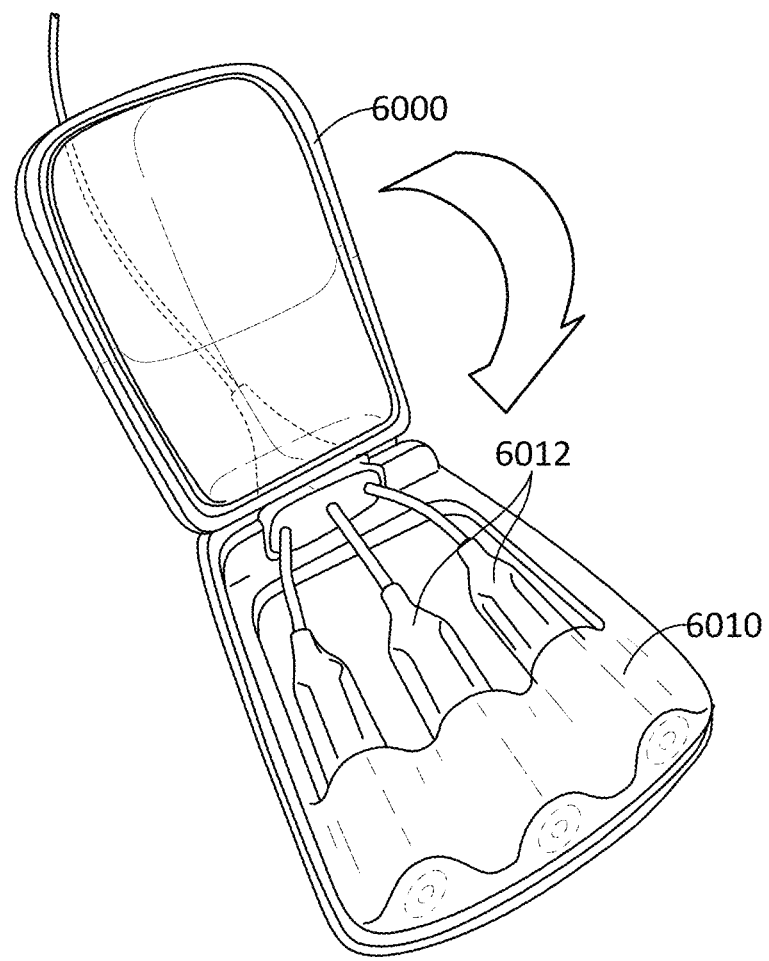
FIG. 60 is perspective view of an embodiment of a rear hinged mounting base configured to receive a manifold adapter configured to secure three lumens.

FIG. 60 is a perspective view of a rear hinged mounting base 6002 configured to receive a manifold adapter 6010 configured to secure three lumens 6012. The lid is shown in the open configuration and with the three lumens 6012 coupled to the manifold adapter 6010 within the interior. When the lid is closed, the hinged mounting base is configured for disinfection similar to the manner illustrated in FIG. 59 using a hand held disinfecting unit configured for that purpose.

Figure 61A:
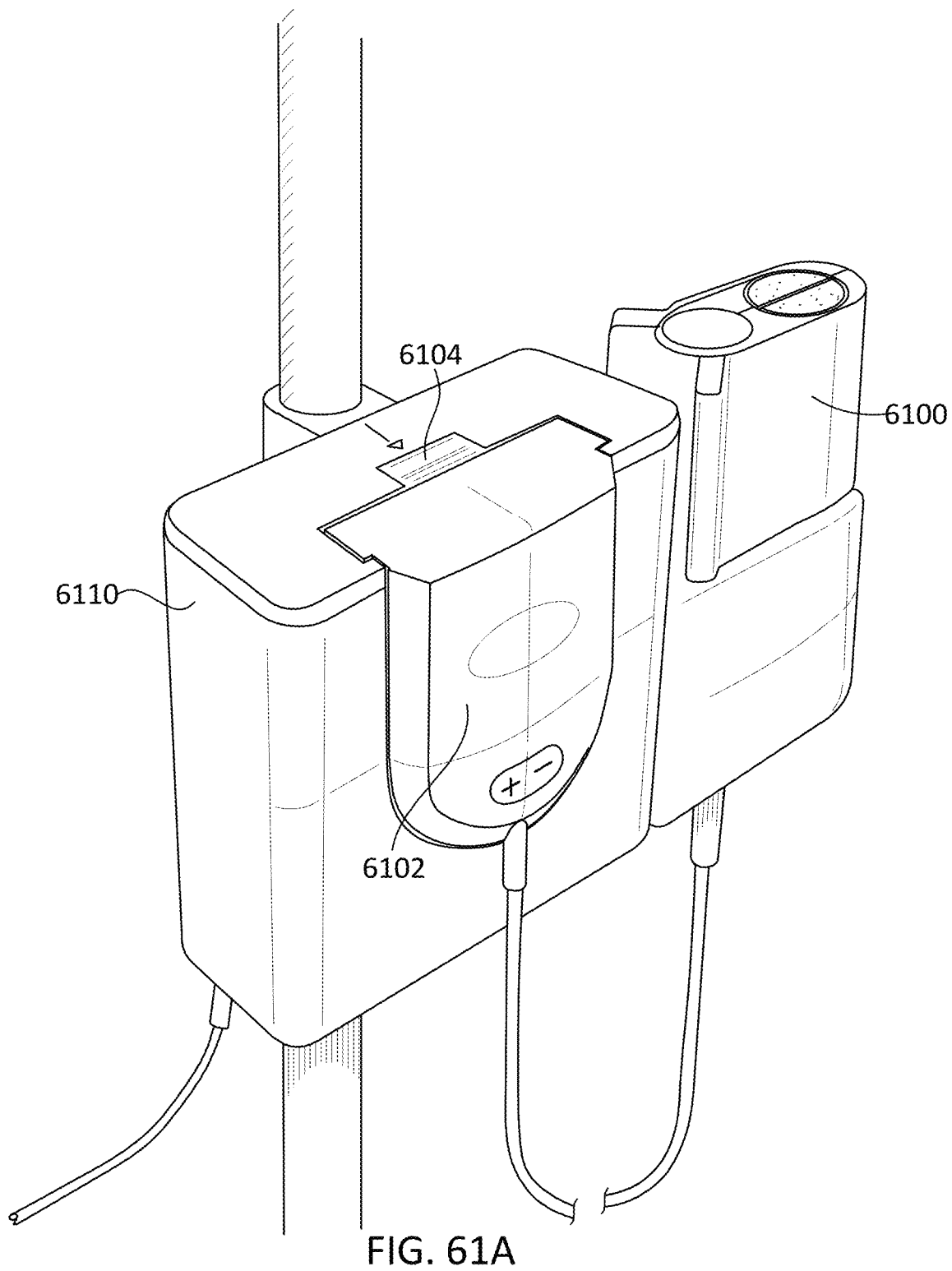
FIGS. 61A and 61B are perspective views of embodiments of a hand held UV disinfecting unit and mobile power pack in a pole mounted power controller base.

FIG. 61A is a perspective view of a hand held UV disinfecting unit 6100 in a pole mounted power controller base 6110 with modifications for portable use. In the view of FIG. 61A, the handheld UV disinfecting unit 6100 and the mobile power pack 6102 are shown in the stowed position within specifically configured receptacles of the power controller base 6110. A quick release feature 6104 allows release of the mobile power pack 6102.

Figure 61B:
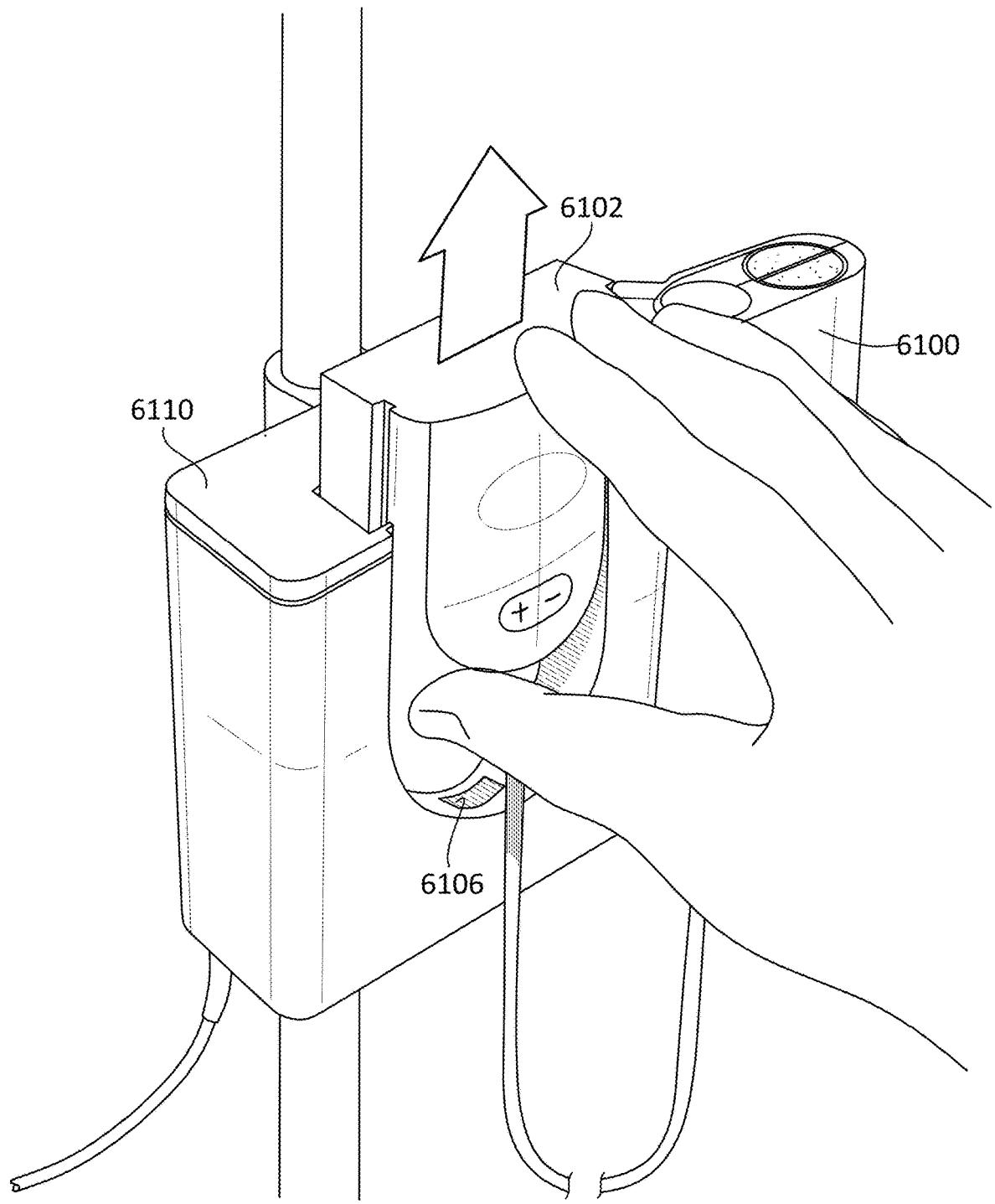

FIG. 61B is a perspective view of the mobile disinfecting unit 6100 illustrating the operation of a power pack 6102 quick release and movement of the mobile power pack 6102 out of the configured receptacle in the power controller base 6110. Also visible in this view is the power charging contact 6106 in the lower portion of the power pack receptacle.

Figure 61C:
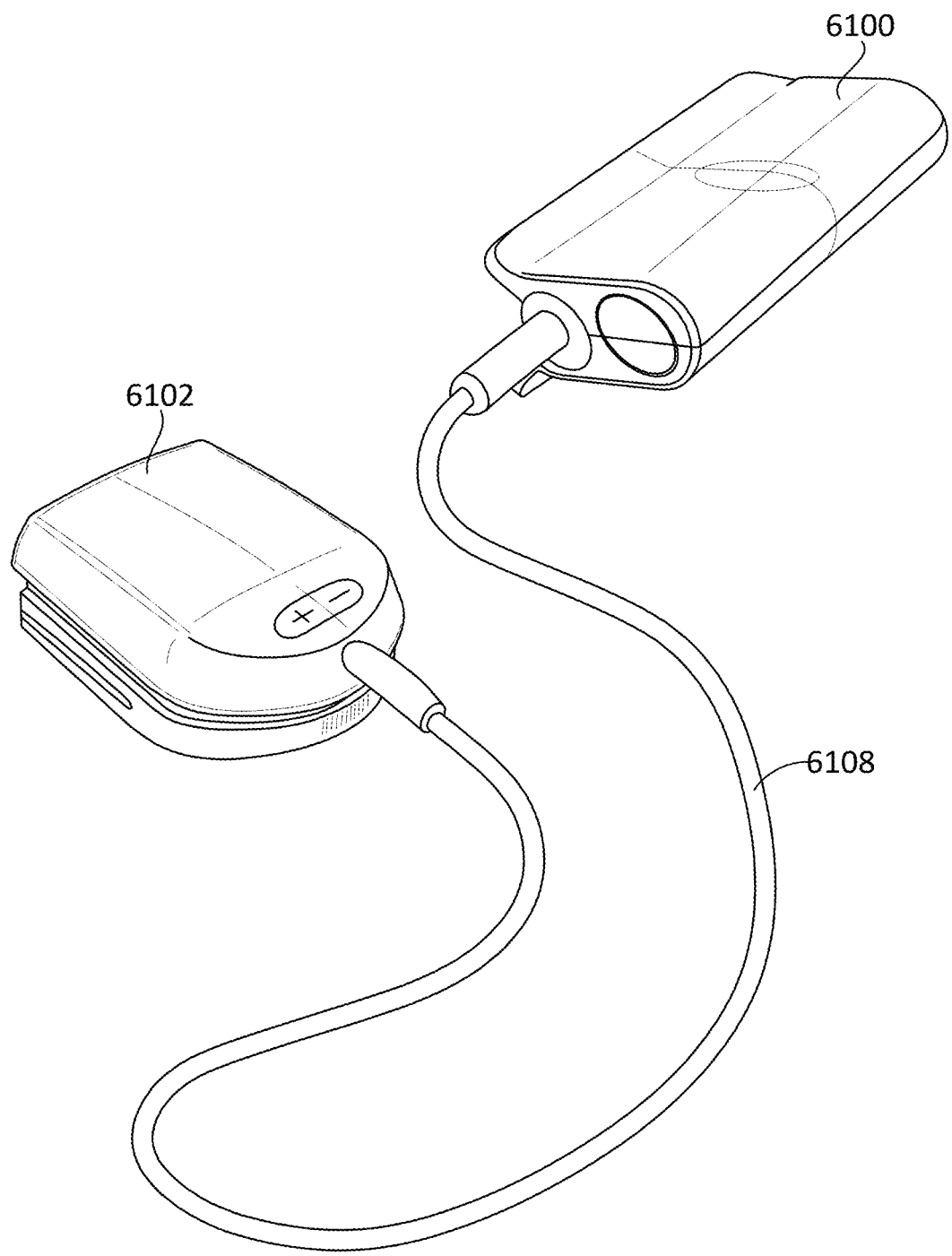
FIG. 61C is a perspective view of the handheld UV disinfecting unit and mobile power pack of FIG. 61A.

FIG. 61C is a perspective view of the handheld UV disinfecting unit 6100 and mobile power pack 6102 after each has been removed from the specific receptacles formed in the power controller base 6110. A power cable 6108 connects the two.

Figure 61D:
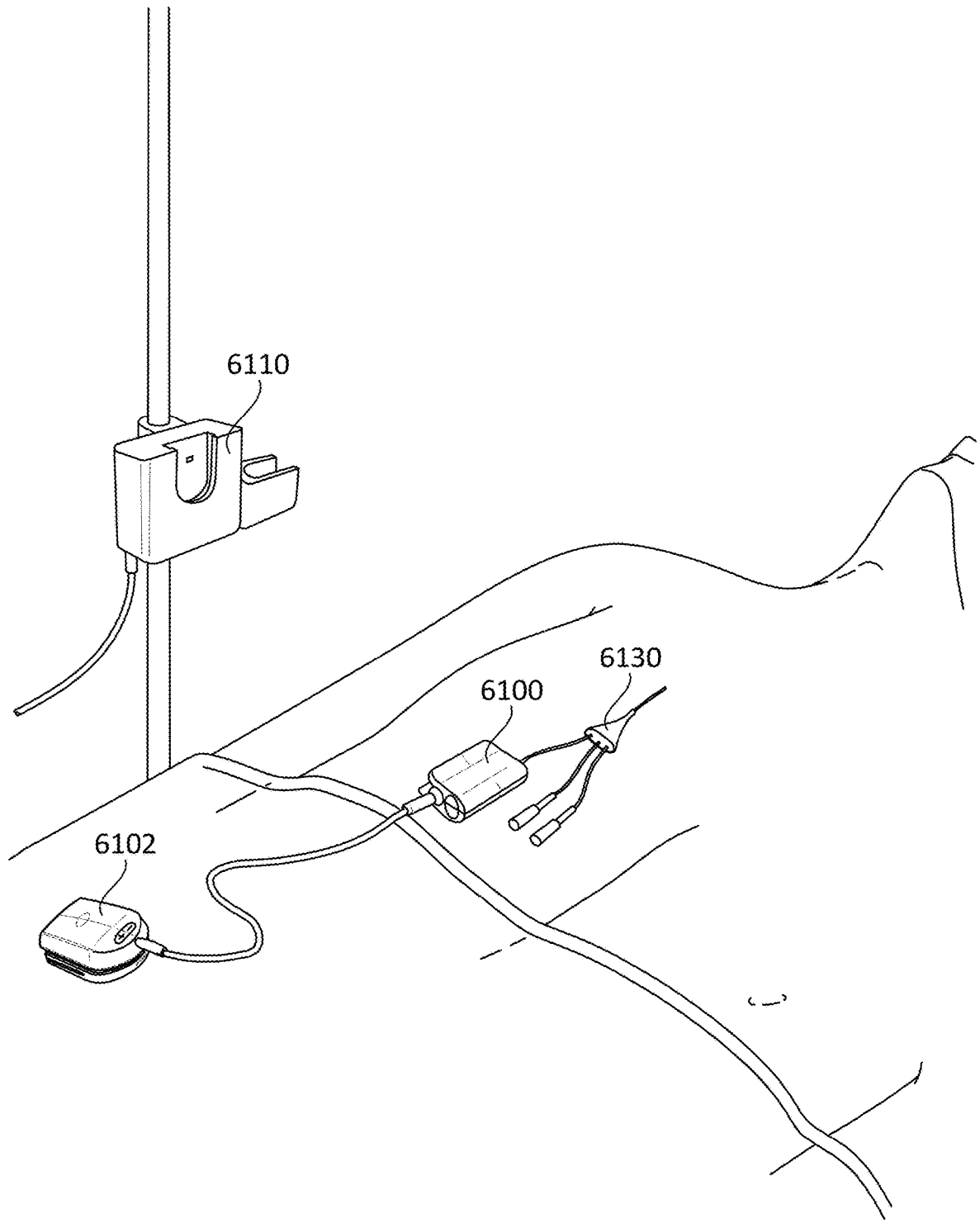
FIG. 61D is a perspective view of a patient having an implanted catheter hub with the portable disinfecting unit of FIG. 61C in position to disinfect one of the lumens of the catheter hub.

FIG. 61D is a perspective view of a patient having an implanted catheter hub with the portable disinfecting unit 6100 in position to disinfect one of the lumens of the catheter hub. The disinfecting unit 6100 is connected to the mobile power pack 6102 and can travel with the patient. The pole mounted power controller and base 6110 is shown in this view adjacent to the patient's hospital bed.

Figure 62A:
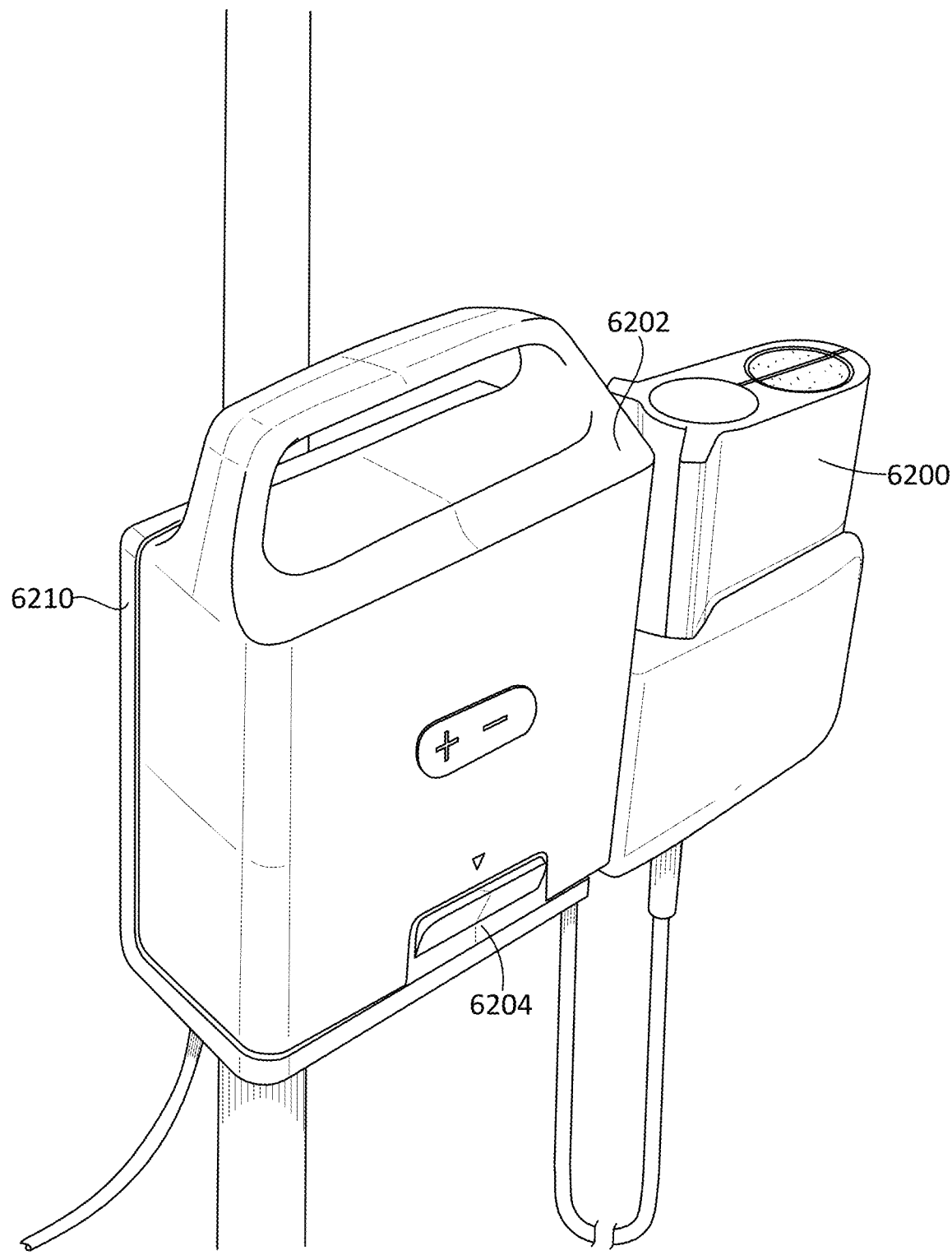
FIGS. 62A-62C are perspective views of another embodiment of a hand held UV disinfecting unit and mobile power pack in a pole mounted power controller base.

FIG. 62A is a perspective view of another hand held UV disinfecting unit 6200 in a pole mounted power controller base 6210 similar to those of FIGS. 62A-D with other modifications for portable use. Mobile power pack 6202 is shown mounted to the power controller base 6210. Quick release feature 6204 allows release of the mobile power pack 6202. In the view of FIG. 62A the handheld UV disinfecting unit 6200 and the mobile power pack 6202 are shown in the stowed position within specifically configured receptacles of the power controller base 6210.

Figure 62B:
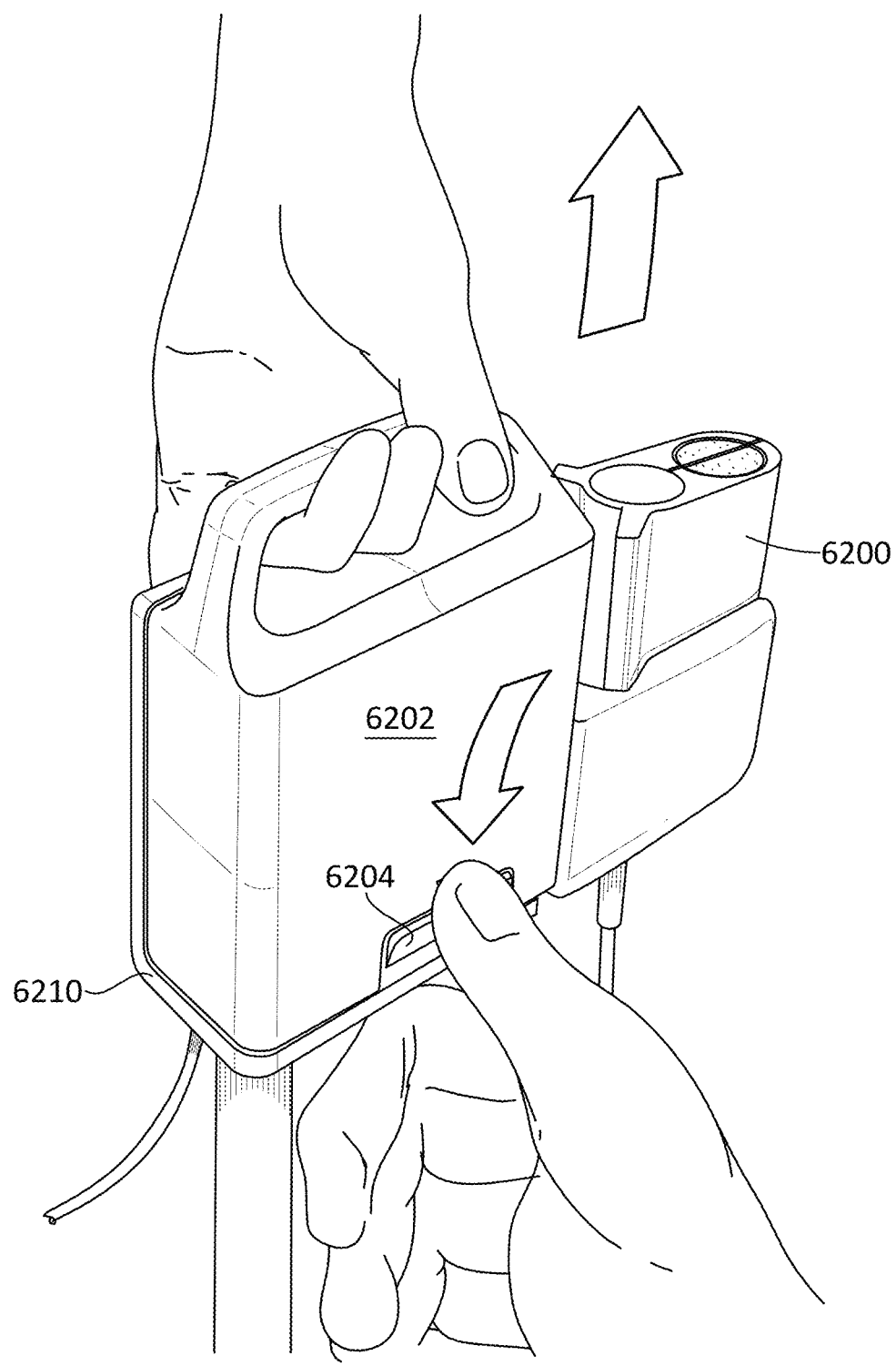
Figure 62C:
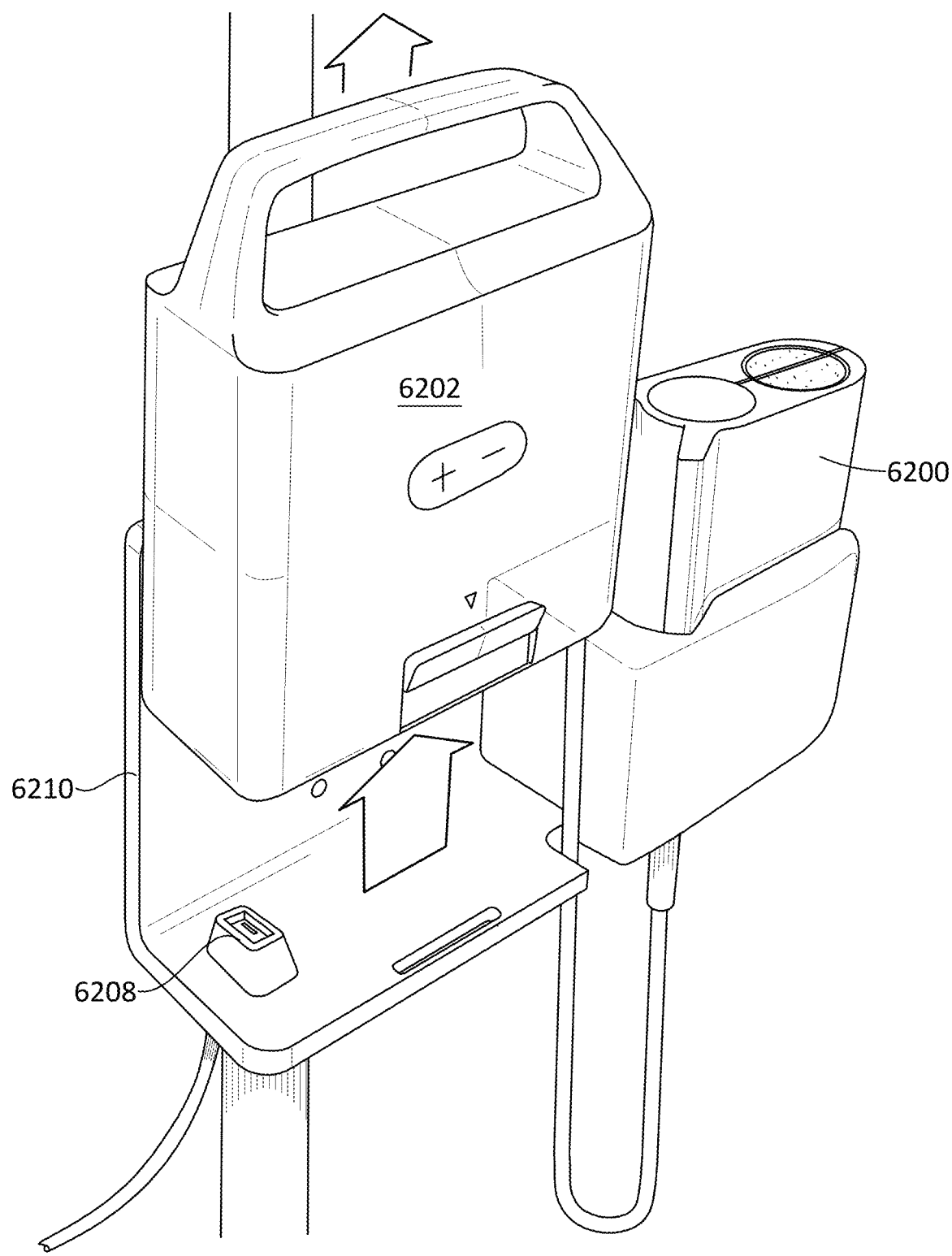

FIGS. 62B and C are perspective views of the mobile disinfecting unit 6200 illustrating the operation of a power pack quick release 6204 (FIG. 62B) and movement of the mobile power pack 6202 out of the configured receptacle in the power controller base 6210 (FIG. 62C). Also visible in this view is the power charging contact 6208 in the lower portion of the power pack receptacle.

Figure 62D:
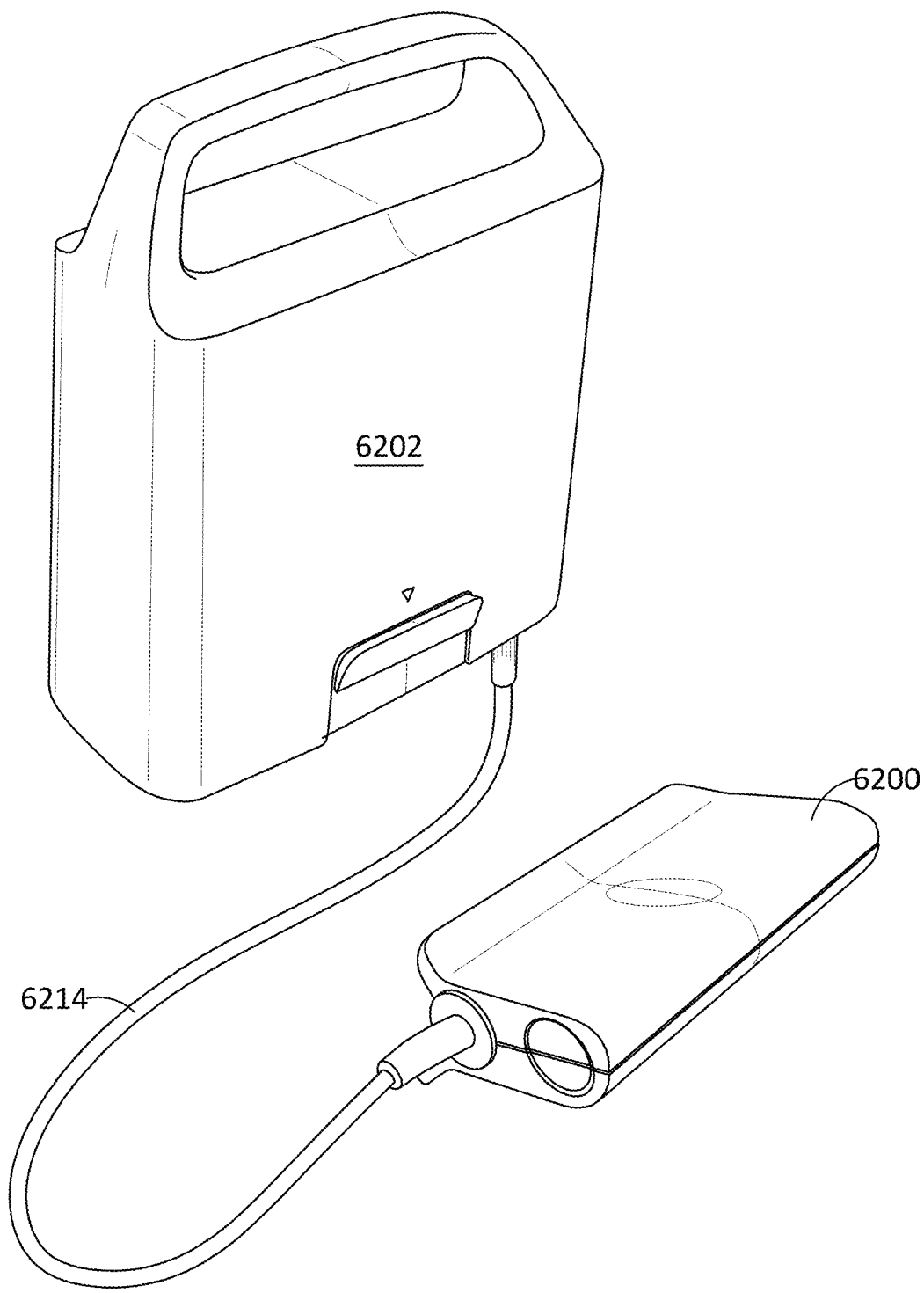
FIG. 62D is a perspective view of the handheld UV disinfecting unit and mobile power pack of FIG. 62A.

FIG. 62D is a perspective view of the handheld UV disinfecting unit 6200 and mobile power pack 6202 of FIG. 62A after each has been removed from the specific receptacles formed in the power controller base. A cable 6214 connects the two, forming a self contained portable system.

Figure 62E:
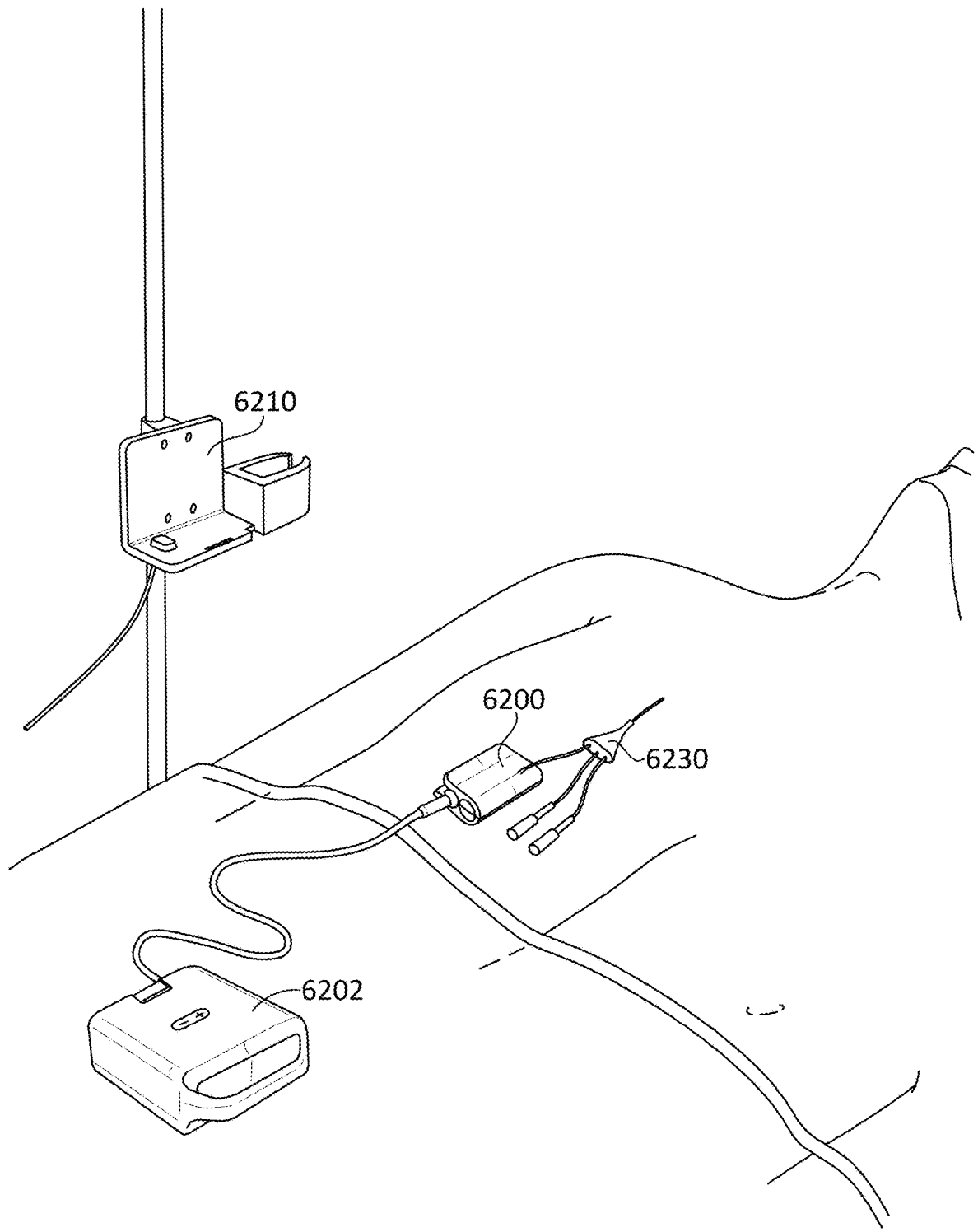
FIG. 62E is a perspective view of a patient having an implanted catheter hub with the portable disinfecting unit of FIG. 62D in position to disinfect one of the lumens of the catheter hub.

FIG. 62E is a perspective view of a patient having an implanted catheter hub 6230 within the portable disinfecting unit 6200 of FIG. 62D in position to disinfect one of the lumens of the catheter hub 6240. The pole mounted power controller and base 6210 is shown in this view adjacent to the patient's hospital bed.

LED Configuration

In developing the configuration of the LEDs for the disinfection units described herein, LEDs were obtained from various manufacturers. Their spot sizes and power were compared to each other and against the manufacturer's specification. The best spot size was found to be approximately 15 mm for a single LED when shined onto a flat surface from a fixed distance of about 0.4 inches. The spot size and distance from a UV sensitive film was used to calculate the effective viewing angle at which the UV dosage is sufficient for microbiological disinfection. The effective viewing angle was found to be about 80-90 degrees, and not the 100-110 degrees of the manufacturer's specification.

There is a tradeoff in design between the intensity from a point light source (e.g., LED) and the spread of light on the target. The intensity decreases exponentially as the distance from the target increases. The spread of light or spot size increases as the distance increases. The intensity of the light source is always strongest in the center of the spot. As described above, in the embodiments described herein, one or more light sensors (not shown) can be used to verify light output from any of the UV light sources, providing the system controller with a feedback signal that is compared to a threshold to determine the sufficiency of the irradiative power and intensity for proper disinfection. Further, the duration of the disinfection cycle can be as short as about 1 second.

Various LED configurations were tested to see how they would disinfect a generally cylindrical shaped connector or component to be disinfected, for example in the disinfection device shown in and described with respect to FIGS. 1A-17C. In some embodiments, the connector to be disinfected has a diameter of about 10 mm and a length of about 30 mm. As in the configuration shown in FIGS. 1E and 1F, in some embodiments, the LEDs are positioned around a generally cylindrical shaped kill zone within the connector insertion opening. Configurations other than cylindrically shaped are also possible. The kill zone comprises an axial dimension or length and a cross sectional shape. In generally cylindrically shaped embodiments of kill zone, the cross sectional shape is a circle. Other cross sectional shapes (e.g., oval, rectangle, square, polygon, etc.) are also possible. As shown in FIG. 63D, the LEDs 6322 are equidistantly spaced around a circumference 6324 of the kill zone at two circumferential planes 6236, 6328 positioned along an axial dimension of the kill zone. The two circumferential planes have a vertical spacing 6330. The LEDs 6322 have a circumferential or horizontal spacing 6332 between LEDs within a circumferential plane. In some embodiments, the LEDs can be positioned at 1, 2, 3, 4, 5, 6, or more circumferential planes positioned along a length of the kill zone. At each circumferential plane, there can be 3, 4, 5, 6, or more LEDs positioned equidistantly around a circumference of the kill zone. In some embodiments, different circumferential planes can have a different number of LEDs.

Figure 63A:
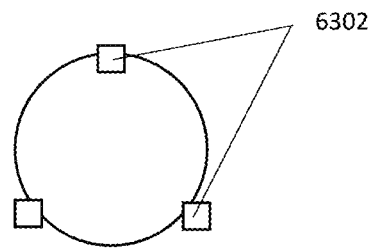
FIGS. 63A-D illustrate various LED configurations for UV disinfection unit.

As shown in FIG. 63A, an LED configuration comprising three pairs of LEDs 6302 spaced about a target component (e.g., connector) with 120 degrees spacing for a total of 6 LEDs was observed. In this configuration, three LEDs are positioned equidistantly around a circumference of the kill zone at two circumferential planes along a length of the kill zone. In other words, pairs of LEDs, each pair comprising two LEDs spaced along an axial length of the kill zone, are positioned equidistantly around a circumference of the kill zone. It was found that this configuration did not provide sufficient coverage as the viewing angle did not cover the width of the horizontal or circumferential spacing between the LEDs.

The space between circumferential planes vertical spacing of the LEDs was between about 10-15 mm. (spot size radius of 2 spots=7.5 mm×2=15 mm maximum distance with no gaps)

Figure 63B:
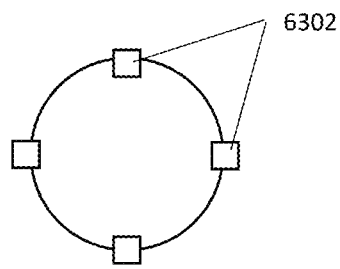
Figure 63C:
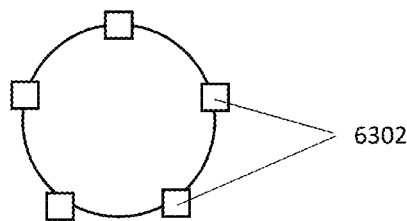
Figure 63D:
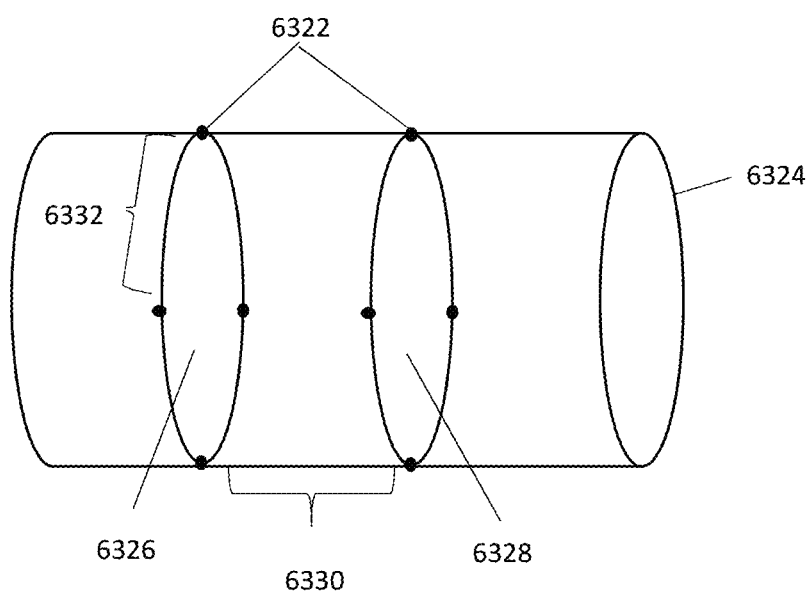

Configurations with 4 and 5 concentric, equally spaced LED pairs 6302, as shown in FIGS. 63B and C showed efficacy in their UV coverage.

Figure 64G:
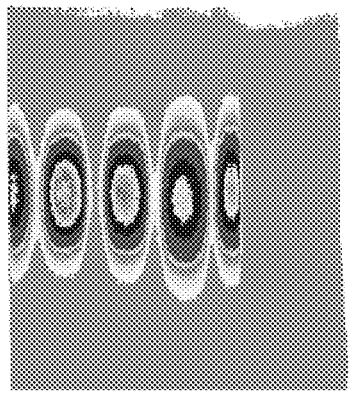
FIGS. 64A-S show data from testing conducted on various LED configurations.
Figure 64H:
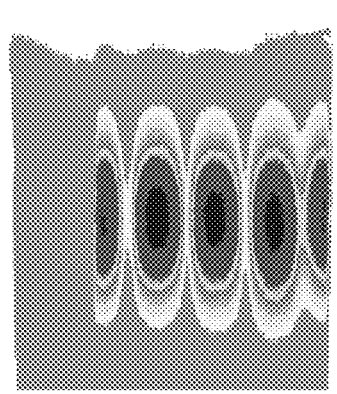
Figure 64I:
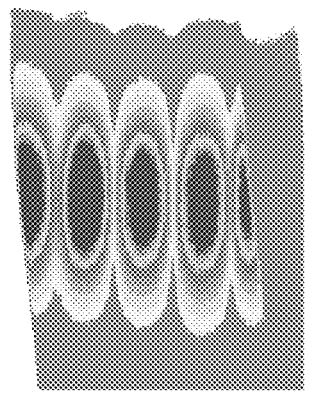
Figure 64J:
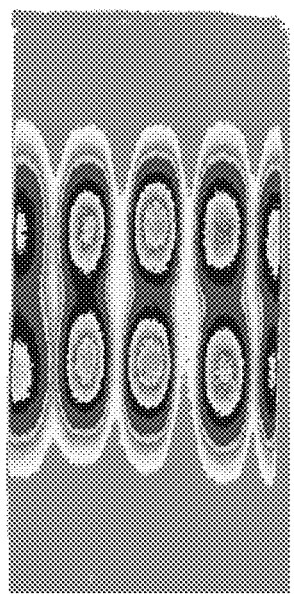
Figure 64K:
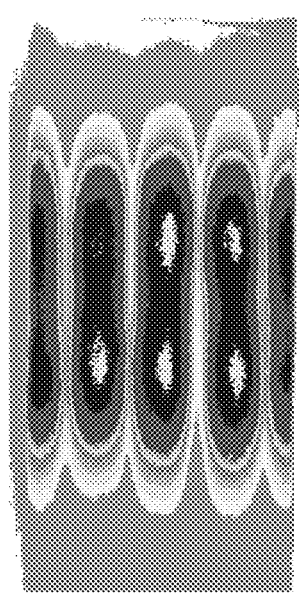
Figure 64L:
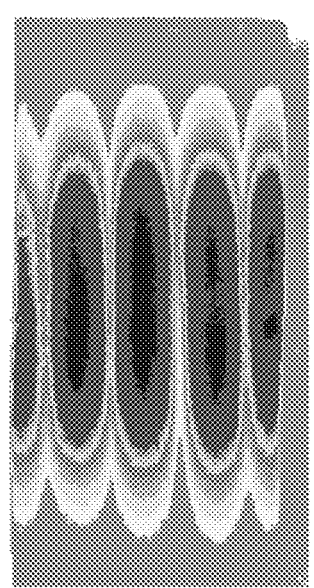
Figure 64R:
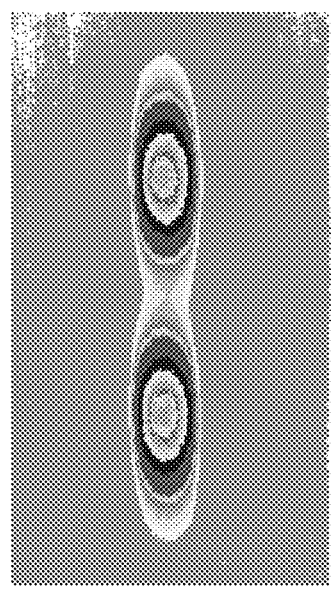
Figure 64S:
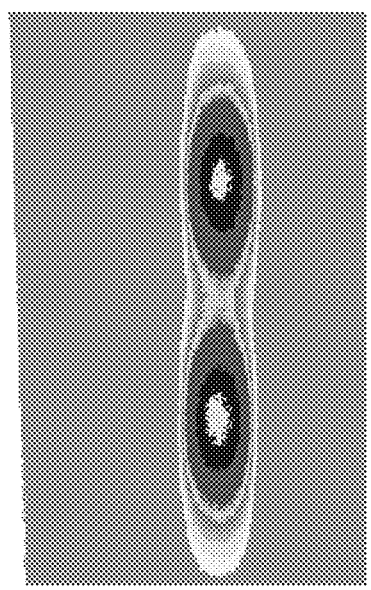

Test data for various LED configurations spaced 90 degrees around a tube is shown in FIGS. 64A-S. Each table showing testing data for a particular LED configuration shows data for various spacing of the LEDs. The data associated with '0.72 in. diameter' is associated with LEDs positioned such that they are concentric about a circle having a diameter of 0.72 in. The data associated with '0.92 in. diameter' is associated with LEDs positioned such that they are concentric about a circle having a dimeter of 0.92 in. The data associated with '1.12 in. diameter' is associated with LEDs positioned such that they are concentric about a circle having a dimeter of 1.12 in. The data associated with '1.32 in. diameter' is associated with LEDs positioned such that they are concentric about a circle having a dimeter of 1.32 in.

FIGS. 64A-C show UV sensitive film strips for a 20 mW Crystal IS 280 nm with 1 LED placed each 90 degrees around the circumference and a 15 sec exposure time. FIG. 64A shows the 0.92 in. configuration. FIG. 64B shows the 1.12 in. configuration. FIG. 64C shows the 1.32 in. configuration. Data is shown in Table 1 below.

TABLE 1

|  | 0.92 in. diameter | 1.12 in. diameter | 1.32 in. diameter |
| --- | --- | --- | --- |
| Max UVC Dose (mJ/cm$^2$) | 465.32 | 206.64 | 125.43 |
| Avg UVC Dose (mJ/cm$^2$) | 155.37 | 118.94 | 95.617 |
| UV exposed area (mm$^2$) | 55.35 | 46.773 | 23.37 |
| Horizontal Gap (mm) | 2.0625 | 2.625 | 4.3125 |
| Total Height (mm) | 10.563 | 9 | 6 |

FIGS. 64D-F show UV sensitive film strips for a 30 mW LG 280 nm LED with 1 LED placed each 90 degrees around the circumference and a 15 s exposure time. FIG. 64E shows the 0.92 in. configuration. FIG. 64E shows the 1.12 in. configuration. FIG. 64F shows the 1.32 in. configuration. Data is shown in Table 2 below.

TABLE 2

|  | 0.92 in. diameter | 1.12 in. diameter | 1.32 in. diameter |
| --- | --- | --- | --- |
| Max UVC Dose (mJ/cm$^2$) | 1270.49 | 490.37 | 249.92 |
| Avg UVC Dose (mJ/cm$^2$) | 294.043 | 168.31 | 127.41 |
| UV exposed area (mm$^2$) | 79.132 | 87.423 | 79.97 |
| Horizontal Gap (mm) | 1.4375 | 1.3125 | 1.375 |
| Total Height (mm) | 14.083 | 14.917 | 14.375 |

FIGS. 64G-I show UV sensitive film strips for a 30 mW Nikkiso 285 nm LED with 1 LED placed each 90 degrees around the circumference and a 15 s exposure time. FIG. 64G shows the 0.92 in. configuration. FIG. 64I shows the 1.12 in. configuration. FIG. 64I shows the 1.32 in. configuration. Data is shown in Table 3 below.

TABLE 3

|  | 0.92 in. diameter | 1.12 in. diameter | 1.32 in. diameter |
| --- | --- | --- | --- |
| Max UVC Dose (mJ/cm$^2$) | 831.37 | 281.8 | 167.45 |
| Avg UVC Dose (mJ/cm$^2$) | 229.38 | 139.31 | 110.03 |
| UV exposed area (mm$^2$) | 78.187 | 83.287 | 57.47 |
| Horizontal Gap (mm) | 1.6562 | 1.5938 | 2.5625 |
| Total Height (mm) | 14.031 | 14.938 | 12.969 |

FIGS. 64J-L show UV sensitive film strips for a 30 mW Nikkiso 285 nm LED with 2 LEDs placed each 90 degrees around the circumference and a 15 s exposure time. FIG. 64J shows the 0.92 in. configuration. FIG. 64K shows the 1.12 in. configuration. FIG. 64L shows the 1.32 in. configuration. Data is shown in Table 4 below.

TABLE 4

|  | 0.92 in. diameter | 1.12 in. diameter | 1.32 in. diameter |
| --- | --- | --- | --- |
| Max UVC Dose (mJ/cm$^2$) | 1135.34 | 407.41 | 205.88 |
| Avg UVC Dose (mJ/cm$^2$) | 298.11 | 179.5 | 144.12 |
| UV exposed area (mm$^2$) | 82.673 | 91.829 | 88.757 |
| Horizontal Gap (mm) | 3.0625 | 1.625 | 1.3125 |
| Total Height 1 LED (mm) | 14.583 | 15.438 | 15.042 |
| Total Height PAIR LED (mm) | 29 | 30.625 | 29.593 |

FIGS. 64M-O show UV sensitive film strips for a 30 mW Nikkiso 285 nm LED with 2 LEDs placed with a vertical spacing of 15 mm and a 15 s exposure time. FIG. 64M shows the 0.72 in. configuration. FIG. 64N shows the 0.92 in. configuration. FIG. 64O shows the 1.12 in. configuration. Data is shown in Table 5 below.

TABLE 5

|  | 0.72 in. diameter | 0.92 in. diameter | 1.12 in. diameter |
| --- | --- | --- | --- |
| Max UVC Dose (mJ/cm$^2$) | 2912.45 | 1011.47 | 300.36 |
| Avg UVC Dose (mJ/cm$^2$) | 753.01 | 257.05 | 158.925 |
| UV exposed area (mm$^2$) | 40.361 | 73 | 74.915 |
| Total Height (mm) | 9 | 13.5625 | 13.9375 |
| Vertical Gap (mm) | 5.125 | 0 | 0 |

FIGS. 64P-Q show UV sensitive film strips for a 30 mW LG 280 nm LED with 2 LEDs placed with a vertical spacing of 15 mm and a 15 s exposure time. FIG. 64P shows the 0.72 in. configuration. FIG. 64Q shows the 0.92 in. configuration. Data is shown in Table 6 below.

TABLE 6

|  | 0.72 in. diameter | 0.92 in diameter |
| --- | --- | --- |
| Max UVC Dose (mJ/cm$^2$) | 3027.71 | 1518.25 |
| Avg UVC Dose (mJ/cm$^2$) | 705.905 | 311.805 |
| UV exposed area (mm$^2$) | 47.413 | 81.896 |
| Total Height (mm) | 10.25 | 14.875 |
| Vertical Gap (mm) | 5.625 | 0 |

FIGS. 64R-S show UV sensitive film strips for a 30 mW LG 280 nm LED with 2 LEDs placed with a vertical spacing of 20 mm and a 15 s exposure time. FIG. 64R shows the 0.92 in. configuration. FIG. 64S shows the 1.12 in. configuration. Data is shown in Table 7 below.

TABLE 7

|  | 0.92 in. diameter | 1.12 in. diameter |
| --- | --- | --- |
| Max UVC Dose (mJ/cm$^2$) | 1247.965 | 426.93 |
| Avg UVC Dose (mJ/cm$^2$) | 282.565 | 155.03 |
| UV exposed area (mm$^2$) | 73.666 | 88.731 |
| Total Height (mm) | 13.375 | 15.4375 |
| Vertical Gap (mm) | 7 | 4.25 |

In the LG and Nikkiso tests, the 0.4 in spacing was slightly better than the 0.5 in spacing for reducing horizontal gap and maximizing total end to end height. An optimal center to center spacing can be around 15 mm for vertical LEDs, with potential to stretch to 16 or 17 mm. An optimal configuration may be 2 LEDs per 90 degrees with a 15-16 mm vertical spacing, and about 1.12 in. in diameter. Other configurations are also possible.

All UV LED manufacturers are improving their products, which will be advantageous in increasing the dosage delivered in this product The LEDs used can have a wavelength of about 250-300 nm. Light of this wavelength is disruptive to microbial cell walls and DNA and has been shown to effectively kill bacteria, fungus, and viruses. Other possible parameters for LEDs operating parameters. Operating parameters of the device and LEDs can comprise delivering current of about 200-800 mA. Voltage can be delivered at about 3-10V. By optimizing the selection of UVC power and geometry the system can be optimized for disinfection times as fast as 1 second or less. For instance, the Nikkiso UVC LEDs produced a maximum 2912 mJ/cm$^2$ and 753 mJ/cm$^2$ at 0.72 mm distance and 1.5 cm spacing. At 1 second this would be equivalent to 194 mJ/cm$^2$ and 50 mJ/cm$^2$ at 1 second Compliance Any of the disinfection units described herein provide the ability for tracking of compliance and logging of data. As described elsewhere herein, the components to be disinfected (e.g., a connector of an in-dwelling catheter implanted in patient) can comprise a chip or tag (e.g., RFID tag, near field tag, etc.) that allows for recognition of the component by the disinfection unit. The disinfection unit has a complementary sensor or reader (RFID sensor, NFC sensor, etc.) that allows it to sense or recognize the tagged component as a unique component. In some embodiments, the component is tied to a patient ID, and the compliance and disinfection information logged by the disinfection unit can be associated with a patient (e.g., patient database, patient chart, hospital records, etc.).

The sensor on the disinfection unit allows the unit to log each time the component is inserted into the disinfection unit. Once the component is inserted into the unit, the unit is able to determine whether or not a complete disinfection cycle has been performed. If a complete disinfection cycle is run, the unit is able to log the time and date of the disinfection cycle. In some embodiments, the unit may also be able to log the ID of the clinician performing the disinfection. In some instances, the disinfection cycle may not be properly run (e.g., due to component not properly inserted within disinfection unit, component not inserted for sufficient time, malfunction of disinfection unit, etc.). In such instances, the disinfection unit can log that an improper disinfection cycle was run and provide a visual and/or audible alert that the component is not properly disinfected. In some embodiments, the alert may be ongoing until a clinician provides a manual override to stop the alert or the clinician properly completes a disinfection cycle.

The disinfection unit is able to log the date and time of the completed and attempted disinfection cycles. The unit can transfer this information to a computer, tablet, or other handheld device through a wired or wireless (e.g., wifi, Bluetooth, etc.) connection. In some embodiments, the wired connection is provided by the data and charging bases or consoles described herein. In some embodiments, the data/charging bases can provide wireless connectivity to the disinfection unit.

The system is able to keep a record of the disinfection cycle frequency. This information can be used to verify compliance with device standards, hospital standards, and the like. This information can also be used to alert a clinician when an additional disinfection cycle is or may be needed based on device standards, hospital standards, infusion protocols, etc. A visual and/or audible alert can be used. In some embodiments, the alert may be ongoing until a clinician provides a manual override to stop the alert or the clinician properly completes a disinfection cycle.

The system can also be used to manually drive user behavior. For example, if a hospital were experiencing an event making disinfection desirable, for example, an infection outbreak, the system can be used to alert the clinician to disinfect or change out the connector being used. The system can also be used to update alerts based on device or hospital standards. For example, if the hospital decides to institute stricter disinfection protocols, the change in protocol can be disseminated to the units and the clinician users can be alerted when action is required.

Detailed features and functionality of the various disinfection units were described with regard to a specific embodiment for clarity in the explanation of the particular feature or functionality. It is to be appreciated that other combinations and sub-combinations of functionalities and features of one disinfecting unit may be adapted to provide similar or specific advantages to alterative embodiments of other disinfection units described herein. By way of example, the portable features described in regard to FIGS. 61A-62E may be advantageously applied to other disinfection unit designs. In much the same way, various status indications, editable electronic displays, and the like illustrated and described in, for example and not limited to FIGS. 38C, 45B, 46B, 48C, 38A, 55B, 3B, 5A, 7A, 7C, 8B, 9A, 9B, 10B, 11A, 11D, 13C, 13D, 13E, 13F, 14B, 15B, 16A, 16B, and/or 16C, may be applied to other disinfection units to provide, modify, or enhance any display or indication that exists in or may be added to a specific configuration.

In some embodiments, there is provided a UV light source as a means for providing UV illumination to disinfect a needleless connector or manifold or component. In some instances, a disinfection unit includes a power control whereby to regulate the power provided to a UV source. Increasing the power of a UV light source may increase illumination intensity and thereby accelerate a disinfection process. Accordingly, some implementations of the disinfecting devices described herein include electronic and/or programmable power control units or systems which regulates, modify, or maintain power supplied to the UV light source from a battery or other power source, depending on configuration. Supplied power can be continuous, pulsed, or otherwise varied.

In some embodiments, the disinfection system contains no user operated power or activation button. Instead, in these alternative embodiments, a detection system, method or process is used to allow or inhibit system operation.

On one aspect, a step accomplished by the user to load a disinfection chamber is detected by the system to automatically initiate a disinfection cycle or process. One specific example of a disinfecting unit of this configuration is the sliding lid chamber design illustrated and described with respect to FIGS. 45A and 45B. Once a manifold, component, adapter or connector is properly positioned within the unit (FIG. 45A), disinfection begins when the user completes the step of sliding the lid to the closed position (FIG. 45B).

In some embodiments, detection by the system includes one or more steps or a proper sequence of steps to be completed before initiating the disinfection cycle. In some other embodiments, detection used to initiate a disinfection cycle includes indications from both the user and the system. One example includes a user step of aligning a manifold over a chamber and then inserting first one end into an alignment slot before snapping a second end into another portion of the chamber. One or both of these user actions may be used by a sensor to indicate that the action was completed or completed correctly according to sequence. For example, a proximity sensor or position detection sensor could be placed in the alignment slot in the preceding example. When the user correctly inserts the manifold, the sensor provides a signal to the disinfection unit controller to indicate the correct presence of the manifold. Other examples are possible such as a latching mechanism, mechanical, magnetic, optical or other type that is used to indicate that the chamber lid is closed or otherwise indicate proper interaction of a component, adapter, connector or manifold with an appropriate portion of a disinfecting unit. In still other embodiments with moving lids or portions of a chamber must engage before operation of the unit, the system may include one or more of sensors, limit switches, position indicators, intended to trigger or otherwise permit a disinfection operation to proceed. In a similar way, a lid or chamber component may include one or more mechanical, electrical, optical, or magnetic feature or component used to ensure, guide or indicate, including electronically to a system controller, the presence of a permitted or properly inserted adapter, connector, component or manifold. Optionally or additionally, one or more of these features may be adapted to prevent removal of component undergoing disinfection until the entire disinfection sequence is completed.

In one specific aspect, a disinfection unit embodiment is adapted and configured to detect whether a permitted or authorized component, connector, adapter or manifold is present in the unit. If a permitted or authorized component, connector, adapter or manifold is detected, then a disinfection cycle starts automatically without further user action. As a result of the detection capability of the disinfection unit, the auto cycle mode would only work when the unit detects a permitted or authorized component, connector, adapter or manifold. Since this disinfection unit is configured without an ON/OFF button, the unit's detection capability prevents use/misuse by a user attempting to operate the unit improperly or with non-permitted or unauthorized component, connector, adapter or manifold. The interoperability of the unit with a permitted or authorized component, connector, adapter or manifold may be accomplished in a number of ways. The detection system may utilize colored band/s, patterns, stripes, bar codes, metallic rings, or radiopaque materials alone or in combination with other electrically, optically or magnetically recognizable or detectable features. These detectable features are included in permitted or authorized components, connectors, adapters or manifolds so as to be detectable by electrical, optical or magnetic or other appropriate sensors within the UV light source housing, disinfecting unit or other component of an embodiment described herein.

In some embodiments, the detection capability includes an input interface such as an optical reader (i.e., a barcode scanner or other device which is capable of reading a computer-readable symbols) appropriately integrated into the disinfection unit so as to read/detect a computer readable authorization, authentication or permission symbol placed in a detectable location on a permitted or authorized component, connector, adapter or manifold. In still other embodiments, an input interface may also include an inductive or near field communication system, a magnetic card reader, or an optical camera which is capable of retrieving information stored within a magnetic stripe or a computer-readable code, respectively, on a permitted or authorized component, connector, adapter or manifold. In one specific example, the detection capability or system of a disinfection unit includes a QR code indicating a permitted or authorized component, connector, adapter or manifold capable of being detected and deciphered using an optical camera and computer-executable software operable by the disinfecting unit to retrieve information from the QR code. In one specific example, the detection capability or detection system of a disinfection unit incorporates the use of an RFID tag and appropriate RFID reader. In this implementation of the detection system, operation of the disinfection unit proceeds only when the detection capability indicates a permitted or authorized RFID tag on a component, a connector, an adapter or a manifold present in the disinfection unit.

In other aspects, a disinfection unit may further comprise a printed circuit board that includes various input, output, monitoring and feedback circuitry to control proper disinfection of a connector or component. The electronic circuit board can be electronically coupled to battery and/or UV light source or other components depending on configuration. For example, in some embodiments printed circuit board includes a power sensor configured to monitor and measure power supplied to a light source. Additionally or alternatively, a printed circuit board may also include a status indicator controller. A status indicator controller may be adapted and configured to control any of the various status indicators, displays, including lights and others described herein. In still further aspects, a printed circuit board may also include a timer used to measure or count a time lapse or interval over which UV illumination is provided during a disinfection operation. In some instances, sufficient disinfection is a factor of illumination power and time. For example, in some embodiments, complete disinfection requires that the minimum power threshold be maintained for a minimal length of time, such as from about 1 second to about 15 seconds or other duration such as 20 30, 40, or 50 seconds depending upon application. In some other embodiments, complete disinfection requires that the minimum power threshold be maintained from a minimum length of time of about 5 seconds or less. Thus, timer can be used to control the length of time during which a disinfection process operates.

As described above, the various embodiments of disinfection units described herein can be used to disinfect a catheter connector, for example, a needleless connector at the end of an indwelling catheter. The connectors used in the disinfection unit can comprise a UV transmissive material so that they allow UV disinfection of internal components. The connector can comprise a valve having an external flow path. In other words, fluid flows around the core segment of the valve, allowing exposure of UV light to the portion of the connector or valve contacted by fluid.

The devices described herein can be used to disinfect connectors for various tubes used in a clinical setting. For example, tracheal tubes and feeding tubes can end at a connector adapted to be disinfected by devices described herein. The connector can be positioned at the end of the tube that is open to air or accessed to provide fluids to a patient. In such embodiments, this connector can be disinfected at a desired frequency and desired settings used the distinction devices described herein.

As appreciated in the description above, a needleless connector is comprised in general terms of an inlet port on the top side, an outlet port on the bottom side and a body between the top side and the bottom side. The inlet port is formed to include any of a variety of suitable threaded or friction fittings suited to the field that the connector is purposed. In one example, the inlet port is a standard female threaded Luer connector configured to connect to a male threaded Luer connector. Such connector pairs are often found in a syringe or an infusion tubing set. In much the same way, the outlet port is also formed to provide any of a variety of suitable threaded or fitted connections based on the field of use. By way of example, the outlet port is formed by a standard male threaded Luer connector that is configured to connect to a female Luer connector. One common example of such connectors is found on the typical vascular catheter hub. In such a configuration, a needleless connector is configured to be connected to the hub of a vascular catheter to provide quick and easy access without the need for a needle for blunt infusion devices such as a syringe or infusion tubing set. The standard female threaded Luer connector comprises one or more male threads that can be continuous or partial. The standard male threaded Luer connector comprises a plurality of full or partial female threads. In some configurations, the needleless connector can also comprise a base section with base ribs near the bottom side to facilitate connecting and disconnecting the needleless connector to the hub of a vascular catheter. The needleless connector may also comprise a neck section near the top side that is generally of a smaller diameter than the diameter of the body.

In accordance with additional aspects of the inventive needless connectors described herein, the needleless connector's body, base, and neck are made from a moldable polymer material adapted for selectivity of ultraviolet light. In one aspect, selective transmissivity of ultraviolet light is selective to UV-C light. In one aspect, a suitable moldable polymer adapted for the purposes herein is one that when formed into an embodiment of a needless connector allows sufficient ultraviolet light with a wavelength from about 250 nm-300 nm in length to penetrate through the material. Light of this wavelength is disruptive to microbial cell walls and DNA and has been shown to effectively kill bacteria, fungus, and viruses. Exemplary moldable polymer materials include a cyclic olefin copolymer such as Topas® available from Advance Polymers, GmbH, Frankfurt Germany, or a polymethylpentene such as TPX® commercially available from Mitsui Chemicals America, Rye Brook, NY.

In each of the exemplary existing needless connector modifications, the exemplary existing or current needleless connector designs are not configured for light based disinfection. Instead, the designs mentioned below and incorporated by reference are desired for and select materials for chemical based disinfection. As a result, the existing designs are made from standard, medical grade moldable polymers which due to their crystalline structure do not allow sufficient doses of the desired antibacterial UV-C light such as the short 250 nm-300 nm wavelength light to propagate through. As a result, it is common for current needleless connectors to be often associated with microbial infections as the fluid and residual blood trapped inside the connector in between uses can provide a good environment for microbial growth and colonization.

The advantageous designs of the various compact, portable LED UV-C disinfection units described along with the improved selective transmissivity fabrication process herein enable the existing needleless connector designs to be newly fabricated to access and receive the benefits of light based disinfection. As a result of the invested cost to design, set up injection molding systems along with other cost of manufacture and integration with existing products, the initial process of conversion, by way of overview, is to first fabricate the previous needleless connector using the precursor materials and process adapted for controllable selectivity of UV-C for light based disinfection. As a result, by using the UV-C transmissive moldable polymer material and adapted fabrication methods for the existing needleless connector body, base, and neck of the current design will then have greatly improved transmissivity to ultraviolet light. Thereafter, a UV-C transmissive variant of the existing needleless connector will achieve the desired disinfection performance when placed in a disinfection chamber keyed to the particular transmissivity signature of that connector. In summary, as a result of fabrication using precursor materials and processes to selectively enhance the UV-C transmissivity of the connector, sufficient UV-C light now propagates through the outside walls of the needleless connector structure in order to disrupt microbes on the inside of the connector to prevent microbial infections. Additionally, if needed, some design aspects may be modified in the existing design to remove shadowing effects caused by thickness of the material or curvature or other factors. In some cases, there may be business justification to modify the existing design to improve the UV-C transmissivity of the needless connector once the decision to shift to a light based disinfection mode is taken. The approach for modification may be particularly attractive for those needless connector designs which have already recovered cost of manufacturing design or are retired from commercial use. In this way, design work for previous needless connectors may be recovered anew by only making the modest investment in new tooling based on the UV-C transmissivity signature for the older or retired needless connector design.

Against this background, we turn FIG. 65, showing an exemplary embodiment of a method 6500 of providing a selective transmissivity connector for use in a light based disinfection system.

First, at step 6505, there is a step of providing existing needleless connector design adapted for non-light-based disinfection. The step refers to the process of using an existing design that was envisioned to have chemical based disinfection but now is being reconfigured for light-based disinfection.

Next, at step 6510, there is a step of fabricating a needleless connector using precursor materials and process adapted for controllable transmissivity to enable UV-C based disinfection. During this step, the existing manufacturing design and injection molds for the existing needleless connector are used during a fabrication process modified to produce an article having enhanced transmissivity in the UV-C spectrum. Applicants have determined that fabrication of connectors using the manufacturer recommended process for a moldable polymer produced a resulting article with poor transmissivity to UV-C wavelengths. As a result, Applicants have determined that variations from the recommended process parameters unexpectedly produced improvements in UV-C transmissivity. One parameter that adversely affected UV-C transmissivity was the dwell time for the material in the mold. Applicants found that a dwell time approximating the manufacturer recommended maximum impeded UV-C transmissivity. However, Applicants discovered that a dwell time that is roughly one third or less of the manufacturer recommended maximum dwell time improved UV-C transmissivity in the finished product. In another aspect, the manufacturer recommended injection pressure also led to a degradation of final UV-C transmissivity. Instead, Applicants found that increasing the injection pressure beyond the recommended range led to improvements in UV-C transmissivity of the finished product.

After fabricating the needleless connector in step 6510, the next step (step 6515) is to obtain a UV-C transmissivity signature for the needleless connector that has been fabricated for control transmissivity UV-C based disinfection. In this step, the connector is exposed to an appropriate testing rig where UVC light is directed against the various portions of the connector structure to determine the transmissivity characteristics of the connector. As a result of this processing step, the particular portions of the connector that are less transmissive are identified so that dosing specifically in those areas may be accommodated to ensure sufficient UV-C light is transmitted to achieve the desired dosing profile.

Next, at step 6520, modeling and adaption processes are performed for UV-C sources, placement and the dosing profile for the fabricated needleless connector. In this step, the type, number and placement of one or more UV-C sources are explored in order to overcome any shadowing, bending or other losses in UV-C transmission based on the use of the prior design. It is to be appreciated that this step is provided to ensure that an appropriate, targeted higher dose or more powerful UV-C light is provided as needed to specifically overcome those areas of bending, shadowing or higher than expected losses resulting from the use of a pre-existing connector design.

Next, at step 6525, select an appropriate UV-C disinfecting unit. An appropriate disinfecting unit would be one that is readily adopted for use in the workflow of the connector. Other additional factors for an appropriate connector include the form factor and the desired degree of portability. It is to be appreciated that any of the embodiments of the disinfecting units described herein may be adapted to benefit from this exemplary method.

Once the disinfecting unit has been selected, the next step, step 6530, is to modify the UV-C sources of the selected disinfecting unit for specific use with the selective transmissivity connector. As a result, the type of sources, placement array and those parameters in the disinfection unit will key the disinfection chamber to meet or exceed the disinfection profile for the fabricated connector. In this way, the use of the connector with the appropriate keyed disinfection chamber ensures the appropriate disinfection profile is provided to the keyed connector.

Next at step 6535, testing is performed to confirm that the keyed UVC disinfection unit provides the desired disinfection profile dosing parameters and achieves the desired disinfection and point for the keyed connector. In some embodiments, as a result of the advantageous design and coupling of disinfection dose to connector transmissivity signature, a selectively transmissive needleless connector may achieve a disinfection endpoint of 4 log reduction in bacteria in less than 15 seconds, in less than 10 seconds or in as little as 5 seconds. Optionally or additionally, embodiments of the selectively transmissive connectors described herein may achieve desirous disinfection points in a particular workflow utilizing less power than conventional disinfection endpoint systems or achieve the disinfection endpoint using lower cost components, such as UV-C LED in different UV-C wavelengths or other beneficial as a result of the optimized keying between connector and disinfection chamber.

Finally, at step 6540, the confirmed keyed connector and disinfection unit are released into the desired needless connector workflow subject to quality control, regulatory and other approvals, as needed for a particular connector and workflow.

In one alternative aspect, the steps of obtaining a signature and modeling/adaption (steps 6515 and 6520) may be performed using software models that generate the UV-C doses provided in any of the disinfection chambers of any of the UV-C disinfection units described herein. In this way, the size, type, placement and array configuration including radial and axial spacing of individual UV sources or clusters of UV sources may be adjusted to compensate for the obtained UV-C transmissivity signature for a connector. In another aspect, physical testing units of the various UV-C disinfection units may be constructed where the disinfection chamber includes a dense array of closely spaced and individually controllable UV-C sources. In use, the connector is placed within the physical testing unit along with appropriate detectors. The individual UV-C sources are then operated individually or sequentially to determine the signature and derive the desired dosing profile for the connector. In one aspect, an automated computer controlled program may be used to operate the UV-C sources, receive input from one or more detectors and then adjust source parameters until desired dosing parameters are achieved. As a result, whether through the use of software modeling or actual test fixture, the type, number, size and placement of the UV-C sources for the keyed disinfection chamber to connector is obtained. This information is then used in the fabrication process of the keyed unit along with the control algorithm for driving the particular selected configuration of the UV-C sources in relation to the disinfection chamber and keyed connector disposed therein. It is to be appreciated that physical or electronic features discussed elsewhere herein may also be provided in one or both of the keyed connector or keyed disinfection unit to ensure the proper type of connector is inserted and in the desired orientation, if specific orientation is needed for a keyed connector/disinfection unit set.

In still additional alternative embodiments, the selective transmissivity fabrication process 100 is adapted for use with the various connector embodiments illustrated and described with regard to FIGS. 2, 3A, 3B, and 6 of U.S. Pat. No. 5,569,235, which is incorporated herein by reference in its entirety.

In still additional alternative embodiments, the selective transmissivity fabrication process 100 is adapted for use with the various connector embodiments illustrated and described with regard to FIGS. 4-8 of U.S. Pat. No. 6,482,188 which is incorporated herein by reference in its entirety.

In still additional alternative embodiments, the selective transmissivity fabrication process 100 is adapted for use with the various connector embodiments illustrated and described with regard to FIGS. 1, 2, 3, 6, and 7-11 of U.S. Pat. No. 7,837,658 which is incorporated herein by reference in its entirety.

In still additional alternative embodiments, the selective transmissivity fabrication process 100 is adapted for use with the various connector embodiments illustrated and described with regard to FIGS. 1-10, 11-13, 15-20, 27-44F and 47-52 of U.S. Pat. No. 8,038,123 which is incorporated herein by reference in its entirety.

In still additional alternative embodiments, the selective transmissivity fabrication process 100 is adapted for use with the various connector embodiments illustrated and described with regard to FIGS. 1-6D of U.S. Pat. No. 8,074,964 which is incorporated herein by reference in its entirety.

In still additional alternative embodiments, the selective transmissivity fabrication process 100 is adapted for use with the various connector embodiments illustrated and described with regard to FIGS. 1A-6 of U.S. Pat. No. 9,375,561 which is incorporated herein by reference in its entirety.

In still additional alternative embodiments, the selective transmissivity fabrication process 100 is adapted for use with the various connector embodiments illustrated and described with regard to FIGS. 1-22 of U.S. Pat. No. 6,682,509 which is incorporated herein by reference in its entirety.

In still additional alternative embodiments, the selective transmissivity fabrication process 100 is adapted for use with the various connector embodiments illustrated and described with regard to FIGS. 1-11 of U.S. Pat. No. 8,876,784 which is incorporated herein by reference in its entirety.

In still additional alternative embodiments, the selective transmissivity fabrication process 100 is adapted for use with the various connector embodiments illustrated and described with regard to FIGS. 1-5C of U.S. Pat. No. 9,061,130 which is incorporated herein by reference in its entirety.

In still additional alternative embodiments, the selective transmissivity fabrication process 100 is adapted for use with the various connector embodiments illustrated and described with regard to FIGS. 1A-6B of U.S. Pat. No. 9,370,651 which is incorporated herein by reference in its entirety.

In one aspect, the selective transmissivity fabrication process 100 is adapted for use with needleless connectors having negative, positive or neutral displacement. In another aspect, the selective transmissivity fabrication process 100 is adapted for use with needleless connectors that are Luer activated, are cannula activated or activated by coupling to an additional connector. In still another aspect, the selective transmissivity fabrication process 100 is adapted for use with needleless connectors having a priming volume from about 0.1 mL to about 0.01 mL.

In still another aspect, the selective transmissivity fabrication process 100 is adapted for use with needleless connectors having a split septum and/or interior flow pathways. In embodiments where the connector fluid pathway includes a flow path structure within the connector body the materials selection, fabrication, transmissivity signature and other steps of method 100 are part of the adaptation of those designs to the advantageous light based disinfection methods and systems described herein. As a result either or both of the material selection or the fabrication process for components of the internal connector fluid flow path to receive light-based disinfection are governed by the selection criteria above in method 100. In these specific embodiments, both the exterior connector body along with the interior flow path material are adapted for selective transmissivity and the signature for both the connector body and interior components are obtained and utilized as part of steps 110, 115 and 120 above so that light based disinfection may be advantageously provided in these connector designs as well. An additional alternative embodiments, the needleless connectors described in "Needleless Connectors: A Primer on Technology" by Lynn Hadaway and Deb Richardson are fabricated, modified or adapted as described herein for conversion to appropriate light based disinfection. The article "Needleless Connectors: A Primer on Technology" by Lynn Hadaway and Deb Richardson, Journal of Infusion Nursing, Vol. 33 Number 1, January 2010, is incorporated herein by reference in its entirety.

In still further additional aspects, a wide variety of embodiments of the fabrication, transmissivity signature and disinfection unit keying process may be advantageously applied to a wide variety of connectors where easy to perform, rapid UV-C based disinfection would be desirous. Exemplary applications include uses such as fluid connectors and other components in fresh water systems, food and beverage processing systems and pharmaceutical composition manufacturing systems. In still other examples within the medical arts, the adoption of the use of selectively transmissive UV-C components may benefit health care work flows in dialysis, blood drawing, processing and handling. Still further, the method of evaluation and adaptation of existing medical components to selectively transmissive components suited to UV-C disinfection includes, by way of example and not limitation, feeding tubes, tracheotomy tubes, chest tubes, external components of a colostomy system, or other medical components where infection concerns would benefit from adoption of an embodiment of one of the easy to use, effective light based disinfection systems described herein.

In some other embodiments, any of the disinfection units, components, adapters, manifolds and the like may be modified or adapted so as to enable interaction with an input interface and/or an output interface to facilitate collection and reporting of information related to a cleaning event, a disinfection event, a change of a component, a patient condition, a patient status change, a delivery of a medicine or a use of a component, disinfection device or connector as disclosed herein. For example, in some embodiments input interface may be an optical reader such as for example barcode scanner or other device which is capable of reading a computer-readable barcode that is placed on a needleless connector, and/or an identification tag or label of the patient and/or the identification of the disinfecting unit or component or manifold described herein. In still other embodiments, an input interface may also include an inductive or near field communication system, a magnetic card reader, or an optical camera which is capable of retrieving information stored within a magnetic stripe or a computer-readable code, respectively. For example, a patient may have an identification card having a magnetic stripe which contains the identity of the patient and other related medical information. The patient, a disinfection unit and/or needleless connector or component may further include a QR code which is capable of being detected and deciphered using an optical camera and computer-executable software configured to retrieve information from the QR code. In still other alternative embodiments, the patient, the disinfecting unit, component, manifold, or connector may further include RFID tag which can be read by a RFID reader on the disinfection device.

In still other alternative embodiments, any of the disinfecting systems, components, manifolds or connectors described herein may be modified so as to be operably connected to a local, remote, cloud, distributed or other computer network via a hardwired and/or wireless link. In some embodiments, link includes a portion of an output interface. When information is acquired, the information is transmitted to network where the information is made accessible to various remote computer devices also operably connected to network. In still other aspects, acquired information related to the use and operation and other appropriate details of the patient use of the catheter or disinfection system is stored in a database, such as an electronic medical record (EMR). An EMR generally comprises a computerized medical record for a patient, as known in the art. In some embodiments, an EMR is configured to receive and store information relating to the disinfection event, including information directly from a disinfecting unit or a unit integrated into a patient bed. For example, an EMR for a patient utilizing a disinfection unit described herein may receive information such as the date of the disinfection event, a final status of the disinfection event, the identity of the clinician, nurse or health care provider who performed the disinfection event or changed a component intended to interaction with or be disinfected by the disinfection system, the make and model and type of a component, a needleless connector, manifold or hub as well a time and/or duration of the disinfection event, including date and time of start and date and time of stop of one or more disinfection events.

Additionally, a computer network may include a server on which a computer executable program is loaded having instructions for receiving, analyzing, and storing information received from disinfection device. The network may further include network security software or other precautionary software as may be required to comply with Health Information Patient Privacy Act requirements. In some embodiments, network comprises a local area network. In other embodiments, network is a global area network, or a distributed, a remote or a cloud based network.

Optionally, the various alternative disinfection units, connectors, components or manifolds described above may be modified to include or substitute components, features, or functionalities from the various disinfection systems, components and methods set forth in: United States Patent Application Publication Number US 2015/0165185 entitled "UV Sterilization Catheters and Catheter Connectors"; United States Patent Application Publication Number US 2013/0323120 entitled "UV Disinfection System for Needleless Connector"; United States Patent Application Publication Number US 2012/0053512 entitled "UV-C Antimicrobial Device for Intravenous Therapy"; U.S. Pat. No. 8,197,087 entitled "Peritoneal Dialysis Patient Connection System using Ultraviolet Light Emitting Diodes; U.S. Pat. No. 7,834,328 entitled "Method and Apparatus for Sterilizing Intraluminal and Percutaneous Access Sites"; U.S. Pat. No. 8,779,386 entitled, "Assembly and Method for Disinfecting Lumens of Devices"; and United States Patent Application Publication Number US 2008/0051736 entitled "Sterilizable Indwelling Catheters", each of which is incorporated by reference in its entirety for all purposes.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A UV disinfection device for disinfecting catheter connectors, comprising:
    a body having a first end and a second end, the body shaped to be held in a hand of a user;
    a generally barrel shaped chamber positioned at or near the first end of the body and configured to receive a catheter connector therein;
    a plurality of UV-C LEDs positioned along a perimeter of a cross-section of the generally barrel shaped chamber; and
    one or more electrical contact switches that are each operable to establish electrical contact with a corresponding contact on a catheter connector disposed in the generally barrel shaped chamber.

2. The UV disinfection device of claim 1, wherein the one or more electrical contact switches comprise pogo pin type contacts.

3. The UV disinfection device of claim 1, wherein the catheter connector has a plurality of contacts thereon, and the number of electrical contact switches corresponds to the number of contacts on the catheter connector.

4. The UV disinfection device of claim 1, wherein the UV disinfection device is configured to receive information specific to the corresponding catheter connector by way of the electrical contact between the one or more electrical contact switches of the UV disinfection device and corresponding contacts of the catheter connector.

5. The UV disinfection device of claim 4, wherein the information relates to one or more of connector identity, disinfection, or time out.

* * * * *